(12) United States Patent
Nakanishi et al.

(10) Patent No.: US 11,834,667 B2
(45) Date of Patent: Dec. 5, 2023

(54) GENE EXPRESSION SYSTEM USING STEALTHY RNA, AND GENE INTRODUCTION/EXPRESSION VECTOR INCLUDING SAID RNA

(71) Applicants: NATIONAL INSTITUTE OF ADVANCED INDUSTRIAL SCIENCE AND TECHNOLOGY, Tokyo (JP); TOKIWA-BIO INC., Tsukuba (JP)

(72) Inventors: Mahito Nakanishi, Tsukuba (JP); Minoru Iijima, Tsukuba (JP)

(73) Assignees: NATIONAL INSTITUTE OF ADVANCED INDUSTRIAL SCIENCE AND TECHNOLOGY, Tokyo (JP); TOKIWA-BIO INC., Tsukuba (JP)

( * ) Notice: Subject to any disclaimer, the term of this patent is extended or adjusted under 35 U.S.C. 154(b) by 1022 days.

(21) Appl. No.: 16/692,771

(22) Filed: Nov. 22, 2019

(65) Prior Publication Data
US 2020/0190537 A1 Jun. 18, 2020

Related U.S. Application Data

(62) Division of application No. 15/544,084, filed as application No. PCT/JP2016/051336 on Jan. 18, 2016, now Pat. No. 10,544,431.

(30) Foreign Application Priority Data

Jan. 16, 2015 (JP) .................................. 2015-007288

(51) Int. Cl.
| | |
|---|---|
| *C12N 15/63* | (2006.01) |
| *C12N 15/86* | (2006.01) |
| *C12N 5/14* | (2006.01) |
| *C12N 15/09* | (2006.01) |
| *C07K 16/28* | (2006.01) |
| *C07K 16/32* | (2006.01) |
| *C07K 16/46* | (2006.01) |
| *C12N 5/074* | (2010.01) |
| *C12N 9/12* | (2006.01) |

(52) U.S. Cl.
CPC .......... *C12N 15/86* (2013.01); *C07K 16/2863* (2013.01); *C07K 16/32* (2013.01); *C07K 16/468* (2013.01); *C12N 5/0696* (2013.01); *C12N 5/14* (2013.01); *C12N 9/127* (2013.01); *C12N 15/09* (2013.01); *C12Y 207/07048* (2013.01); *C07K 2317/14* (2013.01); *C07K 2317/21* (2013.01); *C07K 2317/31* (2013.01); *C12N 2506/02* (2013.01); *C12N 2510/00* (2013.01); *C12N 2760/18843* (2013.01); *C12N 2800/22* (2013.01); *C12N 2800/70* (2013.01); *C12N 2820/60* (2013.01); *C12N 2830/60* (2013.01)

(58) Field of Classification Search
None
See application file for complete search history.

(56) References Cited

U.S. PATENT DOCUMENTS

| | | |
|---|---|---|
| 7,561,973 B1 | 7/2009 | Welch et al. |
| 8,326,547 B2 | 12/2012 | Liu et al. |
| 8,401,798 B2 | 3/2013 | Welch et al. |
| 2009/0068742 A1 | 3/2009 | Yamanaka |
| 2009/0087883 A1 | 4/2009 | Lin |
| 2010/0311171 A1 | 12/2010 | Nakanishi et al. |

(Continued)

FOREIGN PATENT DOCUMENTS

| | | |
|---|---|---|
| EP | 2 322 611 A1 | 5/2011 |
| EP | 2 434 012 A1 | 3/2012 |
| EP | 2639297 A1 | 9/2013 |

(Continued)

OTHER PUBLICATIONS

Larson (Neuromuscular Disorder: 2014, vol. 24, pp. 693-706). (Year: 2014).*

(Continued)

*Primary Examiner* — Celine X Qian
(74) *Attorney, Agent, or Firm* — WHDA, LLP

(57) ABSTRACT

The present invention enables simultaneous and stable expression of a plurality of foreign genes by using a stealthy RNA gene expression system that is a complex that does not activate the innate immune mechanism and is formed from an RNA-dependent RNA polymerase, a single-strand RNA binding protein, and negative-sense single-strand RNAs including the following (1) to (8): (1) a target RNA sequence that codes for any protein or functional RNA; (2) an RNA sequence forming a noncoding region and derived from mRNA expressed in animal cells; (3) a transcription initiation signal sequence recognized by the RNA-dependent RNA polymerase; (4) a transcription termination signal sequence recognized by the polymerase; (5) an RNA sequence containing a replication origin recognized by the polymerase; (6) an RNA sequence that codes for the polymerase and of which codons are optimized for the species from which an introduction target cell is derived; (7) an RNA sequence that codes for a protein for regulating the activity of the polymerase and of which codons are optimized for the species from which the introduction target cell is derived; and (8) an RNA sequence that codes for the single-strand RNA binding protein and of which codons are optimized for the species from which the introduction target cell is derived.

3 Claims, 23 Drawing Sheets
Specification includes a Sequence Listing.

(56) References Cited

U.S. PATENT DOCUMENTS

2013/0210150 A1      8/2013    Ban et al.

FOREIGN PATENT DOCUMENTS

| JP | 2009-82130 | A | | 4/2009 | | |
|----|---|---|---|---|---|---|
| WO | 01/81596 | A2 | | 11/2001 | | |
| WO | 2005/085456 | A1 | | 9/2005 | | |
| WO | WO-2005085456 | A1 | * | 9/2005 | ............ | C12N 15/64 |
| WO | 2007/069666 | A1 | | 6/2007 | | |
| WO | 2008/118820 | A2 | | 10/2008 | | |
| WO | 2010/008054 | A1 | | 1/2010 | | |
| WO | 2010/134526 | A1 | | 11/2010 | | |
| WO | 2012/029770 | A1 | | 3/2012 | | |
| WO | 2012/063817 | A1 | | 5/2012 | | |

OTHER PUBLICATIONS

Kuno et al., "Characterization of Self-Cleaving RNA Sequences on the Genome and Antigenome of Human Hepatitis Delta Virus", (1988) December, Journal of Virology, vol. 62, No. 12, pp. 4439-4444. Cited in Specification. (7 pages).

Sengupta et al., "Relative Efficiency of Utilization of Promoter and Termination Sites by Bacteriophage T3 RNA Polymerase", Aug. 25, 1989, The Journal of Biological Chemistry, vol. 264, No. 24, p. 14246-14255. Cited in Specification. (10 pages).

Melton et al., "Efficient in vitro synthesis of biologically active RNA and RNA hybridization probes from plasmids containing a bacteriophage SP6 promoter", (1984), Nucleic Acids Research, vol. 12, No. 18, pp. 7035-7056. Cited in Specification. (22 pages).

Hampel et al., "RNA Catalytic Properties of the Minimum (-)s TRSV Sequence", (1989), Biochemistry, vol. 28, No. 12, pp. 4929-4933. Cited in Specification. (5 pages).

Tuschl et al., "Targeted mRNA degradation by double-stranded RNA in vitro", Mar. 7, 2017, Genes & Development, 13, pp. 3191-3197. Cited in Specification. (8 pages).

Chang et al., "Construction and Characterization of Amplificable Multicopy DNA Cloning Vehicles Derived from the P15A Cryptic Miniplasmid", Jun. 1978, Journal of Bacteriology, vol. 134, No. 3, pp. 1141-1156. Cited in Specification. (16 pages).

Garcin et al., "A highly recombinogenic system for the recovery of infectious Sendai paramyxovirus from cDNA: generation of a novel copy-back nondefective interfering Virus", (1995), The EMBO Journal, vol. 14, No. 24, pp. 6087-6094. Cited in Specification. (8 pages).

Gotoh et al., "Rescue of Sendai Virus from Viral Ribonucleoprotein-Transfected Cells by Infection with Recombinant Vaccinia Viruses Carrying Sendai Virus L and P/C Genes", (1989), Virology, 171, pp. 434-443. Cited in Specification. (10 pages).

Lopez et al., "The C-terminal half of RNase E, which organizes the *Escherichia coli* degradosome, participates in mRNA degradtion but not rRNA processing in vivo", (1999), Molecular Microbiology, 33, pp. 188-199. Cited in Specification. (12 pages).

Kozak et al., "Point Mutations Define a Sequence Flanking the AUG Initiator Codon That Modulates Translation by Eukaryotic Ribosomes", Jan. 31, 1986, Cell, vol. 44, pp. 283-292. Cited in Specification. (10 pages).

Kozak et al., "Effects of Intercistronic Length on the Efficiency of Reinitiation by Eukaryotic Ribosomes", Oct. 1987, Molecular and Cellular Biology, vol. 7. No. 10, pp. 3438-3445. Cited in Specification. (8 pages).

Vara et al., "Cloning and expression of a puromycin N-acetyl transferase gene from *Streptomyces alboniger* in *Streptomyces lividans* and *Escherichia coli*", (1985), Gene, 33, pp. 197-206. Cited in Specification. (10 pages).

Nakajima et al., "cDNA Cloning and Characterization of a Secreted Luciferase from the Luminous Japanese Ostracod, Cypridina noctiluca", (2004), Biosci. Biotechnol. Biochem., 68, pp. 565-570. Cited in Specification. (6 pages).

Ai et al., "Exploration of New Chromophore Structures Leads to the Identification of Improved Blue Fluorescent Proteins", Apr. 20, 2007, Biochemistry, vol. 46, No. 20, pp. 5904-5910. Cited in Specification. (7 pages).

Drocourt et al., "Cassettes of the Spreptoalloteichus hindustanus ble gene for transformation of lower and higher eukaryotes to phleomycin resistance", (1990), Nucleic Acids Research, vol. 18, No. 13, pp. 4009. Cited in Specification. (1 page).

Kogure et al., "A fluorescent variant of a protein from the stony coral Montipore facilitates dual-color single-laser fluorescence cross-correlation spectroscopy", May 2006, Nature Biotechnology, vol. 24, No. 5, pp. 577-581. Cited in Specification. (7 pages).

Gritz et al., "Plasmid-encoded hygromycin B resistane: the sequence of hygromycin B phosphotransferase gene and its expression in *Escherichia coli Saccharomyces cerevisiae*", (1983), Gene, 25, pp. 179-188. Cited in Specification. (10 pages).

Studier et al., "Use of Bacteriophage T7 RNA Polymerase to Direct Selective High-level Expression of Cloned Genes", (1986), J. Mol. Bio., 189, pp. 113-130. Cited in Specification. (18 pages).

Nawa et al., "Inactivation of Blasticidin S by *Bacillus cereus*. VI. Structure and Comparison of the bsr Gene from a Blasticidin S-Resistant Bacillus cereus", (1998) September, Biol. Pharm. Bull., 21, pp. 893-898. Cited in Specification. (6 pages).

Karasawa et al., "Cyan-emitting and orange-emitting fluorescent proteins as a donor/acceptor pair for fluorescence resonance energy transfer", (2004), Biochem. J., 381, pp. 307-312. Cited in Specification. (6 pages).

Yoneyama et al., "The RNA helicase RIG-I has an essential function in double-stranded RNA-induced innate antiviral resopnse", (2004) July, Nature Immunology, vol. 5, No. 7, pp. 730-737. Cited in Specification. (13 pages).

Sakaguchi et al., "Analysis of interaction of Sendai virus V protein and melanoma differentiation-associated gene 5", (2011), Microbiology and Immunology, 55, pp. 760-767. Cited in Specification. (8 pages).

Jia et al., "Negative Regulation of MAVS-Mediated Innate Immune Response by PSMA7[1] ", Sep. 2009, J. Immunol., 183, pp. 4241-4248. Cited in Specification. (9 pages).

Akagi et al., "Refractory nature of normal human diploid fibroblasts with respect to oncogene-mediated transformation", Nov. 11, 2003, Proc. Natl. Acad. Sci. USA, vol. 100, No. 23, pp. 13567-13572. Cited in Specification. (6 pages).

Hatsuzawa et al., "Structure and Expression of Mouse Furin, a Yeast Kex2-related Protease", Dec. 25, 1990, The Journal of Biological Chemistry, vol. 265, No. 36, p. 22075-22078. Cited in Specification. (4 pages).

Boshart et al., "A Very Strong Enhancer is Located Upstream of an Immediate Early Gene of Human Cytomegalovirus", Jun. 1985, Cell, vol. 41, pp. 521-530. Cited in Specification. (10 pages).

Taira et al., "Transfection of Sendai virus F gene cDNA with mutations at its cleavage site and HN gene cDNA into COS cells induces cell fusion", (1995), Arch. Virol., 140, pp. 187-194. Cited in Specification. (8 pages).

Takebe et al., "SRa Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Jan. 1988, Molecular and Cellular Biology, vol. 8, No. 1, pp. 466-472. Cited in Specification. (7 pages).

Recillas-Targa et al., "Position-effect protection and enhancer blocking by the chicken Beta-globin insulator are separable activities", May 14, 2002, Proc. Natl. Acad. Sci. USA, vol. 99, No. 10, pp. 6883-6888. Cited in Specification. (6 pages).

Fujita et al., "Delimitation and Properties of DNA Sequences Required for the Regulated Expression of Human Interferon-B Gene", (1985) June, Cell, vol. 41, pp. 489-496. Cited in Specification. (8 pages).

Yi et al., "3' Nontranslated RNA Signals Required for Replication of Hepatitis C Virus RNA", Mar. 2003., Journal of Virology, vol. 77, No. 6, pp. 3557-3568. Cited in Specification. (12 pages).

You et al., "3' RNA Elements in Hepatitis C Virus Replication: Kissing Partners and Long Poly (U)", Jan. 2008, Journal of Virology, vol. 82, No. 1, pp. 184-195. Cited in Specification. (12 pages).

(56) References Cited

OTHER PUBLICATIONS

Chromikova et al., "Evaluating the bottlenecks of recombinant IgM production in mammalian cells", (2015), Cytotechnology, 67, pp. 343-356. Cited in Specification. (14 pages).
BRändlein et al., "Natural IgM antibodies, the ignored weapons in tumour immunity", (2004), Histol. Histopathol., 19, pp. 897-905. Cited in Specification. (9 pages).
Okada et al., "Human IgM Monoclonal Antibodies Reactive with HIV-1-Infected Cells Generated Using a Trans-Chromosome Mouse", (2005), Microbiol. Immunol., 49, pp. 447-459. Cited in Specification. (13 pages).
Lewis et al., "Generation of bispecific IgG antibodies by structure-based design of an orthogonal Fab interface", Feb. 2014, Nature Biotechnology, vol. 32, No. 2, pp. 191-198. Cited in Specification. (45 pages).
WURM., "Production of recombinant protein therapeutics in cultivated mammalian cells", Nov. 2004, Nature Biotechnology, vol. 22, No. 11, pp. 1393-1398. Cited in Specification. (6 pages).
International Preliminary Report on Patentability (Form PCT/IB/373) of International Application No. PCT/JP2016/051336 dated Jan. 18, 2016, with Form PCT/ISA/237. (12 pages).
Cheng, X. et al., "CpG Usage in RNA Viruses: Data and Hypotheses", PLOS ONE, Sep. 23, 2013, vol. 8, No. 9, pp. 1-6; cited in Extended (supplementary) European Search Report dated Jun. 1, 2018. (10 pages).
Extended (supplementary) European Search Report dated Jun. 1, 2018, issued in counterpart European Application No. 16737476.8. (8 pages).
International Search Report dated Apr. 19, 2016, issued in counterpart of International Application No. PCT/JP2016/051336 (2 pages).
Nishimura et a., "Development of defective and persistent Sendai virus vector: a unique gene delivery/expression system ideal for cell reprogramming", J. Boil. Chem., Feb. 11, 2011, vol. 286, No. 6, pp. 4760-4771. Cited in Specification & ISR. (19 pages).
Vabret et al., The biased nucleotide composition of HIV-1 triggers type I interferon response and correlates with subtype D increased pathogenicity., PLoS One, (2012) 04, vol. 7, No. 4, e33502, pp. 1-7. Cited in ISR. (7 pages).
Takahashi et al., "Induction of Pluripotent Stem Cells from Adult Human Fibroblasts by Defined Factors", (2007) Nov. 30, Cell 131, 1-12, pp. 861-872. Cited in Specification . (28 pages).
Yu et al., "Induced Pluripotent Stem Cell Lines Derived from Human Somatic Cells", Dec. 21, 2007, Science, vol. 318, pp. 1917-1920. Cited in Specification. (28 pages).
Huang et al., "Direct Reprogramming of Human Fibroblasts to Functional and Expandable Hepatocytes", (2014) Mar. 6, 2014, Cell Stem Cell 14, pp. 370-384. Cited in Specification. (51 pages).
Son et al., "Conversion of Mouse and Human Fibroblasts into Functional Spinal Motor Neurons", Sep. 2, 2011, Cell Stem Cell 9, pp. 205-218. Cited in Specification. (23 pages).
Qian et al., "In vivo reprogramming of murine cardiac fibroblasts into induced cardiomyocytes", May 31, 2012, Nature, vol. 485, pp. 593-598. Cited in Specification. (30 pages).
Song et al., "Heart repair by reprogramming non-myocytes with cardiac transcription factors", May 31, 2012, Nature, vol. 485, pp. 599-604. Cited in Specification. (8 pages).
Carey et al., "Reprogramming of murine and human somatic cells using a single polycistronic vector", Then National Academy of Sciences of the USA, Jan. 6, 2009, vol. 106, pp. 157-162. Cited in Specification. (11 pages).
Singhal et al., "Chromatin-Remodeling Components of the BAF Complex Facilitate Reprogramming", Jun. 11, 2010, Cell 141, pp. 943-955. Cited in Specification. (21 pages).
Tonge et al., "Divergent reprogramming routes lead to alternative stem-cell states", Dec. 11, 2014, Nature, vol. 516, pp. 192-197. Cited in Specification. (18 pages).
Miura et al., "Variation in the safety of induced pluripotent stem cell lines", (2009) August, Nature Biotechnology, vol. 27, No. 8, pp. 743-745. Cited in Specification. (17 pages).
Randall et al., "Interferons and viruses: an interplay between induction, signalling, antiviral responses and virus countermeasures", Journal of General Virology, (2008), 89, pp. 1-47. Cited in Specification. (47 pages).
Sommer et al., "Excision of Reprogramming Transgenes Improves the Differentiation Potential of iPS Cells Generated with a Single Excisable Vector", (2010), Stem Cells, 28, pp. 64-74. Cited in Specification. (16 pages).
Kaji et al., "Virus-free induction of pluripotency and subsequent excision of reprogrammin factors", (2009), Nature, 458, pp. 771-775. Cited in Specification. (24 pages).
Grabundzija et al., "Sleeping Beauty Transposon-based system for cellular reprogramming and targeted gene insertion in induced pluripotent stem cells", (2013), Nucleic Acids Research, vol. 41, No. 3, pp. 1829-1847. Cited in Specification. (19 pages).
Hacein-Bey-Abina et al., "LMO2-Associated Clonal T Cell Proliferation in Two Patients after Gene Therapy for SCID-X1", Oct. 17, 2003, Science, vol. 302, pp. 415-419. Cited in Specification. (6 pages).
Wu et al., "Efficient germ-line transmission obtained with transgene-free induced pluripotent stem cells", Jul. 22, 2014, Proc. Natl. Acad. Sci. USA, vol. 111, p. 10678-10683. Cited in Specification. (15 pages).
Hiratsuka et al., "Integration-Free iPS Cells Engineered Using Human Artificial Chromosome Vectors", Oct. 2011, Plos One, vol. 6, issue 10, e25961. Cited in Specification. (14 pages).
Hurley et al., "When Epstein-Barr Virus Persistently Infects B-Cell Lines, It Frequently Integrates", Mar. 1991, Journal of Virology, vol. 65, No. 3, pp. 1245-1254. Cited in Specification. (10 pages).
Yahata et al., "cHS4 Insulator-mediated Alleviation of Promoter Interference during Cell-based Expression of Tandemly Associated Transgenes", (2007) , J. Mol. Biol. 374, pp. 580-590. Cited in Specification. (11 pages).
Nishiumi et al., "Simultaneous Single Cell Stable Expression of 2-4 cDNAs in HeLaS3 Using fC31 Integrase System", (2009), Cell Structure and Function, 34, pp. 47-59. Cited in Specification. (13 pages).
Balvay et al., "Structural and functional diversity of viral IRESes", (2009), Biochimica et Biophysica Acta, 1789, pp. 542-557. Cited in Specification. (16 pages).
Felipe et al., "E unum pluribus: multiple proteins from a self-processing polyprotein", Feb. 2006, Trends in Biotechnology, vol. 24, No. 2, pp. 68-75. Cited in Specification. (21 pages).
Lengler et al., "FMDV-2A sequence and protein arrangement contribute to functionality of CYP2B1-reporter fusion protein", (2005), Analytical Biochemistry, 343, pp. 116-124. Cited in Specification. (9 pages).
Yoshioka et al., "Efficient Generation of Human iPSCs by a Synthetic Self-Replicative RNA", Aug. 1, 2013, Cell Stem Cell, 13, pp. 246-254. Cited in Specification. (9 pages).
Warren et al., "Highly Efficient Reprogramming to Pluripotency and Directed Differentiation of Human Cells with Synthetic Modified mRNA", Nov. 5, 2010, Cell Stem Cell, 7, pp. 1-13. Cited in Specification. (27 pages).
Fusaki et al., "Efficient induction of transgeen-fee human pluripotent stem cells using a vector based on Sendai virus, an RNA virus that does not integrate into the host genome" (2009), Proc. Jpn. Acad., Ser. B 85, vol. 85, pp. 348-362. Cited in Specification. (15 pages).
Ban et al., "Efficient generation of transgene-free human induced pluripotent stem cells (iPSCs) by temperature-sensitive Sendai virus vectors", Aug. 23, 2011, Proc. Natl. Acad. Sci. USA, vol. 108, No. 34, p. 14234-14239. (Cited in Specification. (6 pages).
Fujie et al., "New Type of Sendai Virus Vector Provides Transgene-Free iPS Cells Derived from Chimpanzee Blood", Dec. 5, 2014, Plos On, 9, e113052. Cited in Specification. (25 pages).
Hua et al., "Cytokines induced by Sendai virus in human peripheral blood leukocytes", (1996), J. Leukocyte Biol., 60, pp. 125-128. Cited in Specification. (4 pages).
Sakai et al., "Accommodation of foreign genes into the Sendai virus genome: sizes of inserted genes and viral replication", (1999), FEBS Letters, 456, pp. 221-226. Cited in Specification. (6 pages).
Kondo et al., "Temperature-sensitive Phenotype of a Mutant Sendai Virus Strain is Caused by its Insufficient Accumulation of the M

(56) References Cited

OTHER PUBLICATIONS

Protein", Oct. 15, 1993, The Journal of Biological Chemistry, vol. 268, No. 29, pp. 21924-21930, Cited in Specification. (7 pages).

Ward et al., "RNA editing enzyme adenosine deaminase is a restriction factor for controlling measles virus replication that also is required for embryogenesis", Jan. 4, 2011, Proc. Natl. Acad. sci. USA, vol. 108, No. 1, pp. 331-336. Cited in Specification. (6 pages).

Saito et al., "Innate immunity induced by composition-dependent RIG-I recognition of hepatitis C virus RNA", Jul. 24, 2008, Nature, vol. 454, pp. 523-527. Cited in Specification. (27 pages).

Rehwinkel et al., "RIG-I Detects Viral Genomic RNA during Negative-Strand RNA Virus Infection", Feb. 5, 2010, Cell, 140, pp. 397-408. Cited in Specification. (22 pages).

Shioda et al., "Determination of the complete nucleotide sequence of the Sendai virus genome RNA and the predicted amino acid sequences of the F, HN and L proteins", (1986), Nucleic Acids Research, vol. 14, No. 4, pp. 1545-1563. Cited in Specification. (19 pages).

Vidal et al., "Editing of the Sendai Virus P/C mRNA by G Insertion Occurs during mRNA Synthesis via a Virus-Encoded Activity", (1990) Jan., Journal of Virology, vol. 64, No. 1, pp. 239-246. Cited in Specification. (9 pages).

Irie et al., "Inhibition of Interferon Regulatory Factor 3 Activation by Paramyxovirus V Protein", Jul. 2012, Journal of Virology, vol. 86, No. 13, pp. 7136-7145. Cited in Specification. (11 pages).

Kato et al., "The paramyxovirus, Sendai virus, V protein encodes a luxury function required for viral pathogenesis", (1997), The EMBO Journal, vol. 16, No. 3, pp. 578-587. Cited in Specification. (10 pages).

Tapparel et al., "The Activity of Sendai Virus Genomic and Antigenomic Promoters Requires a Second Element Past the Leader Template Regions: a Motif (GNNNNN)3 Is Essential for Replication", Apr. 1998, Journal of Virology, vol. 72, No. 4, pp. 3117-3128. Cited in Specification. (12 pages).

Park et al., "Rescue of a foreign gene by Sendai virus", Jul. 1991, Proc. Natl. Acad. sci. USA, vol. 88, pp. 5537-5541. Cited in Specification. (5 pages).

Harty et al., "Mutations within Noncoding Terminal Sequences of Model RNAs of Sendai Virus: Influence on Reporter Gene Expression", Aug. 1995, Journal of Virology, vol. 69, No. 8, pp. 5128-5131. Cited in Specification. (4 pages).
Willenbrink et al., "Long-Term Replication of Sendai Virus Defective Interfering Particle Nucleocapsides in Stable Helper Cell Lines", Dec. 1994, Journal of Virology, vol. 68, No. 12, pp. 8413-8417. Cited in Specification. (5 pages).
Sharp et al., "The Codon adaptation index—a measure of directional synonymous codon usage bia, and its potential applications", (1987), Nucleic Acids Research, vol. 15, No. 3, pp. 1281-1295. Cited in Specification. (15 pages).

Guigó et al., "Distinctive Sequence Features in Protein Coding Genic Non-coding, and Intergenic Human DNA", (1995), J. Mol. Biol., 253, pp. 51-60. Cited in Specification. (10 pages).
Vabret et al., "Large-Scale Nucleotide Optimization of Simian Immunodeficiency Virus Reduces Its Capacity To Stimulate Type I Interferon In Vitro", Apr. 2014, Journal of Virology, vol. 88, No. 8, pp. 4161-4172. Cited in Specification. (26 pages).
Raab et al., "The GeneOptimizer Algorithm: Using a sliding window approach to cope with the vast sequence space in multiparameter DNA sequence optimization", (2010) Syst. Synth. Biol., 4, pp. 215-225. Cited in Specification. (11 pages).
Alan et al., "Vectors for selective expression of cloned DNAs by T7 RNA polymerase", (1987), Gene, 56, pp. 125-135. Cited in Specification. (11 pages).

* cited by examiner

Genome Structure of Stealth RNA Vector #2

1. Firefly Luciferase (FLuc)
2. *Renilla* Luciferase (RLuc)
3. EGFP
4. Puromycin Resistant
5. *Cypridina noctiluca* Luciferase (CLuc)
6. E2-Crimson
7. EBFP2
8. Zeocin Resistant
9. Keima-Red
10. Hygromycin B Resistant ▨ Genes Optimized with GGEOT Method

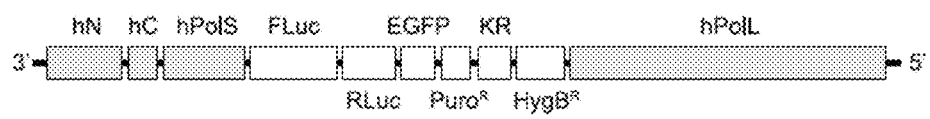

| | Luciferase | Luciferase Activity (% of control) |
|---|---|---|
| 5' ccacc | AUG | 100 |
| 5' ccaccAUGAAAUUGCCAGAAGACUGAcacuagagccgccacc | AUG | 40 |
| 5' caccAUGgcccaggcuucaua | AUG | 23 |

B

Diagram: 3'— hN hC hPolS FLuc EGFP KR hPolL —5'
           RLuc Puro^R HygB^R

| | Translation Efficiency | | F.Luciferase Activity (Relative value) |
|---|---|---|---|
| | NP | C | |
| Stealth RNA gene expression system #6 | 100 | 100 | 1.0 |
| Stealth RNA gene expression system #7 | 100 | 23 | 8.8 |
| Stealth RNA gene expression system #8 | 40 | 23 | 79.0 |

FIG. 21

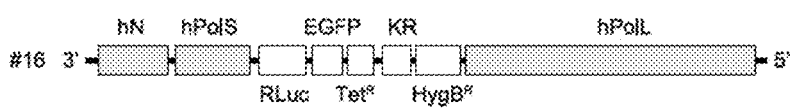

16: 3'— hN hPolS EGFP KR hPolL —5'
         RLuc Tet^R HygB^R

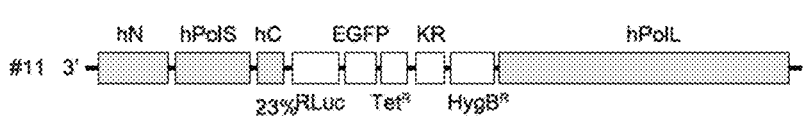

11: 3'— hN hPolS hC EGFP KR hPolL —5'
         23%RLuc Tet^R HygB^R

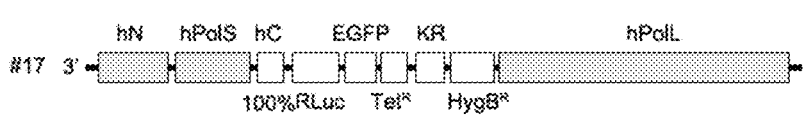
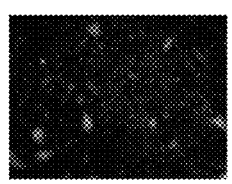

17: 3'— hN hPolS hC EGFP KR hPolL —5'
         100%RLuc Tet^R HygB^R

Expression of EGFP

FIG. 22

```
        hN  hC  hPolS  FLuc     EGFP   KB              hPolL
    3'━■──■━━━━━━━━■━━━━━■━■━━■━■━■━━━━━━━━━━━━━━5'
                              RLuc  Puro^R  HygB^R
    ┌─────────────┐
   (AAAGAAACGACGGUUUCA)
     Sequence D
```

| | | Expression of EGFP in packaging cells | Number of vector particles in packaging cell supernatant (x 10⁶ /mL) |
|---|---|---|---|
| Stealth RNA gene expression system #9 | Remove Sequence D From #6 | +++ | 2 |
| Stealth RNA gene expression system #6 | | +++ | 210 |
| Stealth RNA gene expression system #10 | Remove Sequence D From #7 | ++++ | 7 |
| Stealth RNA gene expression system #7 | | ++++ | 450 |

SEQUENCE LISTING

```
<160> NUMBER OF SEQ ID NOS: 116

<210> SEQ ID NO 1
<211> LENGTH: 10
<212> TYPE: RNA
<213> ORGANISM: Artificial Sequence
<220> FEATURE:
<223> OTHER INFORMATION: Sendai virus transcription initiation signal,
      minus strand sequence

<400> SEQUENCE: 1
cuuucacccu                                                                10

<210> SEQ ID NO 2
<211> LENGTH: 10
<212> TYPE: RNA
<213> ORGANISM: Artificial Sequence
<220> FEATURE:
<223> OTHER INFORMATION: Sendai virus transcription initiation signal,
      minus strand sequence

<400> SEQUENCE: 2
cuuuaucccu                                                                10

<210> SEQ ID NO 3
<211> LENGTH: 10
<212> TYPE: RNA
<213> ORGANISM: Artificial Sequence
<220> FEATURE:
<223> OTHER INFORMATION: Sendai virus transcription initiation signal,
      minus strand sequence

<400> SEQUENCE: 3
cauucacccu                                                                10

<210> SEQ ID NO 4
<211> LENGTH: 10
<212> TYPE: RNA
<213> ORGANISM: Artificial Sequence
<220> FEATURE:
<223> OTHER INFORMATION: Sendai virus transcription termination signal,
      minus strand sequence

<400> SEQUENCE: 4
uuuuucuuaa                                                                10

<210> SEQ ID NO 5
<211> LENGTH: 10
```

```
<212> TYPE: RNA
<213> ORGANISM: Artificial Sequence
<220> FEATURE:
<223> OTHER INFORMATION: Sendai virus transcription termination signal,
      minus strand sequence

<400> SEQUENCE: 5
uuuuucuuac                                                              10

<210> SEQ ID NO 6
<211> LENGTH: 10
<212> TYPE: RNA
<213> ORGANISM: Artificial Sequence
<220> FEATURE:
<223> OTHER INFORMATION: Sendai virus transcription termination signal,
      minus strand sequence

<400> SEQUENCE: 6
uuuuucuuau                                                              10

<210> SEQ ID NO 7
<211> LENGTH: 10
<212> TYPE: RNA
<213> ORGANISM: Artificial Sequence
<220> FEATURE:
<223> OTHER INFORMATION: human parainfluenza virus III transcription
      initiation signal, minus strand sequence

<400> SEQUENCE: 7
cuuuaauccu                                                              10

<210> SEQ ID NO 8
<211> LENGTH: 11
<212> TYPE: RNA
<213> ORGANISM: Artificial Sequence
<220> FEATURE:
<223> OTHER INFORMATION: human parainfluenza virus III transcription
      termination signal

<400> SEQUENCE: 8
uuuuucuuau u                                                            11

<210> SEQ ID NO 9
<211> LENGTH: 11
<212> TYPE: RNA
<213> ORGANISM: Artificial Sequence
<220> FEATURE:
<223> OTHER INFORMATION: Newcastle disease virus transcription
      initiation signal, minus strand sequence

<400> SEQUENCE: 9
cuucuacccg u                                                            11

<210> SEQ ID NO 10
<211> LENGTH: 10
<212> TYPE: RNA
<213> ORGANISM: Artificial Sequence
<220> FEATURE:
<223> OTHER INFORMATION: Newcastle disease virus transcription
      termination signal, minus strand sequence

<400> SEQUENCE: 10
uuuuuucuaa                                                              10

<210> SEQ ID NO 11
<211> LENGTH: 12
<212> TYPE: RNA
```

```
<213> ORGANISM: Artificial Sequence
<220> FEATURE:
<223> OTHER INFORMATION: Sendai virus genomic RNA 3' end replication
      origin, minus strand sequence

<400> SEQUENCE: 11
cucuugucug gu                                                            12

<210> SEQ ID NO 12
<211> LENGTH: 12
<212> TYPE: RNA
<213> ORGANISM: Artificial Sequence
<220> FEATURE:
<223> OTHER INFORMATION: Sendai virus genomic RNA 3' end replication
      origin, minus strand sequence

<400> SEQUENCE: 12
cucuuguuug gu                                                            12

<210> SEQ ID NO 13
<211> LENGTH: 12
<212> TYPE: RNA
<213> ORGANISM: Artificial Sequence
<220> FEATURE:
<223> OTHER INFORMATION: Sendai virus genomic RNA 5' end replication
      origin, minus strand sequence

<400> SEQUENCE: 13
accagacaag ag                                                            12

<210> SEQ ID NO 14
<211> LENGTH: 12
<212> TYPE: RNA
<213> ORGANISM: Artificial Sequence
<220> FEATURE:
<223> OTHER INFORMATION: Sendai virus genomic RNA 5' end replication
      origin, minus strand sequence

<400> SEQUENCE: 14
accaaacaag ag                                                            12

<210> SEQ ID NO 15
<211> LENGTH: 18
<212> TYPE: RNA
<213> ORGANISM: Artificial Sequence
<220> FEATURE:
<223> OTHER INFORMATION: Sendai virus (CNNNNN)3-BOX, minus strand
      sequence
<220> FEATURE:
<221> NAME/KEY: misc_feature
<222> LOCATION: (1)..(5)
<223> OTHER INFORMATION: n is a, c, g, or u
<220> FEATURE:
<221> NAME/KEY: misc_feature
<222> LOCATION: (7)..(11)
<223> OTHER INFORMATION: n is a, c, g, or u
<220> FEATURE:
<221> NAME/KEY: misc_feature
<222> LOCATION: (13)..(17)
<223> OTHER INFORMATION: n is a, c, g, or u

<400> SEQUENCE: 15
nnnnncnnnn ncnnnnnc                                                      18

<210> SEQ ID NO 16
<211> LENGTH: 18
<212> TYPE: RNA
<213> ORGANISM: Artificial Sequence
<220> FEATURE:
```

```
<223> OTHER INFORMATION: Sendai virus (NNNNNG)3-BOX, minus strand
      sequence
<220> FEATURE:
<221> NAME/KEY: misc_feature
<222> LOCATION: (2)..(6)
<223> OTHER INFORMATION: n is a, c, g, or u
<220> FEATURE:
<221> NAME/KEY: misc_feature
<222> LOCATION: (8)..(12)
<223> OTHER INFORMATION: n is a, c, g, or u
<220> FEATURE:
<221> NAME/KEY: misc_feature
<222> LOCATION: (14)..(18)
<223> OTHER INFORMATION: n is a, c, g, or u

<400> SEQUENCE: 16
gnnnnngnnn nngnnnnn                                                  18

<210> SEQ ID NO 17
<211> LENGTH: 18
<212> TYPE: RNA
<213> ORGANISM: Artificial Sequence
<220> FEATURE:
<223> OTHER INFORMATION: Sendai virus packaging signal, minus strand
      sequence

<400> SEQUENCE: 17
acuuuggcag caaagaaa                                                  18

<210> SEQ ID NO 18
<211> LENGTH: 5
<212> TYPE: RNA
<213> ORGANISM: Artificial Sequence
<220> FEATURE:
<223> OTHER INFORMATION: non-coding sequence from Homo sapiens
      glyceraldehyde-3-phosphate dehydrogenase

<400> SEQUENCE: 18 ccacc                                                                 5

<210> SEQ ID NO 19
<211> LENGTH: 27
<212> TYPE: DNA
<213> ORGANISM: Artificial Sequence
<220> FEATURE:
<223> OTHER INFORMATION: non-coding sequence from Homo sapiens
      eukaryotic translation elongation factor 1 alpha-1

<400> SEQUENCE: 19
acgaggcctc agtttgtcta cttggtc                                        27

<210> SEQ ID NO 20
<211> LENGTH: 24
<212> TYPE: DNA
<213> ORGANISM: Artificial Sequence
<220> FEATURE:
<223> OTHER INFORMATION: non-coding sequence from Homo sapiens
      hydroxymethylbilane synthase

<400> SEQUENCE: 20
cctcagtgcc ccattctcac tgct                                           24

<210> SEQ ID NO 21
<211> LENGTH: 30
<212> TYPE: DNA
<213> ORGANISM: Artificial Sequence
<220> FEATURE:
<223> OTHER INFORMATION: non-coding sequence from Homo sapiens
      glyceraldehyde-3-phosphate dehydrogenase
```

<400> SEQUENCE: 21
ggagccgcac cttgtcatgt accatcaata                                    30

<210> SEQ ID NO 22
<211> LENGTH: 15
<212> TYPE: DNA
<213> ORGANISM: Artificial Sequence
<220> FEATURE:
<223> OTHER INFORMATION: non-coding sequence from Homo sapiens
      glyceraldehyde-3-phosphate dehydrogenase

<400> SEQUENCE: 22
tctcccctcc tcaca                                                    15

<210> SEQ ID NO 23
<211> LENGTH: 29
<212> TYPE: DNA
<213> ORGANISM: Artificial Sequence
<220> FEATURE:
<223> OTHER INFORMATION: non-coding sequence from Homo sapiens
      mitochondrial ribosomal protein L32

<400> SEQUENCE: 23
taatagccca cttactcctg aatctttaa                                     29

<210> SEQ ID NO 24
<211> LENGTH: 30
<212> TYPE: DNA
<213> ORGANISM: Artificial Sequence
<220> FEATURE:
<223> OTHER INFORMATION: non-coding sequence from Homo sapiens beta-
      actin

<400> SEQUENCE: 24
cgttacaccc tttcttgaca aaacctaact                                    30

<210> SEQ ID NO 25
<211> LENGTH: 29
<212> TYPE: DNA
<213> ORGANISM: Artificial Sequence
<220> FEATURE:
<223> OTHER INFORMATION: non-coding sequence from Homo sapiens beta-
      actin

<400> SEQUENCE: 25
cttccccctt ttttgtcccc caacttgag                                     29

<210> SEQ ID NO 26
<211> LENGTH: 29
<212> TYPE: DNA
<213> ORGANISM: Artificial Sequence
<220> FEATURE:
<223> OTHER INFORMATION: non-coding sequence from Homo sapiens
      phosphoglycerate kinase 1

<400> SEQUENCE: 26
cgacctctct ccccagctgt atttccaaa                                     29

<210> SEQ ID NO 27
<211> LENGTH: 29
<212> TYPE: DNA
<213> ORGANISM: Artificial Sequence
<220> FEATURE:
<223> OTHER INFORMATION: non-coding sequence from Homo sapiens
      phosphoglycerate kinase 1

```
<400> SEQUENCE: 27
aggctctgtt ccacatatat ttccacttc                                              29

<210> SEQ ID NO 28
<211> LENGTH: 29
<212> TYPE: DNA
<213> ORGANISM: Artificial Sequence
<220> FEATURE:
<223> OTHER INFORMATION: non-coding sequence from Homo sapiens
      peptidylprolyl isomerase A

<400> SEQUENCE: 28
accgccgagg aaaaccgtgt actattagc                                              29

<210> SEQ ID NO 29
<211> LENGTH: 29
<212> TYPE: DNA
<213> ORGANISM: Artificial Sequence
<220> FEATURE:
<223> OTHER INFORMATION: non-coding sequence from Homo sapiens
      peptidylprolyl isomerase A

<400> SEQUENCE: 29
gtttgacttg tgttttatct taaccacca                                              29

<210> SEQ ID NO 30
<211> LENGTH: 29
<212> TYPE: DNA
<213> ORGANISM: Artificial Sequence
<220> FEATURE:
<223> OTHER INFORMATION: non-coding sequence from Homo sapiens tubulin,
      alpha-1b

<400> SEQUENCE: 30
tgtctgctcc tgtcgccttc gcctcctaa                                              29

<210> SEQ ID NO 31
<211> LENGTH: 29
<212> TYPE: DNA
<213> ORGANISM: Artificial Sequence
<220> FEATURE:
<223> OTHER INFORMATION: non-coding sequence from Homo sapiens tubulin,
      beta-1

<400> SEQUENCE: 31
agcactgcca tctcttccag caccatcag                                              29

<210> SEQ ID NO 32
<211> LENGTH: 29
<212> TYPE: DNA
<213> ORGANISM: Artificial Sequence
<220> FEATURE:
<223> OTHER INFORMATION: non-coding sequence from Homo sapiens
      transferrin receptor

<400> SEQUENCE: 32
cccaactcct ataattccct atcttttag                                              29

<210> SEQ ID NO 33
<211> LENGTH: 29
<212> TYPE: DNA
<213> ORGANISM: Artificial Sequence
<220> FEATURE:
<223> OTHER INFORMATION: non-coding sequence from Homo sapiens
      eukaryotic translation elongation factor 2

<400> SEQUENCE: 33
```
gatgtccaaa ctaattttaa caaacgcat                                              29

<210> SEQ ID NO 34
<211> LENGTH: 29
<212> TYPE: DNA
<213> ORGANISM: Artificial Sequence
<220> FEATURE:
<223> OTHER INFORMATION: non-coding sequence from Homo sapiens ubiquitin
      C

<400> SEQUENCE: 34
gtatcagcag aaggacattt taggacggg                                              29

<210> SEQ ID NO 35
<211> LENGTH: 29
<212> TYPE: DNA
<213> ORGANISM: Artificial Sequence
<220> FEATURE:
<223> OTHER INFORMATION: non-coding sequence from Homo sapiens
      transferrin receptor

<400> SEQUENCE: 35
gagttacttc ctatcaagcc agtacgtgc                                              29

<210> SEQ ID NO 36
<211> LENGTH: 29
<212> TYPE: DNA
<213> ORGANISM: Artificial Sequence
<220> FEATURE:
<223> OTHER INFORMATION: non-coding sequence from Homo sapiens TATA box
      binding protein

<400> SEQUENCE: 36
ctaggaaaaa attgaatagt gagacgagt                                              29

<210> SEQ ID NO 37
<211> LENGTH: 29
<212> TYPE: DNA
<213> ORGANISM: Artificial Sequence
<220> FEATURE:
<223> OTHER INFORMATION: non-coding sequence from Homo sapiens lamin B2

<400> SEQUENCE: 37
cagaaccccc caccctacat ttgccttgg                                              29

<210> SEQ ID NO 38
<211> LENGTH: 29
<212> TYPE: DNA
<213> ORGANISM: Artificial Sequence
<220> FEATURE:
<223> OTHER INFORMATION: non-coding sequence from Homo sapiens alpha-
      actin, cardiac muscle 1

<400> SEQUENCE: 38
cgccgacgaa cccctgaag ctgtgccaa                                               29

<210> SEQ ID NO 39
<211> LENGTH: 29
<212> TYPE: DNA
<213> ORGANISM: Artificial Sequence
<220> FEATURE:
<223> OTHER INFORMATION: non-coding sequence from Homo sapiens alpha-
      actin, cardiac muscle 1

<400> SEQUENCE: 39
gatgccttct ctctccatct accttccag                                              29

<210> SEQ ID NO 40
<211> LENGTH: 29
<212> TYPE: DNA
<213> ORGANISM: Artificial Sequence
<220> FEATURE:
<223> OTHER INFORMATION: non-coding sequence from Homo sapiens tubulin,
      beta-1

<400> SEQUENCE: 40
gacaggcaga aagcagagaa gggccagga                              29

<210> SEQ ID NO 41
<211> LENGTH: 29
<212> TYPE: DNA
<213> ORGANISM: Artificial Sequence
<220> FEATURE:
<223> OTHER INFORMATION: non-coding sequence from Homo sapiens tubulin,
      beta-1

<400> SEQUENCE: 41 cacccccccaa aatgctctgc agcctctct                             29

<210> SEQ ID NO 42
<211> LENGTH: 29
<212> TYPE: DNA
<213> ORGANISM: Artificial Sequence
<220> FEATURE:
<223> OTHER INFORMATION: non-coding sequence from Homo sapiens
      1-acylglycerol-3-phosphate O-acyltransferase 1

<400> SEQUENCE: 42
ccaacctccc actcccacct cccctccat                              29

<210> SEQ ID NO 43
<211> LENGTH: 21
<212> TYPE: DNA
<213> ORGANISM: Artificial Sequence
<220> FEATURE:
<223> OTHER INFORMATION: non-coding sequence from Homo sapiens
      1-acylglycerol-3-phosphate O-acyltransferase 1

<400> SEQUENCE: 43
ccactcttga cccccacctc c                                      21

<210> SEQ ID NO 44
<211> LENGTH: 13
<212> TYPE: DNA
<213> ORGANISM: Artificial Sequence
<220> FEATURE:
<223> OTHER INFORMATION: non-coding sequence from Homo sapiens tubulin,
      alpha-1b

<400> SEQUENCE: 44
taaagctttc tgg                                               13

<210> SEQ ID NO 45
<211> LENGTH: 46
<212> TYPE: DNA
<213> ORGANISM: Artificial Sequence
<220> FEATURE:
<223> OTHER INFORMATION: non-coding sequence from Homo sapiens
      glyceraldehyde-3-phosphate dehydrogenase

<400> SEQUENCE: 45
agccgcacct tgtcatgtac catcaataaa gtaccctgtg ctcaac           46

<210> SEQ ID NO 46
<211> LENGTH: 19
<212> TYPE: RNA
<213> ORGANISM: Artificial Sequence
<220> FEATURE:
<223> OTHER INFORMATION: siRNA target sequence for hPolL suppression

<400> SEQUENCE: 46
gggacagaug agauuucuu                                              19

<210> SEQ ID NO 47
<211> LENGTH: 600
<212> TYPE: DNA
<213> ORGANISM: Artificial Sequence
<220> FEATURE:
<223> OTHER INFORMATION: codon optimized Puromycin resistance gene

<400> SEQUENCE: 47
atgaccgagt acaagcctac cgtgcggctg gccacaaggg atgacgtgcc tcgggccgtg     60
aggaccctgg ccgccgcttt cgccgactac cccgccacaa gacacaccgt ggacccagac    120
agacacatcg agagggtgac cgagctgcag gagctgttcc tgaccagagt gggcctggac    180
atcggaaagg tgtgggtggc cgacgacggc gccgccgtgg ctgtgtggac aaccccgag    240 tccgtggagg ccggcgctgt gttcgctgag atcgacctc ggatggccga gctgagcgga    300
agcagactgg ccgcccagca gcagatggag ggcctgctgg ctcctcacag acctaaggag    360
ccagcttggt tcctggctac cgtgggcgtg tcccctgatc accagggcaa gggcctgggc    420
agcgccgtgg tgctgcctgg agtggaggcc gccgagcgcg ccggagtgcc tgcttttctg    480
gagaccagcg cccctcgcaa cctgccattc tatgagagac tgggcttcac cgtgacagct    540
gacgtggagg tgcctgaggg ccccagaaca tggtgtatga cccggaagcc tggcgcctga    600

<210> SEQ ID NO 48
<211> LENGTH: 678
<212> TYPE: DNA
<213> ORGANISM: Artificial Sequence
<220> FEATURE:
<223> OTHER INFORMATION: E2-Crimson fluorescent protein gene

<400> SEQUENCE: 48
atggatagca ctgagaacgt catcaagccc ttcatgcgct tcaaggtgca catggagggc     60
tccgtgaacg gccacgagtt cgagatcgag ggcgtgggcg agggcaagcc ctacgagggc    120
acccagaccg ccaagctgca agtgaccaag ggcggccccc tgcccttcgc ctgggacatc    180
ctgtcccccc agttcttcta cggctccaag gcgtacatca agcaccccgc cgacatcccc    240
gactacctca gcagtccctt ccccgagggc ttcaagtggg agcgcgtgat gaacttcgag    300
gacggcggcg tggtgaccgt gacccaggac tcctccctgc aggacggcac cctcatctac    360
cacgtgaagt tcatcggcgt gaacttcccc tccgacggcc ccgtaatgca gaagaagact    420
ctgggctggg agccctccac tgagcgcaac taccccgcg acggcgtgct gaagggcgag    480
aaccacatgg cgctgaagct gaagggcggc ggccactacc tgtgtgagtt caagtccatc    540
tacatggcca agaagcccgt gaagctgccc ggctaccact acgtggacta caagctcgac    600
atcacctccc acaacgagga ctacaccgtg gtggagcagt acgagcgcgc cgaggcccgc    660
caccacctgt tccagtag                                                 678

<210> SEQ ID NO 49
<211> LENGTH: 375

```
<212> TYPE: DNA
<213> ORGANISM: Artificial Sequence
<220> FEATURE:
<223> OTHER INFORMATION: codon optimized Zeocin resistance gene

<400> SEQUENCE: 49
atggctaagc tgaccagcgc cgtgcccgtg ctgacagcga gggacgtggc tggagctgtg      60
gagttctgga cagacaggct gggcttcagc agggacttcg tggaggacga cttcgccggc     120
gtggtgaggg acgacgtgac cctgttcatc agcgccgtgc aggaccaggt ggtgcccgac     180
aacacactgg cttgggtgtg ggtgagggga ctggatgagc tgtatgctga gtggtctgag     240
gtggtgagca ccaacttcag ggatgcttct ggacctgcta tgacagagat tggagagcag     300
ccttggggaa gagagtttgc cctgagggac cctgctggaa actgcgtgca ctttgtggct     360
gaggagcagg actga                                                     375

<210> SEQ ID NO 50
<211> LENGTH: 1026
<212> TYPE: DNA
<213> ORGANISM: Artificial Sequence
<220> FEATURE:
<223> OTHER INFORMATION: codon optimized Hygromycin resistance gene

<400> SEQUENCE: 50
atgaagaagc ccgagctgac cgctaccagc gtggagaagt tcctgatcga gaagttcgac      60
agcgtgagcg acctgatgca gctgagcgag ggcgaggaga caggggcctt cagcttcgac     120
gtgggcggca ggggctacgt gctgagggtg aacagctgcg ccgacggctt ctacaaggac     180
agatacgtgt acagacactt tgctagcgcc gccctgccca tccctgaggt gctggacatt     240
ggagagttca gcgagagcct gacctactgc atcagcagga gagctcaggg agtgaccctg     300
caggacctgc ctgagacaga gctgcctgcc gtgctgcagc ctgtggctga ggctatggat     360
gctattgctg ccgcagacct gagccagacc agcggatttg acccttcggg ccctcagggt     420
atcggacagt acaccacctg gagggacttc atctgcgcca tcgccgaccc ccacgtgtac     480
cactggcaga ccgtgatgga tgacaccgtg agcgcctctg tggctcaggc cctggatgag     540
ctgatgctgt gggctgagga ctgccctgag gtgaggcacc tggtgcacgc cgacttcggc     600
agcaacaacg tgctgaccga caacggcagg atcaccgccg tgatcgactg gagcgaggcc     660
atgttcggcg acagccagta cgaggtggcc aacatcttct ctggaggcc  ctggctggcc     720 tgcatggagc agcagaccag gtactttgag aggaggcacc ctgagctggc tggaagccca     780
aggctgaggg cttacatgct gaggattgga ctggaccagc tgtaccagag cctggtggac     840
ggcaacttcg acgatgctgc ttgggctcag ggaaggtgcg atgctatcgt gaggagcgga     900
gctggcaccg tggaaggac  ccagattgct aggaggagcg ccgccgtgtg gacagatgga     960
tgcgtggagg tgctggctga ctctggaaac cgtaggccta gcacccgacc aagagctaag    1020
gagtga                                                             1026

<210> SEQ ID NO 51
<211> LENGTH: 25
<212> TYPE: DNA
<213> ORGANISM: Artificial Sequence
<220> FEATURE:
<223> OTHER INFORMATION: recombination sequence attB1

<400> SEQUENCE: 51
acaagtttgt acaaaaaagc aggct                                          25
```

```
<210> SEQ ID NO 52
<211> LENGTH: 25
<212> TYPE: DNA
<213> ORGANISM: Artificial Sequence
<220> FEATURE:
<223> OTHER INFORMATION: recombination sequence attB2

<400> SEQUENCE: 52
acccagcttt cttgtacaaa gtggt 25

<210> SEQ ID NO 53
<211> LENGTH: 4212
<212> TYPE: DNA
<213> ORGANISM: Artificial Sequence
<220> FEATURE:
<223> OTHER INFORMATION: A DNA fragment including hN gene, hCgene and hPolS gene
<400> SEQUENCE: 53
accagacaag agtttaagag atatgtatcc ttttaaattt tcttaagaaa aacttagggt 60
gaaagtatcc accctgagga gcaggttcca gatccttttc tttgctgcca aagtccacca 120
tggctggcct gctgtcaacc ttcgatacct tttcaagtag gaggagcgag tcaatcaaca 180
aatctggggg cggagctgtc atccctggac agcggtccac cgtgtctgtc ttcgtgctgg 240
gcccctctgt gacagacgat gccgacaagc tgttcatcgc caccacattt ctggctcaca 300
gtctggacac agataaacag cattcacaga gaggcgggtt tctggtgagc ctgctggcta 360
tggcatacag ctccccagaa ctgtatctga ctaccaacgg agtgaatgcc gacgtgaagt 420
acgtgatcta taacattgag aaggacccca aaaggactaa gaccgatggc ttcatcgtga 480
agacacggga tatggaatac gagagaacaa ctgagtggct gttcgggcct atggtgaaca 540
agagcccact gtttcaggga cagcgagacg cagctgaccc cgataccctg ctgcaaatct 600
acggctatcc tgcctgcctg gggctatca ttgtccaagt gtggatcgtc ctggtgaaag 660
caattacctc tagtgccggc ctgcggaagg ggttctttaa ccgcctggag gctttccgac 720
aggatggaac agtgaagggc gcactggtct ttaccggcga aacagtggag ggaatcggct 780
ctgtcatgag aagtcagcag tcactggtca gcctgatggt ggaaactctg gtcaccatga 840
acacagccag aagtgacctg accacactgg agaaaaacat ccagattgtg ggaattaca 900
tcagggatgc cggcctggcc agcttcatga ataccatcaa gtatggggtg gaaacaaaga 960
tggcagccct gactctgtcc aacctgagac ccgacatcaa caagctgcgg agcctgattg 1020
atacctacct gtctaagggc cccagggccc ctttcatctg tattctgaaa gacccagtgc 1080
acggggagtt tgctccagga aactaccccg cactgtggtc ctatgcaatg ggcgtggccg 1140
tggtccagaa taaggccatg cagcagtacg tcactggccg cacctatctg gacatggaaa 1200
tgtttctgct ggggcaggcc gtggctaaag atgccgagag caagatcagc agcgccctgg 1260
aggacgagct gggagtcaca gatactgcca aggggcgact gcggcaccat ctggcaaacc 1320
tgtccggagg cgacggagca tatcacaaac ctacaggggg aggcgctatc gaagtggcac 1380
tggataatgc cgacattgat ctggagacta aggcacatgc agaccaggat gctcgcggat 1440
ggggaggaga ttccggcgaa agatgggcca ggcaggtgtc tggcgggcac tttgtcactc 1500
tgcatggcgc tgagcgactg gaggaagaga ccaatgacga agatgtgagt gacatcgagc 1560
ggagaattgc tatgcgactg gcagaaaggc gccaggagga ctcagccacc catggggatg 1620
agggacggaa caatggagtg gaccatgacg aagatgatga cgccgccgca gtcgcaggca 1680
```

-continued

```
ttggaggaat tgaggatct acgaggcctc agtttgtcta cttggtctta agaaaaactt     1740
agggtgaaag cctcagtgcc ccattctcac tgctactaga ggagcccacc atgcccagct     1800
ttctgaagaa gattctgaaa ctgagaggac gaagacagga agatgagtct cgaagtcgga     1860
tgctgtccga cagctccatg ctgtcttgca gggtgaacca gctgactagc gagggaaccg     1920
aagctggctc aaccacaccc agcacactgc ctaaagacca ggccctgctg atcgagccaa     1980
aggtccgggc taaggaaaaa tcccagcacc ggagacccaa gatcattgat caggtgaggc     2040
gcgtcgagag tctgggggaa caggcatcac agcggcagaa acatatgctg agaccctga      2100 tcaacaaaat ctacacaggc cctctggggg aggaactggt gcagactctg tatctgagaa     2160
tctgggccat ggaggaaacc ccagagtctc tgaaaatcct gcagatgcgc gaagacattc     2220
gagatcaggt cctgaagatg aaaacagaga gatggctgag gactctgatt aggggcgaaa     2280
agaccaaact gaaggatttc cagaagcggt acgaggaagt gcacccctat ctgatgaaag     2340
agaaggtgga acaggtcatc atggaagagg cttggtcact ggcagctcat attgtgcagg     2400
agtaatgact cgacggagcc gcaccttgtc atgtaccatc aatattaaga aaaacttagg     2460
gtgaaagtct ccctcctca cacctagagc cgccaccatg gaccaggacg ctttattct      2520 gaaggaggat tctgaagtgg aacggaggc accaggggga agggagagtc tgagtgatgt      2580
cattggcttc ctggacgccg tgctgagctc cgagccaaca gatatcggag gggaccggag     2640
ctggctgcac aacactatta ataccccca ggggcctgga agtgcacata gagccaagtc      2700
agagggcgaa ggggaggtgt caacacccag cactcaggat aacaggtctg gggaggaatc     2760
cagagtctct ggaaggacca gtaagcctga agcagaggcc cacgctggca acctggacaa     2820
acagaatatc catcgagctt ttggaggccg gaccgggaca aactctgtga gtcaggacct     2880
gggagatggg ggagactctg gcatcctgga aaaccccct aatgagcgcg ctaccctcg      2940 atccgggatt gaagatgaga atagggagat ggccgctcac ccagataagc gaggagaaga    3000
ccaggcagag ggactgcctg aggaagtgcg gggctcaacc agcctgccag acgaaggaga    3060
gggaggagcc tccaacaatg gccggtctat ggaacctggg tctagtcatt ccgctagagt    3120
gacaggcgtg ctggtcattc cttctccaga gctggaggaa gcagtcctgc ggagaaacaa    3180
gaggcgccca accaattccg gatctaaacc actgaccca gcaacagtgc ccggcacacg      3240
gagcccaccc ctgaacagat ataatagtac cgggtcacct ccaggaaagc ccccttctac    3300
acaggatgag cacatcaaca gtggggacac tccagctgtg cgggtcaagg atagaaaacc    3360
acccattgga actcggagcg tgagcgactg cccagcaaac ggaagaccta tccacccccgg    3420 cctggagact gattccacca agaaaggaat tggcgaaaat acctcaagca tgaaggagat    3480
ggccacactg ctgactagcc tgggcgtgat ccagtccgca caggaattcg agagcagccg    3540
ggacgccagt tacgtctttg ctcgacgggc actgaaatca gccaactatg ctgagatgac    3600
cttcaacgtg tgcggcctga ttctgagcgc cgaaaagagt tcagctagaa aagtggatga    3660
gaataagcag ctgctgaaac agatccagga aagcgtcgag tccttcagag acatctacaa    3720
gaggttttca gaatatcaga agagcagaa cagcctgctg atgtctaatc tgagtacact    3780
gcacatcatt actgataggg gaggcaagac cgataacaca gacagcctga cacgcagccc    3840
ttccgtgttc gctaagtcca agagaataa gactaaagca acccgctttg acccctccat     3900
ggaaactctg gaggatatga agtacaaacc tgacctgatc cgggaagatg agtttaggga    3960
cgaaattcgc aacccagtgt atcaggaacg cgatactgag ccccgagcat caaatgccag    4020
cagactgctg ccctccaagg agaaacctac catgcattct ctgaggctgg tcatcgaaag    4080
```

```
ctccccactg agccgcgctg agaaggtggc atacgtcaaa tctctgagta agtgcaaaac    4140
cgaccaggag gtgaaggctg tgatggaact ggtggaggaa gacattgaat ctctgacaaa    4200
ctaaatcccg gg                                                        4212

<210> SEQ ID NO 54
<211> LENGTH: 6884
<212> TYPE: DNA
<213> ORGANISM: Artificial Sequence
<220> FEATURE:
<223> OTHER INFORMATION: A DNA fragment including hPolL gene

<400> SEQUENCE: 54
gcggccgctt aagaaaaact tagggtgaat gtaaagcttt ctggccacca tggacgggca      60
ggagtcatcc cagaatcctt ccgatatcct gtatcccgaa tgtcatctga actcacctat     120
tgtgcgaggc aaaatcgccc agctgcacgt gctgctggac gtgaaccagc catataggct     180
gaaggacgat tccatcatta atatcacaaa gcataagatt cgcaacggcg ggctgtctcc     240
cagacagatc aagatcagga gtctgggcaa ggccctgcag agaactatca aggatctgga     300
caggtacaca ttcgagcctt acccaactta ttctcaggaa ctgctgcggc tggacattcc     360
agagatctgc gataaaatcc ggagcgtgtt cgccgtcagt gaccggctga ccagagagct     420
gagctccggc ttccaggatc tgtggctgaa tatcttcaag cagctgggga acatcgaggg     480
acgcgaaggc tatgatccac tgcaggacat tggcacaatc cccgagatta ctgacaaata     540
ctcacgcaac cgatggtatc ggcccttcct gacctggttt agcatcaaat acgacatgag     600
gtggatgcag aagacccgcc ccggaggacc tctggataca agtaactcac acaatctgct     660
ggagtgcaag agctacacac tggtgactta tggagatctg attatgatcc tgaacaagct     720
gactctgacc ggctacatcc tgacccccga actggtgctg atgtattgtg acgtggtcga     780
gggaagatgg aacatgagcg ccgctggcca tctggacaag aagtccattg gcatcacaag     840
caagggggag gaactgtggg aactggtgga cagcctgttc tctagtctgg agaggaaat     900 ctataatgtc attgccctgc tggagcctct gagcctggct ctgattcagc tgaacgatcc     960
agtgatcccc ctgcgcggcg cattcatgcg acacgtcctg accagctgc aggccgtgct    1020 gacctccagg gatgtctaca cagacgcaga ggccgatact atcgtggaat ccctgctggc    1080
tatctttcat gggacatcta ttgacgagaa ggcagaaatc ttcagttct ttaggacctt    1140 tggacacccc tcactggagg ccgtgacagc agccgataaa gtccgcgctc atatgtacgc    1200
acagaaggcc atcaaactga agactctgta tgaatgccac gccgtgttct gtaccatcat    1260
tatcaatggc taccgggaga gacacggagg acagtggcca ccttgcgatt tcctgaccca    1320
cgtgtgcctg gaactgcgca acgctcaggg gtccaatact gcaatctctt acgagtgtgc    1380
cgtggacaac tataccagct tcattggatt caaatttcgc aagtttatcg agccacagct    1440
ggatgaagac ctgaccatct acatgaaaga taaggcactg agcccccgga aggaagcctg    1500
ggacagcgtg taccctgatt caaatctgta ctataaagcc ccagagagcg aggaaacacg    1560
gagactgatc gaggtgttca ttaatgacga aaactttaat cccgaggaaa ttatcaacta    1620
cgtcgaaagc ggggactggc tgaaagatga aagttcaac attagctatt ccctgaaaga    1680
gaaggaaatc aagcaggaag gaagactgtt tgccaaaatg acatacaaga tgagggctgt    1740
gcaggtcctg gcagagactc tgctggccaa aggaatcggc gagctgttct ccgaaaacgg    1800
gatggtgaaa ggagagattg acctgctgaa gaggctgacc acactgtctg tgagtggcgt    1860
```

```
ccctcgcacc gatagcgtgt ataacaattc caaatcaagc gagaagagga atgaagggat    1920
gaagaaaaag aactctggcg ggtattggga cgagaaaaag aggagtcgcc acgaattcaa    1980
ggccacagac tcctctactg atggctacga gactctgagc tgctttctga ctaccgatct    2040
gaaaaagtat tgtctgaatt ggcgcttcga aagcaccgct ctgtttgggc agcgatgcaa    2100
tgagatcttc ggcttcaaga ccttcttcaa ctggatgcat cccgtgctgg agagatgcac    2160
catctacgtg ggcgacccct attgtccagt cgccgatagg atgcaccgcc agctgcagga    2220
tcatgctgac agcgggattt tcatccacaa ccctagggga ggcatcgagg atactgtca     2280 gaagctgtgg accctgattt caatcagcgc aattcatctg ctgcagtgc gggtcggagt     2340 gagagtcagt gccatggtgc agggcgacaa tcaggctatc gcagtcactt caagagtgcc    2400
cgtcgcccag acctataagc agaaaaagaa ccacgtgtat aaggagatta caaagtattt    2460
cggcgctctg aggcacgtga tgtttgatgt cgggcatgag ctgaaactga atgaaactat    2520
catcagttca aagatgttcg tgtactccaa gagaatctac tatgacggca aaatcctgcc    2580
acagtgcctg aaggcactga cacggtgcgt gttctggtct gagactctgg tcgatgaaaa    2640
cagatccgcc tgctctaata tctccacttc tattgccaag gctatcgaga acggctactc    2700
ccccatcctg gggtactgta ttgccctgta taaaacctgc cagcaggtgt gcatctcact    2760
gggcatgacc attaatccca caatcagccc tactgtgcga gaccagtact tcaaagggaa    2820
gaactggctg cgatgcgctg tgctgatccc agcaaacgtc gggggattca attatatgag    2880
tacctcaagg tgttttgtgc gcaacatcgg ggaccctgca gtcgccgctc tggctgatct    2940
gaagcgattc attcgggccg atctgctgga caaacaggtg ctgtaccgcg tgatgaatca    3000
ggagcctgga gatagctcct ttctggactg ggcttctgat ccctatagtt gcaacctgcc    3060
tcacagccag tccatcacaa ctattatcaa gaatatcacc gcaaggtctg tgctgcaaga    3120
aagtcccaac cctctgctga gcgggctgtt cacagagact ccggagagg aagacctgaa     3180 tctggcttcc tttctgatgg atcgaaaagt gatcctgcca cgggtcgcac atgaaatcct    3240
gggaaactct ctgaccggcg tgcgggaggc aatcgcagga atgctggaca ccacaaagag    3300
tctggtgaga tctagtgtca aaagggcgg gctgtcatac ggcatcctga gcgcctggt      3360 gaattacgac ctgctgcagt atgaaaccct gacaagaact ctgaggaaac ccgtgaagga    3420
taacatcgag tacgaatata tgtgcagcgt ggagctggca gtcggactga cagaagat     3480 gtggattcac ctgacatacg ggaggcctat ccatggactg gagactccag atcccctgga    3540
actgctgagg ggcaccttca tcgagggtc agaagtgtgc aagctgtgcc gcagcgaggg    3600
agcagaccct atctacacct ggtttttatct gccagataat attgatctgg acaccctgac   3660
aaacggatgt cctgctattc gcatcccata cttcggctct gctacagacg agcgaagtga    3720
agcacagctg ggctatgtgc ggaatctgag caaacctgcc aaggcagcca ttcggatcgc    3780
tatggtgtat acctgggcat atgggacaga tgagatttct tggatggaag ctgcactgat    3840
cgcacagaca agagccaacc tgagtctgga gaatctgaag ctgctgactc cagtgtctac    3900
tagtaccaac ctgtcccaca ggctgaaaga cacagccact cagatgaagt tctcaagcgc    3960
aactctggtg cgcgccagcc ggttcatcac catcagcaac gacaatatgg ctctgaaaga    4020
ggcaggagaa tctaaggata caaatctggt gtaccagcag atcatgctga ctggcctgag    4080
cctgttcgag tttaacatgc gctataaaaa ggggtccctg ggaaagcctc tgatcctgca    4140
cctgcatctg aacaatggct gctgtattat ggagtcccca caggaagcca atcccacc     4200 ccggtctacc ctgacctgg agattacaca ggaaaacaac aagctgatct atgatcctga    4260
```

```
cccactgaag gatgtggacc tggaactgtt ctccaaagtg cgggacgtgg tccacaccgt    4320
cgatatgaca tactggagcg acgatgaagt gatcagagcc acctccattt gcaccgccat    4380
gacaatcgct gacacaatga gccagctgga tcgggacaac ctgaaggaaa tgattgctct    4440
ggtgaacgac gatgacgtga atagcctgat taccgagttc atggtcatcg atgtcccact    4500
gttctgttcc acatttggag gcatcctggt gaatcagttt gcctactctc tgtatggact    4560
gaacattcga ggccgggagg aaatctgggg ccacgtggtc cgcatcctga aagacaccag    4620
ccatgcagtg ctgaaggtcc tgtcaaatgc cctgagccac ccaaaattt tcaagcggtt     4680 ttggaacgca ggagtggtcg agccagtgta cggacccaac ctgagcaatc aggataagat    4740
cctgctggcc ctgtcagtgt gcgaatatag cgtggacctg ttcatgcacg attggcaggg    4800
gggagtgccc ctggagatct tcatctgtga taatgaccct gatgtcgctg acatgcgacg    4860
gtcctctttc ctggcacgcc atctggccta cctgtgctcc gtggcagaaa tcagccggga    4920
cggaccacga ctggagagta tgaactcact ggagaggctg gaaagcctga agtcctacct    4980
ggagctgact ttcctggatg accccgtgct gcgctattct cagctgaccg gcctggtcat    5040
caaggtcttt cctagtaccc tgacatacat ccggaaaagt tcaattaagg tgctgagaac    5100 caggggggatt ggagtgcccg aggtcctgga agactgggat cctgaagctg acaatgcact    5160
gctggatggc attgccgctg agatccagca gaacattcca ctgggacacc agacacgcgc    5220
cccattttgg ggactgcgag tgtcaaagag ccaggtcctg cgcctgcgag ggtacaaaga    5280
gatcaccaga ggcgaaattg ggagaagcgg cgtggggctg acactgccat cgacggccg     5340 gtatctgtcc catcagctga gactgtttgg gatcaattcc acatcttgcc tgaaggccct    5400
ggaactgact tacctgctgt ccccctggt ggacaaagat aaggacagac tgtacctggg    5460
agagggcgct ggggcaatgc tgtcttgcta tgacgctacc ctgggccctt gtatcaacta    5520
ctataattcc ggcgtgtact cttgtgatgt caacgggcag agagagctga atatctaccc    5580
agccgaagtg gctctggtcg ggaaaaagct gaacaatgtg acctcactgg acagagggt     5640 gaaggtcctg ttcaacggaa atcccggcag cacatggatt ggaaacgacg agtgcgaagc    5700
cctgatctgg aacgagctgc agaatagctc cattggcctg gtgcactgtg acatggaagg    5760
cggggatcat aaggatgacc aggtggtcct gcacgagcat tacagcgtga ttaggatcgc    5820
ctatctggtc ggcgatcgcg acgtggtcct gatctccaaa attgctccta ggctggggac    5880
tgactggacc cgccagctgt ctctgtacct gcgatattgg gatgaagtga atctgatcgt    5940
cctgaagact agtaacccag cctcaaccga aatgtacctg ctgagtaggc accccaaatc    6000
agacattatc gaggattcca agaccgtgct ggcttctctg ctgccactga gcaaggagga    6060
cagcatcaag atcgaaaagt ggattctgat cgagaaagcc aaggctcacg aatgggtgac    6120
cagagagctg agagaagggt ctagttcaag cggaatgctg cggccttacc atcaggccct    6180
gcagacattc ggctttgagc caaacctgta taagctgagc agagacttcc tgtccacaat    6240
gaacattgct gatactcata attgcatgat cgcattcaac agggtgctga aggacaccat    6300
ttttgagtgg gcccggatca cagaatccga taaaagactg aagctgacag gaaaatacga    6360
cctgtatcct gtgcgcgatt ctggcaaact gaagactgtg agtagaaggc tggtcctgtc    6420
atggatcagt ctgtcaatga gcactcggct ggtgaccggg agtttcccag accagaagtt    6480
tgaagccaga ctgcagctgg gaatcgtgtc tctgtcctct agggagattc gcaatctgcg    6540
agtcatcact aaaaccctgc tggaccgctt cgaagatatt atccacagca tcacttaccg    6600
```

```
atttctgacc aaagagatta agatcctgat gaaaattctg ggagccgtga agatgtttgg    6660
cgctcggcag aacgagtaca ccactgtgat tgacgacggc agcctgggcg acattgaacc    6720
ttacgattcc tcctaaaccg gtagccgcac cttgtcatgt accatcaata aagtaccctg    6780
tgctcaacga agtcttggac tgatccatat gacaatagta agaaaaactt acaagaagac    6840
aagaaaattt aaaagaatac atatctctta aactcttgtc tggt                    6884
```

<210> SEQ ID NO 55
<211> LENGTH: 1575
<212> TYPE: DNA
<213> ORGANISM: Artificial Sequence
<220> FEATURE:
<223> OTHER INFORMATION: codon optimized N gene for expression in E.Coli

<400> SEQUENCE: 55

```
atggcaggtt tactcagcac gttcgacact tttagcagca gacgcagcga gagcatcaac      60
aaatccggtg gtggcgcggt gatccctggt cagcgctcta ccgtgagcgt gtttattctg     120
ggcccgtctg tcaccgatga tgccgataag ctgttcattg ccaccacctt tctgcccac     180 agcctggaca cggacaaaca gcactctcaa cgtggcggtt tcctggtttc gttgctggcg     240
atggcgtata gcagcccgga gctgtacttg accaccaacg gcgtgaacgc ggatgtgaag     300
tatgtgattt acaacatcga gaaagatccg aagcgtacga aaccgacgg ttttatcgtt     360 aagacccgcg atatggaata cgagcgtacc acggagtggc tgttcggtcc gatggtcaat     420
aagagcccgc tgttccaagg ccagcgcgac gcagcggacc cggacaccct gctgcagatc     480
tatggctacc ctgcgtgtct gggcgcgatc attgttcaag tatggatcgt tctggtcaag     540
gcgattacca gcagcgcagg tctgcgtaag gcttttttca atcgcctgga ggcgttccgt     600
caggatggca ccgtgaaagg tgcactggtt tttaccggtg aaaccgtcga aggtattggc     660
tctgttatgc gttcccagca gagcttggtc agcctgatgg ttgagactct ggttacgatg     720
aatactgccc gcagcgatct gacgaccctg gagaaaaaca ttcaaattgt cggcaactac     780
atccgtgatg cgggtctggc atccttcatg aatacgatca aatatggcgt ggaaacgaag     840
atggcggcct tgaccctgtc caatctgcgt ccggacatta caaaattgcg tagcctgatt     900
gacacgtacc tgagcaaagg tccgcgtgcc ccgttcatct gcattctgaa agatccagtt     960
cacggtgagt tcgcaccggg taactatccg gccctgtgga gctatgcaat gggcgtggct    1020
gtcgtccaga acaagagcat gcagcagtac gttacgggtc gtacctacct ggatatggag    1080
atgtttctgc tgggtcaagc agttgcaaaa gacgcggagt ccaaaatcag cagcgccctg    1140
gaggacgagt tgggtgtcac cgacaccgcg aaggaacgtc tgcgtcatca tctggctaat    1200
ctgagcggtg gtgatggcgc gtaccacaag ccgacgggtg gtggtgctat cgaagttgcg    1260
ctggataatg cggacatcga tttggaaact gaagcacacg cggatcaaga cgcgcgtggc    1320
tggggtggtg atagcggcga acgctgggcg cgtcaagtgt cgggcggtca ctttgtgacc    1380
ctgcatggtg cggagcgtct ggaagaagaa accaatgatg aggacgttag cgatattgag    1440
cgccgtattg ctatgcgcct ggcggaacgt cgtcaagagg acagcgctac gcacggtgac    1500
gagggccgca acaatggcgt cgaccatgaa gaggacgacg acgctgcagc cgcagcgggt    1560
attggtggca tctaa                                                      1575
```

<210> SEQ ID NO 56
<211> LENGTH: 423
<212> TYPE: DNA
<213> ORGANISM: Artificial Sequence

```
<220> FEATURE:
<223> OTHER INFORMATION: Blastcidin S resistance gene

<400> SEQUENCE: 56
atgaagacct tcaatattag ccagcaggac ctggagctgg tggaggtggc caccgagaaa      60
atcaccatgc tgtacgagga caataagcac cacgtggggg ccgccattcg caccaagaca     120
ggcgagatca tcagcgccgt gcacatcgag gcctacatcg gcgggtgac cgtgtgcgcc      180 gaggccatcg ccatcggctc cgccgtgtcc aacggccaga aggattttga taccattgtg     240
gccgtgaggc acccatacag cgacgaggtg gatcggagca tccgggtggt gtccccttgc     300
gggatgtgca gagagctgat ttccgattac gcccctgact gcttcgtgct gatcgagatg     360
aatgggaagc tggtgaaaac aacaatcgag gagctgatcc ccctgaagta taccaggaac     420
tga                                                                    423

<210> SEQ ID NO 57
<211> LENGTH: 5
<212> TYPE: DNA
<213> ORGANISM: Artificial Sequence
<220> FEATURE:
<223> OTHER INFORMATION: Kozak sequence

<400> SEQUENCE: 57 ccacc                                                                    5

<210> SEQ ID NO 58
<211> LENGTH: 42
<212> TYPE: DNA
<213> ORGANISM: Artificial Sequence
<220> FEATURE:
<223> OTHER INFORMATION: 5' non-coding sequence #1

<400> SEQUENCE: 58
ccaccatgaa attgccagaa gactgacact agagccgcca cc                           42

<210> SEQ ID NO 59
<211> LENGTH: 21
<212> TYPE: DNA
<213> ORGANISM: Artificial Sequence
<220> FEATURE:
<223> OTHER INFORMATION: 5' non-coding sequence #2

<400> SEQUENCE: 59
caccatggcc caggcttcat a                                                  21

<210> SEQ ID NO 60
<211> LENGTH: 1440
<212> TYPE: DNA
<213> ORGANISM: Artificial Sequence
<220> FEATURE:
<223> OTHER INFORMATION: codon optimized human KLF4 gene

<400> SEQUENCE: 60
atgcgacagc ctcctggcga atccgatatg gccgtctccg atgctctgct gccttctttc      60
tctacttttg cctctggacc tgctggcagg gagaagacac tgcgacaggc aggagctccc     120
aacaatcgat ggcgggagga actgtctcac atgaaaagac tgcccctgt cctgcctggg      180 aggccatacg acctggccgc tgcaaccgtg gccacagatc tggagtccgg aggagctgga     240
gcagcttgcg gaggaagcaa cctggcacca ctgcctcgga gagaaccga ggaattcaac      300 gatctgctgg acctggattt tatcctgtct aatagtctga cccacccacc agtccgtc       360
```

```
gcagcaacag tgagctcctc tgcatctgcc agttcaagct cctctccaag ttcaagcggc    420
ccagcttcag cacccagcac ttgttccttc acctacccca ttcgggcagg gaatgaccct    480
ggagtggccc caggggaaac aggaggggga ctgctgtatg cagagaatc tgcacctcca    540 cccactgccc ctttcaacct ggctgacatc aatgatgtct caccaagcgg aggatttgtg    600
gcagagctgc tgaggcccga actggatcct gtctatattc ctccacagca gcctcagccc    660
cctggaggag gactgatggg caagttcgtg ctgaaagcct ccctgtctgc tccaggcagc    720
gagtacggga gtccctcagt catcagcgtg tccaagggat ctcctgacgg aagtcaccca    780
gtggtcgtgg caccatataa cggaggccca cccaggactt gccccaagat caagcaggaa    840
gctgtgtcct cttgtaccca tctgggggca ggacctccac tgagcaatgg ccaccgcccc    900
gctgcacatg actttcctct ggggcgacag ctgccttccc ggaccacacc aaccctggga    960
ctggaggaag tgctgagttc acgcgattgc cacccagccc tgcctctgcc ccctgggttc   1020
cacccacatc ccggacctaa ctacccaagc tttctgccag accagatgca gccacaggtg   1080 ccaccctgc actatcagga gctgatgcct ccaggaagtt gtatgcccga ggaaccaaag   1140
ccaaaacggg gcaggcgcag ctggcctaga aagaggactg ctacccatac atgcgattac   1200
gcaggctgtg ggaagactta taccaaaagc tcccacctga ggcccatct gagaacacac   1260 actggcgaga aaccttacca ctgcgactgg gatggatgtg gctggaagtt cgctcgctcc   1320
gacgaactga cacgccatta tcgaaagcac actgggcatc gaccattcca gtgccagaaa   1380
tgtgaccggg cattttctag aagtgatcat ctggccctgc acatgaaacg gcatttttga   1440
```

<210> SEQ ID NO 61
<211> LENGTH: 1083
<212> TYPE: DNA
<213> ORGANISM: Artificial Sequence
<220> FEATURE:
<223> OTHER INFORMATION: codon optimized human OCT4 gene

<400> SEQUENCE: 61

```
atggccggac acctggcttc agattttgcc ttctcaccac cacctggggg aggggggcgac    60 ggacctgggg gacccgaacc tggatgggtg gaccccagaa cctggctgag ctttcaggga   120 cccctggcg ggccaggaat cggccctggc gtgggacctg gctccgaggt ctgggggatt   180
ccaccctgcc ctccacccta cgaattctgc ggaggcatgg cttattgtgg accacaagtg   240
ggagtcggac tggtgcctca ggggggactg agacatctc agcctgaggg agaagcagga   300
gtgggagtcg agagcaactc cgatggcgct agtcccgaac cttgcaccgt gactccaggg   360
gcagtcaagc tggagaagga aaaactggag cagaatcccg aggaatccca ggacatcaag   420
gctctgcaga aagagctgga acagtttgca aagctgctga gcagaaacg cattaccctg   480 ggctacacac aggccgatgt ggggctgact ctgggagtgc tgttcggcaa agtcttttcc   540
cagaccacaa tctgccgatt cgaggcactg cagctgagct tcaagaacat gtgtaaactg   600
aggcccctgc tgcagaagtg ggtggaggaa gccgacaaca atgagaatct gcaggaaatc   660
tgcaaagcag aaaacactgg tgcaggccagg aagcgcaaac gaactagcat tgagaaccgg   720
gtcagaggca acctggaaaa tctgtttctg cagtgcccaa agcccacact gcagcagatc   780
agccacattg cccagcagct ggggctggag aaagatgtgg tccgggtgtg gttctgtaat   840
cggagacaga aggaaaaaag gagctcctct gactatgctc agcgcgagga tttcgaagcc   900
gctggctctc cttttagtgg cgggccagtg agtttccccc tggcacctgg ccacactttt   960
ggaactcctg gatacggctc accacatttc accgccctgt atagttcagt gccctttccct  1020
```

| | |
|---|---|
| gagggagaag cttttcctcc agtgtctgtc actaccctgg gctcaccaat gcatagcaac | 1080 |
| tga | 1083 |

<210> SEQ ID NO 62
<211> LENGTH: 954
<212> TYPE: DNA
<213> ORGANISM: Artificial Sequence
<220> FEATURE:
<223> OTHER INFORMATION: codon optimized human SOX gene

<400> SEQUENCE: 62

| | |
|---|---|
| atgtataata tgatggaaac cgaactgaag ccacctggac cacagcagac aagcggggga | 60 |
| ggggggggaa actcaacagc agcagcagcc ggcgggaacc agaagaatag tccagacaga | 120 |
| gtgaaaaggc ccatgaacgc attcatggtc tggtcccgag ccagcggag aaagatggcc | 180 |
| caggagaacc ccaaaatgca caatagtgaa atctcaaagc ggctggggc cgagtggaaa | 240 |
| ctgctgagcg agactgaaaa agaccttttt attgacgaag caaaacgact gcgggccctg | 300 |
| cacatgaagg agcatcctga ttacaaatat cgcccaaggc gcaagaccaa acactgatg | 360 |
| aagaaagaca gtacaccct gcccggagga ctgctggctc tgggggaaa cagcatggca | 420 |
| tccggagtgg gagtcggagc tggactggga gcaggagtga atcagaggat ggactcatat | 480 |
| gcccacatga cgggtggag caatggaagt tactcaatga tgcaggatca gctgggctat | 540 |
| ccccagcacc ctggactgaa cgctcatggc gccgctcaga tgcagcctat gcatcgctac | 600 |
| gatgtgtctg cactgcagta taacagtatg actagctccc agacctacat gaatggctct | 660 |
| cctacctaca gcatgtccta ttctcagcag ggcacaccag ggatggccct gggatctatg | 720 |
| ggcagtgtgg tcaagtccga agcttctagt tcaccccctg tggtcacaag ctcctctcac | 780 |
| tcccgcgccc catgccaggc tggggacctg cgagatatga tctctatgta cctgccagga | 840 |
| gcagaggtgc cagaaccagc agcaccctca agactgcaca tgagccagca ttatcagtcc | 900 |
| ggccctgtcc cagggacagc tattaatggc actctgcccc tgagccatat gtga | 954 |

<210> SEQ ID NO 63
<211> LENGTH: 1320
<212> TYPE: DNA
<213> ORGANISM: Artificial Sequence
<220> FEATURE:
<223> OTHER INFORMATION: codon optimized human c-Myc gene

<400> SEQUENCE: 63

| | |
|---|---|
| atgcccctga atgtgagctt actaacagaa aactacgacc tggactacga cagcgtgcag | 60 |
| ccctattttt attgtgacga agaagagaac ttctaccagc agcagcagca gagcgagctg | 120 |
| cagccacctg caccttccga ggacatttgg aagaaatttg aactgctgcc tacaccaccc | 180 |
| ctgtctccaa gtcggagaag cggcctgtgc tcacccagct atgtggccgt cactcctttc | 240 |
| agcctgcgag ggacaatga tggaggagga ggatcctttt ctacagccga tcagctggag | 300 |
| atggtgactg aactgctggg gggagacatg gtcaaccaga gcttcatttg cgatccagac | 360 |
| gatgagactt ttatcaagaa tatcatcatc caggactgta tgtggtcagg cttcagcgcc | 420 |
| gctgcaaagc tggtgtctga aaaactggca agttaccagg ccgctcgcaa agatagtggg | 480 |
| tcacctaacc cagccagagg ccactccgtg tgctctacaa gctccctgta cctgcaggac | 540 |
| ctgagcgcag ccgcttccga gtgtattgat ccctccgtgg tcttccccta tcctctgaat | 600 |
| gactctagtt cacccaagag ttgtgcatca caggacagct ccgcctttc accttctagt | 660 |

| | |
|---|---:|
| gatagcctgc tgtcaagcac tgagtcctct ccacagggca gcccagaacc cctggtgctg | 720 |
| catgaggaaa cccctccaac cacaagttca gattccgagg aggagcagga ggacgaagag | 780 |
| gaaatcgatg tggtctctgt ggagaagcgg caggctccag aaaaagaag cgaatccgga | 840 |
| tctccaagtg caggaggaca ctccaagcca cctcattctc ccctggtgct gaaaaggtgc | 900 |
| cacgtctcca cccaccagca taactacgca gccccaccct ctacaagaaa ggactatccc | 960 |
| gctgcaaaga gggtgaaact ggatagcgtg cgcgtcctgc gacagatcag taacaatagg | 1020 |
| aagtgtactt cacctcgcag ctccgacacc gaggaaaacg tgaaaaggcg cacccataat | 1080 |
| gtcctggagc gccagcgacg gaatgaactg aagcgatcct tctttgccct gcgggatcag | 1140 |
| attcctgagc tggaaaacaa tgagaaggct ccaaaagtgg tcattctgaa gaaagccaca | 1200 |
| gcttatatcc tgtctgtgca ggccgaggaa cagaagctga tcagtgagga agacctgctg | 1260 |
| cggaaaagaa gggagcagct gaagcacaaa ctggaacagc tgagaaacag ctgcgcctga | 1320 |

<210> SEQ ID NO 64
<211> LENGTH: 5040
<212> TYPE: DNA
<213> ORGANISM: Artificial Sequence
<220> FEATURE:
<223> OTHER INFORMATION: codon optimized human BRG1 gene

<400> SEQUENCE: 64

| | |
|---|---:|
| atgagcaccc cagaccctcc tctgggcggc acacctagac caggcccaag ccctggacca | 60 |
| gggccaagcc ccggcgctat gctgggacca tcccccggac ctagcccgg ctccgcacat | 120 |
| tctatgatgg gacctagtcc tggaccaccc tcagcaggac acccaatccc aacacaggga | 180 |
| ccaggggct acccacagga taatatgcac cagatgcata agccaatgga gtcaatgcac | 240 |
| gaaaaaggca tgagcgacga tcccaggtat aaccagatga agggcatggg aatgagatcc | 300 |
| ggagggcacg caggaatggg ccctccaccc tctcctatgg accagcatag ccagggatac | 360 |
| ccttccccac tgggcggatc tgagcacgct agctccccag tgcctgcaag cggaccttct | 420 |
| agtggcccac agatgtcaag cggccccggc ggcgcccctc tggatggagc tgacccacag | 480 |
| gcactggggc agcagaacag aggcccaacc cccttcaatc agaaccagct gcaccagctg | 540 |
| cgcgcccaga tcatggctta caagatgctg gcaaggggcc agcctctgcc agaccatctg | 600 |
| cagatggcag tccagggcaa cgaccaatg cctggaatgc agcagcagat gcccacactg | 660 |
| cctccaccca gtgtgtcagc cactggacca gggcccggcc ctggaccagg gcccggccct | 720 |
| ggaccagggc cggctcctcc aaaattattcc agaccacacg gaatgggagg ccaaacatg | 780 |
| cccctccag ggccatctgg agtgcccct ggaatgcctg ggcagccacc cggcggaccc | 840 |
| ccaaagcctt ggccagaggg acctatggcc aacgccgctg caccaacctc tacaccccag | 900 |
| aagctgatcc ctccccagcc tacaggcagg cccagtcctg caccaccgc agtccctcca | 960 |
| gcagctagcc cagtgatgcc ccctcagact cagagcccg gccagcctgc tcagccagca | 1020 |
| cccatggtcc cactgcacca gaagcagagc cgcatcaccc ctattcagaa ccacgaggc | 1080 |
| ctggatcccg tggagattct gcaggaacgc gagtaccgac tgcagggccg aattgctcat | 1140 |
| aggatccagg aactggagaa tctgccccga tccctggccg gggatctgag aactaaggcc | 1200 |
| accatcgagc tgaaagctct gcggctgctg aactttcaga ggcagctgag acaggaggtg | 1260 |
| gtcgtgtgca tgaggagaga caccgcactg gaaacagccc tgaatgcaaa agcctataag | 1320 |
| cggtccaaac gccagtctct gcgagaggct aggattacag aaaagctgga gaaacagcag | 1380 |
| aagatcgaac aggagaggaa gcggcgccag aaacaccagg agtacctgaa cagtattctg | 1440 |

```
cagcacgcca aagacttcaa ggaatatcat agatcagtca ccggcaaaat ccagaagctg   1500
acaaaagctg tggcaactta ccatgctaat accgaacggg agcagaagaa agaaaacgag   1560
cgcattgaaa aggagcgaat gcgaaggctg atggccgagg atgaggaagg ctatcggaag   1620
ctgatcgatc agaagaaaga caaacgcctg gcatacctgc tgcagcagac tgacgagtat   1680
gtcgccaacc tgaccgaact ggtgagacag cacaaggcag cccaggtggc taaggagaag   1740
aaaaagaaaa agaaaaagaa aaaggcagaa aatgcagagg acagacccc agcaatcgga    1800 cctgatggag agccactgga cgaaacaagt cagatgtcag atctgcccgt caaagtgatc   1860
cacgtggagt ccggaaaaat cctgactggg accgacgctc ctaaggcagg gcagctggag   1920
gcttggctgg aaatgaaccc tggctacgag gtggcaccac gcagcgactc cgaggaatct   1980
ggcagtgagg aagaagagga ggaagaggaa gaggaacagc cacaggctgc acagccaccc   2040
acactgcctg tcgaggagaa gaagaagatc cctgatccag acagtgacga tgtctcagag   2100
gtggatgcaa ggcacatcat tgaaaatgcc aagcaggacg tggacgatga gtatggagtg   2160
tctcaggccc tggctagagg gctgcagagt tactatgcag tcgcccatgc tgtgaccgag   2220
cgggtcgata gcagagcgc cctgatggtc aatggcgtgc tgaagcagta ccagatcaag    2280
ggactggagt ggctggtgtc cctgtataac aataacctga cggcatcct ggctgacgaa    2340 atgggcctgg gaaaaacaat ccagactatt gcactgatca cctacctgat ggagcacaag   2400
agaatcaatg acccctttct gatcattgtg cctctgagca cactgtccaa ctgggcttac   2460
gagttcgaca gtgggcacc ctccgtcgtg aaggtgagct ataaaggatc cccagccgct    2520
agacgggctt ttgtccccca gctgcggtct gggaagttca acgtgctgct gaccacatac   2580
gagtacatca ttaaggataa gcatattctg gccaagatcc gctggaaata catgatcgtg   2640
gacgagggac acaggatgaa gaatcaccat tgcaaactga cacaggtcct gaacactcat   2700
tatgtggcac ctcgccgact gctgctgaca gggactccac tgcagaataa gctgcccgag   2760
ctgtgggccc tgctgaactt tctgctgcca actattttca gtcatgtag caccttcgag    2820 cagtggttta tgccccctt cgctatgaca ggcgaaaagg tggatctgaa cgaggaagag    2880
actatcctga tcattaggag actgcacaag gtcctgcggc cctttctgct gcggcgcctg   2940
aagaaagaag tggaggccca gctgcctgaa aaggtcgagt acgtgatcaa atgcgacatg   3000
tctgccctgc agagagtcct gtatcggcat atgcaggcta aggggtgct gctgacagat    3060 ggcagcgaga aggacaagaa aggcaagggc ggcaccaaaa cactgatgaa tactattatg   3120
cagctgcgca agatctgtaa ccacccatac atgttccagc atattgaaga gtccttttct   3180
gagcacctgg gcttcactgg agggatcgtg cagggactgg atctgtatag gcatctggg    3240 aagtttgagc tgctggacag gattctgccc aagctgagag ccaccaacca taagtgctg    3300 ctgttctgcc agatgacttc cctgatgacc atcatggagg attactttgc ctatcggggc   3360
ttcaagtacc tgcgcctgga tggaactacc aaagctgagg accgcgggat gctgctgaag   3420
accttcaacg agcctggctc cgaatatttc attttctgc tgtctactag ggccggcgga    3480 ctggactga atctgcagtc agctgacacc gtgatcattt tcgatagcga ctggaaccct    3540
caccaggatc tgcaggctca ggacagagca catcggatcg ccagcagaa tgaggtccgc    3600 gtgctgcgac tgtgcaccgt caacagcgtg gaagagaaga ttctggcagc cgctaagtac   3660
aaactgaacg tggatcagaa agtcatccag gccggaatgt ttgaccagaa gtcctctagt   3720
cacgagcgaa gggccttcct gcaggctatc ctggagcacg aggagcagga cgaatctcgc   3780
```

```
cattgtagta ccgggagtgg ctcagcaagc ttcgcacata cagctcctcc acccgcagga    3840
gtgaatcctg acctggagga gcctcccctg aaggaagagg acgaggtccc agacgatgaa    3900
accgtgaacc agatgatcgc tcgacacgaa gaggaattcg atctgtttat gcggatggat    3960
ctggacagac ggcgcgagga agcccggaat cccaagagga aacctagact gatggaggaa    4020
gacgagctgc ccagctggat cattaaggac gatgccgaag tggagcgcct gacctgcgag    4080
gaagaggaag agaaaatgtt cggaagggga tcccggcacc gaaggaggt ggattactcc     4140 gactctctga cagaaaaaca gtggctgaag aaaattacag gaaggatat ccatgacact     4200 gcatcaagcg tggcccgagg actgcagttt cagaggggc tgcagttctg tactcgcgca    4260
agcaaggcca ttgaagaggg gaccctgaa gagatcgaag aggaagtgag gcagaagaaa     4320
tcctctcgaa agaggaaaag agattccgac gccggcagtt caaccctac aacttctaca    4380 cggagtcgcg acaaggacga tgagagcaag aagcagaaga acgaggaag gccccctgct    4440 gaaaagctga gcccaaatcc acccaacctg accaagaaaa tgaagaaaat tgtcgatgcc    4500
gtgatcaagt acaagacag ctcctctggc cgccagctga gtgaggtgtt tattcagctg    4560
ccttcaagaa aagaactgcc agagtactat gaactgatcc ggaagcctgt ggatttcaag    4620
aaaattaagg agagaatccg gaatcacaaa tacaggtccc tgaacgatct ggaaaaggac    4680
gtgatgctgc tgtgtcagaa tgcccagact tttaacctgg aggggtctct gatctacgaa    4740
gacagtatcg tgctgcagtc agtcttcacc agcgtgagac agaagattga aaagaggac    4800 gatagtgagg gcgaggaatc agaggaagag gaagagggcg aagaggaagg aagtgaatca    4860
gagagccggt ccgtcaaggt gaaaatcaag ctggggagaa aagagaaggc tcaggaccgg    4920
ctgaaagggg gccgaaggag accttcacgg ggcagccgcg caaagccagt cgtgtccgac    4980
gatgactctg aggaggagca ggaagaggat aggtctggca gtggatcaga agaggactga    5040
```

<210> SEQ ID NO 65
<211> LENGTH: 3318
<212> TYPE: DNA
<213> ORGANISM: Artificial Sequence
<220> FEATURE:
<223> OTHER INFORMATION: codon optimized human BAF155 gene

<400> SEQUENCE: 65

```
atggcagctg cagccggcgg aggggccc ggcacagccg tgggagctac tggatccgga       60
atcgctgcag cagctgcagg actggctgtg taccggagaa agacggagg gcctgcaaca      120 aagttctggg aatctccaga gactgtgtcc cagctggact ctgtgcgggt ctggctgggg     180
aaacactaca agaaatatgt gcatgcagat gcccctacaa acaagactct ggctggcctg     240
gtggtccagc tgctgcagtt ccaggaggat gcatttggaa agcacgtgac caatccagct     300
tttacaaaac tgcccgcaaa gtgcttcatg gactttaagg caggcggagc cctgtgtcat     360
atcctgggag ccgcttacaa atacaagaac gagcagggat ggcgacgatt cgacctgcag     420
aatccctcca ggatggatag aaacgtggaa atgttcatga acatcgagaa gacccctggtc    480 cagaacaatt gcctgacacg gcctaacatc acctgatcc agacattga tctgaaactg      540 gccaacaagc tgaaggacat cattaagcgc accaggaa ccttcacaga tgagaaaagt      600
aaagcttcac accatatcta cccttatagc tcctctcagg acgatgagga atggctgcgg    660
ccagtgatgc gcaaagagaa gcaggtgctg gtccactggg gcttttaccc cgactccctat  720 gataccctggg tccattctaa cgacgtggat gccgaaatcg aggatccccc tattccagag    780
aaaccctgga aggtgcacgt caagtggatc ctggacactg atattttcaa cgagtggatg     840
```

```
aatgaggaag actacgaagt cgatgagaac cggaaacctg tgtcatttcg gcagcgcatc    900
agcacaaaga atgaggaacc tgtgcgatct ccagagcgaa gggacaggaa ggctagtgca    960
aacgcccgaa aaaggaagca tagcccatcc ccaccccctc caactcctac cgagagtcgc   1020
aagaaatcag gaaagaaagg gcaggccagt ctgtatggca aaagacggtc acagaaggag   1080
gaagacgaac aggaggatct gacaaaggac atggaggatc ctactccagt gcccaacatt   1140
gaggaagtgg tcctgcccaa gaacgtcaat ctgaagaaag actctgaaaa tactcctgtc   1200
aagggcggca ccgtggcaga cctggatgag caggatgagg aaacagtgac tgcaggaggg   1260
aaagaagacg aggatccagc caaggggac cagtctagga gtgtggacct gggcgaagat   1320
aacgtgaccg agcagacaaa tcacatcatt atccccagct acgcctcctg gttcgactat   1380
aactgcatcc atgtgattga acgccgagct ctgccagagt tctttaacgg caaaaataag   1440
agcaaaacac ccgagatcta cctggcctat cgcaacttta tgattgatac ttaccgactg   1500
aatcctcagg agtatctgac cagcacagct tgcaggagaa acctgaccgg agacgtgtgt   1560
gccgtcatga gggtgcacgc tttcctggaa cagtgggggc tggtcaacta ccaggtggat   1620
cccgagagca gacctatggc catgggccct cctcccactc cacactttaa tgtcctggct   1680
gacaccccat caggactggt gcccctgcat ctgagaagcc ctcaggtccc agcagcccag   1740
cagatgctga acttcccaga gaagaacaag gagaagcccg tggacctgca gaactttggc   1800
ctgcgaaccg atatctacag caagaaaaca ctggccaaaa gcaagggagc ttccgcagga   1860
cgagagtgga ctgaacagga gaccctgctg ctgctggaag ccctggagat gtataaagac   1920
gattggaata aggtctctga acacgtgggc agtaggaccc aggatgagtg tatcctgcat   1980
ttcctgagac tgccaattga agaccccac ctggagaact ctgatgcaag tctgggacct   2040
ctggcctatc agcctgtgcc attctcacag agcgggaatc cagtcatgag cacagtggct   2100
tttctggcat ccgtggtgga ccccagagtg gcatccgctg cagcaaaggc tgcactggag   2160
gaattctcta gagtccggga ggaagtgccc ctggaactgg tggaggcaca cgtcaagaaa   2220
gtgcaggagg cagctcgcgc cagcggaaag gtggaccccta catacgggct ggagagttca   2280
tgcatcgccg gaactgggcc cgatgaacct gagaaactgg aaggggccga ggaagagaag   2340
atggaggctg accctgatgg ccagcagcca gaaaaagccg agaacaaggt ggaaaatgag   2400
accgacgagg gggataaggc tcaggatggc gaaaacgaga aaatagcga aaaggagcag   2460 gactcagaag tgagcgagga tactaaatcc gaagagaagg aaaccgaaga gaacaaagag   2520
ctgactgaca cctgtaagga aagggagagt gatacaggca agaaaaaggt cgaacacgag   2580
atctcagagg gaaatgtcgc aaccgcagca gctgcagcac tggcttctgc tgcaacaaaa   2640
gcaaagcatc tggccgctgt ggaagagaga aaaattaaga gtctggtcgc cctgctggtg   2700
gaaacccaga tgaaaaagct ggagatcaag ctgcggcact tcgaggagct ggagacaatt   2760
atggaccgcg aaaaggaggc cctggaacag cagagacagc agctgctgac cgagcggcag   2820
aactttcaca tggaacagct gaagtacgcc gagctgcgcg ctcgacagca gatggagcag   2880
cagcagcatg ggcagaatcc acagcaggca caccagcatt ccggcggacc tggcctggct   2940
ccactgggcg cagcaggaca ccccggcatg atgcctcatc agcagccccc tccatatcct   3000
ctgatgcacc atcagatgcc ccctccccac cctccccagc caggccagat ccccggccct   3060
ggatctatga tgcctggcca gcacatgcct ggaaggatga tcccaactgt ggctgcaaac   3120
attcatccat ccggatctgg acctaccccct cccggcatgc ctccaatgcc aggaaacatt   3180
```

```
ctgggaccaa gagtgccact gaccgcacca aatggcatgt accctccccc tccccagcag    3240
cagcctccac ccctccacc cgctgacggc gtgcctccac ccctgcacc cggaccaccc      3300 gccagcgccg ctccttga                                                   3318

<210> SEQ ID NO 66
<211> LENGTH: 1431
<212> TYPE: DNA
<213> ORGANISM: Artificial Sequence
<220> FEATURE:
<223> OTHER INFORMATION: codon optimized human Immunoglobulin G H chain
      gene

<400> SEQUENCE: 66
atggattgga cttggagatt cctgttcgtc gtcgcagcag caaccggcgt gcagagccag      60
atgcaggtcg tgcagagcgg ggcagaagtg aagaaaccag gcagctccgt cactgtgagt     120
tgcaaggcct caggcgggac cttcagcaac tacgcaatct cctgggtgcg gcaggccccc     180
ggacagggac tggaatggat gggaggcatc attcccctgt cggaactcc tacctattct     240 cagaattttc agggccgcgt gacaatcact gctgataaga gtacctcaac agcacacatg    300
gagctgattt ctctgcgaag tgaagacact gctgtgtact attgcgcaac cgaccggtac    360
agacaggcca acttcgatag ggctcgcgtg gggtggtttg accttgggg gcagggaacc     420 ctggtcacag tgtctagtgc atctaccaag ggaccaagtg tgtttccact ggcccctca     480 agcaaaagca cttccggagg aaccgcagct ctgggatgtc tggtgaagga ttatttccca    540
gagcccgtca cagtgtcatg aacagcgga gcactgacca gcgggtcca tacatttccc     600 gctgtgctgc agtcctctgg cctgtactcc ctgagttcag tggtcaccgt ccctagctcc    660
tctctgggga ctcagaccta tatctgcaac gtgaatcaca gccttctaa tacaaaagtg     720 gacaagaagg tggaaccaaa gagttgtgac aaaacacata cttgcccccc ttgtcctgca    780
ccagagctgc tgggaggacc aagcgtgttc ctgtttccac ccaagcccaa agataccctg    840
atgattagca ggacaccaga agtcacttgc gtggtcgtgg acgtgtccca cgaggatccc    900
gaagtcaagt tcaactggta cgtggacggc gtcgaggtgc ataatgctaa gaccaaaccc    960
agagaggagc agtacaattc aacctatcgg gtcgtgagcg tcctgacagt gctgcaccag   1020
gattggctga acggcaaaga gtataagtgc aaagtgtcta ataaggcact gccgcccct   1080 atcgagaaaa caattagcaa ggctaaaggg cagcctagag aaccacaggt gtataccctg   1140
cctccaagca gggatgagct gacaaagaac caggtctccc tgacttgtct ggtgaaaggg   1200
ttctatccca gtgacattgc agtggagtgg gaatcaaatg acagcctga aaacaattac    1260 aagaccacac cctgtgct ggactccgat ggatcttct ttctgtattc caagctgact      1320
gtggacaaat ctcggtggca gcagggcaac gtcttttctt gtagtgtgat gcatgaggcc   1380
ctgcacaatc attacacaca gaagtcactg agcctgtccc ccggcaaatg a             1431

<210> SEQ ID NO 67
<211> LENGTH: 708
<212> TYPE: DNA
<213> ORGANISM: Artificial Sequence
<220> FEATURE:
<223> OTHER INFORMATION: codon optimized human Immunoglobulin G L chain
      gene

<400> SEQUENCE: 67
atggcttggg cactgctgct gctgacactg ctgacacagg atactgggtc ttgggcacag     60
agcgcactga cacagcctgc ttccgtgtcc ggctctcctg ggcagtctat caccattagt    120
```

```
tgcaccggga caaacaatga cgtgggaagt tacaacctgg tctcatggta tcagcagcac      180
ccaggcaagg cccccaaaat catgatctac gaggtgtcca agcggccaag tggggtctca      240
aaccggttca gcggatcaaa aagcggcaat acagcctcac tgactatcag cggactgcag      300
gcagaggacg aagccgatta ctattgctgt tcctacgctg gctcttatac agtggtcttc      360
ggcgggggaa ctaagctgac cgtgctgggg cagcctaaag ccgctccatc tgtgactctg      420 tttccccta gctccgagga actgcaggct aataaggcaa ccctggtgtg tctgattagc       480
gacttctacc ccggagctgt gacagtcgcc tggaaggctg attctagtcc cgtgaaagca      540
ggggtcgaga ccacaactcc tagcaagcag tccaacaaca gtacgcagc tcaagctat       600 ctgtccctga ctccagaaca gtggaagtct cacaggtcct attcttgcca ggtgacccat      660
gagggcagta ccgtggaaaa aacagtcgcc cccactgaat gttcctga                  708
```

<210> SEQ ID NO 68
<211> LENGTH: 1773
<212> TYPE: DNA
<213> ORGANISM: Artificial Sequence
<220> FEATURE:
<223> OTHER INFORMATION: codon optimized human Immunoglobulin M H chain gene

<400> SEQUENCE: 68

```
atggaactgg gcctgagatg ggtctttctg gtcgctatcc tggagggagt gcagtgtgaa      60
gtgcagctgg tcgagtctgg cggggactg gtgaaaccag cggatctct gcgactgagt       120 tgcgcagctt caggcttcac cttcagcact tactcaatga actgggtccg acaggccccc      180
ggcaagggac tggaatgggt gagctccatc tctagttcaa gctcctacat ctactatgct      240
gacagcgtga agggcgatt cactatctct cgggataacg caaagaatag cctgtatctg      300
cagatgaatt cactgagagc cgaggacaca gctgtctact attgtgccag ggatctgctg      360
attgctgtgg caggacactg gggacagggg accctggtga cagtctctag tggcagcgcc      420
tccgctccaa ctctgttccc cctggtgtcc tgcgaaaact ctcctagtga cacctcaagc      480
gtggcagtcg gatgtctggc ccaggacttc ctgccagata gcatcacatt tcctggaag     540 tacaaaaaca acagtgatat ttcctctact cgcggcttc cctctgtgct gcgaggaggc     600
aaatatgcag ccaccagtca ggtcctgctg ccttcaaagg acgtgatgca gggacagat     660 gagcacgtgg tctgcaaagt gcagcatccc aacggaaata aggagaagaa cgtcccactg     720
cccgtgatcg ctgagctgcc acctaaggtg agcgtcttcg tgccacccag agacgggttc     780
tttgaaaatc cagaaagag caaactgatc tgtcaggcca ccggctttag ccctaggcag     840
attcaggtgt cctggctgcg cgaagggaag caggtcggat ccggcgtgac cacagatcag     900
gtccaggcag aagccaagga gtctgggccc actacctaca agtgaccctc acactgact     960 atcaaggaga gtgactggct gtcacagagc atgttcaccc tgccgggtgga tcatagagga    1020 ctgacatttc agcagaatgc cagttcaatg tgtgtccctg accaggatac cgctatcagg     1080
gtgttcgcaa ttcctccaag cttcgcttcc attttctga ctaagtccac caaactgaca      1140
tgcctggtca ccgacctgac aacttatgat tctgtgacca tcagttggac acgccagaac     1200
ggcgaagccg tgaagaccca cacaaacatt tccgagtctc atcccaatgc aaccttcagc     1260
gccgtgggcg aagcttccat ctgcgaggac gattggaata gcggggagcg gtttacttgt     1320
accgtgacac acactgacct gccttcacca ctgaagcaga ccattagccg acctaaaggc     1380
gtcgccctgc atcggccaga tgtgtacctg ctgccccctg caagagaaca gctgaacctg     1440
```

-continued

```
agggagagcg ccaccatcac atgtctggtg accggattca gccctgcaga cgtctttgtg    1500
cagtggatgc agcgaggaca gccactgtcc cctgaaaagt acgtgacatc tgcaccaatg    1560
cctgagccac aggccccagg cagatatttt gctcactcca ttctgacagt gtctgaggaa    1620
gagtggaaca ctggggagac ttatacctgc gtggtcgctc atgaagcact gccaaatagg    1680
gtcactgagc gcaccgtgga caagagcact gggaaaccca ccctgtataa cgtctcactg    1740
gtcatgagcg atacagccgg aacttgttat tga                                 1773
```

<210> SEQ ID NO 69
<211> LENGTH: 711
<212> TYPE: DNA
<213> ORGANISM: Artificial Sequence
<220> FEATURE:
<223> OTHER INFORMATION: codon optimized human Immunoglobulin M L chain gene

<400> SEQUENCE: 69

```
atggacatgc gagtgcctgc tcagctgctg ggactgctgc tgctgtggct gcccgataca      60
agatgcgaca ttcagatgac tcagagccca agctccctga gtgcctcagt gggagaccgg    120
gtcaccatca catgcagagc ttcacagggc attagcaact acctggcatg gtatcagcag    180
aagccaggca agtgcccaa gctgctgatc tacgcagctt ccaccctgca gtctggggtg    240
cccagtcgat tcagcggatc cggatctgga acagacttta ctctgaccat ttctagtctg    300
cagcctgagg atgtggctac ttactattgc cagaaataca attctgcacc atataccttc    360
ggccagggga caaaactgga gatcaagagg acagtggcag cccctctgt cttcattttt    420 cccctagcg acgaacagct gaagtccggc accgcttccg tggtctgtct gctgaacaat    480
ttttaccctc gcgaagccaa agtgcagtgg aaggtcgata cgctctgca gagtggcaat    540 tcacaggaga gcgtgactga acaggactcc aaagattcta cctatagtct gtcaagcaca    600
ctgactctga gcaaggcaga ttacgagaag cacaaactgt atgcctgcga agtgacacat    660 cagggggctgt cctctcctgt cactaagtcc ttcaacagag gagagtgttg a            711
```

<210> SEQ ID NO 70
<211> LENGTH: 480
<212> TYPE: DNA
<213> ORGANISM: Artificial Sequence
<220> FEATURE:
<223> OTHER INFORMATION: codon optimized human Immunoglobulin M J chain gene

<400> SEQUENCE: 70

```
atgaagaacc atctgctgtt ttggggagtg ctggctgtgt ttatcaaggc tgtccatgtg     60
aaggctcagg aagacgagag aattgtgctg gtggacaaca gtgcaaatg tgctagaatc    120 acctccagga tcattcgcag ctccgaggac cctaacgaag acatcgtgga gcgaaatatt    180
cggatcattg tccccactga caatcgcgaa atatttctg atcccaccag tcctctgcgg    240
acaagattcg tgtaccacct gagtgacctg tgcaagaaat gtgatcccac agaggtggaa    300
ctggacaacc agatcgtcac cgcaacacag tcaaatattt gcgacgaaga tagcgccact    360
gagacctgct acacttatga taggaacaag tgttacaccg cagtggtccc tctggtgtat    420
ggaggagaaa ctaaaatggt cgagacagcc ctgactccag acgcttgtta tcccgattga    480
```

<210> SEQ ID NO 71
<211> LENGTH: 7056
<212> TYPE: DNA

<213> ORGANISM: Artificial Sequence
<220> FEATURE:
<223> OTHER INFORMATION: codon optimized human coagulation factor VIII gene

<400> SEQUENCE: 71

| | | | | | |
|---|---|---|---|---|---|
| atgcagattg | aactgtccac | ctgtttcttc | ctgtgcctgc | tgagattttg | ttttccgct 60 |
| actcgcagat | actacctggg | ggctgtggaa | ctgtcttggg | attacatgca | gagtgacctg 120 |
| ggagagctgc | cagtggacgc | acgatttcca | cctcgggtgc | caaagtcatt | ccctttaac 180 |
| acaagcgtgg | tctacaagaa | gaccctgttc | gtggagttca | ccgatcacct | gttcaatatc 240 |
| gctaagcccc | ggccaccctg | gatgggactg | ctggggccta | ccatccaggc | agaggtgtac 300 |
| gacaccgtgg | tcattacact | gaaaaacatg | gcatcacacc | cagtgagcct | gcatgccgtc 360 |
| ggagtgtctt | actggaaggc | tagtgagggc | gcagaatatg | acgatcagac | ctctcagaga 420 |
| gagaaggaag | acgataaagt | gtttcccggc | gggagccata | catatgtctg | gcaggtgctg 480 |
| aaggagaacg | cccaatggc | tagcgacccc | ctgtgcctga | cctactcata | tctgagccac 540 |
| gtggacctgg | tgaaggatct | gaatagcgga | ctgatcggcg | ccctgctggt | gtgcagggag 600 |
| ggatccctgg | ctaaagaaaa | gacacagact | ctgcataagt | tcattctgct | gttcgccgtg 660 |
| tttgacgagg | ggaaatcctg | gcactctgaa | accaagaact | cactgatgca | ggaccgagat 720 |
| gcagctagcg | cacgagcctg | gcccaaaatg | cacacagtca | acggctacgt | gaatagatca 780 |
| ctgcctgggc | tgatcggatg | ccacaggaag | tctgtctatt | ggcatgtgat | cgggatggga 840 |
| accacaccag | aggtccacag | cattttcctg | gaagggcata | cctttctggt | gcgcaaccac 900 |
| cgacaggctt | ccctggagat | ctctcccatt | acattcctga | ctgcacagac | cctgctgatg 960 |
| gatctgggcc | agttcctgct | gttttgccac | atcagctccc | accagcatga | tgggatggag 1020 |
| gcttacgtca | agtggactc | ctgtcctgag | gaaccacagc | tgcggatgaa | gaacaatgag 1080 |
| gaagccgaag | actatgacga | tgacctgaca | gactctgaga | tggatgtggt | caggttcgat 1140 |
| gacgataaca | gccctccctt | tatccagatt | cgcagcgtcg | ccaagaaaca | ccctaagacc 1200 |
| tgggtgcatt | acatcgcagc | cgaggaagag | gactgggatt | atgctcctct | ggtgctggca 1260 |
| ccagacgata | aagttacaa | atcacagtat | ctgaacaatg | ccctcagcg | gattgggaga 1320 |
| aagtacaaga | aagtgcgatt | catggcatac | acagatgaaa | cttttaagac | cagagaggcc 1380 |
| atccagcacg | aaagcggcat | tctggggcca | ctgctgtacg | agaagtggg | cgacactctg 1440 |
| ctgatcatct | tcaagaacca | ggccagccgg | ccctacaata | tctatcctca | tggaattacc 1500 |
| gatgtcagac | cactgtactc | ccggagactg | cccaaaggag | tgaagcacct | gaaagacttc 1560 |
| cccatcctgc | ctggcgaaat | cttcaagtat | aagtggaccg | tcacagtgga | ggatggccca 1620 |
| actaagtccg | accccagatg | cctgaccagg | tactattcta | gtttcgtgaa | catggaaagg 1680 |
| gatctggcct | ctgggctgat | cggaccactg | ctgatttgtt | acaaagagag | tgtggatcag 1740 |
| aggggcaacc | agatcatgtc | agacaagcgc | aatgtcattc | tgttcagcgt | gtttgacgag 1800 |
| aatcgctcct | ggtatctgac | cgaaaacatc | cagcgattcc | tgccaaatcc | cgctggcgtg 1860 |
| cagctggagg | atcccgaatt | tcaggcatca | aacatcatgc | atagcattaa | tggctacgtg 1920 |
| ttcgacagtc | tgcagctgtc | agtctgcctg | cacgaggtgg | cttactggta | tatcctgagc 1980 |
| attggggcac | agacagattt | cctgagcgtc | ttcttttccg | gatacacttt | taaacataag 2040 |
| atggtgtacg | aggacactct | gaccctgttc | ccattttctg | gcgagaccgt | gtttatgagt 2100 |
| atggaaaacc | ccggactgtg | gatcctgggc | tgccacaact | ccgatttcag | gaatcgcgga 2160 |

-continued

```
atgactgccc tgctgaaagt gtcaagctgt gacaagaata ccggcgacta ctatgaggat     2220
tcctacgaag acatctctgc ttatctgctg agtaaaaaca atgcaattga gccacgctct     2280
tttagtcaga actctaggca ccccagtacc cgccagaagc agttcaacgc cactaccatc     2340
cctgagaata tattgaaaa aacagaccca tggtttgctc atcggactcc tatgccaaag     2400
atccagaacg tgagcagcag cgatctgctg atgctgctga gacagagccc cactcctcac     2460
gggctgtcac tgagcgacct gcaggaggca aagtacgaaa ccttctcaga cgatccaagc     2520
cccggagcca tcgattccaa caattccctg tctgagatga cccacttccg gccacagctg     2580
caccattccg gggacatggt gtttacaccc gagtctggac tgcagctgag actgaacgaa     2640
aaactgggca caactgctgc aacagagctg aagaaactgg actttaaggt gtcaagcact     2700
agcaacaatc tgatctccac cattccctct gataacctgg ccgctgggac agacaatact     2760
tcctctctgg acctccatc aatgcctgtg cactacgata gccagctgga caccacactg     2820
ttcggcaaga aaagttcacc tctgaccgag tctggaggcc cactgagtct gtcagaagag     2880
aacaatgatt caaaactgct ggagagcgga ctgatgaact cccaggaaag ctcctggggc     2940
aagaacgtga gcagcaccga gtccgggcgg ctgtttaaag aaagagagc ccatggccct     3000 gctctgctga ctaaagacaa cgctctgttc aaggtgagca tctccctgct gaagaccaac     3060
aaaacaagca caattccgc aactaatcgg aagacccaca tcgatggccc atccctgctg     3120
attgagaact ctcccagtgt ctggcagaat atcctggagt ctgacacaga gttcaagaag     3180
gtcactccac tgattcatga tcggatgctg atggacaaga atgctaccgc actgagactg     3240
aaccacatga gcaataagac tacctcaagc aaaaacatgg agatggtgca gcagaagaaa     3300
gaaggaccta tccccctga tgcacagaat ccagacatga gcttctttaa aatgctgttc     3360
ctgcctgagt ccgcccgctg gattcagcga acacacggca agaactctct gaatagtggc     3420
caggggcctt ccccaaaaca gctggtctct ctgggcccag agaagagtgt ggaagggcag     3480
aactttctgt ccgagaaaaa taaggtggtc gtgggaaagg gcgaattcac caaagatgtc     3540
ggcctgaagg agatggtgtt cccctcctct aggaatctgt ttctgactaa cctggacaat     3600
ctgcacgaga acaataccca taaccaggaa aagaaaatcc aggaagagat tgagaagaaa     3660
gaaacactga tccaggagaa cgtcgtgctg ccccagattc acacagtgac tggcaccaag     3720
aacttcatga aaaatctgtt tctgctgtct acccgccaga atgtcgaggg cagttacgac     3780
ggggcctatg ctcctgtgct gcaggatttt cgcagtctga acgactcaac taatcgaacc     3840
aagaaacaca ccgcccattt cagcaagaaa ggggaagagg aaaacctgga agggctggga     3900
aatcagacaa aacagatcgt ggagaagtac gcttgcacaa ctagaattag cccaaacaca     3960
tcccagcaga atttcgtgac tcagaggagc aagcgcgccc tgaaacagtt taggctgccc     4020
ctggaggaaa ctgagctgga aaagcgcatc attgtggacg atacatctac tcagtggagc     4080
aagaacatga agcatctgac cccctccacc ctgacacaga tcgattataa cgagaaagaa     4140
aagggcgcca ttacccagtc acctctgagc gactgtctga cacgatcaca cagcatccca     4200
caggccaacc ggtctcccct gcctattgct aaggtgagtt cattccctag catcaggcca     4260
atctacctga cccgcgtgct gtttcaggat aatagctccc atctgcctgc agcctcatat     4320
aggaagaaag acagcggggt gcaggagtct agtcacttcc tgcagggagc aaagaaaaac     4380
aatctgtccc tggccatcct gacactggag atgactgggg atcagcgcga agtcggctca     4440
ctggggacaa gcgccactaa ctccgtgacc tacaagaaag tcgaaaatac agtgctgcca     4500
aagcccgacc tgcctaagac atctggaaaa gtcgagctgc tgccaaaagt gcatatctat     4560
```

```
cagaaggatc tgtttcccac tgaaacctcc aacggatctc ctggccacct ggacctggtg   4620
gagggaagcc tgctgcaggg gaccgaggga gcaatcaaat ggaacgaagc caatcggccc   4680
ggcaaggtcc ctttcctgag agtggccacc gagtcaagcg ccaagacacc ctccaaactg   4740
ctggatcctc tggcttggga caatcattac ggcacccaga tcccaaagga ggaatggaaa   4800
tctcaggaga agagtcccga aaaaactgcc ttcaagaaaa aggacaccat tctgtccctg   4860
aacgcttgcg aatctaatca cgcaatcgct gcaattaacg aggggcagaa caagcccgag   4920
atcgaagtga catgggccaa gcagggacga actgagcggc tgtgcagcca gaacccaccc   4980
gtgctgaaga gacatcagag ggagattaca aggaccacac tgcagtccga tcaggaggaa   5040
atcgactacg acgatactat ttctgtggag atgaaaaagg aagacttcga tatctatgac   5100
gaggatgaaa atcagagtcc tagatcattc cagaaaaaga ccaggcatta ctttattgcc   5160
gctgtggagc gcctgtggga ttatgggatg tcctctagtc ctcacgtcct gcgaaaccgg   5220
gcccagtccg gatctgtgcc acagttcaaa aaggtcgtgt tccaggagtt tactgacggc   5280
agctttaccc agccactgta ccggggggag ctgaatgaac cctgggact gctgggacca   5340 tatatccgag ctgaggtcga agataacatt atggtgacat tccgaaatca ggcatcacgg   5400
ccctacagct tttattcaag cctgatctcc tacgaggaag accagcgaca gggcgctgaa   5460
ccccggaaga acttcgtcaa gcctaacgag acaaagactt acttctggaa ggtgcagcac   5520
catatggccc ctaccaaaga cgaattcgat tgcaaggcat gggcctattt ttctgacgtg   5580
gacctggaga aggacgtgca cagtggactg atcggcccct gctggtgtg ccataccaac   5640 acactgaatc cagcacacgg ccggcaggtc acagtgcagg aattcgctct gttctttaca   5700
atctttgatg agactaagag ctggtacttc actgagaaca tggaacgcaa ttgccgagcc   5760
ccatgtaaca ttcagatgga ggaccccact ttcaaggaaa actacagatt tcacgccatc   5820
aatggctata ttatggatac cctgcccggc ctggtcatgg ctcaggacca gagaatcagg   5880
tggtatctgc tgagcatggg ctccaacgag aatatccact ccattcattt ctctgggcat   5940
gtctttacag tgcggaaaaa ggaggaatat aaaatggccc tgtataacct gtatcccgga   6000
gtcttcgaga ctgtggaaat gctgccttcc aaggcaggca tctggagagt ggagtgcctg   6060
attggagaac acctgcatgc cggcatgtcc acccttgtttc tggtgtactc taacaagtgt   6120
cagacacctc tgggaatggc aagtggccat atcagggatt tccagattac cgcatccgga   6180
cagtacggac agtgggcacc aaaagctggc cgcctgcact atagtgggtc aatcaatgcc   6240
tggagtacca aagagcctt ctcatggatt aaggtggacc tgctggcccc tatgatcatt   6300
cacgggatca aaacacaggg agctaggcag aagttctcct ctctgtatat cagtcagttt   6360
atcatcatgt attcactgga tggaaaaaag tggcagacct accgcgggaa tagcactgga   6420
accctgatgg tcttctttgg gaacgtggac agttcaggaa tcaagcataa cattttcaat   6480
cctccaatca ttgcccggta catcagactg cacccaccc attattctat tcggagtaca   6540
ctgagaatgg aactgatggg ctgcgatctg aacagctgtt ccatgcctct ggggatggag   6600
agtaaggcta tctcagacgc acagattacc gccagctcct attcaccaa catgtttgcc   6660 acatggtctc ccagtaaagc tagactgcac ctgcagggca gaagcaatgc ctggaggcct   6720
caggtcaaca atccaaagga gtggctgcag gtggattttc agaagaccat gaaagtcaca   6780
ggcgtgacta cccaggggt caaaagcctg ctgacttcca tgtacgtgaa ggagttcctg   6840
atctctagtt cacaggacgg ccaccagtgg acctgttct ttcagaacgg aaaagtcaag   6900
```

-continued

```
gtgttccagg gcaatcagga tagctttaca cctgtcgtga actccctgga ccccctctg     6960 ctgactaggt atctgcgcat ccatccacag tcctgggtgc atcagattgc tctgcgaatg    7020
gaagtgctgg ggtgcgaagc tcaggacctg tattga                              7056
```

<210> SEQ ID NO 72
<211> LENGTH: 11058
<212> TYPE: DNA
<213> ORGANISM: Artificial Sequence
<220> FEATURE:
<223> OTHER INFORMATION: codon optimized human dystrophin gene

<400> SEQUENCE: 72

```
atgctgtggt gggaagaggt cgaggattgc tacgagagag aagatgtcca agaagagact     60
tttactaaat gggtcaacgc tcagttctca aaattcggca agcagcatat cgagaacctg    120
tttagcgacc tgcaggatgg gcggagactg ctggacctgc tggagggact gactggccag    180
aaactgccca agaaaaggg ctctaccaga gtgcacgccc tgaacaatgt caataaggct    240
ctgagggtgc tgcagaacaa taacgtggat ctggtcaata tcgggagcac cgacattgtg    300
gatggaaacc acaagctgac actgggcctg atctggaata tcattctgca ttggcaggtg    360
aaaaatgtca tgaagaacat catggccggc ctgcagcaga caaacagcga aagattctg     420 ctgtcctggg tgaggcagtc tactcgcaat taccctcaag tgaatgtcat caacttcacc    480
acaagctggt ccgacggact ggccctgaac gctctgattc actcccatcg cccagacctg    540
ttcgattgga attccgtggt ctgccagcag tctgccaccc agaggctgga gcacgccttt    600
aacatcgctc gctatcagct gggcattgag aagctgctgg acccagaaga cgtggatact    660
acctaccccg acaagaagtc catcctgatg tatattacaa gtctgttcca ggtgctgcca    720
cagcaggtca gcatcgaggc cattcaggaa gtggagatgc tgccccggcc ccctaaagtc    780
accaaggagg aacactttca gctgcaccat cagatgcatt acagtcagca gatcaccgtg    840
agcctggctc agggatatga gcgaaccagc tccccaaaac cccggttcaa gtcctacgca    900
tatacacagg ccgcttacgt gacaacttct gacccaacta gatccccttt cccatctcag    960
catctggagg ctccccgaaga caagtctttt ggctctagtc tgatggaaag tgaggtgaac   1020
ctggataggt atcagactgc cctggaggaa gtcctgagtt ggctgctgtc agccgaggat   1080
accctgcagg ctcagggcga gatcagcaac gacgtggaag tggtcaagga tcagttccac   1140
acacatgagg ggtacatgat ggacctgact gcccaccagg ggagagtggg aaatatcctg   1200
cagctggggt caaaactgat tggaaccggc aagctgagcg aggatgagga acagagggtg   1260
caggaacaga tgaatctgct gaactcccgg tgggagtgcc tgagagtggc cagtatggaa   1320
aagcagtcaa atctgcatag ggtcctgatg gacctgcaga atcagaaact gaaggagctg   1380
aacgattggc tgaccaagac agaggaaagg acccgcaaaa tggaggagga gcccctggga   1440
ccagacctgg aggatctgaa gcggcaggtg cagcagcaca agtcctgca ggaagacctg   1500 gaacaggagc aggtgagagt caacagcctg acacacatgg tggtcgtggt ggacgagtca   1560
agcggagatc atgctactgc cgccctggag gagcagctga aggtgctggg cgatcgctgg   1620
gcaaatatct gtaggtggac tgaggaccgc tgggtgctgc tgcaggatat tctgctgaag   1680
tggcagcggc tgaccgagga gcagtgcctg ttcagcgcct ggctgtccga aaagaggac   1740 gcagtgaaca gatccacac cacaggcttt aaggatcaga atgagatgct gtcctctctg   1800
cagaaactgg cagtgctgaa ggccgacctg gagaagaaaa agcagagcat ggggaaactg   1860
tactccctga gcaggatct gctgtctaca ctgaaaaaca agagtgtgac tcagaagacc   1920
```

| | |
|---|---|
| gaggcatggc tggacaattt cgccagatgt tgggataacc tggtgcagaa actggagaag | 1980 |
| tccaccgcac agatctccca ggccgtgact accacacagc ctagcctgac ccagactacc | 2040 |
| gtcatggaga cagtgacaac tgtcaccaca cgcgaacaga ttctggtgaa gcatgcacag | 2100 |
| gaggagctgc caccacctcc accacagaaa agcggcaga tcaccgtgga ctccgagatt | 2160 |
| cgaaagcggc tggacgtgga catcactgaa ctgcactctt ggattaccag gagtgaggcc | 2220 |
| gtgctgcaga gcccagaatt cgctatcttt cgcaaggagg ggaatttctc cgatctgaaa | 2280 |
| gagaaggtga acgctattga agagagaaa gcagaaaagt ttaggaaact gcaggacgcc | 2340 |
| tctcgcagtg ctcaggcact ggtggagcag atggtcaatg aaggagtgaa cgccgattca | 2400 |
| atcaagcagg ctagcgagca gctgaactcc aggtggattg aattctgcca gctgctgagc | 2460 |
| gagcgcctga actggctgga ataccagaat aacatcattg ccttctacaa tcagctgcag | 2520 |
| cagctggaac agatgactac cacagccgag aactggctga aaatccagcc cactacccct | 2580 |
| tcagagccaa cagccatcaa gagccagctg aagatttgta agacgaagt gaatagactg | 2640 |
| tctggcctgc agcctcagat tgagaggctg aagatccaga gtattgccct gaaagaaaag | 2700 |
| gggcagggac caatgtttct ggacgctgat ttcgtggcct tcaccaacca cttcaagcag | 2760 |
| gtcttttccg acgtgcaggc tcgcgaaaaa gagctgcaga caatcttcga tactctgcct | 2820 |
| ccaatgcgat accaggagac tatgtctgcc attcggacct gggtgcagca gtctgaaaca | 2880 |
| aagctgagta tccctcagct gtcagtcact gactatgaga ttatggaaca gcggctggga | 2940 |
| gagctgcagg ctctgcagag ttcactgcag gaacagcagt caggactgta ctatctgagc | 3000 |
| acaactgtga aagagatgtc aaaaaaggcc ccatccgaaa tctctcgcaa gtaccagagc | 3060 |
| gagtttgaag agattgaagg acgatggaaa aagctgagct cccagctggt ggagcattgt | 3120 |
| cagaagctgg aggagcagat gaataagctg cgcaaaatcc agaaccacat tcagacactg | 3180 |
| aaaaagtgga tggccgaggt ggacgtgttc ctgaaggaag agtggcctgc tctgggcgat | 3240 |
| tctgagatcc tgaaaaagca gctgaagcag tgccggctgc tggtgagtga catccagacc | 3300 |
| attcagccaa gtctgaattc agtcaacgag ggcgggcaga aaatcaagaa cgaagctgag | 3360 |
| cccgaatttg caagcagact ggagacagaa ctgaaggagc tgaatactca gtgggaccat | 3420 |
| atgtgccagc aggtgtacgc caggaaagaa gctctgaagg gaggcctgga gaaaaccgtc | 3480 |
| tcctgcagaa ggatctgtc tgagatgcac gaatggatga cacaggccga agaggaatac | 3540 |
| ctggagcggg acttcgaata taagactcca gatgagctgc agaaagccgt ggaggaaatg | 3600 |
| aagagagcaa aagaggaagc ccagcagaag gaggctaaag tgaagctgct gacagaaagc | 3660 |
| gtgaactccg tcatcgcaca ggctccacct gtggcacagg aggccctgaa aaaggagctg | 3720 |
| gaaactctga ccacaaatta ccagtggctg tgcacccggc tgaacggcaa atgcaagaca | 3780 |
| ctggaggaag tgtgggcatg ctggcatgag ctgctgtcct atctggaaaa ggccaacaag | 3840 |
| tggctgaacg aggtggaatt caaactgaag actaccgaga acatccccgg cggagccgag | 3900 |
| gaaattagcg aggtgctgga ctccctggaa aatctgatgc gccacagcga ggataatcct | 3960 |
| aaccagatcc gaattctggc acagactctg accgacggag gcgtgatgga tgaactgatc | 4020 |
| aatgaggaac tggagacctt taactccaga tggagggagc tgcatgagga agctgtgagg | 4080 |
| cgccagaaac tgctggaaca gtctatccag agtgcacagg agacagaaaa gtccctgcac | 4140 |
| ctgatccagg agtctctgac tttcattgac aagcagctgg ctgcatacat tgctgacaaa | 4200 |
| gtggatgccg ctcagatgcc ccaggaggca cagaagatcc agtctgatct gaccagtcac | 4260 |

-continued

```
gaaatttcac tggaggaaat gaaaaagcat aaccagggca aggaggcagc ccagagagtc      4320
ctgtcccaga tcgacgtggc acagaaaaag ctgcaggacg tgagcatgaa attccgactg      4380
tttcagaagc cagccaattt cgagctgcgg ctgcaggaaa gcaagatgat cctggacgag      4440
gtgaaaatgc atctgcccgc cctggaaacc aagtcagtcg agcaggaagt ggtccagagc      4500
cagctgaatc actgcgtgaa cctgtataag tcactgagcg aggtcaagtc cgaggtggaa      4560
atggtcatca agaccggaag gcagattgtg cagaaaaagc agacagagaa cccaaaggag      4620
ctggacgaac gcgtgaccgc cctgaaactg cactataatg agctgggcgc taaagtcaca      4680
gagagaaagc agcagctgga aaagtgtctg aaactgagcc ggaagatgag aaagagatg      4740 aacgtgctga ccgaatggct ggctgcaacc gacatggagc tgacaaagag gtccgccgtg      4800
gaagggatgc ccagcaatct ggattccgag gtcgcttggg aaaaagcaac ccagaaggag      4860
atcgaaaaac agaaggtgca cctgaagtct attacagagg tcggggaagc cctgaaaacc      4920
gtgctgggaa aaaaggagac actggtggaa gacaagctgt ctctgctgaa tagtaactgg      4980
atcgccgtca caagccgcgc tgaggaatgg ctgaacctgc tgctggagta ccagaaacac      5040
atggaaactt ttgaccagaa tgtggatcat attactaagt ggatcattca ggccgacacc      5100
ctgctggatg agagcgagaa gaagaagccc cagcagaaag gacgtgct gaagcggctg       5160 aaagctgaac tgaacgatat ccgacctaag gtggactcta cacgggatca ggccgctaat      5220
ctgatggcca accgagggga ccactgccga agctggtgg agccacagat cagcgaactg       5280
aaccacagat cgcagccat ctcccatagg attaagaccg aaaagcttc tattcccctg        5340 aaggagctgg aacagtttaa ttccgatatc cagaaactgc tggagcctct ggaggccgaa      5400
attcagcagg gcgtgaatct gaaagaggaa gacttcaaca aggatatgaa tgaggacaac      5460
gaagggactg tgaaagagct gctgcagcgc ggagacaacc tgcagcagcg aatcaccgat      5520
gagcgcaagc gagaggaaat caaaattaag cagcagctgc tgcagaccaa acataatgcc      5580
ctgaaggacc tgaggagtca gcgacggaag aaagctctgg agatctcaca ccagtggtat      5640
cagtataagc gccaggctga cgatctgctg aaatgcctgg acgatattga agaaaactg       5700 gcatccctgc ccgagcctag ggacgaacgc aaaatcaagg agattgatag agaactgcag      5760
aagaaaaagg aggaactgaa cgcagtgaga aggcaggccg agggactgtc tgaagacggc      5820
gctgcaatgg ccgtggagcc tacccagatc cagctgtcca agcggtggag agagattgaa      5880
tctaaattcg cacagtttcg ccgactgaat tttgcccaga tccatactgt cagggaggaa      5940
accatgatgg tcatgacaga ggacatgcca ctggaaatct catacgtgcc cagcacatat      6000
ctgactgaga ttacccacgt cagccaggcc ctgctggagg tggaacagct gctgaacgct      6060
cccgacctgt gcgcaaagga cttcgaggat ctgtttaaac aggaagaaag tctgaagaat      6120
atcaaagact cactgcagca gtctagtggg cggattgata tcattcacag taaaaagact      6180
gccgctctgc agtcagctac ccctgtggag agagtcaagc tgcaggaagc actgagtcag      6240
ctggacttcc agtgggagaa ggtgaacaaa atgtataagg accgacaggg acggtttgat      6300
agatcagtcg agaagtggcg gagattccat tacgatatca aaatcttcaa ccagtggctg      6360
actgaggcag aacagttcct gcgcaaaacc cagatccccg agaattggga acacgccaaa      6420
tacaagtggt atctgaagga gctgcaggac ggcattgggc agagacagac cgtggtcagg      6480
acactgaacg ccactggaga ggaaatcatt cagcagtcaa gcaagaccga cgctagcatc      6540
ctgcaggaga aactgggctc cctgaatctg cgctggcagg aagtgtgcaa acagctgagc      6600
gataggaaaa agcgcctgga ggaacagaag aacatcctgt ccgaattcca gcgggacctg      6660
```

```
aatgagtttg tgctgtggct ggaggaagcc gataacatcg cttccattcc cctggagcct   6720
ggcaaagaac agcagctgaa agagaagctg gaacaggtca agctgctggt ggaggaactg   6780
cctctgcggc aggggatcct gaagcagctg aatgaaaccg gaggaccagt gctggtctcc   6840
gccccaattt ctcccgagga acaggacaag ctggagaaca agctgaagca gacaaacctg   6900
cagtggatca aggtgtctag agcactgcct gagaaacagg gcgagatcga agcccagatt   6960
aaggacctgg ggcagctgga gaaaaagctg gaagatctgg aggaacagct gaaccatctg   7020
ctgctgtggc tgagcccaat caggaatcag ctggagatct acaatcagcc aaaccaggaa   7080
ggacccttcg acgtgcagga gacagaaatc gctgtgcagg caaagcagcc cgatgtcgag   7140
gaaattctgt ccaaaggcca gcacctgtat aaagagaagc ccgccaccca gcctgtgaaa   7200
cgcaagctgg aggacctgtc ctctgaatgg aaagctgtca caggctgct gcaggagctg   7260
cgcgcaaagc agccagatct ggcccctggc ctgacaacta tcggagctag tccaacacag   7320
actgtgaccc tggtcaccca gcccgtggtc acaaaagaaa ctgccatttc aaagctggag   7380
atgcctagtt cactgatgct ggaggtgcca gcactggccg acttcaacag ggcctggacc   7440
gaactgacag actggctgtc tctgctggat caggtcatca agagtcagcg cgtgatggtc   7500
ggcgacctgg aggatattaa tgaaatgatc atcaagcaga aggccaccat gcaggatctg   7560
gagcagaggc gcccacagct ggaggaactg atcacagcag cccagaatct gaaaaacaag   7620
actagcaacc aggaggccag gactatcatt accgaccgaa tcgaacggat tcagaatcag   7680
tgggatgagg tgcaggaaca cctgcagaat cgacggcagc agctgaacga gatgctgaag   7740
gactctaccc agtggctgga ggcaaaagag gaagcagaac aggtgctggg acaggctcgc   7800
gcaaaactgg agagttggaa ggaagggccc tacactgtgg acgcaatcca gaaaaagatt   7860
acagagacta aacagctggc caaggatctg cggcagtggc agaccaatgt ggatgtcgct   7920
aacgacctgg cactgaaaact gctgagagac tatagcgccg acgatacaag gaaggtgcac   7980
atgatcactg agaatattaa cgcttcatgg aggagcatcc ataagcgagt gtccgagcgg   8040
gaagctgcac tggaggaaac ccaccgcctg ctgcagcagt ccctctgga cctggagaag   8100
tttctggcat ggctgactga ggccgaaacc acagctaacg tgctgcagga cgccaccaga   8160
aaagagaggc tgctggaaga ttccaaagga gtgaaggagc tgatgaagca gtggcaggat   8220
ctgcagggcg agatcgaagc tcacaccgac gtgtaccata atctggatga aactcccag   8280
aagattctga ggagtctgga aggctcagac gatgccgtgc tgctgcagag aaggctggac   8340
aatatgaact ttaagtggtc tgagctgcgg aaaaagtctc tgaacatcag aagtcacctg   8400
gaagccagct ccgatcagtg gaaaagactg catctgtcac tgcaggagct gctggtgtgg   8460
ctgcagctga aggacgatga gctgagcagg caggctccta tcgggggaga cttcccagca   8520
gtccagaagc agaatgatgt gcacagagcc tttaaaaggg agctgaaaac aaaggaacca   8580
gtgatcatga gcacactgga gactgtcaga attttcctga ctgaacagcc tctggagggc   8640
ctggaaaagc tgtaccagga gccaagggaa ctgccacccg aggaacgcgc acagaacgtg   8700
acccgactgc tgcgaaagca ggctgaggaa gtcaatacag agtgggaaaa actgaacctg   8760
cactccgccg actggcagcg caagatcgat gagaccctgg aacgactgca ggagctgcag   8820
gaagcaacag acgagctgga tctgaagctg aggcaggccg aagtgatcaa aggatcttgg   8880
cagcccgtcg gcgatctgct gattgacagt ctgcaggatc atctggagaa agtgaaggct   8940
ctgcggggg agatcgcacc actgaaggaa aatgtgagcc acgtcaacga cctggccaga   9000
```

| | | | | |
|---|---|---|---|---|
| cagctgacta | ccctgggaat | tcagctgtca | ccctataatc tgagcacact ggaggatctg | 9060 |
| aacactcggt | ggaagctgct | gcaggtggca | gtcgaggaca gggtgcgcca gctgcacgaa | 9120 |
| gcacatagag | atttcggccc | tgcctcccag | cactttctgt ccacatctgt gcagggacca | 9180 |
| tgggagaggg | ccatctctcc | taacaaggtg | ccctactata ttaaccacga gactcagaca | 9240 |
| acttgctggg | accatcccaa | gatgaccgaa | ctgtaccaga gcctggccga tctgaataac | 9300 |
| gtgcgctttt | ccgcatatcg | aaccgccatg | aaactgcgcc gactgcagaa ggccctgtgc | 9360 |
| ctggacctgc | tgagtctgtc | agccgcttgc | gacgccctgg atcagcataa tctgaagcag | 9420 |
| aacgaccagc | ccatggatat | cctgcagatc | attaactgtc tgaccacaat ctacgatcgg | 9480 |
| ctggagcagg | aacacaataa | cctggtgaat | gtccctctgt gcgtggacat gtgcctgaat | 9540 |
| tggctgctga | cgtctatga | taccggcaga | acagggcgaa tccgggtgct gagcttcaag | 9600 |
| actggcatca | tttccctgtg | caaagctcat | ctggaggaca agtacaggta tctgttcaaa | 9660 |
| caggtggcat | ctagtaccgg | cttttgcgac | cagcggagac tgggactgct gctgcacgat | 9720 |
| agcatccaga | ttcccaggca | gctgggagag | gtggctagct tcggcggatc caacatcgaa | 9780 |
| ccctccgtcc | gctcttgctt | ccagtttgcc | aataacaagc ctgagattga agcagccctg | 9840 |
| tttctggact | ggatgcggct | ggagcctcag | agcatggtct ggctgccagt gctgcacaga | 9900 |
| gtcgctgcag | ccgagacagc | taaacatcag | gcaaagtgca acatctgtaa gaatgccct | 9960 |
| atcattggct | tcagatacag | gtccctgaag | cactttaatt acgatatctg tcagtcttgc | 10020 |
| ttctttagtg | gcagagtggc | caaagggcac | aagatgcatt accccatggt cgagtattgt | 10080 |
| accccctacta | cctctgggga | agacgtgcgg | gattttgcca aggtgctgaa aaacaagttc | 10140 |
| cggaccaaaa | gatactttgc | taagcatccc | cggatgggat atctgcctgt gcagacagtc | 10200 |
| ctggagggcg | acaatatgga | aactcccgtg | accctgatca acttctggcc tgtcgatagc | 10260 |
| gcccccgctt | caagccctca | gctgagtcac | gacgataccc attcacgaat tgagcactac | 10320 |
| gcctcccggc | tggctgagat | ggaaaatagt | aacggctcat atctgaatga cagcatctcc | 10380 |
| cctaacgagt | ctattgacga | tgaacacctg | ctgatccagc attactgcca gagtctgaat | 10440 |
| caggatagcc | cactgtccca | gcctaggtca | ccagcccaga tcctgatttc tctggagagt | 10500 |
| gaggaacggg | gggagctgga | aagaatcctg | gctgacctgg aggaagagaa tcggaacctg | 10560 |
| caggcagagt | atgatagact | gaagcagcag | cacgaacata aaggactgtc accactgccc | 10620 |
| agccctccag | agatgatgcc | cacctcacct | cagagcccac gggacgctga gctgatcgca | 10680 |
| gaagccaagc | tgctgagaca | gcacaaagga | cgcctggaag cccgaatgca gattctggag | 10740 |
| gatcacaaca | gcagctgga | aagccagctg | catcgactgc gacagctgct ggagcagcca | 10800 |
| caggctgaag | caaagtgaa | tgcacaact | gtctcctctc cctctaccag tctgcagcgg | 10860 |
| agtgacagtt | cacagcctat | gctgctgaga | gtggtcggat cacagacatc agacagcatg | 10920 |
| ggcgaagagg | atctgctgag | cccccctcag | gatacctcca caggcctgga agaagtgatg | 10980 |
| gagcagctga | ataactcctt | cccatccagc | agaggcagaa tacccccagg aaaaccaatg | 11040 |
| agagaggaca | ctatgtga | | | 11058 |

<210> SEQ ID NO 73
<211> LENGTH: 12
<212> TYPE: DNA
<213> ORGANISM: Artificial Sequence
<220> FEATURE:
<223> OTHER INFORMATION: Part of human ATP synthase, mitochondrial Fo
      complex subunit B1 mRNA

<400> SEQUENCE: 73
gctacctgga ct                                                                12

<210> SEQ ID NO 74
<211> LENGTH: 18
<212> TYPE: DNA
<213> ORGANISM: Artificial Sequence
<220> FEATURE:
<223> OTHER INFORMATION: Part of human ATP synthase, mitochondrial Fo
      complex subunit B1 mRNA

<400> SEQUENCE: 74
gcagcaggcc aggcacag                                                          18

<210> SEQ ID NO 75
<211> LENGTH: 18
<212> TYPE: DNA
<213> ORGANISM: Artificial Sequence
<220> FEATURE:
<223> OTHER INFORMATION: Part of human peptidylprolyl isomerase A
      (cyclophilin A) mRNA

<400> SEQUENCE: 75
tggcctccca aactgctg                                                          18

<210> SEQ ID NO 76
<211> LENGTH: 12
<212> TYPE: DNA
<213> ORGANISM: Artificial Sequence
<220> FEATURE:
<223> OTHER INFORMATION: Part of human ribosomal protein, large, P1
      (RPLP1) mRNA

<400> SEQUENCE: 76
cagccctaca ct                                                                12

<210> SEQ ID NO 77
<211> LENGTH: 2652
<212> TYPE: DNA
<213> ORGANISM: Artificial Sequence
<220> FEATURE:
<223> OTHER INFORMATION: T7 RNA polymerase cDNA

<400> SEQUENCE: 77
atgaacacca tcaacatcgc aaaaaacgac tttagtgaca cgaactggc tgctatcccc             60 ttcaatactc tggctgacca ttacggggag cgactggcca gagagcagct ggctctggag           120
cacgaaagct acgagatggg ggaagcccga ttccggaaga tgtttgagcg gcagctgaaa           180
gctggagaag tggcagacaa cgccgctgca aagccactga ttaccacact gctgcccaaa           240
atgatcgcca gaattaatga ttggttcgag gaagtgaagg caaaagagg caagaggcct            300 accgccttcc agtttctgca ggagatcaag ccagaagcag tggcctacat caccatcaag           360
actaccctgg catgcctgac aagcgccgac aacacaactg tgcaggctgt cgcatccgcc           420
atcgggaggg ctattgagga cgaagcacgc tttggaagaa tcagggatct ggaggccaag           480
cacttcaaga agaacgtgga ggagcagctg aacaagcggg tgggacacgt ctacaagaag           540
gccttcatgc aggtggtcga ggccgacatg ctgtcaaagg gactgctggg aggagaggca           600
tggagctcct ggcacaaaga agatagcatc catgtggggg tcaggtgcat cgagatgctg           660
attgaatcta ccggaatggt gagtctgcac cgacagaacg caggagtggt cggacaggac           720
tctgagacaa tcgaactggc tcccgagtac gctgaagcaa ttgccactag agctggggca           780

```
ctggccggaa tcagtcccat gttccagcct tgcgtggtgc ccctaagcc atggactggc    840 atcaccggag cgggtactg ggctaatggg cggagacccc tggcactggt gaggacacac    900
agcaagaaag ccctgatgcg ctacgaggat gtctatatgc ctgaagtgta taggccatc    960 aacattgctc agaatacagc atggaaaatt aacaagaaag tgctggctgt cgcaaatgtg   1020
atcactaagt ggaaacattg tcctgtggag acatcccag ccattgaaag ggaggaactg    1080
cctatgaagc cagaggacat cgatatgaac cagaagccc tgaccgcttg gaaacgagcc    1140
gctgcagccg tgtatagaaa ggatcgcgcc cgaaaatcca ggcgcatttc tctggagttc   1200
atgctggaac aggccaacaa gtttgctaat cataaagcaa tctggttccc ttacaacatg   1260
gactggcggg ggagagtcta tgccgtgtcc atgttcaacc cacagggaaa tgatatgaca   1320
aagggcctgc tgactctggc taagggcaaa cccattggaa aggagggcta ctattggctg   1380
aaaatccacg gagcaaattg cgcaggagtg gacaaggtgc cattcccaga gcggatcaag   1440
ttcatcgagg aaaaccatga aaatattatg gcctgtgcta agtctcccct ggagaacaca   1500
tggtgggccg aacaggatag tcctttctgc tttctggcct tctgttttga gtacgctggg   1560
gtgcagcacc atggactgag ttataattgc tcactgcccc tggccttga cggctcttgt    1620 agtgggatcc agcacttctc cgcaatgctg cgggatgagg tcggaggcag agccgtgaac   1680
ctgctgcctt ctgagactgt gcaggacatc tacggcattg cgccaagaa agtgaatgag    1740 atcctgcagg cagacgccat taacggaacc gataatgagg tggtcaccgt cacagatgaa   1800
aacactggcg agatctctga aaaggtgaaa ctggggacca aggctctggc aggacagtgg   1860
ctggcacatg gagtcacccg ctcagtgaca agcgaagcg tgatgacact ggcttacggc    1920
agcaaagagt cgggtttag acagcaggtg ctggaagaca ccatccagcc cgccattgat    1980
tccgggaagg gacccatgtt tacacagcct aaccaggctg caggctatat ggccaagctg   2040
atctgggagt cagtgagcgt cactgtggtc gccgctgtgg aagctatgaa ttggctgaag   2100
tccgccgcca actgctggc tgcagaggtg aaggacaaga aaactggcga aattctgagg    2160
aaacgctgcg ccgtccactg ggtgaccccca gatgggttcc ccgtgtggca ggagtacaag   2220
aaacctatcc agacccggct gaacctgatg ttcctgggcc agtttagact gcagccaaca   2280
atcaacacta taaggacag tgagattgat gctcataaac aggaatcagg aattgcacca    2340
aattttgtgc acagccagga cggctcccat ctgaggaaga ccgtggtctg ggctcacgag   2400
aaatatggca tcgaatcctt cgcactgatt catgactctt ttgggacaat ccccgccgat   2460
gccgctaatc tgttcaaggc tgtccgcgag actatggtgg acacctacga agttgtgat    2520 gtgctggccg acttctatga tcagtttgct gaccagctgc acgagtcaca gctggataag   2580
atgcctgccc tgcccgctaa gggcaacctg aacctgaggg acattctgga gtctgatttc   2640
gcattcgctt ga                                                       2652
```

<210> SEQ ID NO 78
<211> LENGTH: 4242
<212> TYPE: DNA
<213> ORGANISM: Artificial Sequence
<220> FEATURE:
<223> OTHER INFORMATION: hN-hPolS-hC cDNA

<400> SEQUENCE: 78

```
accagacaag agtttaagag atatgtatcc ttttaaattt tcttaagaaa aacttagggt     60
gaaagtatcc accctgagga gcaggttcca gatccttttc tttgctgcca agtccacca    120 tggccggcct tctgtccact ttcgacacct ttagctcacg gcgctccgag tccatcaaca   180
```

-continued

```
agtccggcgg tggagccgtg atccctggac agcgctccac tgtctccgtg ttcgtcctcg    240
ggccgtcggt gaccgacgac gccgacaagc tgttcatcgc cactactttc ctcgctcatt    300
ccctggatac cgataagcag cactcccagc gcggaggttt tttggtgtct ctcctggcaa    360
tggcctactc gtccccggag ctgtacctga caactaacgg agtgaacgcg gacgtgaaat    420
acgtgatcta caacatcgaa aaggacccga agcggaccaa gaccgacggt ttcattgtca    480
agactcggga tatggagtac gagaggacca ccgagtggct tttcggccca atggtcaaca    540
agagcccgct gttccaagga cagcgggacg ccgcggaccc cgacaccctg ctgcaaatct    600
acggctaccc tgcttgcctg ggagccatca tcgtccaagt ctggattgtg ctcgtgaagg    660
ccattaccag ctccgccggt ctgagaaagg ggttttttcaa ccgcctggag gcgttcagac    720
aggacggcac cgtgaagggg gcactggtgt tcaccggcga aaccgtggaa ggaatcggct    780
cagtgatgcg gtcccagcag tccctggtgt cgctgatggt ggaaactctc gtgaccatga    840
acacggcccg gtcggacctg accaccctgg agaagaacat ccagattgtg ggcaactaca    900
ttcgggatgc cggactcgct agcttcatga acactattaa gtacggagtg gaaaccaaga    960
tggccgccct gactctctcc aacctgaggc ccgatatcaa caagctgcgc tcgctgatcg   1020 ataccta cct gtcaaagggg cccagggccc cattcatttg catacttaaa gaccctgtgc   1080
acggagagtt cgcccctgga aactatcccg ctctgtggag ctacgcaatg ggagtggccg   1140
tggtgcagaa caaggccatg cagcaatacg tcaccgggag gacctatctc gatatggaga   1200
tgttcctgct ggggcaggcc gtggcgaagg acgcagaaag caaaatctcg tcggcccttg   1260
aagatgaact gggtgtcact gacaccgcga agggcagact cagacaccac ttggccaacc   1320
tcagcggagg agatggagct taccacaagc cgactggggg tggagcgatt gaagtcgccc   1380
tggataacgc cgacatcgac cttgagacta aggcgcatgc ggaccaggac gccagggga t   1440 ggggcgggga cagcggcgaa cgctgggccc gccaagtgtc cggcggtcac ttcgtgacct   1500
tgcatggcgc ggagcgcctg gaagaggaaa ccaatgatga ggacgtgtca gacatcgaaa   1560
gacggatcgc catgcgactg gctgaacggc gccaggagga ttccgcgacg cacggggacg   1620
agggacggaa caatggagtg gaccacgacg aagatgacga cgccgcagcc gtggccggaa   1680
tcggcggaat ctagcggttt atttattgat ccttatttat tcaaagatct acgaggcctc   1740
agtttgtcta cttggtctta agaaaaactt agggtgaaag cctcagtgcc ccattctcac   1800
tgctactagt cgccaacatg gaccaggacg cattcattct gaaagaagat tcagaagtcg   1860
aacgcgaagc ccccggtgga agggagtctc tcagcgacgt gatcggattc ctggacgccg   1920
tgctgtcatc ggaaccgacc gacattgggg gagacaggtc gtggctgcac aacactatca   1980
acaccccgca agggcctggc tccgcgcatc gggccaagtc ggaggagaa ggagaagtgt   2040 caaccccgag cacccaggac aaccgctcag gggaagagtc cagagtctcc ggtagaacgt   2100
caaagcctga agccgaggcc catgccgaa acctggataa gcagaacatt caccgggcct   2160
ttggtggccg caccgggaca aactccgtgt cgcaagacct gggcgatggc ggcgattccg   2220
gtatcctgga gaatccccca aacgagaggg gataccaag atccggaatc gaggacgaaa   2280
accgggaaat ggcagcccac cctgataagc ggggcgaaga tcaggccgaa ggcctgcctg   2340
aggaggtccg gggatcgacc tccttgcctg acgaagggga aggcggcgcc tcgaacaacg   2400
gccggtcaat ggagcccggc agctcccatt ccgctcgggt cactggagtc ctcgtgattc   2460
cttccccgga actggaggaa gccgtgctga ggcggaacaa gcggcggccg accaactccg   2520
```

-continued

| | |
|---|---|
| gatcaaagcc tctgactccc gccaccgtgc ccggaactag gtccccgccc ctgaaccgat | 2580 |
| acaactcgac cgggtcacca cccggaaagc cgccgtccac ccaagacgag cacatcaaca | 2640 |
| gcggggacac tccggccgtg cgcgtgaagg accggaagcc acccatcggc actcggagcg | 2700 |
| tgtctgactg tcctgcgaat ggtagaccca tccaccctgg cctggaaacc gactccacca | 2760 |
| agaagggaat aggggagaac acctccagca tgaaggagat ggctactctg ctcacctcgc | 2820 |
| ttggcgtgat ccagtccgcg caagagttcg aatccagccg cgacgcctcc tacgtgttcg | 2880 |
| cgcggcgcgc cctgaagtcc gcgaactacg ccgagatgac tttcaacgtg tgcggattga | 2940 |
| tcctgtccgc ggaaaagagc tccgcaagaa agtggacga gaacaagcag ctgctcaagc | 3000 |
| agatccagga gagcgtggag tccttccgcg acatctacaa acgcttctcc gagtatcaga | 3060 |
| aggagcagaa ctcccttctc atgtccaacc tgtccaccct tcacatcatc actgatcggg | 3120 |
| gtggaaagac ggataacacc gattcgttga cccgctcccc gagcgtgttc gccaagtcca | 3180 |
| aagaaacaa gactaaggcc accagatttg atccttcgat ggaaaccctg gaggacatga | 3240 |
| agtacaagcc cgacctcatt cgggaggacg aattccggga cgagatcaga aacccggtgt | 3300 |
| accaagagag ggacaccgaa ccccgcgcta gcaatgctag ccgcctcctg ccgtcaaagg | 3360 |
| agaagccaac catgcactcg ctgcggctgg tcattgaaag ctctcccctg tcccgcgcgg | 3420 |
| aaaaggtcgc ctacgtgaaa agcctctcga agtgcaagac cgaccaggaa gtgaaggccg | 3480 |
| tgatggaact ggtggaggag gacatcgaat ccctcaccaa ttgaaccggt gtcgacggag | 3540 |
| ccgcaccttg tcatgtacca tcaatattaa gaaaaactta gggtgaaagt ctcccctcct | 3600 |
| cacacctagg agaccaccat gcccagcttt ctcaagaaga ttttgaaact cggggacga | 3660 |
| cgccaggagg acgagtcgcg gagccggatg ctttccgatt cctcaatgtt gtcatgccgc | 3720 |
| gtgaatcagc tgcacatcaga agggacggaa gccggatcga cgacgccctc gactttgccg | 3780 |
| aaagaccagg cattgctgat cgagccgaaa gtccgcgcga agaaaagtc gcagcaccga | 3840 |
| aggcccaaga ttatcgatca agtgagaagg gtcgaatccc ttggtgagca ggcgagccag | 3900 |
| agacaaaaac atatgcttga aacgctgatc aacaagattt acaccgggcc tcttggagaa | 3960 |
| gagctggtgc agacactcta tcttcggatt tgggcgatgg aagagactcc ggaatcgctg | 4020 |
| aagatcctcc aaatgagaga ggacattcgc gatcaggtac tgaagatgaa accgaaaga | 4080 |
| tggttgagga ctctcatcag gggcgagaaa acaaagttga aagacttcca aaagcgatac | 4140 |
| gaggaggtgc atccctatct catgaaggaa aaggtagaac aggtcattat ggaggaggcg | 4200 |
| tggtcactcg ccgcacacat cgtgcaagag tgataacccg gg | 4242 |

<210> SEQ ID NO 79
<211> LENGTH: 6884
<212> TYPE: DNA
<213> ORGANISM: Artificial Sequence
<220> FEATURE:
<223> OTHER INFORMATION: hPolL cDNA

<400> SEQUENCE: 79

| | |
|---|---|
| gcggccgctt aagaaaaact tagggtgaat gtaaagcttt ctggccacca tggacggtca | 60 |
| ggaatcaagc cagaatccgt ccgacatcct ctacccggag tgccatctta acagcccgat | 120 |
| cgtacgcggg aagatcgcac agcttcacgt cctgttggat gtcaatcagc cgtacagatt | 180 |
| gaaagatgac tcaatcatta acattaccaa gcacaagatt cgaaatggag gtttgtcacc | 240 |
| tcggcagatt aaaatccggt cactggggaa ggcgcttcag aggaccatca agaccttga | 300 |
| ccgctacacc ttcgagccct acccgacgta ctcccaagaa cttttgcggc tcgacatccc | 360 |

```
ggagatctgc gataagatcc ggtcggtgtt tgccgtatcc gataggctta cgcgcgagtt      420
gtcgtcgggg ttccaagacc tctggctcaa tatctttaaa cagcttggga atatcgaagg      480
ccgagaaggc tacgacccgc ttcaggatat cggcacgatt cccgagatca ccgacaaata      540
ctcaaggaat cgatggtaca gacccttcct tacatggttc tcaatcaaat acgatatgag      600
gtggatgcag aaaactaggc cgggagggcc tcttgacacg agcaattcgc ataacctctt      660
ggagtgtaag tcctacacgc tggtgacgta cggcgacctt atcatgattt tgaacaaact      720
cacgcttacg gggtacatct tgacaccaga attggtactt atgtactgtg acgtagtgga      780
aggaaggtga acatgtcag cagcgggcca cctcgacaag aagtccatcg gaattacttc       840
caaaggggag gaattgtggg agttggtgga ctcgttgttt agcagccttg gtgaggagat      900
ctacaacgta atcgcccttt tggagccgct ttcactcgcg ttgatccaac tcaacgatcc      960
cgtcattcct ttgcggggtg cgtttatgag acacgtactg actgagcttc aggcagtgtt     1020
gacatcgaga gatgtctaca cggatgccga agcggatact atcgtggagt cactccttgc     1080
aatcttccac ggcaccagca tcgacgagaa agctgaaatc tttagcttct ttcggacttt     1140
cgggcacccc tcacttgaag ccgtcaccgc ggctgacaaa gtacgggcgc acatgtacgc     1200
gcagaaggcg attaaactta agacgttgta cgagtgccat gctgtgttct gcacaatcat     1260
tattaatggt tacagagagc ggcacggggg tcagtggccc ccttgcgact ttccagacca     1320
cgtctgcttg gagctcagaa atgcacaggg ttcgaacacg gcgatcagct acgaatgtgc     1380
ggtggacaac tatactagct tcatcgggtt caaattcagg aaattcatcg aaccacagct     1440
ggacgaagac ctgactatct acatgaagga taaggcgctg tcaccgagga agaagcatg      1500 ggatagcgtg tacccgact caaatttgta ctataaagcg ccagagtccg aggagacacg      1560
gcggttgatt gaggtgttca ttaacgatga aatttttaac ccagaagaga tcatcaacta     1620
tgtcgagtcg ggcgactggc tcaaggacga gaagttcaac atctcgtact ccttgaaaga     1680
aaaagaaatc aagcaggagg ggcgactgtt cgctaagatg acatacaaga tgcgagccgt     1740
gcaagtcttg gcgaaaacct tgttggcaaa ggggatcgga gaattgttct cggaaaacgg     1800
aatggtcaag ggagagatcg accttttgaa acgcctgaca accttgtcgg tctcgggagt     1860
cccgcgcact gactcggtgt ataacaacag caagtcctcg gagaagcgaa acgaggggat     1920
gaagaagaag aattcaggtg gatactggga cgagaaaaag agatccaggc atgagttcaa     1980
ggccacagac tcgtcaacgg atggttatga acgctttcg tgcttcctga cgaccgatct      2040
caaaaagtac tgcctcaact ggcggttcga agcacagca cttttttgggc agagatgtaa      2100 cgaaatcttt gggtttaaga ccttctttaa ctggatgcac cccgtcttgg agcggtgcac     2160
aatctacgta ggagatccat actgtccggt ggctgaccga atgcataggc aactccagga     2220
ccatgcggat tccggaattt tcatccacaa cccgagagga ggaatcgagg ggtattgcca     2280
gaaactctgg accctgattt cgattagcgc gattcacctt gctgcggtgc gagtgggggt     2340
cagggtgtca gcgatggtgc agggagataa tcaggcaatc gcggtcactt cgcgagtgcc     2400
ggtcgcgcag acgtacaaac agaagaaaaa tcatgtatac aaggaaatca ccaagtactt     2460
tggggctctg cggcacgtca tgtttgacgt gggacacgag ttgaaactta atgaaacgat     2520
catcagctcg aaaatgtttg tatacagcaa gagaatttac tacgacggaa agattctccc     2580
gcagtgcttg aaggctctga ctcgatgtgt attctggagc gaaacgctgg tcgatgaaaa     2640
caggtcagca tgtagcaata tctcgacatc gatcgcaaaa gcgattgaaa atggttattc     2700
```

```
gccaatttg  ggatactgta  tcgcgctta  caaaacgtgt  cagcaagtgt  gtatctcgct  2760
gggtatgacc  attaacccca  ccatttcgcc  tacggtgcgg  gatcagtact  tcaagggaaa  2820
gaattggctg  aggtgcgcgg  tgttgatccc  agcaaatgtg  ggaggtttta  actatatgtc  2880
cacgtcacga  tgctttgtcc  ggaatatcgg  tgatccagcc  gtggccgctc  tggccgattt  2940
gaaaagattc  atccgagctg  acttgctcga  caagcaggtg  ttgtatcggg  tgatgaatca  3000
ggagccgggt  gactcctcat  ttttggattg  ggcgtccgac  ccgtactcgt  gcaatctgcc  3060
gcactcccaa  tcgatcacca  ctatcatcaa  gaacatcaca  gccaggtcag  tgttgcaaga  3120
aagcccgaat  cctctgttgt  caggtctctt  cacagagact  tcggggagg  aagatttgaa  3180 cttggcgtcg  tttctcatgg  atcgcaaggt  gatcctccca  cgggtcgcgc  atgagatcct  3240
tggaaacagc  ctgacagggg  tgcgagaagc  gattgcgggc  atgttggata  ctacgaagag  3300
cctcgtccgc  tcctccgtga  aaagggagg  actctcgtac  gggatcttgc  ggagacttgt  3360
caattacgac  ttgctccagt  atgagacgct  gacaaggaca  ctgaggaaac  ccgtgaagga  3420
caatatcgaa  tacgaataca  tgtgctcagt  ggaattggcc  gtggggctga  ggcaaaagat  3480
gtggatccac  ctgacatacg  gacgcccgat  ccacggactg  gagacacctg  accctcttga  3540
gttgttgagg  gggacgttca  tcgaagggtc  ggaggtctgc  aaactctgta  gatcggaggg  3600
agccgacccc  atctacacgt  ggttttatct  ccccgataat  attgatcttg  acacacttac  3660
aaatggatgc  cctgcgatta  gaatcccgta  tttcgggtca  gcaacggacg  agaggtccga  3720
ggctcagctt  gggtacgtgc  gcaaccttag  caagcccgcg  aaagccgcca  tcagaatcgc  3780
tatggtgtat  acgtgggcct  acgggaccga  tgaaatttca  tggatggaag  ccgcgctcat  3840
tgctcagaca  agagcgaatc  tctcgctgga  aaatctgaag  ctcctgacac  ccgtatcaac  3900
atccacgaac  ctttcccatc  ggttgaaaga  caccgccacc  cagatgaagt  tttcctcggc  3960
aacgctcgtc  agggcgtcac  gcttcatcac  gatctcgaat  gataacatgg  cgcttaaaga  4020
agccggagag  tcgaaagaca  cgaacctcgt  ctatcaacag  atcatgttga  ctggactgtc  4080 gcttttgag  ttcaatatga  ggtacaagaa  gggatcgctc  ggcaaacctc  tcatcctcca  4140
cttgcacctc  aataacgggt  gctgcatcat  ggagtcacct  caagaggcga  acatcccgcc  4200
tagaagcaca  ttggacttgg  agattacaca  agagaataac  aaactcatct  acgatcccga  4260 tccctcaag  gatgtggacc  ttgaacttt  ctcgaaagta  cgcgatgtcg  tccacaccgt  4320
tgacatgaca  tattggtccg  acgacgaggt  aatccgcgca  acctcgatct  gcaccgcgat  4380
gacaatcgca  gacaccatgt  cccagcttga  ccgggataac  cttaaggaga  tgattgcgct  4440
ggtcaatgac  gacgacgtaa  actcgctgat  tacggagttc  atggtcatcg  acgtgcctct  4500
cttctgcagc  acattcggag  gcatcctggt  caaccagttc  gcctacagcc  tttatggtct  4560
taacatccga  ggaagagaag  agatttgggg  gcacgtggtg  agaatcttga  aggacacgtc  4620
ccatgcggta  cttaaggtgc  tgagcaacgc  cctcagccac  cccaaaattt  ttaagagatt  4680
ttggaatgcc  gggggtggtgg  aacctgtgta  cggacccaat  cttcgaatc  aagacaaaat  4740 cctgcttgca  ctcagcgtct  gtgagtattc  cgtggacctt  tcatgcacg  attggcaagg  4800 gggagtcccc  ttggaaatct  tcatctgcga  caatgacccc  gacgtggcgg  atatgcggag  4860
atcgtcattt  cttgctcgcc  atcttgcata  cttgtgctcc  gtagcagaga  tctcacggga  4920
cgggcctcgc  ctggagtcaa  tgaactcatt  ggaacggctc  gaatccctga  aatcgtacct  4980
cgaattgact  ttcctggacg  atccggtcct  taggtattcg  cagctcactg  gcttgtaat  5040 caaggtattt  ccctcgacat  tgacgtacat  caggaagtcg  tccattaaag  tattgcgcac  5100
```

```
tcgcgggatc ggcgtaccgg aagtgcttga ggattgggac ccggaggcgg ataacgcatt    5160
gctcgatggt atcgctgcgg agattcagca gaatatcccc ctcgggcatc agaccagagc    5220
tcccttttgg gggctgcggg tatcgaaaag ccaggtcctc cgactgaggg gatacaaaga    5280
gattaccaga ggagagattg ggagatcagg agtcggattg acacttccgt ttgacggacg    5340
ctatctctcc caccaactgc gcctctttgg gattaactcg acttcgtgcc tcaaggccct    5400
tgagcttacg tatctcctgt ccccgttggt ggacaaggac aaagaccgct tgtatctggg    5460
ggaaggggcg ggtgcaatgc tttcgtgtta cgatgcgacg cttggtccgt gcattaacta    5520
ttacaactcg ggagtgtact cgtgtgacgt caacggccaa agagaattga atatctaccc    5580
agcagaggta gcgctcgtgg aaagaaact gaacaatgtc acctcactcg gacagcgcgt    5640
gaaggtgctc ttcaatggta accccggatc gacgtggatt ggtaatgatg agtgcgaagc    5700
tttgatttgg aacgaactcc aaaattcctc gattggattg gtgcactgtg acatggaggg    5760
aggggaccac aaggatgatc aagtagtact ccacgagcac tacagcgtga ttcggatcgc    5820
ttatttggtg ggcgatcggg acgtcgtact catctccaag atcgcccctc gactgggaac    5880
agactggact cgccaattgt ccctctacct ccgctactgg gatgaagtca atcttatcgt    5940
ccttaagaca tcgaacccgg cttcgactga aatgtacctc ctcagcagac accccaagtc    6000
ggacatcatt gaggatagca aaacagtact cgcgtcactg ctccccctct cgaaggagga    6060
ttccattaag atcgagaaat ggattctcat cgagaaagca aaggcccatg aatgggtaac    6120
gagagagctg cgcgagggaa gctcgtcatc gggcatgctt agaccctacc accaggcgct    6180
gcagactttt ggattcgaac ccaatctgta taaacttagc cgcgacttcc tcagcaccat    6240
gaacatcgct gacacacata actgcatgat cgctttcaac cgggtactca agacacgat    6300 ttttgagtgg gccagaatca cggagtcgga caagcggctg aaacttacag ggaagtacga    6360
cctttatccc gtcagagaca gcggtaaact gaaaacagtg tccagaagac tggttctgtc    6420
atggatctca ctgtcaatga gcacgcgatt ggtcacgggt tcgttccctg atcaaaagtt    6480
tgaggcgaga ctccaattgg gcattgtctc gctctcgtca agagagatca ggaacctccg    6540
agtcattact aaaacgctcc tcgacagatt cgaggacatt attcacagca tcacttatcg    6600 attttttgacg aaggagatca agatccttat gaagattctc ggtgccgtga aaatgttcgg    6660
ggcgagacaa aatgagtaca caacagtcat tgatgacggt tcgctcggag atatcgagcc    6720
atacgatagc tcgtgaaccg gtagccgcac cttgtcatgt accatcaata aagtaccctg    6780
tgctcaacga agtcttggac tgatccatat gacaatagta agaaaaactt acaagaagac    6840
aagaaaattt aaaagaatac atatctctta aactcttgtc tggt                    6884
```

<210> SEQ ID NO 80
<211> LENGTH: 4248
<212> TYPE: DNA
<213> ORGANISM: Artificial Sequence
<220> FEATURE:
<223> OTHER INFORMATION: hN-hPolS-hC cDNA

<400> SEQUENCE: 80

```
accaaacaag agaaaaaaca tgtatgggat atgtaatgaa gtttaagaaa aacttagggt      60
gaaagtatcc accctgagga gcaggttcca gatcctttc tttgctgcca aagtccacca     120
tggctggcct gctgtcaacc ttcgataect tttcaagtag gaggagcgag tcaatcaaca     180
aatctggggg cggagctgtc atccctggac agcggtccac cgtgtctgtc ttcgtgctgg     240
```

-continued

```
gcccctctgt gacagacgat gccgacaagc tgttcatcgc caccacattt ctggctcaca    300
gtctggacac agataaacag cattcacaga gaggcgggtt tctggtgagc ctgctggcta    360
tggcatacag ctccccagaa ctgtatctga ctaccaacgg agtgaatgcc gacgtgaagt    420
acgtgatcta taacattgag aaggacccca aaaggactaa gaccgatggc ttcatcgtga    480
agacacggga tatggaatac gagagaacaa ctgagtggct gttcgggcct atggtgaaca    540
agagcccact gtttcaggga cagcgagacg cagctgaccc cgatacccctg ctgcaaatct    600
acggctatcc tgcctgcctg ggggctatca ttgtccaagt gtggatcgtc ctggtgaaag    660
caattacctc tagtgccggc ctgcggaagg ggttctttaa ccgcctggag ctttccgac    720
aggatggaac agtgaagggc gcactggtct ttaccggcga acagtggag ggaatcggct    780
ctgtcatgag aagtcagcag tcactggtca gcctgatggt ggaaactctg gtcaccatga    840
acacagccag aagtgacctg accacactgg agaaaaacat ccagattgtg gggaattaca    900
tcagggatgc cggcctggcc agcttcatga ataccatcaa gtatgggtg gaaacaaaga    960
tggcagccct gactctgtcc aacctgagac ccgacatcaa caagctgcgg agcctgattg   1020
atacctacct gtctaagggc ccagggccc ctttcatctg tattctgaaa gacccagtgc   1080
acggggagtt tgctccagga aactaccccg cactgtggtc ctatgcaatg ggcgtggccg   1140
tggtccagaa taaggccatg cagcagtacg tcactggccg cacctatctg gacatggaaa   1200
tgtttctgct ggggcaggcc gtggctaaag atgccgagag caagatcagc agcgccctgg   1260
aggacgagct gggagtcaca gatactgcca aggggcgact gcggcaccat ctggcaaacc   1320
tgtccggagg cgacggagca tatcacaaac ctacaggggg aggcgctatc gaagtggcac   1380
tggataatgc cgacattgat ctggagacta aggcacatgc agaccaggat gctcgcggat   1440
ggggaggaga ttccggcgaa agatgggcca ggcaggtgtc tggcgggcac tttgtcactc   1500
tgcatggcgc tgagcgactg gaggaagaga ccaatgacga agatgtgagt gacatcgagc   1560
ggagaattgc tatgcgactg gcagaaaggc gccaggagga ctcagccacc catggggatg   1620
agggacggaa caatggagtg gaccatgacg aagatgatga cgccgccgca gtcgcaggca   1680
ttggaggaat ttgacggttt atttattgat ccttatttat tcaaagatct acgaggcctc   1740
agtttgtcta cttggtctta agaaaaactt agggtgaaag cctcagtgcc ccattctcac   1800
tgctactagt cgccaccatg gaccaggacg ctttttattct gaaggaggat tctgaagtgg   1860
aacgggaggc accaggggga agggagagtc tgagtgatgt cattggcttc ctggacgccg   1920
tgctgagctc cgagccaaca gatatcggag gggaccggag ctggctgcac aacactatta   1980
ataccccccca ggggcctgga agtgcacata gagccaagtc agagggcgaa ggggaggtgt   2040
caacacccag cactcaggat aacaggtctg ggaggaatc cagagtctct ggaaggacca   2100
gtaagcctga agcagaggcc cacgctggca acctggacaa acagaatatc catcgagctt   2160
ttggaggccg accgggaca aactctgtga gtcaggacct gggagatggg ggagactctg   2220
gcatcctgga aacccccct aatgagcgcg gctaccctcg atccgggatt gaagatgaga   2280
ataggagat ggccgctcac ccagataagc gaggagaaga ccaggcagag ggactgcctg   2340
aggaagtgcg gggctcaacc agcctgccag acgaaggaga gggaggagcc tccaacaatg   2400
gccggtctat ggaacctggg tctagtcatt ccgctagagt gacaggcgtg ctggtcattc   2460
cttctccaga gctggaggaa gcagtcctgc ggagaaacaa gaggcgccca accaattccg   2520
gatctaaacc actgaccccca gcaacagtgc ccggcacacg gagcccaccc ctgaacagat   2580
ataatagtac cgggtcacct ccaggaaagc ccccttctac acaggatgag cacatcaaca   2640
```

```
gtggggacac tccagctgtg cgggtcaagg atagaaaacc acccattgga actcggagcg    2700
tgagcgactg cccagcaaac ggaagaccta tccaccccgg cctggagact gattccacca    2760
agaaaggaat tggcgaaaat acctcaagca tgaaggagat ggccacactg ctgactagcc    2820
tgggcgtgat ccagtccgca caggaattcg agagcagccg ggacgccagt tacgtctttg    2880
ctcgacgggc actgaaatca gccaactatg ctgagatgac cttcaacgtg tgcggcctga    2940
ttctgagcgc cgaaaagagt tcagctagaa aagtggatga gaataagcag ctgctgaaac    3000
agatccagga aagcgtcgag tccttcagag acatctacaa gaggttttca gaatatcaga    3060
aagagcagaa cagcctgctg atgtctaatc tgagtacact gcacatcatt actgataggg    3120
gaggcaagac cgataacaca gacagcctga cacgcagccc ttccgtgttc gctaagtcca    3180
aagagaataa gactaaagca acccgctttg acccctccat ggaaactctg gaggatatga    3240
agtacaaacc tgacctgatc cgggaagatg agtttaggga cgaaattcgc aacccagtgt    3300
atcaggaacg cgatactgag ccccgagcat caaatgccag cagactgctg ccctccaagg    3360
agaaacctac catgcattct ctgaggctgg tcatcgaaag ctccccactg agccgcgctg    3420
agaaggtggc atacgtcaaa tctctgagta agtgcaaaac cgaccaggag gtgaaggctg    3480
tgatggaact ggtggaggaa gacattgaat ctctgacaaa ctaagtcgac ggagccgcac    3540
cttgtcatgt accatcaata ttaagaaaaa cttagggtga agtctcccc tcctcacacc    3600 taggaccatg gcccaggctt cataatgccc agctttctga agaagattct gaaactgaga    3660
ggacgaagac aggaagatga gtctcgaagt cggatgctgt ccgacagctc catgctgtct    3720
tgcagggtga accagctgac tagcgaggga accgaagctg gctcaaccac acccagcaca    3780
ctgcctaaag accaggccct gctgatcgag ccaaaggtcc gggctaagga aaaatcccag    3840
caccggagac ccaagatcat tgatcaggtg aggcgcgtcg agagtctggg ggaacaggca    3900
tcacagcggc agaaacatat gctggagacc ctgatcaaca aaatctacac aggccctctg    3960
ggggaggaac tggtgcagac tctgtatctg agaatctggg ccatggagga aaccccagag    4020
tctctgaaaa tcctgcagat gcgcgaagac attcgagatc aggtcctgaa gatgaaaaca    4080
gagagatggc tgaggactct gattaggggc gaaaagacca aactgaagga tttccagaag    4140
cggtacgagg aagtgcaccc ctatctgatg aaagagaagg tggaacaggt catcatggaa    4200
gaggcttggt cactggcagc tcatattgtg caggagtaat gacccggg    4248
```

<210> SEQ ID NO 81
<211> LENGTH: 4242
<212> TYPE: DNA
<213> ORGANISM: Artificial Sequence
<220> FEATURE:
<223> OTHER INFORMATION: hPolS-hN-hC cDNA

<400> SEQUENCE: 81

```
accagacaag agtttaagag atatgtatcc ttttaaattt tcttaagaaa aacttagggt      60
gaaagtatcc accctgagga gcaggttcca gatccttttc tttgctgcca aagtccacca    120
tggaccagga cgcattcatt ctgaaagaag attcagaagt cgaacgcgaa gcccccggtg    180
gaagggagtc tctcagcgac gtgatcggat tcctggacgc cgtgctgtca tcggaaccga    240
ccgacattgg gggagacagg tcgtggctgc acaacactat caacaccccg caagggcctg    300
gctccgcgca tcgggccaag tcggaggag aaggagaagt gtcaacccccg agcacccagg    360 acaaccgctc aggggaagag tccagagtct ccggtagaac gtcaaagcct gaagccgagg    420
```

```
cccatgccgg aaacctggat aagcagaaca ttcaccgggc ctttggtggc cgcaccggga    480
caaactccgt gtcgcaagac ctgggcgatg gcggcgattc cggtatcctg gagaatcccc    540
caaacgagag gggataccca agatccggaa tcgaggacga aaaccgggaa atggcagccc    600
accctgataa gcggggcgaa gatcaggccg aaggcctgcc tgaggaggtc cggggatcga    660
cctccttgcc tgacgaaggg gaaggcggcg cctcgaacaa cggccggtca atggagcccg    720
gcagctccca ttccgctcgg gtcactggag tcctcgtgat tccttcccg gaactggagg    780
aagccgtgct gaggcggaac aagcggcggc cgaccaactc cggatcaaag cctctgactc    840
ccgccaccgt gcccggaact aggtccccgc ccctgaaccg atacaactcg accgggtcac    900
cacccggaaa gccgccgtcc acccaagacg agcacatcaa cagcggggac actccggccg    960
tgcgcgtgaa ggaccggaag ccacccatcg gcactcggag cgtgtctgac tgtcctgcga   1020
atggtagacc catccaccct ggcctggaaa ccgactccac caagaaggga ataggggaga   1080
acacctccag catgaaggag atggctactc tgctcacctc gcttggcgtg atccagtccg   1140
cgcaagagtt cgaatccagc cgcgacgcct cctacgtgtt cgcgcggcgc gccctgaagt   1200
ccgcgaacta cgccgagatg actttcaacg tgtgcggatt gatcctgtcc gcggaaaaga   1260
gctccgcaag aaaagtggac gagaacaagc agctgctcaa gcagatccag gagagcgtgg   1320
agtccttccg cgacatctac aaacgcttct ccgagtatca aaggagcag aactcccttc   1380
tcatgtccaa cctgtccacc cttcacatca tcactgatcg gggtggaaag acggataaca   1440
ccgattcgtt gacccgctcc ccgagcgtgt tcgccaagtc caaagagaac aagactaagg   1500
ccaccagatt tgatccttcg atggaaaccc tggaggacat gaagtacaag cccgacctca   1560
ttcgggagga cgaattccgg gacgagatca gaaacccggt gtaccaagag agggacaccg   1620
aaccccgcgc tagcaatgct agccgcctcc tgccgtcaaa ggagaagcca accatgcact   1680
cgctgcggct ggtcattgaa agctctcccc tgtcccgcgc ggaaaaggtc gcctacgtga   1740
aaagcctctc gaagtgcaag accgaccagg aagtgaaggc cgtgatggaa ctggtggagg   1800
aggacatcga atccctcacc aattgaaccg gtagatctac gaggcctcag tttgtctact   1860
tggtcttaag aaaaacttag ggtgaaagcc tcagtgcccc attctcactg ctactagtcg   1920
ccaacatggc cggccttctg tccactttcg acacctttag ctcacggcgc tccgagtcca   1980
tcaacaagtc cggcggtgga gccgtgatcc ctggacagcg ctccactgtc tccgtgttcg   2040
tcctcgggcc gtcggtgacc gacgacgccg acaagctgtt catcgccact actttcctcg   2100
ctcattccct ggataccgat aagcagcact cccagcgcgg aggttttttg gtgtctctcc   2160
tggcaatggc ctactcgtcc ccggagctgt acctgacaac taacgagtg aacgcggacg   2220
tgaaatacgt gatctacaac atcgaaaagg acccgaagcg gaccaagacc gacggtttca   2280
ttgtcaagac tcgggatatg gagtacgaga ggaccaccga gtggcttttc ggcccaatgg   2340
tcaacaagag cccgctgttc caaggacagc gggacgccgc ggaccccgac accctgctgc   2400
aaatctacgg ctaccctgct tgcctgggag ccatcatcgt ccaagtctgg attgtgctcg   2460
tgaaggccat taccagctcc gccggtctga aaagggggtt tttcaaccgc ctggaggcgt   2520
tcagacagga cggcaccgtg aagggggcac tggtgttcac cggcgaaacc gtggaaggaa   2580
tcggctcagt gatgcggtcc cagcagtccc tggtgtcgct gatggtggaa actctcgtga   2640
ccatgaacac ggcccggtcg gacctgacca ccctggagaa gaacatccag attgtgggca   2700
actacattcg ggatgccgga ctcgctagct tcatgaacac tattaagtac ggagtggaaa   2760
ccaagatggc cgccctgact ctctccaacc tgaggcccga tatcaacaag ctgcgctcgc   2820
```

```
tgatcgatac ctacctgtca aagggcccca gggccccatt catttgcata cttaaagacc      2880
ctgtgcacgg agagttcgcc cctggaaact atcccgctct gtggagctac gcaatgggag      2940
tggccgtggt gcagaacaag gccatgcagc aatacgtcac cgggaggacc tatctcgata      3000
tggagatgtt cctgctgggg caggccgtgg cgaaggacgc agaaagcaaa atctcgtcgg      3060
cccttgaaga tgaactgggt gtcactgaca ccgcgaaggg cagactcaga caccacttgg      3120
ccaacctcag cggaggagat ggagcttacc acaagccgac tggggtgga gcgattgaag       3180 tcgccctgga taacgccgac atcgaccttg agactaaggc gcatgcggac caggacgcca      3240
ggggatgggg cggggacagc ggcgaacgct gggcccgcca agtgtccggc ggtcacttcg      3300
tgaccttgca tggcgcggag cgcctggaag aggaaaccaa tgatgaggac gtgtcagaca      3360
tcgaaagacg gatcgccatg cgactggctg aacggcgcca ggaggattcc gcgacgcacg      3420
gggacgaggg acggaacaat ggagtggacc acgacgaaga tgacgacgcc gcagccgtgg      3480
ccggaatcgg cggaatctag cggtttattt attgatcctt atttattcaa gtcgacggag      3540
ccgcaccttg tcatgtacca tcaatattaa gaaaaactta gggtgaaagt ctcccctcct      3600
cacacctagg agaccaccat gcccagcttt ctgaagaaga ttctgaaact gagaggacga      3660
agacaggaag atgagtctcg aagtcggatg ctgtccgaca gctccatgct gtcttgcagg      3720
gtgaaccagc tgactagcga gggaaccgaa gctggctcaa ccacacccag cacactgcct      3780
aaagaccagg ccctgctgat cgagccaaag gtccgggcta aggaaaaatc ccagcaccgg      3840
agacccaaga tcattgatca ggtgaggcgc gtcgagagtc tgggggaaca ggcatcacag      3900
cggcagaaac atatgctgga gaccctgatc aacaaaatct acacaggccc tctgggggag      3960
gaactggtgc agactctgta tctgagaatc tgggccatgg aggaaacccc agagtctctg      4020
aaaatcctgc agatgcgcga agacattcga gatcaggtcc tgaagatgaa aacagagaga      4080
tggctgagga ctctgattag gggcgaaaag accaaactga aggatttcca gaagcggtac      4140
gaggaagtgc acccctatct gatgaaagag aaggtggaac aggtcatcat ggaagaggct      4200
tggtcactgg cagctcatat tgtgcaggag taatgacccg gg                         4242
```

<210> SEQ ID NO 82
<211> LENGTH: 6884
<212> TYPE: DNA
<213> ORGANISM: Artificial Sequence
<220> FEATURE:
<223> OTHER INFORMATION: hPolL cDNA

<400> SEQUENCE: 82

```
gcggccgctt aagaaaaact tagggtgaat gtaaagcttt ctggccacca tggacggaca       60
ggaatctagc cagaatccca cgacatcct gtatcccgag tgccacctga atagcccaat       120
cgtgagagga aaaatcgccc agctgcacgt gctgctggac gtgaaccagc catataggct      180
gaaggacgat ccatcatta atatcacaaa gcataagatt cgcaacgcg gctgtctcc        240 ccgccagatt aagatccgaa gtctgggcaa agccctgcag cgcactatca agatctgga       300 ccgatacacc ttcgagcctt acccaacata tagccaggaa ctgctgaggc tggacattcc      360
agagatctgc gataagatcc gcagcgtgtt tgctgtctcc gaccggctga ccagagagct      420
gagctccggc ttccaggatc tgtggctgaa tatcttcaag cagctgggga acatcgaggg      480
aagagaaggc tatgatccac tgcaggacat tggcaccatc cccgagatta cagacaagta      540
ctctcgcaac cgatggtata ggcccttcct gacctggttt agtatcaagt acgacatgcg      600
```

```
atggatgcag aaaacacggc ccggaggccc tctggatact tccaactctc acaatctgct    660
ggagtgcaaa agctacacac tggtgactta tggagatctg gtcatgatcc tgaataagct    720
gactctgacc ggctacattc tgaccccga actggtgctg atgtattgtg acgtggtcga    780
gggaagatgg aacatgagcg ccgctggcca tctggacaag aagagcattg gcatcaccag    840 taaggggag gaactgtggg aactggtgga ctccctgttc tctagtctgg gagaggaaat    900
ctataatgtg attgccctgc tggagcctct gtctctggct ctgattcagc tgaacgatcc    960
agtgatcccc ctgcggggcg ccttcatgag acacgtcctg accgagctgc agaccgtgct   1020
gacaagcagg gatgtctaca ctgacgcaga ggccgatacc atcgtggaat ccctgctggc   1080
aatctttcat gggacatcta ttgacgagaa ggccgaaatc ttcagtttct ttcggacatt   1140
tggacacccc tcactggagg ccgtgactgc agccgataag gtcagagctc atatgtacgc   1200
acagaaagcc atcaagctga aaccctgta tgaatgccac gccgtgttct gcaccatcat   1260
tatcaatggc taccgggaga cacggggg acagtggcca ccttgcgatt ttcctgacca   1320
cgtgtgcctg gaactgcgca cgctcaggg gtcaaatact gcaatcagct acgagtgtgc   1380
cgtggacaac tataccagct tcattggatt caagtttaga aagttcatcg agccacagct   1440
ggatgaagac ctgaccatct acatgaagga taaagcactg tcccccagga agaagcctg   1500 ggactccgtg tatcctgatt ctaatctgta ctataaggcc ccagagtctg aggaaacacg   1560
gagactgatc gaggtgttca ttaatgacga aaactttaat cccgaggaaa ttatcaacta   1620
cgtggagagc ggggactggc tgaaggatga ggaattcaac attagttatt cactgaagga   1680
gaaagaaatc aagcaggaag acgcctgtt tgccaagatg acatacaaaa tgcgagctgt   1740
gcaggtcctg gcagagactc tgctggccaa gggaatcggc gagctgttct ccgaaaatgg   1800
gatggtgaag ggagagattg acctgctgaa acgactgacc acactgagcg tgtccggcgt   1860
ccctcggacc gatagcgtgt ataacaattc aaagtcaagc gagaaaagga acgaggggat   1920
ggaaaacaaa aattctggcg ggtattggga cgagaagaaa aggagtcgcc acgaattcaa   1980
ggccaccgac tcctctacag atggctacga gactctgagt tgctttctga ctaccgatct   2040
gaagaaatat tgtctgaatt ggcggttcga atctaccgct ctgtttggc agagatgcaa   2100 tgagatcttc ggcttcaaga ccttcttcaa ctggatgcat cccgtgctgg agagatgcac   2160
catctacgtg ggcgacccct attgtccagt cgctgatagg atgcaccgcc agctgcagga   2220
tcatgcagac tccgggattt tcatccacaa ccctagggga ggcatcgagg atactgtca   2280 gaagctgtgg accctgattt ctatcagtgc cattcatctg ctgcagtgc gggtcggagt   2340 gagagtctcc gctatggtgc agggcgacaa tcaggctatc gcagtcacct ctcgcgtgcc   2400
cgtcgctcag acatataaac agaagaaaaa ccacgtgtac gaggaaatta caaagtattt   2460
cggcgcactg cggcacgtga tgtttgatgt cgggcatgag ctgaaactga atgaaactat   2520
catcagttca aagatgttcg tgtactccaa aagaatctac tatgacgca agatcctgcc   2580 acagtgcctg aaggccctga ctaaatgcgt gttctggagc gagaccctgg tcgatgaaaa   2640
caggtcagct tgcagcaata tctcaactag cattgccaaa gctatcgaga acggctacag   2700
ccccatcctg gggtactgta ttgccctgta taagacctgc cagcaggtgt gcatctcact   2760
gggcatgact attaatccca ccatcagccc tacagtgaga accagtact tcaaggggaa   2820 aaactggctg aggtgcgctg tgctgatccc cgcaaacgtc gggggattca attatatgtc   2880
cacctctagg tgttttgtgc gcaacatcgg ggacctgca gtcgccgctc tggctgatct   2940
gaaacgattc attcgggccg atctgctgga caagcaggtg ctgtaccgcg tgatgaatca   3000
```

```
ggagcctgga gatagctcct ttctggactg ggcaagcgat ccctattcct gcaacctgcc    3060
tcacagtcag tcaatcacaa ctattatcaa gaatatcacc gccaggagcg tgctgcagga    3120
atcccccaac cctctgctga gcgggctgtt cacagagact tccggagagg aagacctgaa    3180
tctggccagc ttcctgatgg atagaaaagt gatcctgcca agggtcgccc atgaaatcct    3240
gggaaacagc ctgaccggcg tgagagaggc aatcgccgga atgctggaca ccacaaagtc    3300
tctggtgcga gccagtgtcc ggaaaggagg actgagctac ggcatcctga ggcgcctggt    3360
gaattacgac ctgctgcagt atgaaaccct gacaagaact ctgaggaagc ccgtgaaaga    3420
taacatcgag tacgaatata tgtgcagcgt ggagctggca gtcggactgc gacagaagat    3480
gtggattcac ctgacttacg gcgacctat ccacggcctg gagacccag atccctgga     3540 actgctgagg ggcattttca tcgaggggtc agaagtgtgc aagctgtgcc gcagcgaggg    3600
agctgaccct atctacacct ggttttatct gccagataat attgatctgg acaccctgac    3660
aaacggatgt cctgcaattc gcatcccata cttcggctct gctacagacg agagaagtga    3720
agcacagctg ggctatgtga ggaatctgag caagcctgcc aaagcagcca ttcggatcgc    3780
tatggtgtat acctgggcat atgggaccga tgagattagc tggatggaag ctgcactgat    3840
cgcacagaca cgcgccaacc tgtccctgga gaatctgaag ctgctgactc cagtgagcac    3900
ttccaccaac ctgtcccacc ggctgaagga cacagccact cagatgaaat tctctagtgc    3960
aaccctggtg cgcgccagcc ggttcatcac aatcagcaac gacaatatgg ctctgaagga    4020
ggcaggagaa tctaaagata caaatctggt gtaccagcag atcatgctga ctggcctgag    4080
tctgttcgag tttaacatgc gctacaagaa ggggtcactg ggaaagcctc tgatcctgca    4140
cctgcatctg aacaatggct gctgtattat ggagtcccca caggaagcca atatcccacc    4200
ccggtctaca ctggacctgg agattactca ggaaaacaat aagctgatct atgatcctga    4260
cccactgaaa gatgtggacc tggaactgtt ctccaaggtg agggacgtgg tccacactgt    4320
cgatatgacc tactggagcg acgatgaagt gatccgcgcc acctccattt gcactgccat    4380
gaccatcgct gacacaatgt cccagctgga tcgggacaac ctgaaggaaa tgattgctct    4440
ggtgaacgac gatgacgtga attctctgat taccgagttc atggtcatcg atgtcccact    4500
gttctgttca acatttggag gcatcctggt gaatcagttt gcctacagcc tgtatggact    4560
gaacattcga ggccgggagg aaatctgggg ccacgtggtc agaatcctga aggacacctc    4620
ccatgcagtg ctgaaagtcc tgtctaatgc cctgagtcac cccaagattt tcaaaaggtt    4680
ttggaacgca ggagtggtcg agccagtgta cggacccaac ctgtctaatc aggataagat    4740
cctgctggct ctgtcagtgt gcgaatatag cgtggacctg ttcatgcacg attggcaggg    4800
gggagtgccc ctggagatct tcatctgtga taatgaccct gatgtcgcag acatgcggcg    4860
gagcagcttc ctggcacgcc atctggccta cctgtgctcc ctggccgaaa tctctagaga    4920
tggccccagg ctggagtcca tgaactctct ggagcggctg gaaagtctga atcatacctc    4980
ggagctgact ttcctggatg accccgtgct gagatatagc cagctgaccg gcctggtcat    5040
caaggtcttt ccttccaccc tgacatacat ccggaagtcc agcatcaagg tgctgagaac    5100
cagggggatc ggagtgcccg aggtcctgga agactgggat cctgaagctg acaatgcact    5160
gctggatggc attgccgctg agatccagca gaacattcca ctgggacacc agacacgggc    5220
cccattttgg ggactgagag tgtctaaaag tcaggtcctg cgcctgcgag ggtacaagga    5280
gatcaccagg ggcgaaattg gcgcagtgg agtgggactg acactgccat tcgacggcag    5340
```

| | |
|---|---:|
| gtatctgtca catcagctgc gcctgtttgg gatcaactca actagctgcc tgaaggccct | 5400 |
| ggaactgacc tacctgctga gcccctggt ggacaaggat aaagacagac tgtacctggg | 5460 |
| agagggcgct ggggcaatgc tgagctgcta tgacgctacc ctgggccctt gtatcaacta | 5520 |
| ctataattca ggcgtgtact cctgtgatgt caacgggcag cgcgagctga atatctaccc | 5580 |
| agccgaagtg gctctggtcg ggaagaaact gaacaatgtg acctctctgg gacagcgggt | 5640 |
| gaaggtcctg ttcaacggaa atcccggcag tacatggatt ggaaacgacg agtgcgaagc | 5700 |
| cctgatctgg aacgagctgc agaatagttc aattggcctg gtgcactgtg acatggaagg | 5760 |
| cggggatcat aaagatgacc aggtggtcct gcacgagcat tacagcgtga ttcgaatcgc | 5820 |
| ttatctggtc ggcgatcggg acgtggtcct gatctcaaag attgcacctc gactgggac | 5880 |
| agactggact cggcagctga gcctgtacct gagatattgg gatgaagtga atctgatcgt | 5940 |
| cctgaaaacc tccaacccag cctctacaga aatgtacctg ctgagtaggc accccaagtc | 6000 |
| agacattatc gaggattcca aaccgtgct ggcttctctg ctgccactga gtaaggagga | 6060 |
| ctcaattaag atcgaaaaat ggattctgat cgagaaggcc aaagctcacg aatgggtgac | 6120 |
| cagagagctg agggaaggga gctcctctag tggaatgctg aggccttacc atcaggccct | 6180 |
| gcagacattc ggctttgagc caaacctgta taagctgagc cgcgacttcc tgtccactat | 6240 |
| gaacattgct gatacccata attgcatgat cgcattcaac cgggtgctga agacacaat | 6300 |
| ttttgagtgg gccaggatca ctgaaagcga taagcgcctg aaactgacag gaaagtacga | 6360 |
| cctgtatcct gtgcgcgata gcggcaagct gaaaactatc agtagaaggc tggtgctgtc | 6420 |
| atggatttcc ctgtctatga gtacacggct ggtcactggg tccttcccag accagaaatt | 6480 |
| tgaagccaga ctgcagctgg gaatcgtgtc tctgtcaagc agggagattc gcaatctgcg | 6540 |
| agtcatcact aagaccctgc tggacagatt cgaagatatt atccacagca tcacatacag | 6600 |
| atttctgact aaggagatca gatcctgat gaagattctg ggagccgtga aaatgtttgg | 6660 |
| cgctcggcag aacgagtaca ccactgtgat tgatgatggc agcctggggg acattgaacc | 6720 |
| ctacgactcc tcctaaaccg gtagccgcac cttgtcatgt accatcaata aagtaccctg | 6780 |
| tgctcaacga agtcttggac tgatccatat gacaatagta agaaaaactt acaagaagac | 6840 |
| aagaaaattt aaaagaatac atatctctta aactcttgtc tggt | 6884 |

<210> SEQ ID NO 83
<211> LENGTH: 2237
<212> TYPE: DNA
<213> ORGANISM: Artificial Sequence
<220> FEATURE:
<223> OTHER INFORMATION: hRIG-IC cDNA

<400> SEQUENCE: 83

| | |
|---|---:|
| ccggtagcag aaatagactg ggaagatgca caacttaaga aaaacttagg gtgaaagcct | 60 |
| gcgacaaaac ctcctccttt tccaagtgta ccaccatgga atgtcagaac ctgtcagaaa | 120 |
| actcctgtcc ccccagcgaa gtgtcagata ctaacctgta ctccccttc aagccacgga | 180 |
| attaccagct ggagctggcc ctgcccgcta tgaagggcaa aaacaccatc atttgcgctc | 240 |
| ctaccggatg tggcaagaca ttcgtgtctc tgctgatttg tgaacaccat ctgaagaaat | 300 |
| ttcctcaggg gcagaaggga aaagtggtct tctttgccaa ccagatccca gtgtatgagc | 360 |
| agcagaagag tgtcttctca aaatactttg aacgacacgg ctatcgggtg acaggcatca | 420 |
| gcgggggcaa ctgccgagaa tgtccccgtcg agcagattgt ggaaaacaat gacatcatta | 480 |
| tcctgacccc acagatcctg gtgaacaatc tgaagaaagg gaccattccc tcactgagca | 540 |

```
tcttcacact gatgattttt gacgagtgcc acaatacatc taagcagcat ccttacaaca    600
tgatcatgtt caactatctg gatcagaaac tgggagggag ctccggacca ctgcctcagg    660
tcatcggcct gacagcaagc gtgggagtcg gagacgccaa gaacactgac gaggctctgg    720
attacatctg caagctgtgc gcttctctgg atgcaagtgt gattgccact gtcaagcaca    780
atctggagga actggagcag gtggtctaca agcctcagaa attctttagg aaggtggaaa    840
gcaggatctc cgataagttc aaatatatta tcgcacagct gatgcgggac accgagagcc    900
tggccaagag aatctgtaaa gatctggaaa acctgtccca gattcagaat agagagtttg    960
ggactcagaa gtatgaacag tggattgtga ccgtccagaa agcctgcatg gtgttccaga   1020
tgccagacaa ggatgaagaa agtcgaatct gtaaggccct gttcctgtat acctcacacc   1080
tgcggaagta taacgacgct ctgattatct cagagcatgc aagaatgaag gacgccctgg   1140
attacctgaa agatttcttt agcaatgtga gggccgctgg cttcgacgag atcgaacagg   1200
atctgactca gaggtttgag gaaaagctcc aggagctgga atccgtgtct cgcgacccaa   1260
gcaacgagaa tcccaaactg gaagatctgt gcttcatcct ccaggaggaa tatcacctga   1320
acccagagac cattacaatc ctgtttgtga agaccgagag tctggtggac gcactgaaaa   1380
actggattga agggaatcct aagctgtcct tcctgaaacc aggaatcctg actggcaggg   1440
ggaagaccaa ccagaatact ggaatgaccc tgcccgctca gaagtgcatt ctggacgcct   1500
tcaaggccag cggagatcat aacattctga tcgccacatc tgtggctgac gagggcattg   1560
atatcgccca gtgtaacctg gtcatcctgt acgaatatgt gggcaatgtc attaagatga   1620
tccagactcg gggaagaggc agggctcgcg gctcaaagtg cttcctgctg accagcaatg   1680
caggcgtgat cgagaaggaa cagattaaca tgtataagga agatgatg aacgacagta    1740 ttctgaggct ccagacatgg gatgaggccg tgttccgcga aaagattctg cacatccaga   1800
ctcatgagaa gttcatccgc gactcccagg aaaagccaaa acccgtgcct gataaggaga   1860
acaagaaact gctgtgccga agtgtaaag ctctggcatg ctacaccgca gacgtgcggg    1920
tcatcgagga atgtcactat acagtgctgg gcgatgcctt caaggagtgc tttgtctccc   1980
ggccacatcc caagcctaaa cagttctcta gtttgaaaa gcgcgctaaa atcttctgcg    2040
cacgacagaa ttgttctcac gactggggca tccacgtgaa gtacaaaacc ttcgagattc   2100
ccgtcattaa gatcgagtct tttgtggtcg aagatatcgc cacaggagtg cagactctgt   2160
atagtaagtg gaaagatttt cattttgaga agattcccct tgacccagca gagatgtcta   2220
agtaactcga ccccggg                                                  2237
```

<210> SEQ ID NO 84
<211> LENGTH: 317
<212> TYPE: DNA
<213> ORGANISM: Artificial Sequence
<220> FEATURE:
<223> OTHER INFORMATION: hV-Unique Region cDNA

<400> SEQUENCE: 84

```
ccggtagcag aaatagactg ggaagatgca caacttaaga aaaacttagg gtgaaagcct      60
gcgacaaaac ctcctccttt tccaagtgta ccaccatggg ccaccgacgg gaacatatca     120
tctacgagcg ggatgggtat atcgtggacg aatcttggtg caatccagtc tgtagtcgca     180
ttcgaatcat tccagaagg gagctgtgcg tgtgtaaaac ctgtcctaag gtctgcaaac      240
tgtgtaggga cgatatccag tgcatgcgcc ccgacccttt ctgtagagaa attttaagga     300
```

```
gctgactcga ccccggg                                                      317
```

<210> SEQ ID NO 85
<211> LENGTH: 857
<212> TYPE: DNA
<213> ORGANISM: Artificial Sequence
<220> FEATURE:
<223> OTHER INFORMATION: hPSMA7 cDNA

<400> SEQUENCE: 85

```
ccggtagcag aaatagactg ggaagatgca caacttaaga aaaacttagg gtgaaagcct         60
gcgacaaaac ctcctccttt tccaagtgta ccaccatgag ttacgataga gcaatcacag        120
tgttctcccc cgatggacat ctgtttcagg tcgagtatgc ccaggaagcc gtcaaaaaag        180
ggtccactgc cgtgggggtc cgaggacggg acatcgtggt cctgggggtg gagaagaaat        240
ctgtcgcaaa gctccaggat gaacgcaccg tgcgaaaaat ttgcgccctg gacgataacg        300
tctgtatggc cttcgctggc ctgacagcag acgcacgaat cgtgattaat agagccaggg        360
tcgagtgcca gagccaccgc ctgactgtgg aggaccccgt gactgtcgaa tacatcacca        420
ggtatattgc cagcctgaag cagcggtaca cccagtccaa cggccggaga cccttcggga        480
tcagcgccct gattgtggga ttcgactttg atggcacacc cagactgtac cagacagacc        540
cttcaggcac ttatcatgcc tggaaagcta cgcaatcgg acggggcgct aagagcgtga         600
gagagttcct ggagaagaac tacaccgatg aggctattga aaccgacgat ctgaccatca        660
agctggtcat caaggccctg ctggaggtgg tccagtctgg agggaagaac atcgaactgg        720
cagtgatgag gcgcgaccag agtctgaaga tcctgaatcc cgaggaaatt gagaaatatg        780
tggctgagat tgagaaagaa aaggaggaga tgagaaaaa gaaacagaag aaagccagtt         840
gataactcga ccccggg                                                      857
```

<210> SEQ ID NO 86
<211> LENGTH: 1707
<212> TYPE: DNA
<213> ORGANISM: Artificial Sequence
<220> FEATURE:
<223> OTHER INFORMATION: hPolS cDNA

<400> SEQUENCE: 86

```
atggaccagg acgcattcat tctgaaagaa gattcagaag tcgaacgcga agcccccggt         60
ggaagggagt ctctcagcga cgtgatcgga ttcctggacg ccgtgctgtc atcggaaccg        120
accgacattg ggggagacag gtcgtggctg cacaacacta tcaacacccc gcaagggcct        180
ggctccgcgc atcgggccaa gtcggaggga aaggagaag tgtcaacccc gagcacccag         240
gacaaccgct caggggaaga gtccagagtc tccggtagaa cgtcaaagcc tgaagccgag        300
gcccatgccg gaaacctgga taagcagaac attcaccggg cctttggtgg ccgcaccggg        360
acaaactccg tgtcgcaaga cctgggcgat ggcggcgatt ccggtatcct ggagaatccc        420
ccaaacgaga ggggataccc aagatccgga atcgaggacg aaaaccggga aatggcagcc        480
caccctgata gcggggcga agatcaggcc gaaggcctgc ctgaggaggt ccggggatcg         540
acctccttgc ctgacgaagg ggaaggcggc gcctcgaaca acggccggtc aatggagccc        600
ggcagctccc attccgctcg ggtcactgga gtcctcgtga ttccttcccc ggaactggag        660
gaagccgtgc tgaggcggaa caagcggcgg ccgaccaact ccggatcaaa gcctctgact        720
cccgccaccg tgcccggaac taggtccccg ccctgaacc gatacaactc gacccggtca         780
ccacccggaa agccgccgtc cacccaagac gagcacatca acagcgggga cactccggcc        840
```

```
gtgcgcgtga aggaccggaa gccacccatc ggcactcgga gcgtgtctga ctgtcctgcg      900
aatggtagac ccatccaccc tggcctggaa accgactcaa caaaaaaggg cataggagag      960
aacacatcat ctatgaaaga gatggctaca ttgttgacga gtcttggtgt aatccagtct     1020
gctcaagaat tcgaatcatc ccgagacgcg agttatgtgt ttgcaagacg tgccctaaag     1080
tctgcaaact atgcagagat gacattcaat gtatgcggcc tgatcctttc tgccgagaaa     1140
tcttccgctc gtaaagtgga cgagaacaag cagctgctca agcagatcca ggagagcgtg     1200
gagtccttcc gcgacatcta caaacgcttc tccgagtatc agaaggagca gaactccctt     1260
ctcatgtcca acctgtccac ccttcacatc atcactgatc ggggtggaaa gacggataac     1320
accgattcgt tgacccgctc cccgagcgtg ttcgccaagt ccaaagagaa caagactaag     1380
gccaccagat ttgatccttc gatggaaacc ctggaggaca tgaagtacaa gcccgacctc     1440
attcgggagg acgaattccg ggacgagatc agaaacccgg tgtaccaaga gagggacacc     1500 gaacccccgcg ctagcaatgc tagccgcctc ctgccgtcaa aggagaagcc aaccatgcac     1560
tcgctgcggc tggtcattga agctctcccc ctgtcccgcg cggaaaaggt cgcctacgtg     1620
aaaagcctct cgaagtgcaa gaccgaccag gaagtgaagg ccgtgatgga actggtggag     1680
gaggacatcg aatccctcac caattga                                         1707

<210> SEQ ID NO 87
<211> LENGTH: 918
<212> TYPE: DNA
<213> ORGANISM: Artificial Sequence
<220> FEATURE:
<223> OTHER INFORMATION: Human NANOG cDNA

<400> SEQUENCE: 87
atgagtgtgg atccagcttg tccccaaagc ttgccttgct ttgaagcatc cgactgtaaa       60
gaatcttcac ctatgcctgt gatttgtggg cctgaagaaa actatccatc cttgcaaatg      120
tcttctgctg agatgcctca cacggagact gtctctcctc ttccttcctc catggatctg      180
cttattcagg acagccctga ttcttccacc agtcccaaag caaacaacc cacttctgca       240 gagaagagtg tcgcaaaaaa ggaagacaag gtcccggtca gaaacagaa gaccagaact       300 gtgttctctt ccacccagct gtgtgtactc aatgatagat ttcagagaca gaaatacctc      360
agcctccagc agatgcaaga actctccaac atcctgaacc tcagctacaa acaggtgaag      420
acctggttcc agaaccagag aatgaaatct aagaggtggc agaaaaacaa ctggccgaag      480
aatagcaatg tgtgacgca gaaggcctca gcacctacct accccagcct ttactcttcc      540
taccaccagg gatgcctggt gaacccgact gggaaccttc aatgtggag caaccagacc       600 tggaacaatt caacctggag caaccagacc cagaacatca gtcctggag caaccactcc       660 tggaacactc agacctggtg cacccaatcc tggaacaatc aggcctggaa cagtcccttc      720
tataactgtg gagaggaatc tctgcagtcc tgcatgcagt tccagccaaa ttctcctgcc      780
agtgacttgg aggctgcctt ggaagctgct ggggaaggcc ttaatgtaat acagcagacc      840
actaggtatt ttagtactcc acaaaccatg gatttattcc taaactactc catgaacatg      900
caacctgaag acgtgtga                                                    918

<210> SEQ ID NO 88
<211> LENGTH: 630
<212> TYPE: DNA
<213> ORGANISM: Artificial Sequence
<220> FEATURE:
```

<223> OTHER INFORMATION: Human LIN28 cDNA

<400> SEQUENCE: 88

| | | | | | |
|---|---|---|---|---|---|
| atgggctccg | tgtccaacca | gcagtttgca | ggtggctgcg | ccaaggcggc | agaagaggcg | 60 |
| cccgaggagg | cgccggagga | cgcggcacgg | gcggcgacg | agcctcagct | gctgcacggt | 120 |
| gcgggcatct | gtaagtggtt | caacgtgcgc | atggggttcg | gcttcctgtc | catgaccgcc | 180 |
| cgcgccgggg | tcgcgctcga | cccccagtg | gatgtctttg | tgcaccagag | taagctgcac | 240 |
| atggaagggt | tccggagctt | gaaggagggt | gaggcagtgg | agttcacctt | taagaagtca | 300 |
| gccaagggtc | tggaatccat | ccgtgtcacc | ggacctggtg | gagtattctg | tattgggagt | 360 |
| gagaggcggc | caaaaggaaa | gagcatgcag | aagcgcagat | caaaaggaga | caggtgctac | 420 |
| aactgtggag | gtctagatca | tcatgccaag | gaatgcaagc | tgccaccca | gcccaagaag | 480 |
| tgccacttct | gccagagcat | cagccatatg | gtagcctcat | gtccgctgaa | ggcccagcag | 540 |
| ggccctagtg | cacagggaaa | gccaacctac | tttcgagagg | aagaagaaga | aatccacagc | 600 |
| cctaccctgc | tcccggaggc | acagaattga | | | | 630 |

<210> SEQ ID NO 89
<211> LENGTH: 1800
<212> TYPE: DNA
<213> ORGANISM: Artificial Sequence
<220> FEATURE:
<223> OTHER INFORMATION: Human IgM 9F11 heavy chain cDNA

<400> SEQUENCE: 89

| | | | | | |
|---|---|---|---|---|---|
| atgtcagtgt | catttctgat | ttttctgcca | gtcctggggc | tgccttgggg | ggtcctgtca | 60 |
| caggtccagc | tgcagcagtc | cgggccagga | ctggtgaaac | ctgctcagac | actgtccctg | 120 |
| acttgcgcaa | tcagtggcga | ctcagtgagc | tccaactctg | ctacctggaa | ttggattaga | 180 |
| cagagtccac | tgaggggact | ggagtggctg | ggacggacat | actatagaag | caaatggtac | 240 |
| aacgactatg | ccgtgagcgt | caagtcccgg | atcaccatta | ccctgatac | aagcaagaat | 300 |
| cagttctccc | tgcagctgaa | ttctgtcacc | ccagaagaca | cagcagtgta | ctattgtgcc | 360 |
| agggagaact | actatggatc | cggccgctac | aattggttcg | atccttgggg | gcagggaaca | 420 |
| ctggtgactg | tctctagtgg | aagcgcatcc | gccccaaccc | tgtttcccct | ggtgagctgc | 480 |
| gaaaactctc | ccagtgacac | atcaagcgtg | gctgtcggct | gtctggcaca | ggacttcctg | 540 |
| cctgattcaa | tcacttttag | ctggaagtac | aaaaacaatt | cagacatcag | cagcaccaga | 600 |
| ggctttccat | ctgtgctgag | aggcgggaaa | tatgccgcta | caagccaggt | cctgctgccc | 660 |
| tccaaggacg | tgatgcaggg | aactgatgag | cacgtggtct | gcaaagtgca | gcatcccaac | 720 |
| ggcaataagg | agaagaacgt | cccactgccc | gtgatcgctg | agctgccacc | taaggtgtcc | 780 |
| gtcttcgtgc | caccccgaga | cggattcttt | ggcaatcccc | ggaagtctaa | actgatctgt | 840 |
| caggccaccg | gttttcacc | tagacagatt | caggtgagct | ggctgaggga | aggaaagcag | 900 |
| gtcggctctg | gggtgaccac | agatcaggtc | caggctgaag | caaggagag | cgggccaact | 960 |
| acctacaaag | tgacctccac | actgactatc | aaggagtctg | actggctgtc | acagagcatg | 1020 |
| ttcacatgca | gggtggatca | ccgcggcctg | acttttcagc | agaatgcaag | ttcaatgtgt | 1080 |
| gtccccgacc | aggataccgc | catcagggtg | ttcgctattc | ctccatcttt | cgccagtatt | 1140 |
| tttctgacca | gtccacaaa | actgacttgc | ctggtcacag | acctgacaac | ttatgattcc | 1200 |
| gtgactatct | cttggaccg | ccagaacggc | gaagccgtga | agacccacac | aaacatttcc | 1260 |
| gagtctcatc | ccaatgcaac | cttctctgcc | gtgggcgaag | ctagtatctg | cgaggacgat | 1320 |

```
tggaatagcg gggagcggtt cacctgtacc gtgacacaca ctgacctgcc tagtccactg    1380
aagcagacca tttcacgccc taaaggcgtc gccctgcatc gaccagatgt gtacctgctg    1440
ccacctgccc gcgaacagct gaacctgcga gagagtgcta ccatcacatg tctggtgacc    1500
ggcttctccc ccgctgatgt ctttgtgcag tggatgcagc gaggacagcc actgagccct    1560
gaaaagtacg tgacatccgc acccatgcct gagccacagg cacctggcag atattttgcc    1620
cacagtattc tgactgtgtc agaggaagag tggaacaccg gggagactta tacctgcgtg    1680
gtcgcccatg aagctctgcc aaatcgagtc accgagcgga cagtggacaa gagcacaggg    1740
aaacccactc tgtataacgt cagtctggtc atgtcagata ctgccggaac ctgttattga    1800

<210> SEQ ID NO 90
<211> LENGTH: 714
<212> TYPE: DNA
<213> ORGANISM: Artificial Sequence
<220> FEATURE:
<223> OTHER INFORMATION: Human IgM 9F11 light chain cDNA

<400> SEQUENCE: 90
atggatatgc gagtgcccgc tcagctgctg ggactgctgc tgctgtggtt ccccggatca     60
agatgcgaca ttcagatgac tcagagccca agctccgtgt ctgcaagtgt cggcgaccga    120
gtgaccatca catgcagagc ctcccagggg atttctagtt ggctggcttg gtatcagcag    180
aagccaggga agctcccaa gctgctgatc tatgatgcat caagcctgca gagtggagtg    240
ccctcacgat tctcaggcag cgggtccgga accgactta ctctgaccat ttcctctctg    300
cagcctgagg atttcgcaac atactattgc cagcaggcca acagcttccc actgaccttt    360 ggcggggaa caaaagtgga gatcaagagg actgtcgccg ctccctctgt gttcattttt    420 cccccctagtg acgaacagct gaaaagcggc acagcttccg tggtctgtct gctgaacaat    480
ttttaccctc gcgaagcaaa agtccagtgg aaggtggata cgccctgca gtctgggaat    540 agtcaggagt cagtgactga acaggacagc aaagattcca cctattctct gagttcaaca    600
ctgactctgt ccaaggctga ctacgagaag cacaaactgt atgcatgcga agtcacacat    660
cagggactga gctcccctgt gactaagtct ttcaatagag gcgagtgttg ataa          714

<210> SEQ ID NO 91
<211> LENGTH: 1410
<212> TYPE: DNA
<213> ORGANISM: Artificial Sequence
<220> FEATURE:
<223> OTHER INFORMATION: Human IgG HC1 heavy chain cDNA

<400> SEQUENCE: 91
atggattgga cttggagatt cctcttcgtc gtagcagcag ctacaggtgt ccagtccgag     60
gtgcagctgg tggaatcagg gggggactg gtgcagcctg agggtcact gcgactgtct    120 tgtgccgctt ctgggttcac ttttaccgac tacacaatgg attgggtgcg caaggcacct    180
ggcaagggac tggagtgggt cgctgatgtg aacccaaata gcggcgggtc catctacaac    240
caggagttca agggcggtt caccctgtcc gtggaccgat ctaaaaacac cctgtatctg    300
cagatgaata gcctgcgagc tgaagatact gcagtgtact attgcgcccg gaatctgggc    360
cccagcttct actttgacta ttggggacag ggcactctgg tcaccgtgag ctccgctagt    420
acaaagggcc cttcagtgtt cccactggca ccctctagta atccacatc tggaggcact    480 gccgctctgg ggtgtctggt gaaggactac ttcccagagc ccgtcaccgt gtcttggaac    540
```

| | |
|---|---|
| agtggggcac tgactagcgg agtcgcaacc ggacctgccg tgctgcagtc aagcggactg | 600 |
| tactccctgt cctctgtggt caccgtccca agttcaagcc tgggcactca gacctatatc | 660 |
| tgcaacgtga atcacaagcc aagtaataca aaagtggaca agaaagtgga gcccaagtct | 720 |
| tgtgataaaa cacatacttg ccccccttgt cctgcaccag aactgctggg gggaccctcc | 780 |
| gtgttcctgt tccacccaa gcctaaagat accctgatga ttagcaggac cccagaggtc | 840 |
| acatgcgtgg tcgtggacgt gagccacgag accccgaag tcaagtttaa ctggtacgtg | 900 |
| gacggcgtcg aagtgcataa tgctaagaca aaacccaggg aggaacagta acagcacc | 960 |
| tatcgcgtcg tgtccgtcct gacagtgctg catcaggatt ggctgaacgg aaaagagtat | 1020 |
| aagtgcaaag tgtccaataa ggcactgccc gccctatcg agaaaacaat ttctaaggcc | 1080 |
| aaaggccagc ctagagaacc acaggtgtat accctgcctc catccaggga tgaactgaca | 1140 |
| aagaaccagg tctctctgac ttgtctggtg aaaggcttct atccctcaga tattgctgtg | 1200 |
| gagtgggaaa gcaatgggca gcctgagaac aattacaaga ccacaccccc tgtgctggac | 1260 |
| tcagatggga gcttctttct gtattctaag ctgaccgtgg acaaaagtcg gtggcagcag | 1320 |
| ggaaatgtct ttagttgttc agtgatgcac gaagcactgc acaaccatta cactcagaaa | 1380 |
| tcactgtcac tgtcccctgg caagtgataa | 1410 |

<210> SEQ ID NO 92
<211> LENGTH: 702
<212> TYPE: DNA
<213> ORGANISM: Artificial Sequence
<220> FEATURE:
<223> OTHER INFORMATION: Human IgG LC1 light chain cDNA

<400> SEQUENCE: 92

| | |
|---|---|
| atggcttggg ctctgctgct gctgacactg ctgacccagg atacaggatc ttgggctcgc | 60 |
| attcagatga cccagtcccc tagttctctg tccgcctctg tgggcgacag ggtcaccatc | 120 |
| acatgcaagg ctagccagga cgtgagcatt ggagtcgcat ggtatcagga taagccaggc | 180 |
| aaagcaccca gctgctgat ctatagtgcc tcataccggt ataccggggt gcccagcaga | 240 |
| ttcagcggat ccgggtctgg aacagacttt actctgacca ttagctccct gcagccagag | 300 |
| gatttcgcca catactattg ccagcagtac tatatctacc cctatacatt tggccagggg | 360 |
| actaaagtgg aaattaaggg ccagcctaaa gccgctccat ccgtcactct gttcccccct | 420 |
| tctagtgagg aactgcaggc taacaaggcc accctggtgt gctacatctc tgactttat | 480 |
| cctgggcag tgaccgtcgc atggaaggct gattcaagcc ccgtgaaagc tggagtcgag | 540 |
| accacaactc ctagcaagca gtccaacaac aagtacgcag cctggtctta ctgagtctg | 600 |
| acaccagaac agtggaaaag ccaccggagt tactcatgtc aggtcactca cgaaggcagc | 660 |
| actgtggaaa aaactgtggc tcctaccgaa tgttcttgat aa | 702 |

<210> SEQ ID NO 93
<211> LENGTH: 1416
<212> TYPE: DNA
<213> ORGANISM: Artificial Sequence
<220> FEATURE:
<223> OTHER INFORMATION: Human IgG HC2 heavy chain cDNA

<400> SEQUENCE: 93

| | |
|---|---|
| atggattgga catggcgctt tctgttcgtc gtcgcagccg caaccggagt gcagtctcag | 60 |
| gtgcagctgt gcagtcagg agccgaggtg aagaaacctg gcgcctccgt caaagtgtct | 120 |
| tgcaaggcta gtgggtacac tttcacctct cactggatgc attgggtgag atatgccct | 180 |

```
gggcagggac tggagtggat cggagaattc aacccaagca atggaaggac taactacaac      240
gagaagttta aatctaaggc tacaatgact gtggatacca gtacaaacac tgcatatatg      300
gagctgagct ccctgaggtc agaggacacc gccgtgtact attgcgcaag ccgggactac      360
gattatgacg gaagatactt cgattattgg ggccagggga cactggtcac cgtgagcagc      420
gccagcacca aaggccctag cgtgtttcca ctggctccct caagcaagag tacctcagga      480
gggacagccg ctctgggatg tctggtgaag gactacttcc cagagccgt caccgtgtct      540 tggaacagtg gagcactgac aagcggcgtc cacacttttc ctgccgtgct gcagtcctct      600
gggctgtact ccctgagttc agtggtcacc gtcccaagct cctctctggg aacccagaca      660
tatatctgca acgtgaatca caaaccaagt aatacaaagg tggacaagaa ggtggaaccc      720
aaaagctgtg acaagactca tacctgccca ccttgtcctg caccagagct gctgggagga      780
ccaagcgtgt tcctgtttcc acccaaacct aaggataccc tgatgattag ccgcactcca      840
gaagtcacct gcgtggtcgt ggacgtgagc acgaggacc ccgaagtcaa gtttaactgg      900
tacgtggacg gcgtcgaggt gcataatgcc aaaacaaagc ccagggagga acagtacaac      960
tccacttatc gcgtcgtgtc tgtcctgacc gtgctgcacc aggattggct gaacggcaag     1020
gaatataaat gcaaggtgtc taacaaggcc ctgcccgccc ctatcgagaa gacaattagc     1080
aaagcaaagg gccagcccag agagccacag gtgtataccc tgcctcccag ccgggacgag     1140
ctgaccaaaa accaggtctc tctgacatgt ctggtgaagg gattctatcc cagcgacatt     1200
gctgtggagt gggaatccaa tggccagcct gagaacaatt acaagaccac accccctgtg     1260
ctggattcag acggcagctt ctttctgtat agtaaactga ccgtggacaa gtcacgatgg     1320
cagcagggga atgtctttag ctgttccgtg atgcatgaag cactgcataa tcactacacc     1380
cagaaatcac tgtcactgag cccaggaaaa taatga                               1416

<210> SEQ ID NO 94
<211> LENGTH: 696
<212> TYPE: DNA
<213> ORGANISM: Artificial Sequence
<220> FEATURE:
<223> OTHER INFORMATION: Human IgG LC2 light chain cDNA

<400> SEQUENCE: 94
atggcttggg ctctgctgct gctgaccctg ctgacccagg acaccgggag ttgggctgac       60
atccagatga cccagtcccc ttcttccctg agtgcatcag tgggcgaccg ggtcaccatc      120
acatgcagcg ccagctcctc tgtgacatac atgtattggt atcagagaaa gccaggaaaa      180
gctcccaagc tgctgatcta cgatacttct aacctggcaa gtggcgtgcc aagcaggttc      240
agcggatccg gatctggaac tgactacact tttaccatca gttcactgca gcccgaggat      300
attgccacct actattgcca gcagtggagc tcccacatct tcacatttgg ccaggggact      360
aaagtggaaa ttaaggggca gcctaaagcg gctccaagcg tcacactgtt cccccccttct     420 agtgaggaac tgcaggctaa taaggccacc ctggtgtgcc tgatctccga ctttttatcct     480 ggggccgtga cagtcgcctg aaaggctgat tcaagcccg tgaaagctgg agtcgagacc      540
acaactccta gcaagcagtc caacaacaag tatgcagcct cctcttacct gtccctgacc      600
cccgaacagt ggaaatctca tcggagttac tcatgtcagg tcactcacga agggagcact      660
gtggaaaaaa ccgtcgcacc aaccgaatgt tcataa                                696

<210> SEQ ID NO 95
```

```
<211> LENGTH: 122
<212> TYPE: RNA
<213> ORGANISM: Artificial Sequence
<220> FEATURE:
<223> OTHER INFORMATION: 3' terminal sequence of the stealth RNA vector
<220> FEATURE:
<221> NAME/KEY: misc_feature
<222> LOCATION: (45)..(57)
<223> OTHER INFORMATION: n is a, c, g, or u
<220> FEATURE:
<221> NAME/KEY: misc_feature
<222> LOCATION: (68)..(110)
<223> OTHER INFORMATION: n is a, c, g, or u

<400> SEQUENCE: 95
caugguggac uuuggcagca agaaaagga ucuggaaccu gcucnnnnnn nnnnnncuu      60 ucacccunnn nnnnnnnnn nnnnnnnnnn nnnnnnnnnn nnnnnnnnnn cucuugucug    120
gu                                                                 122

<210> SEQ ID NO 96
<211> LENGTH: 151
<212> TYPE: RNA
<213> ORGANISM: Artificial Sequence
<220> FEATURE:
<223> OTHER INFORMATION: 5' terminal sequence of the stealth RNA vector
<220> FEATURE:
<221> NAME/KEY: misc_feature
<222> LOCATION: (13)..(57)
<223> OTHER INFORMATION: n is a, c, g, or u
<220> FEATURE:
<221> NAME/KEY: misc_feature
<222> LOCATION: (68)..(78)
<223> OTHER INFORMATION: n is a, c, g, or u
<220> FEATURE:
<221> NAME/KEY: misc_feature
<222> LOCATION: (143)..(148)
<223> OTHER INFORMATION: n is a, c, g, or u

<400> SEQUENCE: 96
accagacaag agnnnnnnnn nnnnnnnnnn nnnnnnnnnn nnnnnnnnnn nnnnnnnuuu    60
uucuuacnnn nnnnnnnngg aucaguccaa gacuucguug agcacagggu acuuuauuga   120
ugguacauga caaggugcgg cunnnnnnuu a                                 151

<210> SEQ ID NO 97
<211> LENGTH: 122
<212> TYPE: RNA
<213> ORGANISM: Artificial Sequence
<220> FEATURE:
<223> OTHER INFORMATION: 3' terminal sequence of the Sendai virus

<400> SEQUENCE: 97
caucgugaac uuuggcagca aagcaaaggg ucuggaaccu gcuccucagg guggauacuu    60
ugacccuaaa auccuguaua acuucauuac auaucccaua cauguuuuuu cucuuguuug   120
gu                                                                 122

<210> SEQ ID NO 98
<211> LENGTH: 122
<212> TYPE: RNA
<213> ORGANISM: Artificial Sequence
<220> FEATURE:
<223> OTHER INFORMATION: 3' terminal sequence of the Stealth RNA vector
      variant 1

<400> SEQUENCE: 98
caucgugaac uuuggcagca aagcaaaggg ucuggaaccu gcuccucagg guggauacuu    60
```
ugacccuaaa auccuguaua gagucuaggu uggaguugga accguggaga cucuuguuug    120
gu    122

<210> SEQ ID NO 99
<211> LENGTH: 122
<212> TYPE: RNA
<213> ORGANISM: Artificial Sequence
<220> FEATURE:
<223> OTHER INFORMATION: 3' terminal sequence of the Stealth RNA vector
      variant 2

<400> SEQUENCE: 99
caucgugaac uuuggcagca aagcaaaggg ucuggaaccu gcuccucagg guggauacuu    60
ucacccuaag uuuuucuuaa acuucauuac auaucccaua cauguuuuuu cucuuguuug    120
gu    122

<210> SEQ ID NO 100
<211> LENGTH: 122
<212> TYPE: RNA
<213> ORGANISM: Artificial Sequence
<220> FEATURE:
<223> OTHER INFORMATION: 3' terminal sequence of the Stealth RNA vector
      variant 3

<400> SEQUENCE: 100
caucgugaac uuuggcagca aagcaaaggg ucuggaaccu gcucagucca gguagcacuu    60
ugacccuaaa auccuguaua acuucauuac auaucccaua cauguuuuuu cucuuguuug    120
gu    122

<210> SEQ ID NO 101
<211> LENGTH: 122
<212> TYPE: RNA
<213> ORGANISM: Artificial Sequence
<220> FEATURE:
<223> OTHER INFORMATION: 3' terminal sequence of the Stealth RNA vector
      variant 4

<400> SEQUENCE: 101
caucgugaac uuuggcagca aagcaacugu gccuggccug cugccucagg guggauacuu    60
ugacccuaaa auccuguaua acuucauuac auaucccaua cauguuuuuu cucuuguuug    120
gu    122

<210> SEQ ID NO 102
<211> LENGTH: 122
<212> TYPE: RNA
<213> ORGANISM: Artificial Sequence
<220> FEATURE:
<223> OTHER INFORMATION: 3' terminal sequence of the Stealth RNA vector
      variant 5

<400> SEQUENCE: 102
caucgugaca gcaguuuggg aggccaaggg ucuggaaccu gcuccucagg guggauacuu    60
ugacccuaaa auccuguaua acuucauuac auaucccaua cauguuuuuu cucuuguuug    120
gu    122

<210> SEQ ID NO 103
<211> LENGTH: 122
<212> TYPE: RNA
<213> ORGANISM: Artificial Sequence
<220> FEATURE:
<223> OTHER INFORMATION: F3' terminal sequence of the Stealth RNA vector variant 6

<400> SEQUENCE: 103
caugguggac uuggcagca aagcaaaggg ucuggaaccu gcuccucagg guggauacuu    60
ugacccuaaa auccuguaua acuucauuac auaucccaua cauguuuuuu cucuuguuug   120
gu                                                                 122

<210> SEQ ID NO 104
<211> LENGTH: 122
<212> TYPE: RNA
<213> ORGANISM: Artificial Sequence
<220> FEATURE:
<223> OTHER INFORMATION: 3' terminal consensus sequence of the Stealth
      RNA vector
<220> FEATURE:
<221> NAME/KEY: misc_feature
<222> LOCATION: (4)..(31)
<223> OTHER INFORMATION: n is a, c, g, or u
<220> FEATURE:
<221> NAME/KEY: misc_feature
<222> LOCATION: (33)..(37)
<223> OTHER INFORMATION: n is a, c, g, or u
<220> FEATURE:
<221> NAME/KEY: misc_feature
<222> LOCATION: (39)..(43)
<223> OTHER INFORMATION: n is a, c, g, or u
<220> FEATURE:
<221> NAME/KEY: misc_feature
<222> LOCATION: (45)..(57)
<223> OTHER INFORMATION: n is a, c, g, or u
<220> FEATURE:
<221> NAME/KEY: misc_feature
<222> LOCATION: (68)..(110)
<223> OTHER INFORMATION: n is a, c, g, or u

<400> SEQUENCE: 104
caunnnnnnn nnnnnnnnnn nnnnnnnnnn ncnnnnncnn nnncnnnnnn nnnnnnncuu    60
ucacccunnn nnnnnnnnnn nnnnnnnnnn nnnnnnnnnn nnnnnnnnnn cucuugucug   120
gu                                                                 122

<210> SEQ ID NO 105
<211> LENGTH: 145
<212> TYPE: RNA
<213> ORGANISM: Artificial Sequence
<220> FEATURE:
<223> OTHER INFORMATION: 5' terminal sequence of the Sendai viurs

<400> SEQUENCE: 105
accagacaag aguuuaagag auauguauuc uuuuaaauuu ucuugucuuc uuguaaguuu    60
uucuuacuau ugucauaugg aucagaccaa gacuuccagg uaccgcggag cuucgaucgu   120
ucugcacgau agggacuaau uauua                                        145

<210> SEQ ID NO 106
<211> LENGTH: 151
<212> TYPE: RNA
<213> ORGANISM: Artificial Sequence
<220> FEATURE:
<223> OTHER INFORMATION: 5' terminal sequence of the Stealth RNA vector
      variant 1

<400> SEQUENCE: 106
accagacaag aguuuaagag auauguauuc uuuuaaauuu ucuugucuuc uuguaaguuu    60
uucuuacuau ugucauaugg aucagaccaa gacuuccagg uaccgcggag cuucgaucgu   120
ucugcacgau agggacuaau uaaccgguuu a                                 151

<210> SEQ ID NO 107
<211> LENGTH: 151
<212> TYPE: RNA
<213> ORGANISM: Artificial Sequence
<220> FEATURE:
<223> OTHER INFORMATION: 5' terminal sequence of the Stealth RNA vector
      variant 2

<400> SEQUENCE: 107
accagacaag aguuuaagag auauguauuc uuuuaaauuu ucuugucuuc uuguaaguuu      60
uucuuacuau ugucauaugg aucaguccaa gacuucguug agcacagggu acuuuauuga    120
ugguacauga caaggugcgg cuaccgguuu a                                   151

<210> SEQ ID NO 108
<211> LENGTH: 151
<212> TYPE: RNA
<213> ORGANISM: Artificial Sequence
<220> FEATURE:
<223> OTHER INFORMATION: 5' terminal sequence of the Stealth RNA vector
      variant 3

<400> SEQUENCE: 108
accagacaag aguuuaagag auauguauuc uuuuaaauuu ucuugucuuc uuguaaguuu      60
uucuuacuau ugucauaugc agcaggccag gcacagcagg uaccgcggag cuucgaucgu    120
ucugcacgau agggacuaau uaaccgguuu a                                   151

<210> SEQ ID NO 109
<211> LENGTH: 151
<212> TYPE: RNA
<213> ORGANISM: Artificial Sequence
<220> FEATURE:
<223> OTHER INFORMATION: 5' terminal sequence of the Stealth RNA vector
      variant 4

<400> SEQUENCE: 109
accagacaag aguuuaagag auauguauuc uuuuaaauuu ucuugucuuc uuguaaguuu      60
uucuuaagug uagggcuggg aucaguccaa gacuuccagg uaccgcggag cuucgaucgu    120
ucugcacgau agggacuaau uaaccgguuu a                                   151

<210> SEQ ID NO 110
<211> LENGTH: 151
<212> TYPE: RNA
<213> ORGANISM: Artificial Sequence
<220> FEATURE:
<223> OTHER INFORMATION: 5' terminal sequence of the Stealth RNA vector
      variant 5

<400> SEQUENCE: 110
accagacaag agaaaaaaca uguauggau auguaaugaa guuauacagg auuuaguuu      60 uucuuacuau ugucauaugg aucaguccaa gacuuccagg uaccgcggag cuucgaucgu    120
ucugcacgau agggacuaau uaaccgguuu a                                   151

<210> SEQ ID NO 111
<211> LENGTH: 145
<212> TYPE: RNA
<213> ORGANISM: Artificial Sequence
<220> FEATURE:
<223> OTHER INFORMATION: 5' terminal consensus sequence of the Stealth
      RNA vector
<220> FEATURE:
<221> NAME/KEY: misc_feature

```
<222> LOCATION: (13)..(57)
<223> OTHER INFORMATION: n is a, c, g, or u
<220> FEATURE:
<221> NAME/KEY: misc_feature
<222> LOCATION: (68)..(78)
<223> OTHER INFORMATION: n is a, c, g, or u
<220> FEATURE:
<221> NAME/KEY: misc_feature
<222> LOCATION: (80)..(84)
<223> OTHER INFORMATION: n is a, c, g, or u
<220> FEATURE:
<221> NAME/KEY: misc_feature
<222> LOCATION: (86)..(90)
<223> OTHER INFORMATION: n is a, c, g, or u
<220> FEATURE:
<221> NAME/KEY: misc_feature
<222> LOCATION: (92)..(142)
<223> OTHER INFORMATION: n is a, c, g, or u

<400> SEQUENCE: 111
accagacaag agnnnnnnnn nnnnnnnnnn nnnnnnnnnn nnnnnnnnnn nnnnnnnuuu      60
uucuuaannn nnnnnnnngn nnnngnnnnn gnnnnnnnnn nnnnnnnnnn nnnnnnnnnn     120
nnnnnnnnnn nnnnnnnnnn nnuua                                          145

<210> SEQ ID NO 112
<211> LENGTH: 11
<212> TYPE: DNA
<213> ORGANISM: Artificial Sequence
<220> FEATURE:
<223> OTHER INFORMATION: SapI recognition sequence, forward strand
<220> FEATURE:
<221> NAME/KEY: misc_feature
<222> LOCATION: (8)..(11)
<223> OTHER INFORMATION: n is a, c, g, or t

<400> SEQUENCE: 112
gctcttcnnn n                                                          11

<210> SEQ ID NO 113
<211> LENGTH: 11
<212> TYPE: DNA
<213> ORGANISM: Artificial Sequence
<220> FEATURE:
<223> OTHER INFORMATION: SapI recognition sequence, reverse strand
<220> FEATURE:
<221> NAME/KEY: misc_feature
<222> LOCATION: (1)..(4)
<223> OTHER INFORMATION: n is a, c, g, or t

<400> SEQUENCE: 113
nnnngaagag c                                                          11

<210> SEQ ID NO 114
<211> LENGTH: 5
<212> TYPE: RNA
<213> ORGANISM: Artificial Sequence
<220> FEATURE:
<223> OTHER INFORMATION: Kozak sequence

<400> SEQUENCE: 114 ccacc                                                                  5

<210> SEQ ID NO 115
<211> LENGTH: 42
<212> TYPE: RNA
<213> ORGANISM: Artificial Sequence
<220> FEATURE:
<223> OTHER INFORMATION: 5' non-coding sequence #1
```

```
<400> SEQUENCE: 115
ccaccaugaa auugccagaa gacugacacu agagccgcca cc                          42

<210> SEQ ID NO 116
<211> LENGTH: 21
<212> TYPE: RNA
<213> ORGANISM: Artificial Sequence
<220> FEATURE:
<223> OTHER INFORMATION: 5' non-coding sequence #2

<400> SEQUENCE: 116
caccauggcc caggcuucau a                                                 21
```

GENE EXPRESSION SYSTEM USING STEALTHY RNA, AND GENE INTRODUCTION/EXPRESSION VECTOR INCLUDING SAID RNA

CROSS-REFERENCE TO RELATED APPLICATION

This application is a Divisional of copending U.S. application Ser. No. 15/544,084, filed on Jul. 17, 2017, which is a 371 of International Application No. PCT/JP2016/051886, filed Jan. 18, 2016, which claims the benefit of priority from the prior Japanese Patent Application No. 2015-007288, filed on Jan. 16, 2015, the entire contents of all of which are incorporated herein by references.

TECHNICAL FIELD

The present invention relates to a vector for introducing and persistently expressing exogenous genes in animal cells.

The sequence listing submitted in a computer readable form under the name of "P170488US01 sequence_listing.txt" is hereby incorporated by reference into the present application. The electronic copy of the sequence listing in the computer readable form, the file size of which is 149 K bytes, was created on Jun. 13, 2023.

BACKGROUND ART

The techniques of externally introducing any given gene into animal cells including human cells, and expressing the gene persistently in the cells are essential techniques in various industries utilizing biotechnologies. For example, industrial mass production of human monoclonal antibodies for use as pharmaceuticals requires the technique of persistently expressing genes of H-chain and L-chain of immunoglobulin at the same level. In gene therapy of congenital metabolic diseases, the technique of introducing a therapeutic gene into human tissue cells, and stably expressing the gene in the body for a long term is required.

1. Regarding Cell-Reprogramming Technology

Recently, a cell-reprogramming technology for producing useful cells by genetically converting the characteristic of normal tissue cells attracts attention. The technique of introducing genes into an animal cell and persistently expressing the genes is also a base technology essential for cell-reprogramming. For example, it is possible to prepare human induced pluripotent stem cells (iPS cells) by introducing a combination of four genes, OCT4, SOX2, KLF4, and c-MYC, or OCT4, SOX2, NANOG, and LIN28 into human normal fibroblasts, and expressing the genes persistently for 21 days (Patent Document 1, Patent Document 2, Non-Patent Document 1, and Non-Patent Document 2). Also, it is possible to prepare hepatic cells by introducing three genes, FOXA3, HNF1A, and HNF4A into human fibroblasts and expressing the gene persistently for 14 days (Non-Patent Document 3). It is also reported that a dopaminergic neuron can be prepared by introducing five genes, ASCL1, BRN2, MYT1L, LMX1A, and FOXA2 into human fibroblasts, and expressing the gene persistently for 24 days (Non-Patent Document 4). Thus, in various cell-reprogramming, there is a need for a technique capable of simultaneously introducing and expressing plural genes into a cell, and keeping the expression for a period required for reprogramming.

It is known that cell-reprogramming can be induced in vivo. For example, it has been reported that when three genes, GATA4, MEF2C, and TBX5, or four genes, GATA4, HAND2, MEF2C, and TBX5 are administered to an infarcted site in a mouse myocardial infarctionmodel, infiltrated fibroblasts transdifferentiate into cardiomyocytes (Non-Patent Document 5, and Non-Patent Document 6). Therefore, the cell-reprogramming technology is expected to become the basis of regenerative medicine for myocardial infarction, spinal cord injury and the like in future.

2. Improvement in Cell-Reprogramming Efficiency

Assuming that in vitro cell-reprogramming is used for medicine, it is desired that the material cells can be collected from a human body without invasion, and can be collected in the condition that they are not contaminated with microorganisms outside the living body. Cells that satisfy these requirements are almost limited to mononuclear cells in peripheral blood, and a gene introduction vector adapted to these cells is desired.

In general, the efficiency with which animal cells are reprogrammed by externally introduced genes is very low, however, the efficiency can be raised by carrying all the genes on one vector, and introducing the genes into cells at once (Patent Document 3, Patent Document 4, Non-Patent Document 7, and Non-Patent Document 8).

Also it is known that the efficiency is raised by increasing the number of genes used in cell-reprogramming. For example, in the technique of converting mouse fibroblasts to induced pluripotent stem cells (iPS cells), it is known that the efficiency of conversion rises five times by using a total of six genes by adding two genes, BRG1 and BAF155, to four genes, OCT4, SOX2, KLF4, and c-MYC (Non-Patent Document 9). Also, in the technique of reprogramming human fibroblasts into motor nerves, it is known that the efficiency of reprogramming rises 100 times by using a total of seven genes by adding three genes, HB9, ISL1, and NGN2 to four genes, LHX3, ASCL1, BRN2, and MYT1L (Non-Patent Document 10).

When the number of genes used in cell-reprogramming is increased, the size of genes that should be carried also increases. Illustrating preparation of iPS cells as an example, the total size of four genes, KLF4, OCT4, SOX2, and c-MYC is 4,774 base pairs, whereas the total size of genes after adding the two genes, BRG1 (5,040 base pairs) and BAF155 (3,318 base pairs) is 13,132 base pairs (Non-Patent Document 9). By adding CHD1 gene (5,133 base pairs) encoding a chromatin remodeling factor that is specifically expressed in embryonic stem cells and is expected to accelerate reprogramming of cells to iPS cells to four genes, KLF4, OCT4, SOX2, and c-MYC, the total size amounts to 9,907 base pairs, and by adding TET1 gene (6,429 base pairs) encoding a DNA demethylase to four genes, KLF4, OCT4, SOX2, and c-MYC, the total size amounts to 11,203 base pairs. The total size of the seven genes, LHX3, ASCL1, BRN2, MYT1L, HB9, ISL1, and NGN2 that are used in the technique of reprogramming human fibroblasts into motor nerves is 9,887 base pairs (Non-Patent Document 10).

Thus, in order to raise the efficiency of the cell-reprogramming, it is desired to use at least six or more genes, and a vector capable of carrying all of these genes at once is desired. Also, desired is a vector capable of expressing introduced exogenous genes even when the total size of the genes is 5,000 or more nucleotides, desirably 8,000 or more nucleotides.

The term vector used herein refers to a recombinant viral or non-viral nucleic acid-macromolecular substance complex that is composed of nucleic acid including exogenous genes, and is capable of introducing the nucleic acid into animal cells and expressing the genes.

It is known that in reprogramming of animal cells by expression of exogenous genes, the expression levels of the genes seriously affect the characteristics of the reprogrammed cells. For example, when four genes, OCT4, SOX2, KLF4, and c-MYC are expressed in mouse fibroblasts, it is known that iPS cells are generated when expression of the genes is weak, whereas cells having a totally different characteristic from iPS cells are generated when the expression of the genes is strong (Non-Patent Document 11). Thus, for the technique of reprogramming animal cells including human cells by expressing externally introduced genes, there is a need for a vector capable of setting the expression of the genes at an optimum level depending on the purpose.

3. Removal of Genes for Reprogramming

Further, in order to make the reprogrammed cells prepared by externally introducing genes completely exert their function, it is necessary to completely remove the reprogramming genes from the cells. Also, when the prepared human cells are used as a material for regenerative medicine, it is necessary to completely remove the genes from the cells for ensuring the safety. For example, in induced pluripotent stem cells (iPS cells) prepared by using four genes, OCT4, SOX2, KLF4, and c-MYC, the pluripotency cannot be functional in the condition that these four genes are expressed, and hence, it is necessary to at least completely suppress the expression of these genes, or preferably completely remove these genes from the cells (Patent Document 1, Patent Document 2, Patent Document 3, Non-Patent Document 1, Non-Patent Document 2, and Non-Patent Document 7). It is also known that if the c-MYC gene used in preparing the iPS cells is left in the iPS cells, the tissue cells that are prepared by differentiation of the iPS cells become tumorigenic with high frequency (Non-Patent Document 12). Therefore, it is necessary to completely remove the c-MYC gene from the iPS cells for ensuring the safety.

Thus, the gene expression technique required for cell-reprogramming needs to have the mutually contradictory characteristics: persistent expression of genes at an optimum levels is desired for achieving the reprogramming, while it can be removed easily and completely once the reprogramming has completed.

4. Importance of Avoiding Activation of Innate Immune System

Most of the gene introduction/expression vectors that are currently used in animal cells are constructed using an animal viruses or plasmid DNAs prepared from microorganisms such as *Escherichia coli* as materials. However, an animal cell has an innate immune system that eliminates invading pathogens from outside (Non-Patent Document 13), and nucleic acids derived from viruses or microorganisms introduced from outside the cell are recognized as foreign substances, and the innate immune system is activated. When the degree of activation of the innate immune system exceeds a certain level, cell death by the apoptosis is induced, and thus the efficiency of the reprogramming is deteriorated. When expression of interferon or inflammatory cytokines is induced by the activation of the innate immune system, inflammation is caused in the living body. In order to prevent such an undesired reaction, gene introduction/expression technique for cell-reprogramming is required to be capable of avoiding the activation of the innate immune system. This characteristic is important particularly in application to the regenerative medicine including in vivo cell-reprogramming as described in the above section 1.

5. Gene Introduction/Expression System for Ideal Cell-Reprogramming

From the foregoing investigation, there is a need for a gene introduction/expression technique satisfying the following at least five requirements as discussed in the above sections 1. to 4. so as to further ameliorate the cell-reprogramming technique for animal cells including human cells by using genes for industrial application.

(1) Capability of efficiently introducing exogenous genes into animal cells including human peripheral blood cells.

(2) Capability of persistently expressing the genes for any required period.

(3) Capability of avoiding the innate immune system possessed by cells in expression of the genes.

(4) Capability of expressing the genes even if the total length of the introduced exogenous genes is 5,000 or more nucleotides, desirably 8,000 or more nucleotides.

(5) Capability of simultaneously expressing at least six, desirably eight or more genes.

Also, it is greatly desired to further achieve the following points.

(6) Capability of regulating the expression levels of the genes. In particular, it is preferred that the expression level of each gene can be regulated individually when plural genes are introduced.

In applying gene-introduced cells, in particular, to transplantation techniques, the following point is also very important.

(7) Capability of removing the gene by a simple technique when the genes become unnecessary.

6. Technique of Introducing Plural Genes into Animal Cells

As a technique for introducing plural genes into animal cells including human cells from outside, and expressing the genes persistently in the cells, that has been reported to be applicable to cell-reprogramming, the following three techniques are known.

(1) Method of integrating the genes into nuclear genomic DNA.

(2) Method of carrying the genes on DNA capable of existing stably and independently from genomic DNA in a nucleus.

(3) Method of carrying the genes on RNA capable of existing in cytoplasm.

6-1. Method for Integrating Plural Genes into Nuclear Genomic DNA

In the method of integrating an exogenous gene into genomic DNA existing in a nucleus of cell by using a lentivirus vector (Non-Patent Document 8, and Non-Patent Document 14), transposon (Non-Patent Document 15, and Non-Patent Document 16), non-homologous recombination, homologous recombination or the like, the gene can exist stably as with the genomic DNA. However, once the gene is integrated into the genomic DNA, complicated operations such as introducing a sequence specific recombinase into cells are required for selectively removing the gene from the genomic DNA, and the gene cannot be removed securely from every cell (Non-Patent Document 15). Further, since integration of exogenous genes into genomic DNA requires DNA replication of host cells, the efficiency of gene introduction into cells having poor proliferation potency such as blood cells is very low. Further, the phenomenon of "insertional mutagenesis" that random integration of exogenous gene into genomic DNA causes disruption or abnormal activation of genes of the host is known, and hence, there exists a concern about the safety for medical application (Non-Patent Document 17).

6-2. Method for Carrying Plural Genes on a DNA that is Independent from Genomic DNA in Nucleus As a method for carrying a exogenous gene on a DNA capable of existing stably in a nucleus of cell independently from genomic DNA, a method of using a circular DNA carrying a replication origin of genome of Epstein-Barr virus (Non-Patent Document 18), and a method of using an artificial chromosome containing a straight-chain giant DNA (Non-Patent Document 19) are known. These DNA molecules continue replication and are kept stably in nuclei of human cells, and the mechanism of this relies on the mechanism with which genomic DNA of host cells is replicated. Therefore, it is impossible to specifically inhibit only replication of the DNA carrying exogenous genes, and a technique for actively removing the DNA from cells has not been reported. Additionally, since division of a host cell is required for introducing the DNA molecule into a cell nucleus, the efficiency of gene introduction into cells having poor proliferation potency such as blood cells is very low. Further, since it is known that circular DNA in a cell nucleus is frequently incorporated into genomic DNA of the cell, the risk of insertional mutagenesis cannot be eliminated (Non-Patent Document 20).

6-3. Technique of Expressing Plural Genes from Single Vector DNA

Further, as described in the above sections 6-1. and 6-2., when DNA is used as a platform for gene expression, a technique of expressing plural genes from the single vector DNA is required. As such a technique, the following three methods are known: 1) a method of simply linking plural independent genes, and expressing the genes, 2) a method of expressing plural proteins from one messenger RNA (mRNA) by using an RNA structure called Internal Ribosome Entry Site (IRES), and 3) a method of expressing a fusion protein in which plural proteins are linked by 2A peptide.

It is known that in the method of linking plural independent genes, expression of genes is strongly suppressed due to mutual interference between genes (Non-Patent Document 21). In order to prevent this, it is necessary to insert a structure called an insulator between genes, and the insertion increases the size of the vector DNA, and complicates the structure of the vector DNA. While the case of expressing four genes installed on one DNA molecule has been reported in this method (Non-Patent Document 22), the case of simultaneously expressing five or more genes has not been reported.

In the method of expressing plural proteins from one messenger RNA (mRNA) by using IRES sequence, the translation efficiency of the protein positioned downstream IRES sequence is lower than, or sometimes 10% or less compared with the translation efficiency of the protein positioned upstream IRES sequence (Non-Patent Document 23). Additionally, since IRES sequence has a relatively large size and has a complicated structure, the method of using IRES sequence is mainly used for simultaneously expressing two proteins.

2A peptide has a structure consisting of 18 to 22 amino acid residues found in a positive-sense single-stranded RNA virus, and a fusion protein in which plural proteins are connected by 2A peptide are automatically cleaved at the time of synthesis and dissociated into the original plural proteins. In this technique, one proline residue is left at the N-terminus of each protein arising after cleavage, and 17 to 21 amino acid residues are left at the C-terminus, and these excess amino acid residues can influence on the function of the protein (Non-Patent Document 24). In addition, since the efficiency of cleavage at a 2A peptide site is largely influenced by the structure of the fusion protein, it is necessary to make trial and error requiring labors for preparing plural proteins efficiently (Non-Patent Document 25). In the method of connecting plural proteins by 2A peptide, the case of simultaneously expressing four proteins (Non-Patent Document 8) and the case of simultaneously expressing five proteins (Non-Patent Document 16) have been reported. Also the case of expressing four proteins by combining IRES sequence and 2A peptide has been reported (Non-Patent Document 14).

6-4. Method for Carrying Plural Genes on One RNA Existing in Cytoplasm

As described in the above sections 6-1. to 6-3., in the existing gene introduction/expression technique that uses DNA as a platform for gene expression, cell-reprogramming using four to five genes has been reported. However, as long as DNA is used as a platform for gene expression, it is not easy to simultaneously carry six or more genes and to achieve removal of the genes in a convenient way, and a technique satisfying at least all the five requirements required for ideal reprogramming shown in the above section 5. has not been reported.

Meanwhile, as a technique of cell-reprogramming by expressing plural genes that are externally introduced into animal cells including human cells using RNA as a platform, techniques of using a positive-sense RNA (Non-Patent Document 26, and Non-Patent Document 27), and techniques of using a negative-sense RNA (Patent Document 3, Patent Document 4, Patent Document 5, Patent Document 6, Non-Patent Document 7, Non-Patent Document 28, Non-Patent Document 29, and Non-Patent Document 30) have been reported.

6-4-1. Method of Using Positive-Sense RNA

As a technique of cell-reprogramming by using a positive-sense RNA capable of existing stably in cytoplasm, a technique of using a positive-sense single-stranded genomic RNA derived from Venezuelan equine encephalomyelitis virus (VEEV) (Non-Patent Document 26) has been reported. In this technique, expression of four proteins is realized by replacing a structural gene on 3' side of genomic RNA of VEEV with genes encoding proteins that are linked by 2A peptide. This system induces extremely strong expression of interferon, and then combination with an anti-interferon substance (B18R protein derived from vaccinia virus) is necessarily required (Non-Patent Document 26). The efficiency of gene introduction depends on the gene introducing reagent to be applied, and cells capable of being reprogrammed is limited to adhesive cells such as fibroblasts. An RNA carrying exogenous genes is unstable, and disappears by removing B18R protein from the culture medium.

As a technique of cell-reprogramming by using a positive-sense RNA, a technique using a chemically synthesized messenger RNA (mRNA) (Non-Patent Document 27) has been reported. In this prior art, after mixing plural mRNAs separately carrying up to five exogenous genes, the plural mRNAs are introduced into cells by using a gene introducing reagent. Since the expressions of the genes are transient, it is necessary to newly introduce the genes into the cells every day. Also, the gene introduction is limited to adhesive cells such as fibroblasts. Also in this technique, since the innate immune system is activated strongly, it is necessary to combine an anti-interferon substance (B18R protein derived from vaccinia virus) (Non-Patent Document 27).

6-4-2. Method of Using Negative-Sense RNA

As a technique of cell-reprogramming using negative-sense RNAs, a method of using mixed vectors separately carrying an exogenous gene on a wild-type strain of Sendai virus which is one species of paramyxoviruses (Patent Document 5, Non-Patent Document 28, and Non-Patent Document 29), and a method of using a vector carrying three genes simultaneously (Patent Document 6, and Non-Patent Document 30) have been reported as prior arts. In these gene expression systems using negative-sense RNA (s), autonomous replication ability of the wild-type virus is attenuated by deleting F gene, and exogenous genes are installed respectively as single gene expression cassettes. Although activation of the innate immune system was not mentioned, the vectors are expected to have ability to activate the innate immune system correspondingly because it has been known that Sendai virus which is a material has strong interferon inducibility (Non-Patent Document 31). Also it has been reported that the vector can be removed by introducing a temperature sensitive mutation into genome of the wild-type virus, and thus increasing the cultivation temperature (Patent Document 6, Non-Patent Document 29, and Non-Patent Document 30). The size of gene that can be expressed by a vector based on wild-type Sendai virus has been reported to be from 3078 base pairs (beta galactosidase from *Escherichia coli*) (Non-Patent Document 32) to 3450 base pairs (sum of three genes, KLF4, OCT4, and SOX2) (Patent Document 6, Non-Patent Document 30).

As a technique of reprogramming cells by using a negative-sense RNA, a technique based on a mutant Sendai virus capable of persistent infection has been reported (Patent Document 3, Patent Document 4, and Non-Patent Document 7). In this technique, plural point mutations responsible for long-term persistence are identified in genome of the virus which is a material of the vector, and it is indicated that these mutations are involved in avoidance of activation of the innate immune system (deterioration in interferon expression). Also by deleting three genes from virus genome, and carrying new genes, it is possible to express four exogenous genes simultaneously. Further, it has been reported that vectors are actively removed from cells by suppressing expression of L gene that encodes an RNA-dependent RNA polymerase by short interfering RNA (siRNA). It has been reported that the size of gene that can be expressed with the use of a vector based on a mutant Sendai virus capable of persistent infection is 4774 base pairs (sum of four genes, KLF4, OCT4, SOX2, and c-MYC) (Patent Document 3, Patent Document 4, and Non-Patent Document 7).

7. Future Challenge in Plural Gene Introducing Techniques

In existent gene introduction/expression techniques using RNA as a platform for gene expression as described in the above section 6-4., cell-reprogramming using four to five genes has been reported. Among these techniques, a defective and persistent expression Sendai virus vector described in the above section 6-4-2. has the most excellent characteristic, however, the number of genes that can be installed on the vector has been reported to be at most four. In the technique using an RNA virus as a material, it is difficult to alter the level of gene expression.

As shown in the above section 6., the technique of externally introducing plural genes into animal cells including human cells and persistently expressing the genes in the cells has been variously modified toward optimization for cell-reprogramming that converts the characteristics of normal tissue cells using genes, and produces useful cells. However, a technique satisfying all the five requirements required for ideal reprogramming shown in the above section 5. has not been reported heretofore.

CITATION LIST

Patent Document

Patent Document 1: WO 2007/069666
Patent Document 2: WO 2008/118820
Patent Document 3: WO 2010/134526
Patent Document 4: WO 2012/063817
Patent Document 5: WO 2010/008054
Patent Document 6: WO 2012/029770
Patent Document 7: U.S. Pat. No. 8,326,547
Patent Document 8: U.S. Pat. No. 8,401,798
Patent Document 9: U.S. Pat. No. 7,561,973

Non-Patent Document

Non-Patent Document 1: Takahashi, et al., Cell, 131, 861-872, 2007
Non-Patent Document 2: Yu, et al., Science, 318, 1917-1920, 2007
Non-Patent Document 3: Huang, et al., Cell Stem Cell, 14370-384, 2014
Non-Patent Document 4: Son, et al., Cell Stem Cell, 9, 205-218, 2011
Non-Patent Document 5: Qian, et al., Nature, 485, 593-598, 2012
Non-Patent Document 6: Song, et al., Nature, 485, 599-604, 2012
Non-Patent Document 7: Nishimura, et al., J. Biol. Chem., 286, 4760-4771, 2011
Non-Patent Document 8: Carey, et al., Proc. Natl. Acad. Sci. USA, 106, 157-162, 2009
Non-Patent Document 9: Singhal, et al., Cell, 141, 943-955, 2010
Non-Patent Document 10: Son, et al., Cell Stem Cell, 9, 205-218, 2011
Non-Patent Document 11: Tonge, et al., Nature, 516, 192-197, 2014
Non-Patent Document 12: Miura, et al., Nature Biotechnology, 27, 743-745, 2009
Non-Patent Document 13: Randall, J. Gen Viral., 89, 1-47, 2008
Non-Patent Document 14: Sommer, et al., Stem Cells, 28, 64-74, 2010
Non-Patent Document 15: Kaji, et al., Nature, 458, 771-775, 2009
Non-Patent Document 16: Grabundzjia, et al., Nuc. Acids Res., 41, 1829-1847, 2013
Non-Patent Document 17: Hacein-Bey-Abina, et al., Science, 302, 415-419, 2003
Non-Patent Document 18: Wu, et al., Proc. Natl. Acad. Sci. USA, 111, 10678-10683, 2014
Non-Patent Document 19: Hiratsuka, et al., Plos One, 6, e25961, 2011
Non-Patent Document 20: Hurley, et al., J. Virol., 65, 1245-1254, 1991
Non-Patent Document 21: Yahata, et al., J. Mol. Biol., 374, 580-590, 2007
Non-Patent Document 22: Nishiumi, et al., Cell Struct. Funct., 34, 47-59, 2009
Non-Patent Document 23: Balvay, et al., Biochi. Biophys. Acta, 1789, 542-557, 2009
Non-Patent Document 24: Felipe, et al., Trends Biotech., 24, 68-75, 2006

Non-Patent Document 25: Lengler, et al., Anal. Biochem., 343, 116-124, 2005

Non-Patent Document 26: Yoshioka, et al., Cell Stem Cell, 13, 246-254, 2013

Non-Patent Document 27: Warren, et al., Cell Stem Cell, 7, 1-13, 2010

Non-Patent Document 28: Fusaki, et al., Proc. Jpn. Acad. Ser. B85, 348-362, 2009

Non-Patent Document 29: Ban, et al., Proc. Natl. Acad. Sci. USA, 108, 14234-14239, 2011

Non-Patent Document 30: Fujie, et al., Plos One, 9, e113052, 2014

Non-Patent Document 31: Hua, et al., J. Leukocyte Biol., 60, 125-128, 1996

Non-Patent Document 32: Sakai, et al., FEBS Lett., 456, 221-226, 1999

Non-Patent Document 33: Kondo, et al., J. Biol. Chem., 268, 21924-21930, 1993

Non-Patent Document 34: Ward, et al., Proc. Natl. Acad. Sci. USA, 108, 331-336, 2011

Non-Patent Document 35: Saito, et al., Nature, 454, 523-527, 2008

Non-Patent Document 36: Vabret, et al., Plos One, 7, e33502, 2012

Non-Patent Document 37: Rehwinkel, et al., Cell, 140, 397-408, 2010

Non-Patent Document 38: Shioda, et al., Nuc. Acids Res., 14, 1545-1563, 1986

Non-Patent Document 39: Vidal, et al., J. Virol., 64, 239-246, 1990

Non-Patent Document 40: Irie, et al., J. Virol., 86, 7136-7145, 2012

Non-Patent Document 41: Kato, et al., EMBO J., 16, 578-587, 1997

Non-Patent Document 42: Tapparel, et al., J. Virol., 72, 3117-3128. 1998

Non-Patent Document 43: Park, et al., Proc. Natl. Acad. Sci. USA, 88, 5537-5541, 1991

Non-Patent Document 44: Harty, et al., J. Viral., 69, 5128-5131, 1995

Non-Patent Document 45: Willenbrink et al., J. Virol., 68, 8413-8417, 1994

Non-Patent Document 46: Sharp, et al., Nuc. Acids Res., 15, 1281-1295, 1987

Non-Patent Document 47: Guigo, et al., J. Mol. Biol., 253, 51-60, 1995

Non-Patent Document 48: Vabret, et al., J. Viral., 88, 4161-4172, 2014

Non-Patent Document 49: Raab, et al., Syst. Synth. Biol., 4, 215-225, 2010

Non-Patent Document 50: Alan, H., Gene, 56 125-135, 1987

Non-Patent Document 51: Kuo, et al., J. Virol., 62, 4439-4444, 1988

Non-Patent Document 52: Sengupta, et al., J. Biol. Chem., 264, 14246-14255, 1989

Non-Patent Document 53: Melton, et al., Nuc. Acids Res., 12, 7035-7056, 1984

Non-Patent Document 54: Hampel, A., et al., Biochemistry 28, 4929-4933, 1989

Non-Patent Document 55: Tuschl, et al., Genes Dev., 13, 3191-3197, 1999

Non-Patent Document 56: Chang, et al., J. Bacteriol., 134, 1141-1156, 1978

Non-Patent Document 57: Garcin, et al., EMBO J., 14, 6087-6094, 1995

Non-Patent Document 58: Gotoh, et al., Virology, 171, 434-443, 1989

Non-Patent Document 59: Lopez, et al., Mol. Microbiol., 33, 188-199, 1999

Non-Patent Document 60: Kozak, Cell, 44, 283-292, 1986

Non-Patent Document 61: Kozak, Mol. Cell Biol., 7, 3438-3445, 1987

Non-Patent Document 62: Vara, et al., Gene, 33, 197-206, 1985

Non-Patent Document 63: Nakajima, et al., Biosci. Biotechnol. Biochem., 68, 565-570, 2004

Non-Patent Document 64: Ai, et al., Biochemistry, 46, 5904-5910, 2007

Non-Patent Document 65: Drocourt, et al., Nuc. Acids Res., 18, 4009, 1990

Non-Patent Document 66: Kogure, et al., Nat. Biotechnol., 24, 577-581, 2006

Non-Patent Document 67: Gritz, et al., Gene, 25, 179-188, 1983

Non-Patent Document 68: Studier, et al., J. Mol. Biol., 189, 113-130, 1986

Non-Patent Document 69: Nawa, et al., Biol. Pharm. Bull, 21, 893-898, 1998

Non-Patent Document 70: Karasawa, et al., Biochem. J., 381, 307-312, 2004

Non-Patent Document 71: Yoneyama, et al., Nature Immunol., 5, 730-737, 2004

Non-Patent Document 72: Sakaguchi, et al., Microbial. Immunol., 55, 760-767, 2011

Non-Patent Document 73: Jia, et al., J. Immunol., 183, 4241-4248, 2009

Non-Patent Document 74: Studier, et al., J. Mol. Biol., 189, 113-130, 1986

Non-Patent Document 75: Akagi, et al., Proc. Natl. Acad. Sci. USA, 100, 13567-13572, 2003

Non-Patent Document 76: Hatsuzawa, et al., J. Biol. Chem., 265, 22075-22078, 1990

Non-Patent Document 77: Boshart, et al., Cell, 41, 521-530, 1985

Non-Patent Document 78: Taira, et al., Arch. Viral., 140, 187-194, 1995

Non-Patent Document 79: Takebe, et al., Mol. Cell Biol., 8, 466-472, 1988

Non-Patent Document 80: Recillas-Targa, et al., Proc. Natl. Acad. Sci. USA, 99, 6883-6888, 2002

Non-Patent Document 81: Fujita, et al., Cell, 41, 489-496, 1985

Non-Patent Document 82: Yi and Lemon, J. Virol., 77, 3557-3568, 2003

Non-Patent Document 83: You and Rice, J. Virol., 82, 184-195, 2008

Non-Patent Document 84: Chromikova, et al., Cytotechnology, 67, 343-356, 2015

Non-Patent Document 85: Brandlein and Vollmers, Histol. Histopathol., 19, 897-905, 2004

Non-Patent Document 86: Okada, et al., Microbiol. Immunol., 49, 447-459, 2005

Non-Patent Document 87: Lewis, et al., Nature Biotech., 32, 191-198, 2014

Non-Patent Document 88: Wurm. Nature Biotech., 22, 1393-1398, 2004

SUMMARY OF THE INVENTION

Problems to be Solved by the Invention

As described above, a problem to be solved by the present invention is developing a gene introduction/expression technique desired for reprogramming animal cells including human cells by the use of genes, and a vector for the technique. It is also an object of the present invention to provide a vector capable of carrying a total length of 5,000 or more nucleotides or at least six or more exogenous genes besides reprogramming genes, and capable of persistently expressing the genes without activating an innate immune system in animal cells. Also provided is an efficient technique for carrying six or more exogenous genes on a vector.

Also provided is a gene introduction/expression technique satisfying the requirements (1) to (5) that are desired especially for reprogramming technology, preferably satisfying the requirements further including the requirements (6) and (7).
- (1) Capability of efficiently introducing exogenous genes into animal cells including human peripheral blood cells.
- (2) Capability of persistently expressing the genes for any required period.
- (3) Capability of avoiding the innate immune system possessed by cells in expression of the genes.
- (4) Capability of expressing the genes even if the total length of the introduced exogenous genes is 5,000 or more nucleotides, desirably 8,000 or more nucleotides.
- (5) Capability of simultaneously expressing at least six, desirably eight or more genes.
- (6) Capability of regulating the levels of the expression of the genes. In particular, when plural genes are introduced, the expression level can be regulated individually.

In applying, in particular, to transplantation techniques, the following point is also important.
- (7) Capability of removing the gene expression system by a simple technique when the genes are no longer necessary.

Means for Solving the Problems

As described in the sections 6-1. to 6-3. of the background art, when DNA is used as a platform for gene expression, it is theoretically very difficult to satisfy all the five requirements, more preferably all the seven requirements required for ideal reprogramming shown as the "Problems to be Solved by the Invention". On the other hand, as described in the section 6-4., when RNA is used as a platform for gene expression, it becomes the primary issue how to avoid the problem of activation of the intracellular innate immune system caused by a virus-derived RNA while increasing the number of genes that can be installed on the single vector to six or more, and the total length of genes to 5,000 or more nucleotides.

Thus, in the present invention, first, using mRNA fragments derived from animal cells that does not activate an innate immune system as materials, a negative-sense single-stranded RNA in which the RNA fragments are combined with transcription start signals, transcription termination signals, and a replication origin that are recognized by an RNA-dependent RNA polymerase was designed. Then in the negative-sense single-stranded RNA, genes encoding four proteins required for transcription and replication such as an RNA-dependent RNA polymerase were installed after the structures thereof were optimized so as not to be recognized as foreign substances by the innate immune system. Further, the present inventors developed a novel method of binding ten genes as designed by using five restriction endonucleases, and ten cRNAs complementary to these ten genes were bound and then installed on the negative-sense single-stranded RNA.

The present inventors succeeded in carrying at least ten exogenous genes (a total size of at least 13.5 kilo nucleotides) and expressing them persistently for a long term without activating the innate immune system by using the negative-sense single-stranded RNA completed by the above method as a platform for gene expression. Further, the present inventors made the levels of expression of the installed genes regulatable within the range of up to 80 times by modifying the expression efficiency of N protein or C protein required for gene expression. Thus, by eliminating the RNA elements having a structure derived from virus as much as possible, the present inventors succeeded in preparing a novel gene expression system greatly beyond the limit of the capability of the conventional gene expression system using genome of RNA virus.

Further, by expressing an envelope protein and a matrix protein of paramyxovirus in cells transfected with the negative-sense single-stranded RNA carrying exogenous genes, prepared in the present invention, according to the method described in Patent Document 3, Non-Patent Document 33, and Non-Patent Document 7, a particle that encapsulates the RNA molecule, and has activity of introducing the RNA molecule into another cell was prepared. This particle could persistently express ten genes installed on the RNA molecule while keeping activation of the innate immune system low in various animal cells including human blood cells. Further, by introducing siRNA that is complementary to the gene of the RNA-dependent RNA polymerase installed on the RNA molecule and of which structure has been optimized, into the cells, the RNA molecule carrying exogenous genes could be eliminated. In the manner as described above, the present inventors confirmed that all the seven requirements including the five requirements (1) to (5) shown in the "Problems to be Solved by the Invention" and the requirements (6) and (7) in the aforementioned preferable case could be satisfied, and accomplished the present invention.

Since the RNA molecule used in the present invention lacks a specific structure required for the innate immune system to recognize as "pathogen-associated molecular pattern, PAMP", the RNA molecule is difficult to be captured by the innate immune system, namely it is "stealthy". Therefore, hereinafter, the RNA molecule is referred to as "stealthy RNA", the gene expression system using the RNA as a material is referred to as "stealth RNA gene expression system", the construct including the gene expression system and having the activity of introducing the gene expression system into animal cells is referred to as "stealth RNA vector".

In other words, the present invention can be described as follows:

[1] A stealth RNA gene expression system comprising:
a negative-sense single-stranded RNA (A) having RNA sequences (1) to (8) below,
a single-stranded RNA binding protein (B), and
an RNA-dependent RNA polymerase (C),
wherein the stealth RNA gene expression system is a complex that does not activate an innate immune system:
- (1) target RNA sequences encoding any given protein or functional RNA,
- (2) RNA sequences constituting noncoding region (s) and derived from mRNA(s) expressed in animal cells,
- (3) transcription start signal sequences recognized by the RNA-dependent RNA polymerase,
- (4) transcription termination signal sequences recognized by the polymerase enzyme, (5) RNA sequences containing replication origins recognized by the polymerase enzyme,
(6) RNA sequences encoding the polymerase enzyme with codons optimized for a biological species from which cells for transfection are derived,
(7) an RNA sequence encoding a protein that regulates activity of the polymerase enzyme with codons optimized for a biological species from which cells for transfection are derived, and
(8) an RNA sequence encoding the single-stranded RNA binding protein with codons optimized for a biological species from which cells for transfection are derived.

Here, since typical cells for transfection are human cells, the preferred cases can be described as follows.

[1'] A stealth RNA gene expression system comprising:
a negative-sense single-stranded RNA (A) having RNA sequences (1) to (8) below,
a single-stranded RNA binding protein (B), and
an RNA-dependent RNA polymerase (C),
wherein the stealth RNA gene expression system is a complex that does not activate an innate immune system:
(1) target RNA sequences encoding any given protein or functional RNA,
(2) human mRNA-derived RNA sequences constituting noncoding region (s),
(3) transcription start signal sequences recognized by the RNA-dependent RNA polymerase,
(4) transcription termination signal sequences recognized by the polymerase enzyme,
(5) RNA sequences containing replication origins recognized by the polymerase enzyme,
(6) RNA sequences encoding the polymerase enzyme with codons optimized for human cells,
(7) an RNA sequence encoding a protein that regulates activity of the polymerase enzyme with codons optimized for human cells, and
(8) an RNA sequence encoding the single-stranded RNA binding protein with codons optimized for human cells.

[2] The stealth RNA gene expression system according to the [1], wherein the target RNA sequences of the (1) contain at least six genes, or are RNA sequences having a total length of 5000 or more nucleotides.

Here, the target RNA sequences can contain seven to ten genes, or are RNA sequences having a total length of 5,000 to 15,000 nucleotides.

[3] The stealth RNA gene expression system according to the [1] or [2], wherein the RNA sequences of the (2) are derived from mRNA of human gene(s) and each of the RNA sequences is having a length of 5 to 49 nucleotides.

Here, as the mRNA sequence of a human gene, preferably a mRNA sequence of a human House-keeping gene, more preferably a noncoding region sequence in a mRNA sequence of a human House-keeping gene, for example, an RNA sequence described in (Table 1), or a partial sequence having a length of consecutive 5 to 49 nucleotides thereof, or a plurality of these sequences linked to each other can be used.

[4] The stealth RNA gene expression system according to any one of the [1] to [3], wherein each of the RNA sequences of the (2) having sequences identical to or different from one another is placed adjacent to 3' terminal site and/or 5' terminal site of each of gene sequences contained in the target RNA sequences of the (1).

[5] The stealth RNA gene expression system according to any one of the [1] to [4], wherein the RNA-dependent RNA polymerase encoded by the RNA sequences of the (6) consists of L protein and P protein derived from an RNA virus belonging to a paramyxovirus family,
the protein that regulates activity of the polymerase enzyme encoded by the RNA sequence of the (7) is C protein derived from the same virus as the RNA virus,
the single-stranded RNA binding protein encoded by the RNA sequence of the (8) is NP protein derived from the same virus as the RNA virus, and
all of the RNA sequences of the (3) to (5) are RNA sequences containing a transcription start signal, a transcription termination signal, or a replication origin sequence derived from a genome of the same virus as the RNA virus.

[6] The stealth RNA gene expression system according to the [5], wherein the RNA sequences encoding the L protein, P protein, C protein and NP protein are optimized for human cells, and have a GC content adjusted within a range of 50 to 60%.

[7] The stealth RNA gene expression system according to the [6], wherein the RNA virus belonging to a paramyxovirus family is an RNA virus selected from the group consisting of Sendai virus, human para influenza virus, and Newcastle disease virus.

[8] The stealth RNA gene expression system according to any one of the [1] to [7], wherein the transcription start signal sequences of the (3) are RNA sequences selected from the group of RNA sequences consisting of 3'-UCCCAC-UUUC-5' (SEQ ID NO: 1), 3'-UCCCUAUUUC-5' (SEQ ID NO: 2), 3'-UCCCACUUAC-5' (SEQ ID NO: 3), 3'-UCC-UAAUUUC-5' (SEQ ID NO: 7), and 3'-UGCCCAUCUUC-5' (SEQ ID NO: 9), and the transcription termination signal sequences of the (4) are RNA sequences selected from the group of RNA sequences consisting of 3'-AAUUCUUUUU-5' (SEQ ID NO: 4), 3'-CAUUCUUUUU-5' (SEQ ID NO: 5), 3'-UAUUCUUUUU-5' (SEQ ID NO: 6), and 3'-UUAUUC-UUUUU-5' (SEQ ID NO: 8).

[9] The stealth RNA gene expression system according to any one of the [4] to [8], wherein each of the transcription start signal sequences of the (3) having sequences identical to or different from one another is placed adjacent to 3' terminal site of each of the RNA sequences of the (2) that is placed adjacent to 3' terminal site of each of gene sequences contained in the target RNA sequences of the (1), and each of the transcription termination signal sequences of the (4) is placed adjacent to 5' terminal site of the RNA sequence that is placed adjacent to 5' terminal site of each of gene sequences contained in the target RNA sequences of the (1).

[10] The stealth RNA gene expression system according to any one of the [7] to [9], wherein the RNA sequences containing a replication origins of the (5) contain the following sequences:

```
      (a) an RNA sequence represented by
                              (SEQ ID NO: 11)
   3'-UGGUCUGUUCUC-5'
   or (SEQ ID NO: 12)
   3'-UGGUUUGUUCUC-5', (b) an RNA sequence represented by
                              (SEQ ID NO: 13)
   3'-GAGAACAGACCA-5'
   or (SEQ ID NO: 14)
   3'-GAGAACAAACCA-5',
```

-continued

```
(c) an RNA sequence represented by
                                    (SEQ ID NO: 15)
3'-(CNNNNN)3-5',
and (d) an RNA sequence represented by
                                    (SEQ ID NO: 16)
3'-(NNNNNG)3-5'.
```

[11] The stealth RNA gene expression system according to the [10], wherein the RNA sequence of the (a) is positioned at the 3' terminus of the negative-sense single-stranded RNA (A), and the RNA sequence of the (b) is positioned at the 5' terminus.

[12] The stealth RNA gene expression system according to the [10] or [11], wherein the RNA sequence of the (c) starts at 79th nucleotide from the 3' terminus of the negative-sense single-stranded RNA (A), and the RNA sequence of the (d) starts at 96th nucleotide from the 5' terminus.

[13] The stealth RNA gene expression system according to any one of the [10] to [12], wherein the RNA sequences containing replication origins of the (5) further contain in a position of 97th to 116th nucleotides from the 3' terminus of the negative-sense single-stranded RNA (A), an RNA sequence of (e) 3'-AAAGAAACGACGGUUUCA-5' (SEQ ID NO: 17) or an RNA sequence having the same length of 18 nucleotides as the (e).

[14] A stealth RNA vector including a complex composed of the stealth RNA gene expression system according to any one of the [1] to [13], and having activity of introducing the complex into animal cells, that does not activate an innate immune system.

[15] The stealth RNA vector according to the [14], that forms a virus particle having ability to infect animal cells.

[16] An animal cell transfected with the stealth RNA vector according to the [14] or [15].

[17] A stealth RNA which is a negative-sense single-stranded RNA (A) having RNA sequences of (1) to (8) below, capable of forming a complex that does not activate an innate immune system together with a single-stranded RNA binding protein (B), and an RNA-dependent RNA polymerase (C):

(1) target RNA sequences encoding any given protein or functional RNA, (2) RNA sequences constituting noncoding region(s) that is unrecognizable by an innate immune system, (3) transcription start signal sequences recognized by an RNA-dependent RNA polymerase, (4) transcription termination signal sequences recognized by the polymerase enzyme, (5) RNA sequences containing replication origins recognized by the polymerase enzyme, (6) RNA sequences encoding the polymerase enzyme and having a structure optimized to be unrecognizable by an innate immune system, (7) an RNA sequence encoding a protein that regulates activity of the polymerase enzyme, and having a structure optimized to be unrecognizable by an innate immune system, and (8) an RNA sequence encoding a single-stranded RNA binding protein and having a structure optimized to be unrecognizable by an innate immune system.

The present invention also includes the following modes.

[17'] A stealth RNA which is a negative-sense single-stranded RNA (A) having RNA sequences of (1) to (8) below, capable of forming a complex that does not activate an innate immune system together with a single-stranded RNA binding protein (B), and an RNA-dependent RNA polymerase (C):

(1) target RNA sequences encoding any given protein or functional RNA, (2) RNA sequences constituting noncoding region(s) and derived from mRNA(s) expressed in animal cells, (3) a transcription start signal sequence recognized by the RNA-dependent RNA polymerase, (4) transcription termination signal sequences recognized by the polymerase enzyme, (5) RNA sequences containing replication origins recognized by the polymerase enzyme, (6) an RNA sequence encoding the polymerase enzyme with codons optimized for a biological species from which cells for transfection are derived, (7) an RNA sequence encoding a protein that regulates activity of the polymerase enzyme with codons optimized for a biological species from which cells for transfection are derived, and (8) an RNA sequence encoding the single-stranded RNA binding protein with codons optimized for a biological species from which cells for transfection are derived.

[17" ] A stealth RNA which is a negative-sense single-stranded RNA (A) having RNA sequences of (1) to (8) below, capable of forming a complex that does not activate an innate immune system together with a single-stranded RNA binding protein (B), and an RNA-dependent RNA polymerase (C):

(1) target RNA sequences encoding any given protein or functional RNA, (2) human mRNA-derived RNA sequences constituting noncoding region (s), (3) transcription start signal sequences recognized by the RNA-dependent RNA polymerase, (4) transcription termination signal sequences recognized by the polymerase enzyme, (5) RNA sequences containing replication origins recognized by the polymerase enzyme, (6) RNA sequences encoding the polymerase enzyme with codons optimized for human cells, (7) an RNA sequence encoding a protein that regulates activity of the polymerase enzyme with codons optimized for human cells, and (8) an RNA sequence encoding the single-stranded RNA binding protein with codons optimized for human cells.

[18] The stealth RNA according to the [17], wherein RNA sequences containing replication origins recognized by the RNA-dependent RNA polymerase of the (5) are located at the 3' terminal site and the 5' terminal site of the negative-sense single-stranded RNA (A), and the RNA sequence located at the 3' terminal site and the RNA sequence located at the 5' terminal site include RNA sequences complementary to each other.

[19] The stealth RNA according to the [17] or [18], wherein each of the transcription start signal sequences of the (3) having sequences identical to or different from one another is placed adjacent to 3' terminal site of each of the RNA sequences of the (2) that is placed adjacent to 3' terminal site of each of plural gene sequences contained in the target RNA sequences of the (1), and each of the transcription termination signal sequences of the (4) is placed adjacent to 5' terminal site of the RNA sequence that is placed adjacent to 5' terminal site of each of plural gene sequences contained in the target RNA sequences of the (1).

[20] The stealth RNA according to any one of the [17] to [19], wherein each of the transcription start signal sequences of the (3) having sequences identical to or different from on another is placed adjacent to 3' terminal site of each of the RNA sequences of the (2) that is placed adjacent to 3' terminal site of each of plural gene sequences contained in the target RNA sequences of the (1); each of the transcription termination signal sequences of (4) is placed adjacent to 5' terminal site of the RNA sequence that is placed adjacent to 5' terminal site of each of plural gene sequences contained in the target RNA sequences of the (1); and both of them constitute a cassette structure together with restriction sites located at both ends of the cassette that can be cleaved by plural restriction endonucleases, and plural cassette structures are bound to each other.

[21] A method for reconstituting a stealth RNA gene expression system, comprising the following processes (1) to (5):
  (1) preparing an *Escherichia coli* expressing T7 RNA polymerase;
  (2) introducing into the *Escherichia coli* host of the (1), at least a vector for *Escherichia coli* carrying an RNA encoding an RNA-dependent RNA polymerase and an RNA binding protein, and a vector for *Escherichia coli* for expressing a DNA encoding RNA binding protein, together with the negative-sense single-stranded RNA (A) according to any one of the [1] to [13] to transform the host,
  (3) forming a complex of the negative-sense single-stranded RNA containing exogenous gene RNA expressed by T7 RNA polymerase, and RNA binding protein in the transformed *Escherichia coli* of the (2),
  (4) preparing animal cells in which an RNA-dependent RNA polymerase is expressed, and
  (5) introducing the complex of the negative-sense single-stranded RNA and the RNA binding protein obtained in the (3) into an animal cell host of the (4) to reconstitute a stealth RNA gene expression system composed of the negative-sense single-stranded RNA, and the complex of the RNA binding protein and the RNA-dependent RNA polymerase.

[22] A DNA-based tandem cassette having two cloning sites A and B,
  the tandem cassette being composed of (1) multimerization site A, (2) transcription start signal A, (3) noncoding sequence A1, (4) cloning site A, (5) noncoding region A2, (6) transcription termination signal A, (7) transcription start signal B, (8) noncoding sequence B1, (9) cloning site B, (10) noncoding region B2, (11) transcription termination signal B, and (12) multimerization site B in order from the 5' terminus,
  the multimerization site A of the (1), and multimerization site B of the 812) being DNAs that are identical to or different from each other and each containing a recognition site by restriction endonuclease and/or a recognition site by site-specific recombinase,
  the transcription start signal A of the (2), and transcription start signal B of the (7) being DNAs that are identical to or different from each other and each containing a transcription start signal recognized by the RNA-dependent RNA polymerase when transcribed to RNA,
  the noncoding sequence A1 of the (3), noncoding region A2 of (5), noncoding sequence B1 of the (8), and noncoding region B2 of the (10) being DNAs that are identical to or different from one another and each becoming RNA that is not recognized by an innate immune system of a host cell when transcribed to RNA,
  the cloning site A of the (4), and cloning site B of the (9) being DNAs that are identical to or different from each other and each containing one or more recognition site by restriction endonuclease and/or recognition site by site-specific recombinase,
  the transcription termination signal A of the (6), and transcription termination signal B of the (11) being DNAs that are identical to or different from each other and each containing a transcription termination signal recognized by the RNA-dependent RNA polymerase when transcribed to RNA.

[23] The tandem cassette according to the [22], wherein
  the cloning site A of the (4) contains a recognition site by restriction endonuclease A, and a recognition site by restriction endonuclease C in order from 5' terminal side, and
  the cloning site B of the (9) contains a recognition site by restriction endonuclease D, and a recognition site by restriction endonuclease B in order from 5' terminal side,
  provided that the restriction endonuclease A and the restriction endonuclease D give single-stranded protruding ends of the same sequence, and the restriction endonuclease C and the restriction endonuclease B give single-stranded protruding ends of the same sequence.

[24] The tandem cassette according to the [22] or [23], wherein both of the multimerization site A of the (1), and multimerization site B of the (12) are DNAs containing a recognition site by a restriction endonuclease giving a single-stranded protruding end of any sequence represented by NN or NNN.

[25] The tandem cassette according to any one of the [22] to [24], wherein the noncoding sequence A1 of the (3), noncoding region A2 of the (5), noncoding sequence B1 of the (8), and noncoding region B2 of the (10) are identical to or different from one another and each of them is cDNA corresponding to a partial sequence of RNA sequence derived from mRNA expressed in animal cells, and
  one of human-derived genes identical to or different from each other is inserted into the cloning site A of the (4), and cloning site B of the (9).

Effects of the Invention

Since the stealth RNA gene expression system of the present invention is difficult to be captured by the innate immune system, it has a very low cytotoxicity, and is capable of carrying ten genes and introducing them into various tissue cells, and expressing them persistently for any required period. The wording of "capable of avoiding an innate immune system" or "not recognized by an immune system" used herein means that the introduced gene or the vector or the like used for introduction does not substantially stimulate the innate immunity of the host. Specifically, it means that the interferon β inducibility as an index is 30 or less, preferably 20 or less, more preferably 10 or less, when the expression amount of IFN-β mRNA in normal cells is 1.0.

Also, since the stealth RNA gene expression system functions in cytoplasm, by using the stealth RNA vector including the gene expression system, it is possible to introduce and express the installed genes into cells of peripheral blood not having proliferating ability and have not undergone cell division. Furthermore, a gene expression system with various expression intensity within a maximum of 80 times can be selected, and easy removal is allowed by suppressing activity of the RNA-dependent RNA polymerase if no longer necessary. Therefore, this technique is suited for the object of efficiently reprogramming characteristics of animal cells including human cells by using six or more genes, that has been impossible heretofore.

For example, application of efficiently preparing iPS cells having high quality for clinical use in regenerative medicine under such a severe condition not containing animal derived components (Xeno-free) and not using feeder cells (Feeder-free) using human peripheral blood cells as a material can be conceived. Also, application to the technology called direct reprogramming for creating useful cells such as nerve cells, neural stem cells, stem cells, pancreatic beta cells and the like from human tissue cells (blood, skin, placenta, etc.) using six or more genes is enabled. Further, since the possibility of causing cell death or inflammation is low, application to gene therapy by various genes including giant genes, and application to regenerative medicine by in vivo reprogramming are expected.

Since the stealth RNA gene expression system can carry plural genes simultaneously, and express them in a certain ratio, it is also effective in production of biopharmaceuticals made up of plural subunits. For example, in production of human immunoglobulin G, it is necessary that each subunit is expressed simultaneously in the same cell. It is also required that H-chain and L-chain are expressed simultaneously in a ratio of 1:1 in the same cell in production of human immunoglobulin G, and H-chain, L-chain, and μ-chain are expressed simultaneously in a ratio of 1:1:0.2 in the same cell in production of human immunoglobulin M. The stealth RNA gene expression system can easily satisfy such a requirement.

Further, since the level of gene expression can be varied in the stealth RNA gene expression system, strong gene expression required for production of biopharmaceuticals can be easily realized. Conventional manufacturing process of biopharmaceuticals using animal cells requires the process of establishing a stable cell strain in which the number of copies of the gene integrated into chromosome is amplified, which requires large amounts of time and labor. However, by employing the stealth RNA gene expression system, such labor is no longer required.

Also, the stealth RNA gene expression system is effective for suppressing gene mutation which is problematic in production of biopharmaceuticals. Recently, it has been reported that the primary cause of occurrence of mutation in genome of an RNA virus is cytosolic adenosine deaminase (Adenosine deaminase acting on RNA, ADAR1) (Non-Patent Document 39). Since ADAR1 is induced by activation of the innate immune system, it is possible to suppress mutation of genes in the stealth RNA gene expression system by controlling induction of ADAR1 as low as possible.

The stealth RNA gene expression system is also suited for expression of a drug-discovery target protein made up of plural subunits. For example, for expression of NADPH oxidase (Nox2) which is a drug-discovery target enzyme, it is necessary to simultaneously express six subunits, gp91phox, p22phox, Rac, p47phox, p67phox, and p40phox, and this can be easily realized by the stealth RNA gene expression system. Further, by using the stealth RNA vector, it is possible to express the drug-discovery target protein in target cells such as primary culture vascular endothelial cells and nerve cells for which gene introduction and expression has been difficult because they do not undergo cell division, and it is possible to achieve the object easily.

Further, since the stealth RNA gene expression system and the stealth RNA vector are less likely to cause cell injury or inflammation, they can be applied as a platform of gene therapy for obtaining a therapeutic effect by in vivo gene expression. In particular, since the stealth RNA gene expression system and the stealth RNA vector can carry and persistently express a giant gene such as cDNA of blood coagulation factor VIII which is a product of a gene responsible for hemophiliaA (7053 nucleotides) and cDNA of dystrophin which a product of a gene responsible for Duchenne muscular dystrophy (11058 nucleotides) unlike conventional gene introduction/expression vectors, application as vectors for gene therapy of these diseases is expected.

Further, since the tandem cassette used in a tandem cassette linking method developed for carrying six or more, preferably eight or more exogenous genes on the vector of the present invention is constructed on a DNA basis, the present technique can be widely applied to common DNA expression vectors besides the stealth RNA vector of the present invention.

BRIEF DESCRIPTION OF DRAWINGS

FIG. 20 illustrates structures of stealth RNA gene expression systems having different gene expression levels (indicated by positive-sense RNA sequences).

FIG. 21 illustrates a genome structure and gene expression of a stealth RNA gene expression system in which C gene is deleted or translation of C gene is suppressed.

FIG. 22 illustrates activity of packaging signal of a stealth RNA gene expression system.

DESCRIPTION OF EMBODIMENTS

Figure 1A:
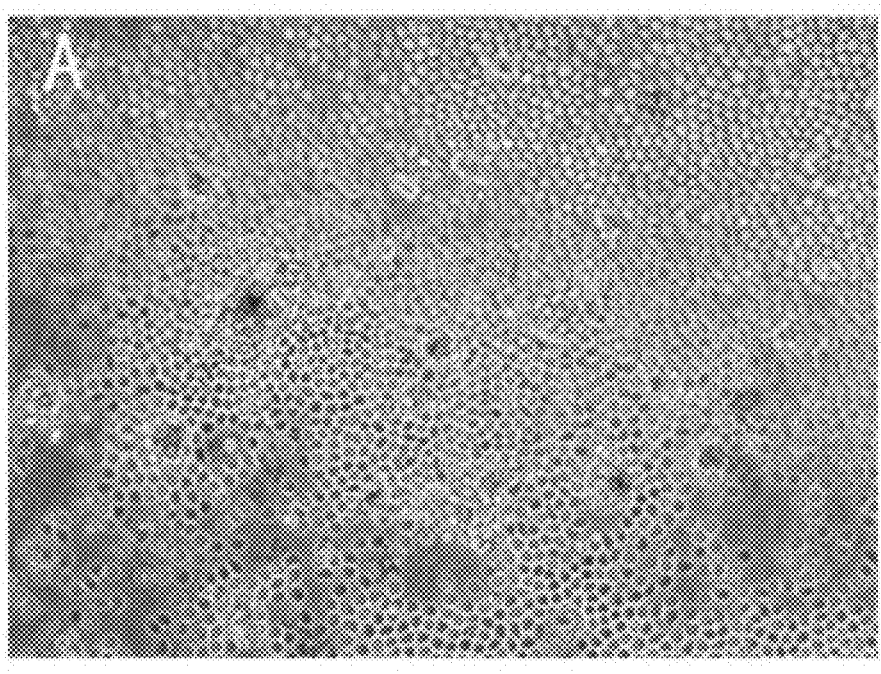
FIG. 1 illustrates a structure of a negative-sense single-stranded RNA molecule prepared by combining RNA derived from mRNA expressed in animal cells, and transcription start signals, transcription termination signals, and replication origins recognized by an RNA-dependent RNA polymerase.
Figure 1B:
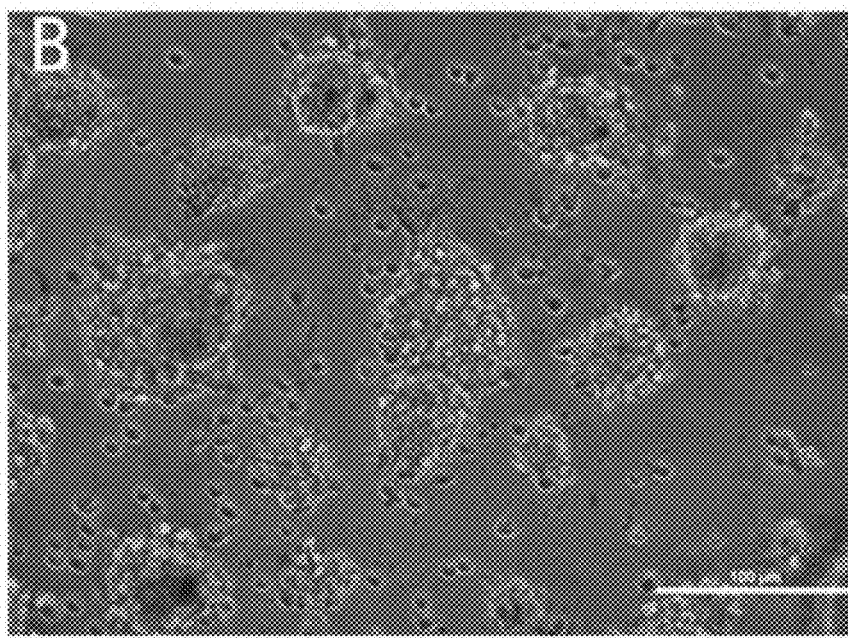
Figure 1C:
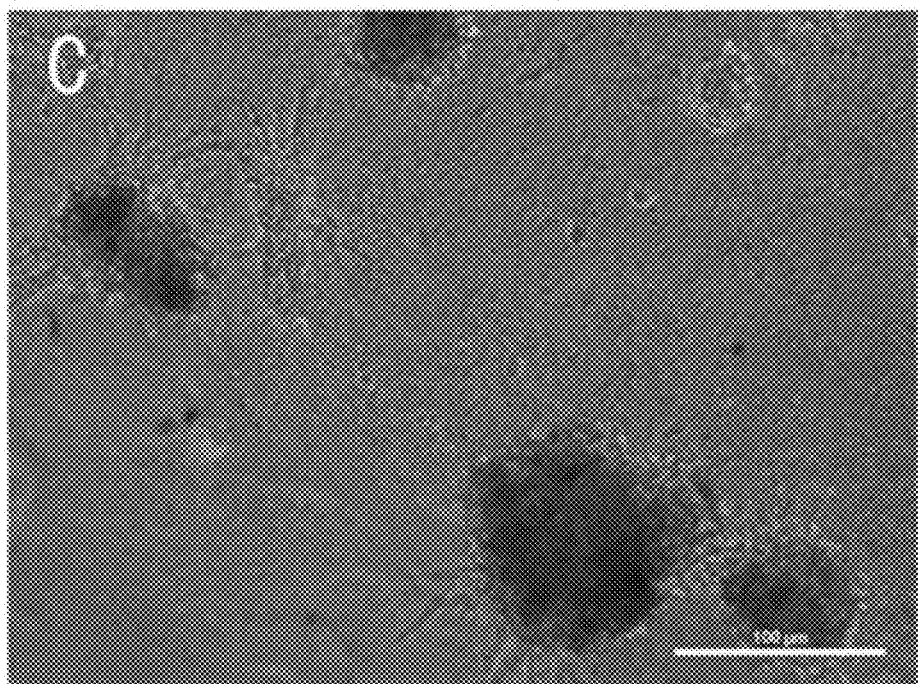
Figure 1D:
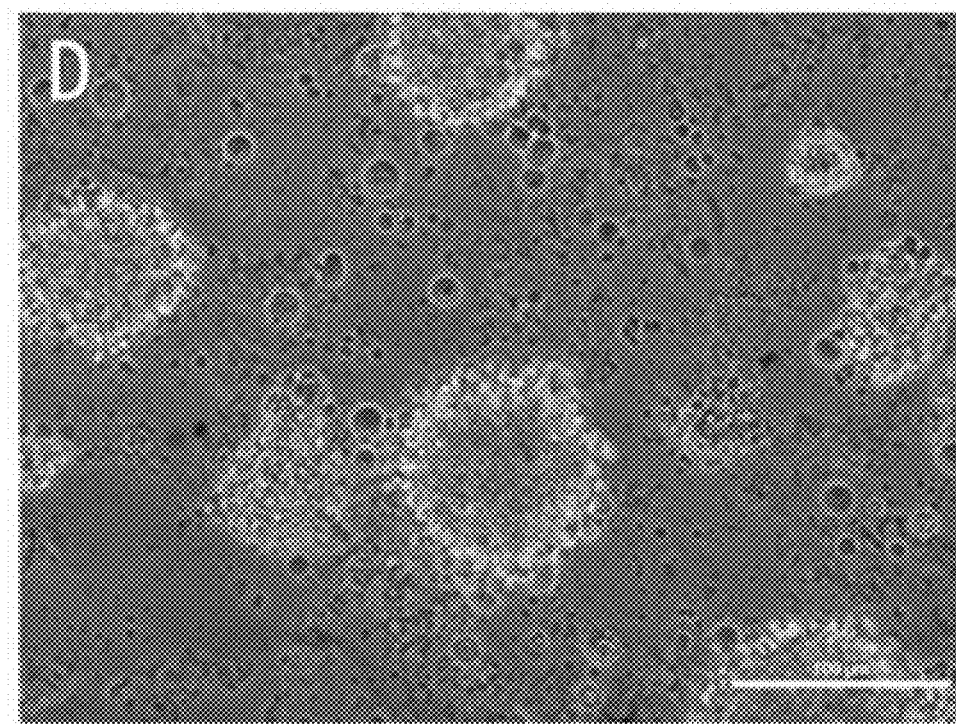

1. Constituents of "stealth RNA gene expression system" of the present invention The RNA molecule used in the present invention is "stealthy", namely it is difficult to be captured by the innate immune system. Therefore, in the present invention, the RNA molecule is referred to as "stealthy RNA", the gene expression system using the RNA as a material is referred to as "stealth RNA gene expression system", the structure including the gene expression system and having the activity of introducing the gene expression system into animal cells is referred to as "stealth RNA vector".

A stealth RNA gene expression system in the present invention is a complex that includes a negative-sense single-stranded RNA (A) containing RNA sequences (1) to (8) below, a single-stranded RNA binding protein (B), and an RNA-dependent RNA polymerase (C), and does not activate an innate immune system. A stealth RNA vector is a particle that contains the complex and has activity of introducing the complex into animal cells. In the present invention, a sequence encoding protein means an RNA sequence of the antisense strand in describing an RNA sequence of negative-sense single-stranded RNA.

(1) target RNA sequences encoding any given protein or functional RNA,
(2) RNA sequences constituting noncoding region(s) that is unrecognizable by an innate immune system,
(3) a transcription start signal sequences recognized by the RNA-dependent RNA polymerase,
(4) transcription termination signal sequences recognized by the polymerase enzyme,
(5) RNA sequences containing replication origins recognized by the polymerase enzyme,
(6) RNA sequences encoding the polymerase enzyme and having a structure optimized to be unrecognizable by an innate immune system,
(7) an RNA sequence encoding a protein that regulates activity of the polymerase enzyme and having a structure optimized to be unrecognizable by an innate immune system, and
(8) an RNA sequence encoding the single-stranded RNA binding protein and having a structure optimized to be unrecognizable by an innate immune system.

(Hereinafter, also referred to as gene RNA or simply referred to as gene.)

Here, each of the RNA sequences of (2) preferably has a length of 5 to 49 nucleotides, and is placed as a noncoding region on 3' terminal side and 5' terminal side of each of the introduced exogenous gene RNAs (1).

While the stealth RNA gene expression system functions even when the introduced exogenous gene RNA of (1) contains less than six genes, for example, one to five genes, or contains a total nucleotide length of less than 5,000 nucleotides, the RNA gene expression system of the present invention exerts a significant effect in particular, when the exogenous gene RNA contains six or more, preferably eight or more, more preferably ten or more genes, or contains RNA of a total nucleotide length of 5,000 nucleotides, preferably 8,000 nucleotides, and more preferably 10,000 nucleotides.

In this description, the wording "gene or gene material" includes a negative-sense RNA or cDNA, and a positive-sense RNA or cDNA that is complementary to the same. In other words, those capable of synthesizing any of the gene or gene material by transcription or reverse transcription are also included in the present invention.

2. Constituents of Stealth RNA Expression System of the Present Invention 2-1. Preparation of Tandem Cassette for Introduction of Exogenous Gene RNA The exogenous gene RNA in the stealth RNA gene expression system of the present invention have "(2) RNA sequences that are not recognized by an innate immune system" within 3' terminal and 5' terminal noncoding regions thereof, wherein each of the RNA sequences is identical to or different from each other and having a length of 5 to 49 nucleotide, and can be prepared as a cassette by providing a "transcription start signal" of (3) and a "transcription termination signal" of (4) on further outer 3' terminal and 5' terminal site respectively, and providing multimerization sites at both outermost terminals.

The negative-sense single-stranded RNA used in the stealth RNA gene expression system of the present invention can be easily constructed by using the DNA-based tandem cassette shown below.

The tandem cassette of the present invention is composed of (1) multimerization site A, (2) transcription start signal A, (3) noncoding sequence A1, (4) cloning site A, (5) noncoding region A2, (6) transcription termination signal A, (7) transcription start signal B, (8) noncoding sequence B1, (9) cloning site B, (10) noncoding region B2, (11) transcription termination signal B, and (12) multimerization site B in order from the 5' terminus. The tandem cassette is schematically shown in the lower diagram of FIG. 7.

The multimerization sites A and B may be identical to or different from each other, and any sequence can be used as long as it can be used for multimerization of the cassette or for binding with other nucleic acid. Preferred examples of the multimerization site include a restriction site by a restriction endonuclease, and a recognition site by a site-specific recombinase. Examples of preferred restriction endonucleases include SapI, BbsI, BbvI, BcoDI, BfuAI, BsaI, BsmBI, BsmFI, BtgZI, EarI, FokI, HgaI, and SfaNI having a characteristic of generating a single-stranded protruding end structure having any sequence indicated, for example, by NN or NNN on the terminus generated by digestion. As other preferred examples, AlwNI, BglI, BstAPI, BstXI, DraIII, SfiI and so on having an indefinite sequence within the recognition site are recited. When homologous recombination is utilized, sequences such as attB1 and attB2 can be recited as a recognition site by a recombinase. Further, when Gibson Assembly System (New England Biolabs, Inc) is utilized, any sequence of 15 or more nucleotides can be used as a multimerization site providing that it has the same sequence as the overlapping sequence at an end of other tandem cassette which is to be a counter part of linkage.

The transcription start signals A and B can be identical to or different from each other, and can be any sequence as long as they are functional as transcription start signals recognized by an RNA-dependent RNA polymerase when they are transcribed to RNA. Examples of the transcription start signals recognized by an RNA-dependent RNA polymerase will be specifically described in the following paragraphs. Preferably, the sequences represented by SEQ ID NOs: 1 to 3 can be recited.

The noncoding sequences A1, A2, B1 and B2 can be identical to or different from one another. Any sequence is acceptable as long as the sequence gives "RNA that is not recognized by an innate immune system" defined in the above when transcribed to RNA, and as a preferred example, sequences having a length of 5 to 49 nucleotides and shown in Table 1 can be recited.

The cloning sites A and B can be any sequence that allows insertion of a desired exogenous gene. Preferably, one cloning site contains one or two or more recognition sites by restriction endonucleases, or contains one or two or more recognition sites by site-specific recombinases. Preferred examples of the cloning site include a sequence containing Acc65I recognition site and SalI recognition site, a sequence containing Acc65I recognition site and XhoI recognition site, a sequence containing BsiWI recognition site and SalI recognition site, and a sequence containing BsiWI recognition site and XhoI recognition site.

The transcription termination signals A and B can be identical to or different from each other, and can be any sequences as long as they are functional as transcription termination signals recognized by an RNA-dependent RNA polymerase when they are transcribed into RNA. Examples of the transcription termination signals recognized by an RNA-dependent RNA polymerase will be specifically described in the following paragraphs. Preferably, the sequences represented by SEQ ID NOs: 4 to 6 can be recited.

In the one tandem cassette, at least two exogenous genes can be inserted. A cassette multimer formed of five linked cassettes each having insertion of two exogenous genes carries ten exogenous genes. In the following Examples, DNA fragments carrying four, six, or ten exogenous genes are prepared by utilizing multimerization of tandem cassettes as described above, and sub-cloned into plasmids. Further, by combining with RNA-dependent RNA polymerase genes derived from virus, and an RNA binding protein gene, an RNA expression system desired in the present invention is constructed.

2-2. RNA-Dependent RNA Polymerase, and Transcription Start Signal and Transcription Termination Signal Recognized by the Polymerase Enzyme Preferably, the "RNA-dependent RNA polymerase", and the transcription start signal and the transcription termination signal recognized by the polymerase enzyme are selected from sequences derived from the same negative-sense RNA virus, and are typically sequences derived from genome of a virus belonging to the paramyxovirus family. Since the combination of "RNA-dependent RNA polymerase" of genome of a virus belonging to the paramyxovirus family, "transcription start signal recognized by the polymerase enzyme", and "transcription termination signal recognized by the polymerase enzyme" has the same basic structure, combinations of sequences derived from any virus can be used.

In Examples of the present invention, a combination of L protein (large subunit of RNA polymerase, PolL) and P protein (small subunit of RNA polymerase, PolS) derived from Sendai virus was selected as "RNA-dependent RNA polymerase", "3'-UCCCACUUUC-5' (SEQ ID NO: 1)" was selected as "RNA which is a transcription start signal recognized by an RNA-dependent RNA polymerase", "3'-AAUUCUUUUU-5' (SEQ ID NO: 4)" was selected as "RNA which is a transcription termination signal recognized by an RNA-dependent RNA polymerase", and the transcription start signal and the transcription termination signal were placed respectively on 3' side and 5' side of each gene (FIG. 1). Then C protein of Sendai virus (C) is used as "protein that regulates activity of RNA polymerase", and NP protein of Sendai virus (N) is used as "single-stranded RNA binding protein".

In the technique disclosed in the present description, since RNA is used mainly in the form of a negative-sense single-stranded RNA, an RNA sequence is disclosed from 3' terminal side as sequence information of a negative strand unless otherwise noted. However, sequence information in the sequencing listings that forms part of the present description is described from 5' terminal side according to the guidelines.

When a combination of L protein and P protein of Sendai virus is selected as "RNA-dependent RNA polymerase", as a transcription start signal, besides "3'-UCCCACUUUC-5' (SEQ ID NO: 1)", "3'-UCCCUAUUUC-5' (SEQ ID NO: 2)", and "3'-UCCCACUUAC-5' (SEQ ID NO: 3)", RNA having an equivalent function as these sequences can be used. Similarly, also as a transcription termination signal, besides "3'-AAUUCUUUUU-5' (SEQ ID NO: 4)" "3'-CAUUCUUUUU-5' (SEQ ID NO: 5)", and "3'-UAUUC-UUUUU-5' (SEQ ID NO: 6)", RNA having an equivalent function as these sequences can be used. When a combination of L protein and P protein of human para influenza viruses type 3 is selected as "RNA-dependent RNA polymerase", "3'-UCCUAAUUUC-5' (SEQ ID NO: 7)" or an RNA having an equivalent function can be used as a transcription start signal, and "3'-UUAUUCUUUUU-5' (SEQ ID NO: 8)" or an RNA having an equivalent function can be used as a transcription termination signal. Further, when a combination of L protein and P protein of Newcastle disease virus is selected as "RNA-dependent RNA polymerase", "3'-UGCCCAUCUUC-5' (SEQ ID NO: 9)" or an RNA having an equivalent function can be used as a transcription start signal, and "3'-AAUCUUUUUU-5' (SEQ ID NO: 10)" or an RNA having an equivalent function can be used as a transcription termination signal.

2-3. Elements for Replication Function of Stealth RNA Gene Expression System of the Present Invention Essential elements for the replication function of the stealth RNA gene expression system of the present invention include replication origins recognized by an RNA-dependent RNA polymerase, and sequences having the structure of $(CNNNNN)_3$-on 3' terminal site, and $(NNNNNG)_3$-on 5' terminal site.

Figure 2A:
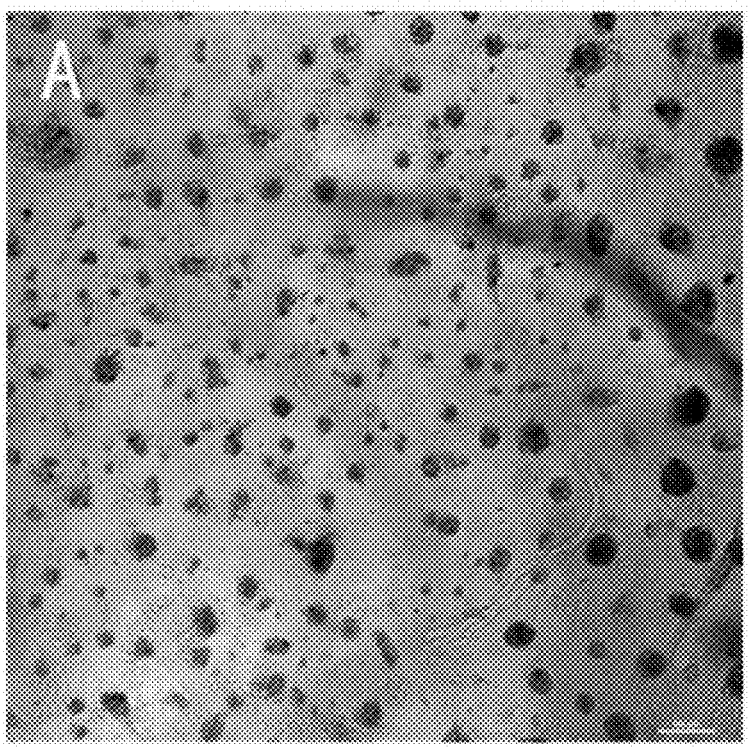
FIG. 2 illustrates structures of 3' terminus and 5' terminus of a nucleic acid required for replication of a negative-sense single-stranded RNA molecule.
Figure 2B:
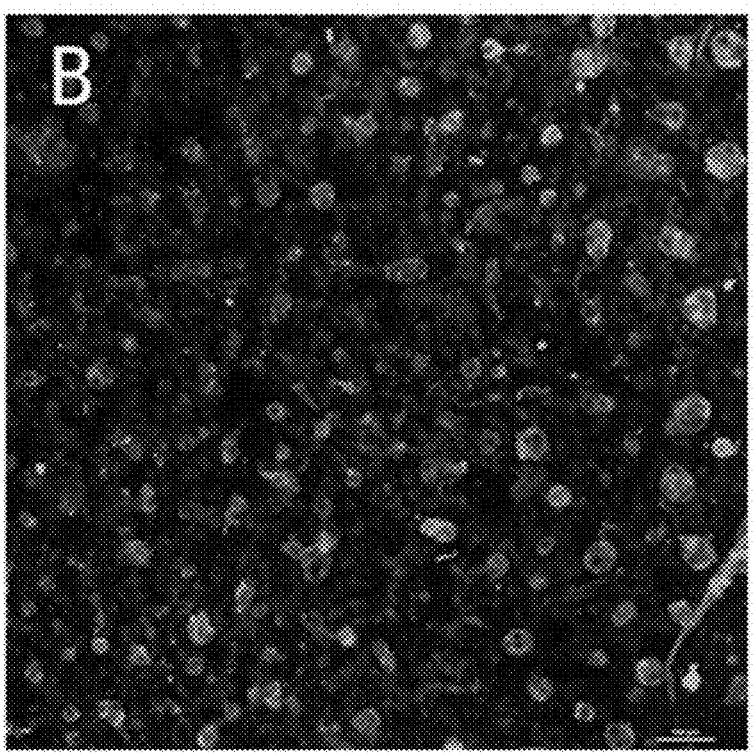
Figure 2C:
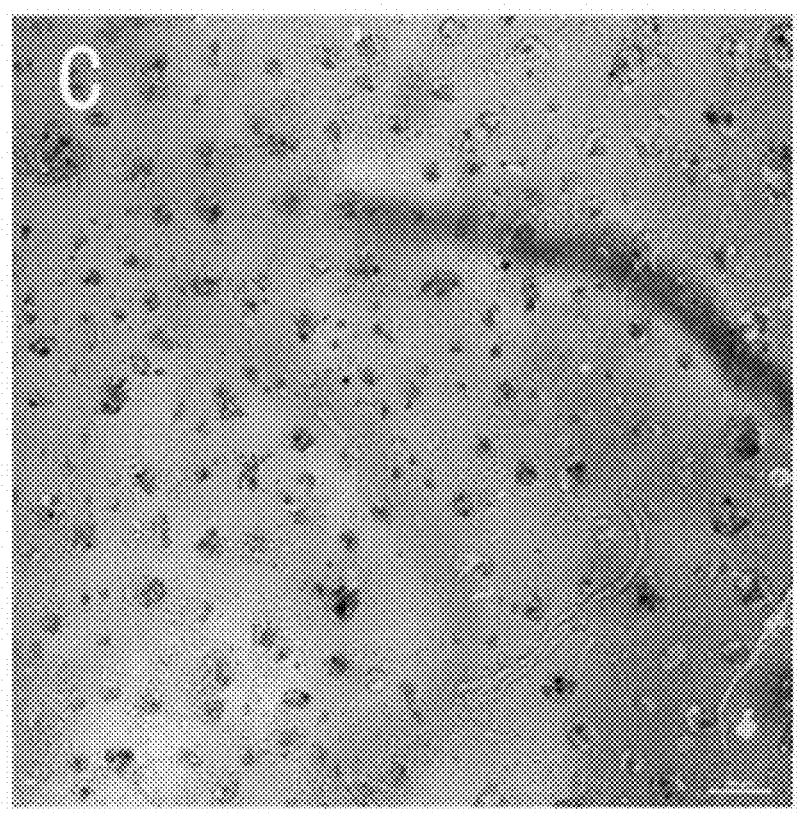
Figure 3A:
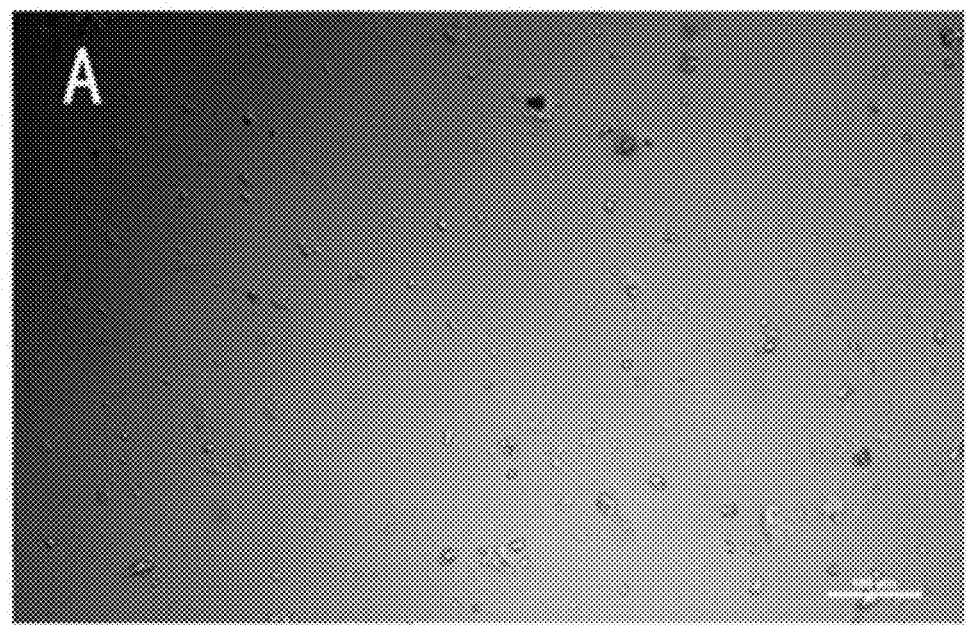
FIG. 3 illustrates a structure of 3' terminus of a nucleic acid required for replication of a negative-sense single-stranded RNA molecule.
Figure 3B:
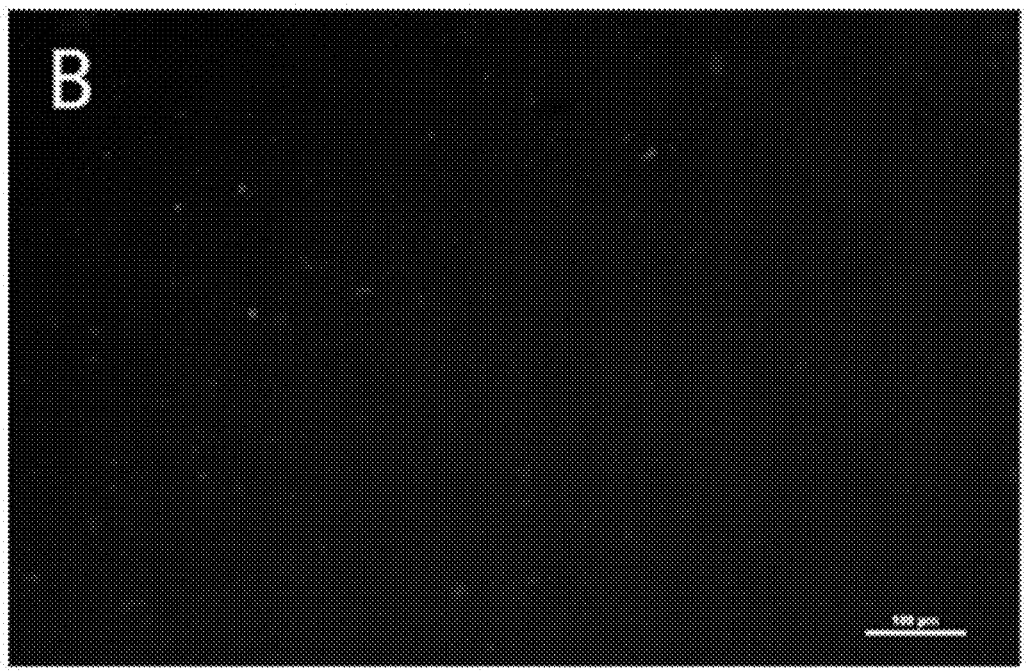
Figure 3C:
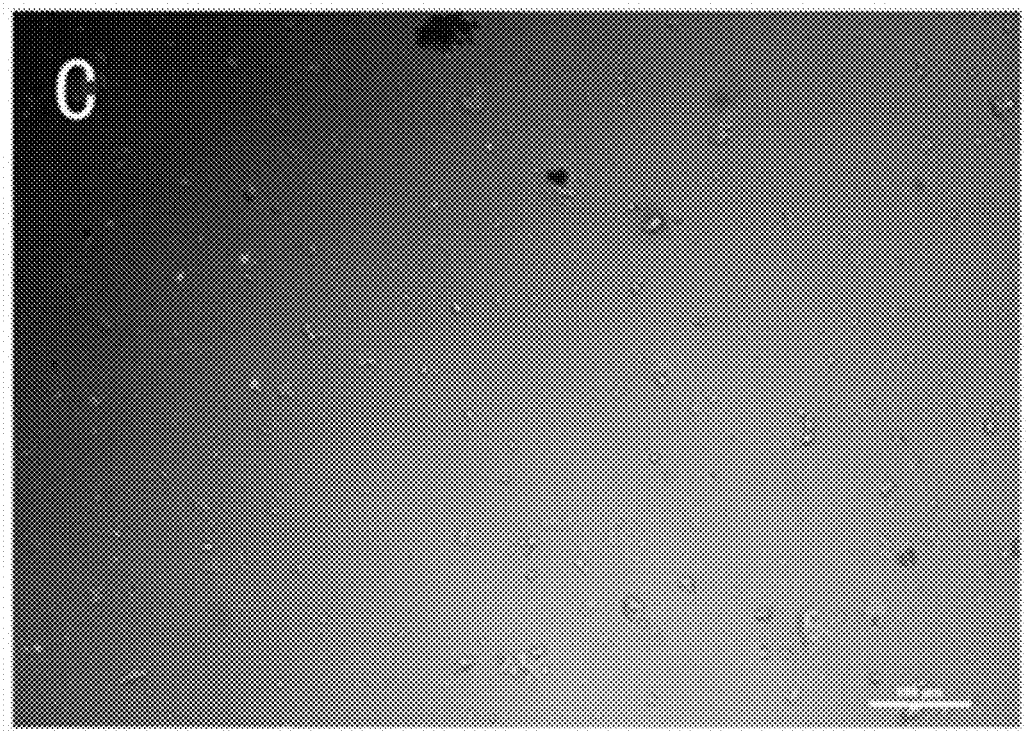
Figure 4:
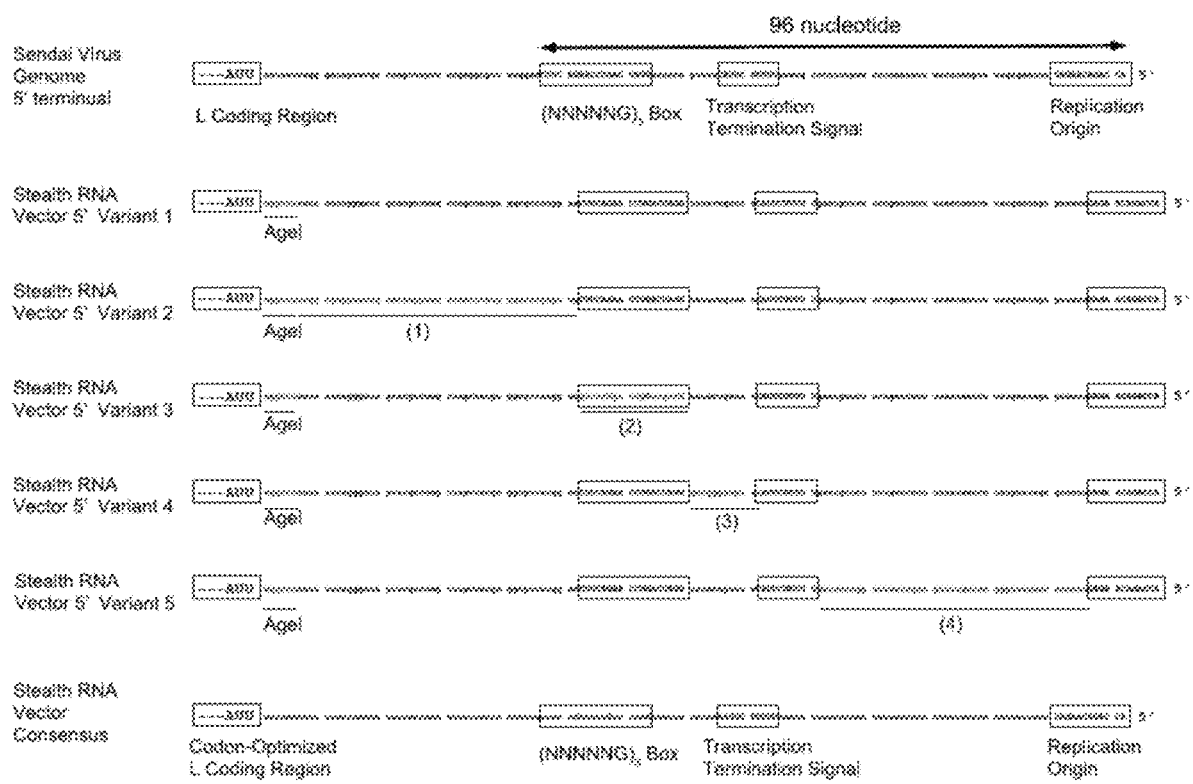
FIG. 4 illustrates a structure of 5' terminus of nucleic acid required for replication of a negative-sense single-stranded RNA molecule.

In Examples of the present invention, since a combination of L protein and P protein of Sendai virus was selected as "RNA-dependent RNA polymerase", RNA of 114 nucleotides existing at 3' terminus of the genome of Sendai virus, and RNA of 96 nucleotides existing at 5' terminus of the genome of Sendai virus were selected as "RNA containing a replication origin recognized by an RNA-dependent RNA polymerase". Among these structures, those essential for the replication function of the stealth RNA gene expression system are as follows (FIG. 2, FIG. 3, FIG. 4).

(1) "3'-UGGUCUGUUCUC-5' (SEQ ID NO: 11)" existing at 3' terminus of the genome or an RNA sequence of 12 nucleotides having an equivalent function (for example, "3'-UGGUUUGUUCUC-5' (SEQ ID NO: 12)"), (2) "3'-GAGAACAGACCA-5' (SEQ ID NO: 13)" existing at 5' terminus of the genome or an RNA sequence of 12 nucleotides having an equivalent function (for example, "3'-GAGAACAAACCA-5' (SEQ ID NO: 14)"), (3) an RNA sequence of 18 nucleotides having a structure of "3'-$(CNNNNN)_3$-5' (SEQ ID NO: 15)" starting from the 79th nucleotide from 3' terminus of the genome, and (4) an RNA sequence of 18 nucleotides having a structure of "3'-$(NNNNNG)_3$-5' (SEQ ID NO: 16)" starting from the 96th nucleotide from 5' terminus of the genome.

Among these, (1) and (2) are considered as replication origins recognized by an RNA-dependent RNA polymerase because they are mutually complementary sequences, and then 3' terminus of the genome RNA and 3' terminus of the anti genome RNA (RNA complementary to the genome RNA) are identical. While the functions of (3) and (4) are unknown, it is known that they are the sequences essential for replication of single-stranded RNA by an RNA-dependent RNA polymerase (Non-Patent Document 42).

2-4. Packaging Signal Region Essential for Particulation in Negative-Sense Single-Stranded RNA In the present invention, the present inventors first identified the region spanning from the 97th nucleotide to the 114th nucleotide of 3' terminus of the genome as a region that is a packaging signal for particle formation in the negative-sense single-stranded RNA.

As shown in Example 18 (FIG. 22), when the whole of the region (indicated as "sequence D") was deleted, the efficiency of particle formation of the stealth RNA vector was significantly deteriorated although gene expression in the packaging cell was not influenced.

This indicates that this sequence of 18 nucleotides, or the region having a length of 18 nucleotides or apart thereof is a sequence or region that is essential for incorporation into a virus-like particle.

Then the present inventors replaced this sequence of 18 nucleotides with a partial sequence that is arbitrarily selected from partial sequences of mRNA derived from Housekeeping gene recited in (Table 1) ((5) of FIG. 3, SEQ ID NO: 75), and confirmed that the efficiency of particle formation was not changed.

On the basis of this result, it is considered that the region having a length of 18 nucleotides from the 97th to 114th nucleotides from 3' terminus of the genome or a region having a partial length thereof is essential for packaging for particle formation in the negative-sense single-stranded RNA. In other words, it can be concluded that the region is "packaging signal region" that is not essential for transcription and replication of the negative-sense single-stranded RNA as a template, but is essential for incorporation of the stealth RNA gene expression system into a virus-like particle.

(5) RNA having a length of 18 nucleotides, corresponding to "3'-AAAGAAACGACGGUUUCA-5' (SEQ ID NO: 17)" from the 97th to 114th nucleotides from 3' terminus of the genome, or any RNA having a length of at least consecutive 8 or more nucleotides, preferably 10 or more nucleotides, more preferably 15 or more nucleotides thereof.

The possibility that the stealth RNA gene expression system lacking the length of 18 nucleotides or a partial region thereof of the above (5) leads production of a virus-like particle containing the stealth RNA gene expression system is very low even if the host cells are infected with a homogeneous or heterogeneous virus.

Thus, the region having a length of 18 nucleotides or a partial region thereof is an essential region when the stealth RNA gene expression system of the present invention is prepared as an infectious particle, and used as a stealth RNA gene expression vector, however, the region is contrarily a sequence that should be eliminated for biopharmaceutical production where it is desired to ultimately eliminate contamination with virus-like particles and to ensure the safety.

2-5. Construction of Template for Gene Expression of Negative-Sense Single-Stranded RNA It is known that an RNA molecule carrying a combination of "RNA which is a transcription start signal recognized by an RNA-dependent RNA polymerase", "RNA which is a transcription termination signal recognized by an RNA-dependent RNA polymerase" and "RNAs containing a replication origin recognized by an RNA-dependent RNA polymerase" existing at 3' terminus and 5' terminus of a negative-sense single-stranded RNA, together with any exogenous gene between the transcription start signal and the transcription termination signal serves as a template for transcription or replication in the presence of essential factors such as an RNA-dependent RNA polymerase derived from a virus supplied in trans (Non-Patent Document 43, Non-Patent Document 44, and Non-Patent Document 45). For example, it is demonstrated that a negative-sense single-stranded RNA having the aforementioned structure carrying a combination of a transcription start signal, a transcription termination signal and replication origins derived from Sendai virus, and Chloramphenicol acetyl transferase (CAT) gene of *Escherichia coli* as a exogenous gene serves as a template for transcription and replication in a cell infected with Sendai virus to produce CAT (Non-Patent Document 43, and Non-Patent Document 44). Also it is indicated that a negative-sense single-stranded RNA having an equivalent structure is persistently replicated in cells in which NP (single-stranded RNA binding protein), P (small subunit of RNA-dependent RNA polymerase) and L (large subunit of RNA-dependent RNA polymerase) proteins of Sendai virus are stably expressed (Non-Patent Document 45).

These reports indicate that the negative-sense single-stranded RNA prepared in the present invention serves as a template for gene expression, however, when such a technique is used as it is, the activity of transcription or replication depends on the NP, P, and L proteins supplied in trans from the cells containing genes of the virus, so that a general gene expression system enabling gene expression in any cell is not obtained. Thus, the present inventors attempted to carry genes required for transcription and replication on an RNA molecule having the structure shown in the above section 2-3. (FIG. 1) and formed of components that are not recognized by an innate immune system.

3. Findings Regarding Avoidance of Activation of Innate Immune System (PAMP) in Animal Cells 3-1. Regarding PAMP of Virus-Derived RNA An innate immune system possessed by an animal cell is activated by recognition of a "molecular pattern characteristic of pathogenic microorganism (Pathogen-associated molecular pattern, PAMP)" existing in genome RNA of a virus that has been entered inside the cell, or mRNA of a virus gene. The structure of PAMP has been identified in hepatitis C virus and human immunodeficiency virus. In hepatitis C virus, it has been reported that a uridine-rich sequence positioned in a noncoding region at 3' terminal of the genome is PAMP (Non-Patent Document 35). Meanwhile, in a human immunodeficiency virus, it has been reported that the region having a high adenine content existing in mRNA transcribed from three genes of Gag, Pol, and Env is PAMP (Non-Patent Document 36). Besides the above, in Sendai virus, strong PAMP activity is detected in a long-chain RNA fraction exceeding 600 nucleotides existing in infected cells (Non-Patent Document 37), and the existence of a high secondary structure that potentially functions as PAMP is known also in a noncoding region of each gene of F, HN and L (Non-Patent Document 38). Thus, it is expected that most of virus-derived RNAs contain PAMP.

3-2. Investigation of Optimization of Virus-Derived RNA

The attempt to disrupt the PAMP structure by optimizing codons of the region encoding a protein in the RNA virus genome for human cells, and thus to avoid the activation of the innate immune system has been often conducted heretofore. For example, it has been reported that since PAMP exists in each mRNA transcribed from each of Gag, Pol, and Env genes of human immunodeficiency virus (HIV), each gene induces interferon when it is expressed as it is in animal cells, whereas interferon induction is suppressed in each of Gag, Pol, and Env proteins that are optimized for human cells and expressed (Non-Patent Document 36). Also in a simian immunodeficiency virus (SIV), likewise in HIV, it is known that PAMP exists in each mRNA of Gag, Pol, and Env, and by optimizing codons in the region containing PAMP in each gene for human cells, the interferon inducibility decreases (Non-Patent Document 48). However, the interferon inducibility of SIV little changes only by optimization of codons in the region containing PAMP in Pol gene in the SIV genome sequence. In light of this, codons of the region containing PAMP of Gag gene were also optimized in addition to optimization of Pol gene, and this resulted in reduction in the replicability of the virus to 1% or less, and significant impairment in functions of transcription and replication of the virus (Non-Patent Document 48). This result not only reveals that Pol gene or Gag gene of SIV encodes Pol protein or Gag protein, but also reveals that the information required for the function of transcription or replication of the virus exists in the nucleic acid sequence itself that encodes the protein.

Also for the region containing PAMP in a noncoding region of 3' terminus of the genome of hepatitis C virus, there is a report that the virus replicability is impaired when the region is disrupted (Non-Patent Document 82, and Non-Patent Document 83).

These results indicate that the "region containing PAMP" in RNA virus genome is very likely to be also a region essential for the functions such as replication of the virus.

Thus, since a universal method for removing the structure having a function of PAMP from genome nucleic acid without impairing the function of the RNA virus is not known, application of the technique for optimizing codons of the region containing PAMP in the virus RNA for human cells to an RNA virus vector contrarily leads a negative result.

3-3. Utilization of Virus Derived Innate Immunity Inhibitory Factor

In conventional techniques using genome of an RNA virus or a synthetic RNA as a platform for gene expression, the cytotoxicity is weakened by inhibiting activation of the innate immune system by PAMP by the action of the factor competing the innate immune system possessed by various viruses, rather than by elucidating the structure recognized as PAMP and removing the structure. For example, B18R protein, which is used as an essential constituent in Non-Patent Document 26 and Non-Patent Document 27, is an interferon binding protein encoded by genomic DNA of vaccinia virus, and has a function of inhibiting activation of the innate immune system by inhibiting the activity of interferon.

Further, in the vectors based on Sendai virus described in Patent Document 3, Patent Document 4, and Non-Patent Document 7, mutation of an RNA-dependent RNA polymerase (L protein and P protein), and expression of V protein derived from Sendai virus serve to suppress the innate immune system. V protein is one of proteins produced from mRNA transcribed from P gene region of Sendai virus, and has an N-terminal region (317 amino acid residues) common to that of P protein, and a basic C-terminal region (67 amino acid residues) having a structure peculiar to V protein (Non-Patent Document 39). V protein inhibits activation of the innate immune system through inhibition of a transcription factor IRF-3 (Non-Patent Document 40). It is known that in a V protein-defective Sendai virus prepared by artificially introducing mutation into a base sequence of P gene, the function of suppressing activation of the innate immune system is lost, and the virus is easily eliminated from the infected individual (Non-Patent Document 40, and Non-Patent Document 41).

In the case of using a virus derived innate immunity inhibitory factor together as described above, there arises a concern in safety that the innate immune system cannot be activated even when the cells into which the exogenous gene is introduced are infected with other species of pathogenic microorganism. For example, in cells stably retaining genome of the Sendai virus vector, V protein is constantly expressed. Thus, when this vector is used in tissue cells of a living body, there is a possibility that the innate immune system cannot be activated even when the cells are infected with other virus. Therefore, a technique of avoiding activation of an innate immune system by a method not relying on suppression of the innate immune system by a virus derived factor is desired.

4. Techniques for Avoiding PAMP in RNA Gene Expression System of the Present Invention 4-1. "RNA that is not Recognized by an Innate Immune System" found within noncoding region sequence The key of the present invention is selection of RNA capable of avoiding activation of an innate immune system possessed by animal cells. As described above, the wording "avoiding activation of an innate immune system" used in the present invention means that the interferon β inducibility as an index is 30 or less, preferably 20 or less, more preferably 10 or less, when the expression amount of IFN-β mRNA in normal cells is 1.0.

Thus, in the present invention, as a material for "RNA that is not recognized by an innate immune system", the present inventors decided to use RNA sequences derived from mRNA expressed in animal cells such as human cells, and selected mRNA derived from House-keeping genes that are expressed in a wide variety of human cells. The mRNA is expressed inmost of human cells in relatively large quantity, and does not contain a motif recognized by the human innate immune system. Further, from noncoding regions in the mRNAs that do not encode protein, RNAs each having a length of 5 nucleotides to 49 nucleotides that do not form a complicated secondary structure were selected (Table 1), and placed in a noncoding region on 5' side and in a noncoding region of 3' side of each gene installed on the vector (FIG. 1).

All of the partial sequences of mRNA derived from House-keeping gene recited below (Table 1) can be used as particularly preferred sequences among "RNA sequences derived from mRNA expressed in animal cells" of "RNA that is not recognized by an innate immune system" in the noncoding region sequence of the present invention. As other examples of such preferred sequences, partial sequences of RNA sequences derived from mRNA of genes that are expressed in large quantity in a living body such as albumin gene can also be preferably used.

As described above, in Examples of the present invention, noncoding region sequences derived from mRNA expressed in human cells are selected, and partial sequences thereof were used in consideration of application to regenerative medicine, however, "RNA that is not recognized by an innate immune system" is not limited to the sequences derived from noncoding region sequences derived from mRNA recited in Examples or (Table 1). For example, in OptimumGen Gene Design System (Patent Document 7, GenScript USA Inc.), partial sequences of a noncoding sequence possessed by human mRNA appropriately selected from a group of human mRNAs that are highly expressed in human, employed for determining a standard CAI value can be used. Besides these, human RNAs other than mRNA, RNAs expressed in cells of other animal species, and non-native synthetic RNAs can also be selected as long as they are not recognized by the innate immune system of the host cells in which the vector is used.

TABLE 1

| Position of cassette | Position in cassette | Animal species from which sequence is derived | Name (abbreviated name) of gene from which sequence is derived | Length (nucleotides) | GenBank accession No. | Sequence ID No. |
|---|---|---|---|---|---|---|
| #1 | 3' | Human | glyceraldehyde-3-phosphate dehydrogenase | 5 | NM_002046 | 18 |
| #1 | 5' | Human | eukaryotic translation elongation factor 1 alpha 1 | 27 | NM_001402 | 19 |
| #2 | 3' | Human | hydroxymethylbilane synthase | 24 | NM_000190 | 20 |
| #2 | 5' | Human | glyceraldehyde-3-phosphate dehydrogenase | 30 | NM_002046 | 21 |
| #3 | 3' | Human | glyceraldehyde-3-phosphate dehydrogenase | 15 | NM_002046 | 22 |
| #3 | 5' | Human | mitochondrial ribosomal protein L32 | 29 | NM_031903 | 23 |
| #4 | 3' | Human | β-actin | 30 | NM_001101 | 24 |
| #4 | 5' | Human | β-actin | 29 | NM_001101 | 25 |
| #5 | 3' | Human | phosphoglycerate kinase 1 | 29 | NM_000291 | 26 |
| #5 | 5' | Human | phosphoglycerate kinase 1 | 29 | NM_000291 | 27 |
| #6 | 3' | Human | peptidylprolyl isomerase A | 29 | NM_021130 | 28 |
| #6 | 5' | Human | peptidylprolyl isomerase A | 29 | NM_021130 | 29 |
| #7 | 3' | Human | tubulin, α-1b | 29 | NM_006082 | 30 |
| #7 | 5' | Human | tubulin, β-1 | 29 | NM_030773 | 31 |
| #8 | 3' | Human | transferrin receptor | 29 | NM_003234 | 32 |
| #8 | 5' | Human | eukaryotic translation elongation factor 2 | 29 | NM_001961 | 33 |
| #9 | 3' | Human | ubiquitin C | 29 | NM_021009 | 34 |
| #9 | 5' | Human | transferrin receptor | 29 | NM_003234 | 35 |
| #10 | 3' | Human | TATA box binding protein | 29 | NM_003194 | 36 |
| #10 | 5' | Human | lamin B2 | 29 | NM_032737 | 37 |
| #11 | 3' | Human | α-actin, cardiac muscle 1 | 29 | NM_005159 | 38 |
| #11 | 5' | Human | α-actin, cardiac muscle 1 | 29 | NM_005159 | 39 |
| #12 | 3' | Human | tubulin, β-1 | 29 | NM_030773 | 40 |
| #12 | 5' | Human | tubulin, β-1 | 29 | NM_030773 | 41 |
| #13 | 3' | Human | 1-acylglycerol-3-phosphate O-acyltransferase 1 | 29 | NM_006411 | 42 |
| #13 | 5' | Human | 1-acylglycerol-3-phosphate O-acyltransferase 1 | 21 | NM_006411 | 43 |
| #14 | 3' | Human | tubulin, α-1b | 13 | NM_006082 | 44 |
| #14 | 5' | Human | glyceraldehyde-3-phosphate dehydrogenase | 46 | NM_002046 | 45 |
| | | Human | ATP synthase, mitochondrial Fo complex subunit B1 | 13 | NM_001688 | 73 |
| | | Human | ATP synthase, mitochondrial Fo complex subunit B1 | 18 | NM_001688 | 74 |
| | | Human | peptidylprolyl isomerase A (cyclophilin A) | 18 | NM_021130 | 75 |
| | | Human | ribosomal protein, large, P1 (RPLP1) | 12 | NM_001003 | 76 |

4-2. Replacement with "RNA that is not Recognized by an Innate Immune System" in 3' Terminal and 5' Terminal Regions of RNA Vector Genome As shown in FIG. 2, FIG. 3 and FIG. 4, among the genome RNA sequences constituting the stealth RNA vector of the present invention, the 3' terminal region and the 5' terminal region include sequence regions of which function is unknown besides the essential constituents involved in transcription, replication and the like shown in the above sections 2-2. to 2-3. and so on, and these sequences include regions that can be replaced with "RNA that is not recognized by an innate immune system" such as partial sequences of mRNA derived from House-keeping gene in plural sites.

For example, as shown in Example of FIG. 3, among the structures existing in 3' terminus of native virus genome, the regions of (1) to (6) can be replaced with other non-homologous base sequences including partial sequences of mRNA derived from House-keeping gene in Table 1, and all of 3' Variant 1 to 3' Variant 6 of the stealth RNA gene expression system are capable of achieving stable gene expression and production of vector particles. Also as shown in Example of FIG. 4, among the structures existing in 5' terminus of native virus genome, the regions of (1) to (4) can be replaced with or inserted by other non-homologous base sequence, and all of 5' Variant 1 to 5' Variant 5 of the stealth RNA gene expression system are capable of achieving stable gene expression.

It would be highly possible that the interferon inducibility is further suppressed by replacing sequences of these positions with "RNA that is not recognized by an innate immune system" such as partial sequences of mRNA derived from House-keeping gene of (Table 1).

5. Techniques for Avoiding Activation of an Innate Immune System (PAMP) by Proteins Essential for Transcription and Replication 5-1. Investigation of Value that Provides Index for PAMP Structure in Gene Encoding Protein Essential for Transcription and Replication In Examples of the present invention, L protein (large subunit of RNA polymerase, PolL) and P protein (small subunit of RNA polymerase, PolS) of Sendai virus were selected as "RNA-dependent RNA polymerase", C protein (C) of Sendai virus was selected as "protein that regulates activity of RNA polymerase", and NP protein (N) of Sendai virus was selected as "single-stranded RNA binding protein". Although these proteins are essential for transcription and replication from a negative-sense single-stranded RNA, it is highly possible that "pathogen-associated molecular pattern (PAMP)" exists in genome RNA or mRNA of Sendai virus encoding these proteins as shown in Non-Patent Document 37. Therefore, it is necessary to remove a structure that is a potential PAMP from the RNA encoding these protein so as to construct a stealth RNA gene expression system that does not activate an innate immune system.

Figure 5:
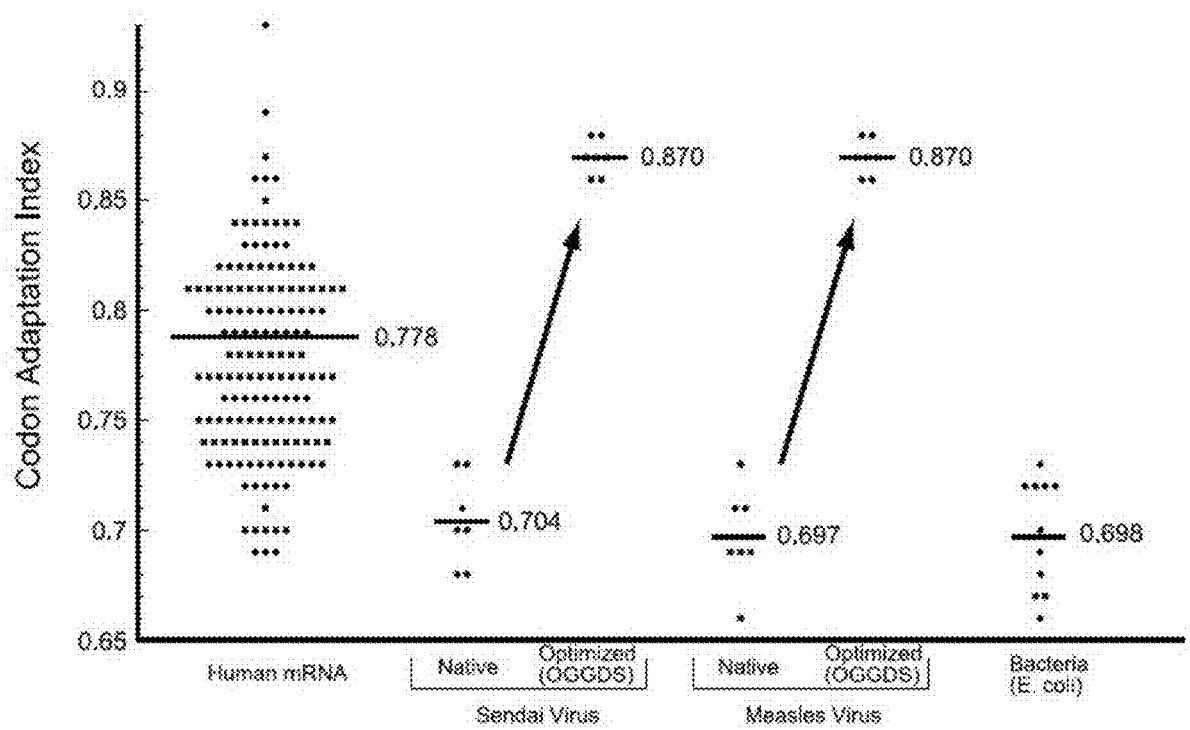
FIG. 5 illustrates analysis of codon adaptation index in mRNAs derived from RNA viruses.

Although it is sure that active PAMPs exist in genome RNA and mRNA constituting Sendai virus, the region where the active PAMP actually exists has not been elucidated. However, RNA having active PAMP must have a structure that is clearly different from that of RNA expressed in host cells. Thus, the present inventors first made comparison according to codon adaptation index (CAI) of coding region as an index in order to examine the difference in structure between mRNA derived from an RNA virus and mRNA of a human cell. CAI is an index for dissociation from the frequency of appearance of codons of mRNAs encoding 100 proteins that are most strongly expressed in cells of a certain biological species, and CAI=1.0 indicates that the codon use frequency is the same as that of mRNAs of these 100 proteins (Non-Patent Document 46). As a result of analysis according to "OptimumGen Gene Design System (Patent Document 7, GenScript USA Inc.)", an average value of CAI of coding regions of arbitrarily selected 151 human mRNAs was 0.778, an average value of CAI of seven mRNAs of Sendai virus was 0.704, and an average value of CAI of seven mRNAs of measles virus belonging to the same paramyxovirus family was 0.697, revealing that the CAI of mRNA of paramyxovirus was significantly lower than the average CAI of mRNAs of human cells (FIG. 5). An average value of CAI of arbitrarily selected eleven mRNAs expressed in *Escherichia coli* analyzed for reference was 0.698 (FIG. 5). This suggests the possibility that in use in human cells, mRNA of paramyxovirus has a structural deviation comparable to that of mRNA of *Escherichia coli* which is a prokaryote, and this is recognized as PAMP.

Figure 6:
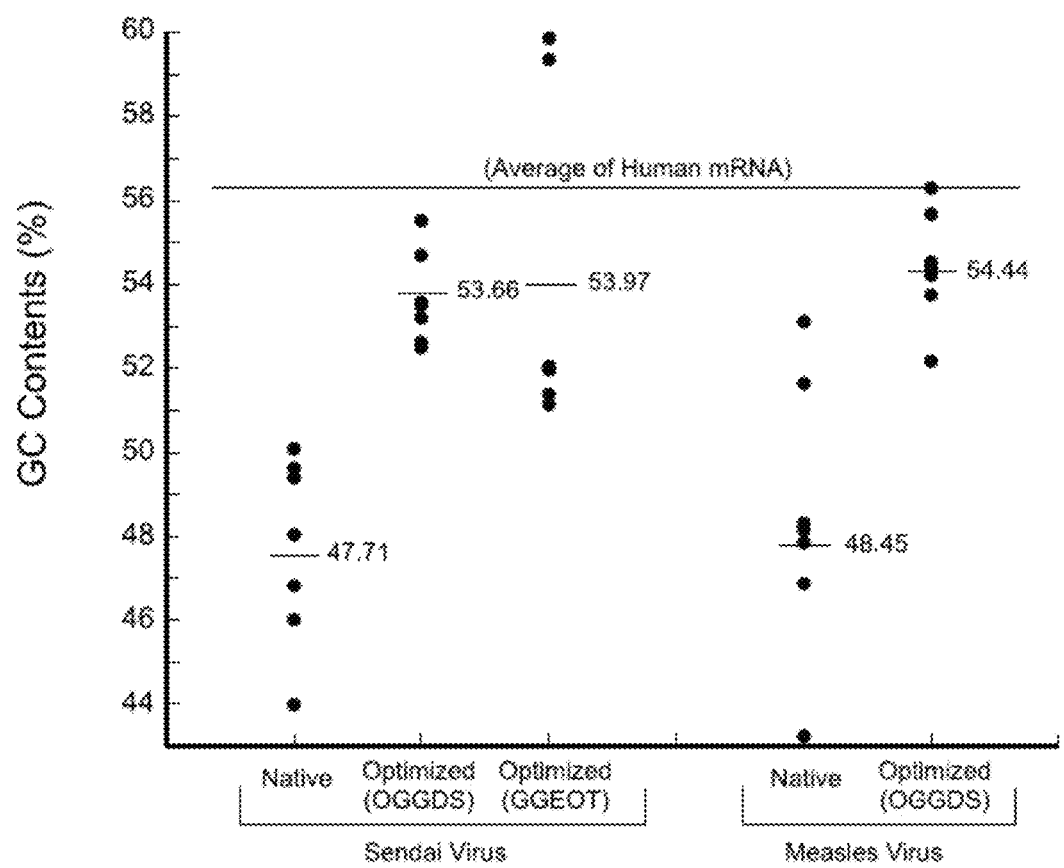
FIG. 6 illustrates analysis of GC contents in mRNAs derived from RNA viruses.

For examining the difference in structure between mRNA derived from RNA virus and mRNA of human cells from other point of view, GC contents of coding regions were calculated. An average value of GC contents of native paramyxovirus-derived RNA was 47.7% to 48.5%, which was significantly lower than 56.3% which was an average value of GC contents of coding regions of human mRNA (Non-Patent Document 47) (FIG. 6). Considering that genome of an RNA virus has a relatively low GC content, and adenine-rich or uridine-rich sequences have high potential to become PAMP (Non-Patent Document 43), the GC content also has potential becomes an index suggesting the existence of PAMP.

5-2. "Codon Optimization" Application Experiment for Genes Involved in Transcription and Replication Derived from Sendai Virus It has been confirmed that "codon optimization" for approximating such CAI values and GC contents to average values of mRNA of human cells is effective for disrupting a PAMP structure in a virus-derived coding region and avoiding PAMP, as shown for HIV, SIV, hepatitis virus and the like in the above section 3-2.

However, the above section 3-2. also indicates the result that the replicability is largely impaired when "codon optimization" is conducted in a PAMP region in a sequence of gene essential for transcription and replication of these viruses. Therefore, it would be conventional common knowledge that PAMP structures in sequences of genes essential for transcription and replication highly possibly serve as secondary structures essential for transcription and replication.

Considering various functions are generally integrated compactly in virus genome, it would be highly possible that a PAMP structure in a gene sequence essential for transcription and replication is important for the function of the virus also in the case of Sendai virus as is the case with these virus genomes from the conventional findings as described above. That is, it was highly expected that when codons in coding regions of proteins involved in transcription and replication, such as Sendai virus-derived "RNA-dependent RNA polymerase" for use in the RNA gene expression system of the present invention are optimized for human cells, the original transcription and replication ability is also largely impaired although PAMP can be avoided.

Under such circumstances, the present inventors dared to optimize codons of all RNAs encoding proteins such as "RNA-dependent RNA polymerase" and "RNA binding protein" involved in transcription and replication for human cells.

In the present invention, since L protein (large subunit of RNA polymerase, PolL) and P protein (small subunit of RNA polymerase, PolS) of Sendai virus are used as "RNA-dependent RNA polymerase", C protein (C) of Sendai virus is used as "protein that regulates activity of RNA polymerase", and NP protein (N) of Sendai virus is used as "single-stranded RNA binding protein", codon optimization was conducted according to "OptimumGen Gene Design System (Patent Document 7, GenScript USA Inc.)" which is one program generally used as a codon optimization method so as to remove PAMP from RNAs encoding these proteins. As a result of this, CAI values fall within the range from 0.86 to 0.88, and showed values approximate to those of mRNAs encoding proteins highly expressed in human cells.

Results of applying codon optimization to genes of L, P, C and N proteins of Sendai virus according to "OptimumGen Gene Design System (also referred to as OGGDS method)" are shown in the following (Table 2).

TABLE 2

|  |  | Before optimization | | After optimization | |
|---|---|---|---|---|---|
| Gene name | Function | Codon Adaptation Index | GC content (%) | Codon Adaptation Index | GC content (%) |
| L | RNA-dependent RNA polymerase | 0.68 | 44.0 | 0.88 | 52.5 |
| P | Protein that regulates activity of RNA polymerase | 0.73 | 49.6 | 0.86 | 54.4 |
| C | Protein that regulates activity of RNA polymerase | 0.73 | 50.1 | 0.88 | 53.5 |
| N | RNA binding protein | 0.71 | 49.4 | 0.88 | 55.5 |

In the above (Table 2), GC contents as well as CAI values were calculated for RNAs after codon optimization so as to analyze the optimized RNAs from other point of view. While GC contents of RNAs before optimization were in the range of 44.0% to 50.1%, GC contents of RNAs after optimization increased to the range of 52.5% to 55.5%, and approximated 56.3% which is an average value of GC contents of coding regions of human mRNA (Non-Patent Document 47) (Table 2) (FIG. 6). In RNA viruses, it is known that adenine-rich or uridine-rich sequences have high potential to become PAMP (Non-Patent Document 36), and the experiment result strongly suggests the possibility that the structure of virus-derived RNA approximates the structure of human mRNA by the technique of codon optimization, and regions having activity of PAMP are removed at the same time.

In the present invention, an RNA vector carrying RNAs encoding NP protein, P protein, C protein, L protein derived from Sendai virus that are optimized for human cells by the above technique together with ten exogenous genes was constructed (FIG. 13) (Example 8), and the vector was expressed in Hela cells, and investigated (Example 9). It was confirmed that all the ten exogenous genes were expressed in adequate quantities that can be observed. Also it was confirmed that the RNA vector is capable of avoiding INF-β induction in human fibroblasts (Example 13, FIG. 17).

This reveals that the RNA vector of the present invention carrying RNA of genes that are involved in transcription and replication derived from Sendai virus and are optimized for human cells functions as an excellent stealth RNA vector having the PAMP avoiding effect.

This result also shows that any PAMP structure existing in genes essential for transcription and replication was not essential for transcription and replication in the case of Sendai virus, and this was an unexpected surprising result for the present inventors who dared to made the experiment.

5-3. Investigation of Codon Optimization Method

The result of the above (Table 2) suggests that for "codon optimization" for suppressing induction of innate immune reaction by removing regions having active PAMP, the two numerical ranges of "CAI value" and "GC content" are important requirements. Thus, the present inventors planned to conduct an experiment by applying other codon optimization method so as to investigate which one of the two requirements is more essential. As a method for codon optimization, since various methods have been proposed as represented by GeneOptimizer Process (Non-Patent Document 49) and GeneGPS Expression Optimization Technology (Patent Document 8, and Patent Document 9) besides the aforementioned OGGDS method, it is possible to confirm that the equivalent effect is achieved when a method other than the aforementioned OGGDS method is applied.

Thus, a codon optimization method based on GeneGPS Expression Optimization Technology (hereinafter, also referred to as a GGEOT method) which is a generally used "codon optimization" technique likewise the OGGDS method was applied to a template DNA encoding NP protein, P protein, C protein, and L protein of Sendai virus, and an RNA vector capable of carrying ten exogenous genes (FIG. 15) was prepared in the same manner. By the verification by the method of Example 9, it was confirmed that the stealth RNA vector was a stealth RNA vector capable of avoiding induction of the innate immune reaction as with the stealth RNA vector optimized by the OGGDS method (data not shown).

Optimization by the OGGDS method and optimization by the GGEOT method use completely different algorithms, and the identity between the base sequences of nucleic acid optimized by these two methods was 77% to 80%, revealing that considerably different nucleotides were selected for codon optimization (Table 4).

The foregoing demonstrated that the method for optimizing the genes encoding "RNA-dependent RNA polymerase", "protein that regulates activity of RNA polymerase", and "single-stranded RNA binding protein" for preparing a stealth RNA gene expression system does not rely on a specific codon optimization method, and any codon optimization method based on any algorithm can be applied as a codon optimization method of the present invention.

The following (Table 3) shows values of GC contents and CAI values after codon optimization by the GGEOT method for L, P, C and N protein genes of Sendai virus, in comparison with the values by the OGGDS method shown in the above (Table 2). Since the GGEOT method lacks a calculation program for "CAI value", the calculation was conducted according to the calculation program for "CAI value" of the OGGDS method.

Also (Table 4) shows the original sequence, and a value of homology (identity) between the sequences after application of OGGDS and the sequences after application of GGEOT for each of L, P, C and N protein genes.

TABLE 3

| | | Before optimization | | After optimization (OptimumGen Gene Design System) | | After optimization (GeneGPS Expression Optimization Technology) | |
|---|---|---|---|---|---|---|---|
| Gene name | Function | Codon Adaptation Index | GC content (%) | Codon Adaptation Index | GC content (%) | Codon Adaptation Index | GC content (%) |
| L | RNA-dependent RNA polymerase | 0.68 | 44.0 | 0.88 | 52.5 | (0.71) | 51.1 |
| P | Protein that regulates activity of RNA polymerase | 0.73 | 49.6 | 0.86 | 54.4 | (0.70) | 59.9 |
| C | Protein that regulates activity of RNA polymerase | 0.73 | 50.1 | 0.88 | 53.5 | (0.72) | 51.4 |
| N | RNA binding protein | 0.71 | 49.4 | 0.88 | 55.5 | (0.70) | 59.4 |

TABLE 4

| | | |
|---|---|---|
| | N (NP) gene | |
| Native Virus Genome | 75.94% | Optimized with OGGDS Method |
| Native Virus Genome | 76.13% | Optimized with GGEOT Method |
| Optimized with OGGDS Method | 80.38% | Optimized with GGEOT Method |
| | C gene | |
| Native Virus Genome | 77.24% | Optimized with OGGDS Method |
| Native Virus Genome | 76.91% | Optimized with GGEOT Method |
| Optimized with OGGDS Method | 77.56% | Optimized with GGEOT Method |
| GENE A | Homology between GENE A & B | GENE B |
| | PolS (P) gene | |
| Native Virus Genome | 74.17% | Optimized with OGGDS Method |
| Native Virus Genome | 74.99% | Optimized with GGEOT Method |
| Optimized with OGGDS Method | 78.09% | Optimized with GGEOT Method |
| | PolL (L) gene | |
| Native Virus Genome | 75.31% | Optimized with OGGDS Method |
| Native Virus Genome | 74.92% | Optimized with GGEOT Method |
| Optimized with OGGDS Method | 76.72% | Optimized with GGEOT Method |

5-4. Essential Index for “Codon Optimization”

While CAI is used as an index for estimating the translation efficiency of mRNA in human cells (Non-Patent Document 46), codon optimization is used as a measure for eliminating a structure having active PAMP from a virus-derived RNA in the present invention, and elevation in the translation efficiency may not be necessarily obtained.

While CAI is an “index for dissociation from the frequency of appearance of codons of mRNAs encoding 100 proteins that are most strongly expressed in cells of a certain biological species”, an objective standard for selecting 100 proteins which forms a standard has not been shown. Optimization by the OGGDS method and optimization by the GGEOT method that could achieve expression of ten genes while suppressing induction of the equivalent innate immune reaction in human-derived culture cells in the present invention were compared from each other, and the CAI value of the latter case (calculated by the OGGDS method) did not significantly vary before optimization and after optimization (Table 3).

Meanwhile, the GC content was 51% or more, and about 60% at most regardless of the employed optimization method. This shows that GC content is more effective than CAI value as an index of the possibility that a structure having active PAMP has been removed. In other words, as an index in “codon optimization” for “stealth RNA gene expression system” in which induction of the innate immune reaction is suppressed, GC content is the most excellent index, and the possibility that the structure having active PAMP has been removed is estimated if the GC content after codon optimization of the virus-derived protein is at least 50.0% or more, desirably 52.0% or more.

From the above, the wording “codon optimization” for an RNA gene expression system used in the present invention means adjusting all of the base sequences encoding proteins required for the RNA gene expression system to have a GC content of 50 to 60%, preferably 52 to 56%.

As a result of modification of the base sequence by codon optimization, the sequences encoding C protein and V protein that had existed in P gene region disappeared, and neither C protein nor V protein was expressed from optimized P gene. The RNAs encoding C protein and V protein are not essential because gene expression is conducted even when the RNAs are completely removed, however, in the case of C protein, in particular, it is preferred to add C protein gene RNA that is optimized as described above into the sequence because C protein is important for properly regulating the expression amount of the RNA vector of the present invention. Also V protein RNA can be added into the sequence as necessary after it appropriately undergoes similar codon optimization.

6. Method for Carrying a Large Number of Exogenous Genes on Stealth RNA in the Present Invention (Transcription Cassette Linking Method)

6-1. Investigation of Method for Carrying Six or More Genes on One Vector

Next, the method for carrying six or more, for example, ten exogenous genes on a stealth RNA in a simple manner was investigated. Since an RNA molecule itself cannot be engineered by gene recombination technique, every construction including carrying of an optimized virus-derived gene in 5-4. was conducted as a cDNA, and RNA was prepared by DNA-dependent RNA polymerase such as T7 RNA polymerase derived from T7 phage using the cDNA as a template.

For preparing a DNA molecule carrying ten genes in the simplest manner, a method of introducing restriction endonuclease cleavage sites peculiar to each gene upstream and downstream the respective cDNA of each gene, and inserting the cDNAs cleaved by restriction endonucleases into sequence is conceivable. However, this method is impractical because at least 20 different restriction endonucleases are required, and it is necessary to prepare every cDNA again for changing the combination of genes or for changing the position on the stealth RNA.

6-2. Preparation of "Tandem Transcription Cassette" Carrying Two Genes

Figure 7:
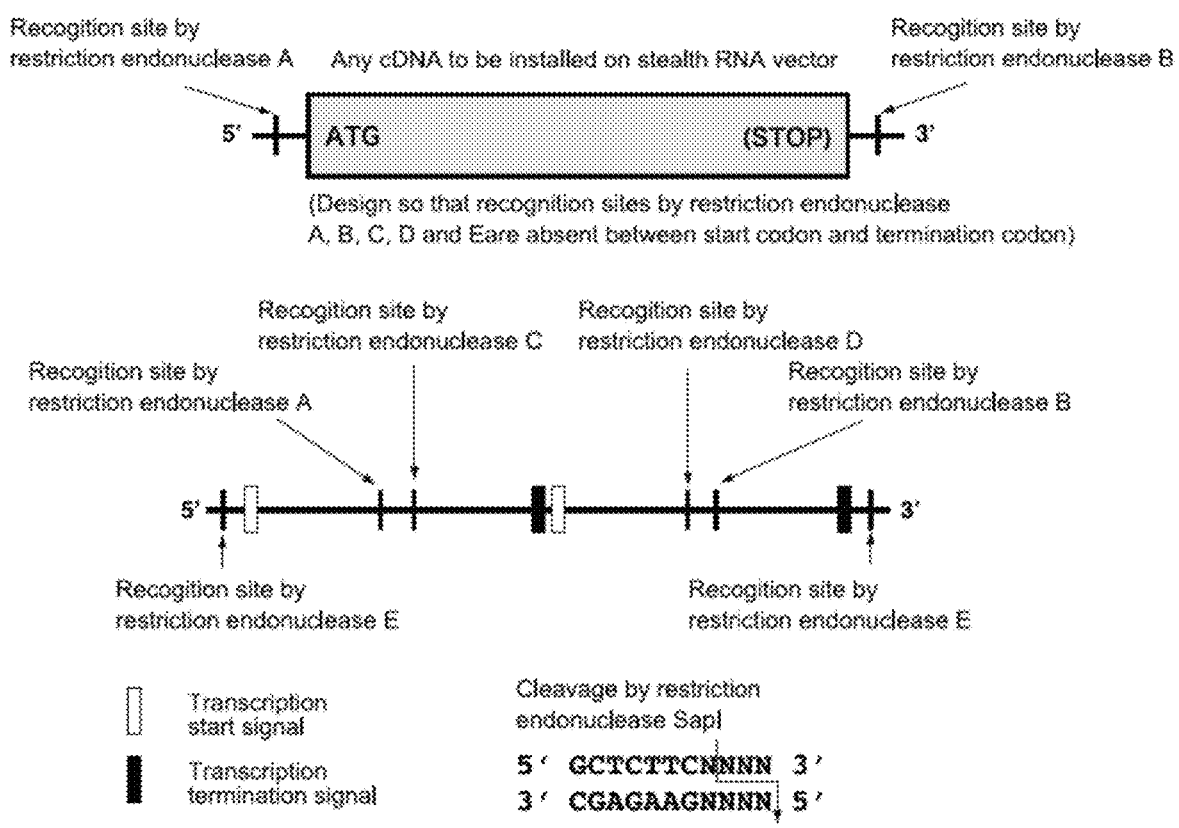
FIG. 7 illustrates a method of designing an exogenous gene cDNA to be installed on a stealth RNA gene expression system. DNA cleaved by restriction endonuclease (RE) A and DNA cleaved by RE D have identical end structure, and can be covalently bound by DNA ligase. Similarly, DNA cleaved by RE B and DNA cleaved by RE C have identical end structure, and can be covalently bound by DNA ligase. Therefore, cDNA fragment cleaved by RE A and RE B can be inserted into a site cleaved either by combination of RE A and RE C or by combination of RE D and RE B.

In the present invention, as described in the above section 2-1. (FIG. 1), the technique of preparing "tandem transcription cassette" carrying two genes, and linking plural tandem transcription cassettes is employed. In this technique, genes to be installed were designed to have the same structure, and designed so that they can be installed at any position in the stealth RNA (FIG. 7). In this designing method, restriction endonuclease cleavage sites are separately provided: restriction endonuclease A cleavage site on 5' upstream side of the gene to be installed, and restriction endonuclease B cleavage site on 3' downstream side of the gene, and cDNA cleaved at these sites is inserted into a DNA molecule which is to be a template. The template DNA into which the cDNA is to be inserted is provided with recognition sites by restriction endonuclease C and restriction endonuclease D, in addition to recognition sites by restriction endonuclease A and restriction endonuclease B. These combinations of restriction endonucleases are selected so that the DNA fragment cleaved by restriction endonuclease A can covalently bind with the DNA fragment cleaved by restriction endonuclease D, and the DNA fragment cleaved by restriction endonuclease B can covalently bind with the DNA fragment cleaved by restriction endonuclease C. There are a large number of such combinations, besides the combination Acc65I and BsiWI and the combination of XhoI and SalI recited in Examples, combination of XbaI, and SpeI or NheI, and combination of BamHI and BglII are conceivable. In this case, any cDNA to be installed is structurally restricted to design so that recognition sites by restriction endonuclease A, restriction endonuclease B, restriction endonuclease C, and restriction endonuclease D are absent within its sequence. By using such combinations of restriction endonucleases, DNA fragments each carrying two cDNAs are first prepared (FIG. 8).

6-3. "Transcription Cassette" Linking Method

Figure 8:
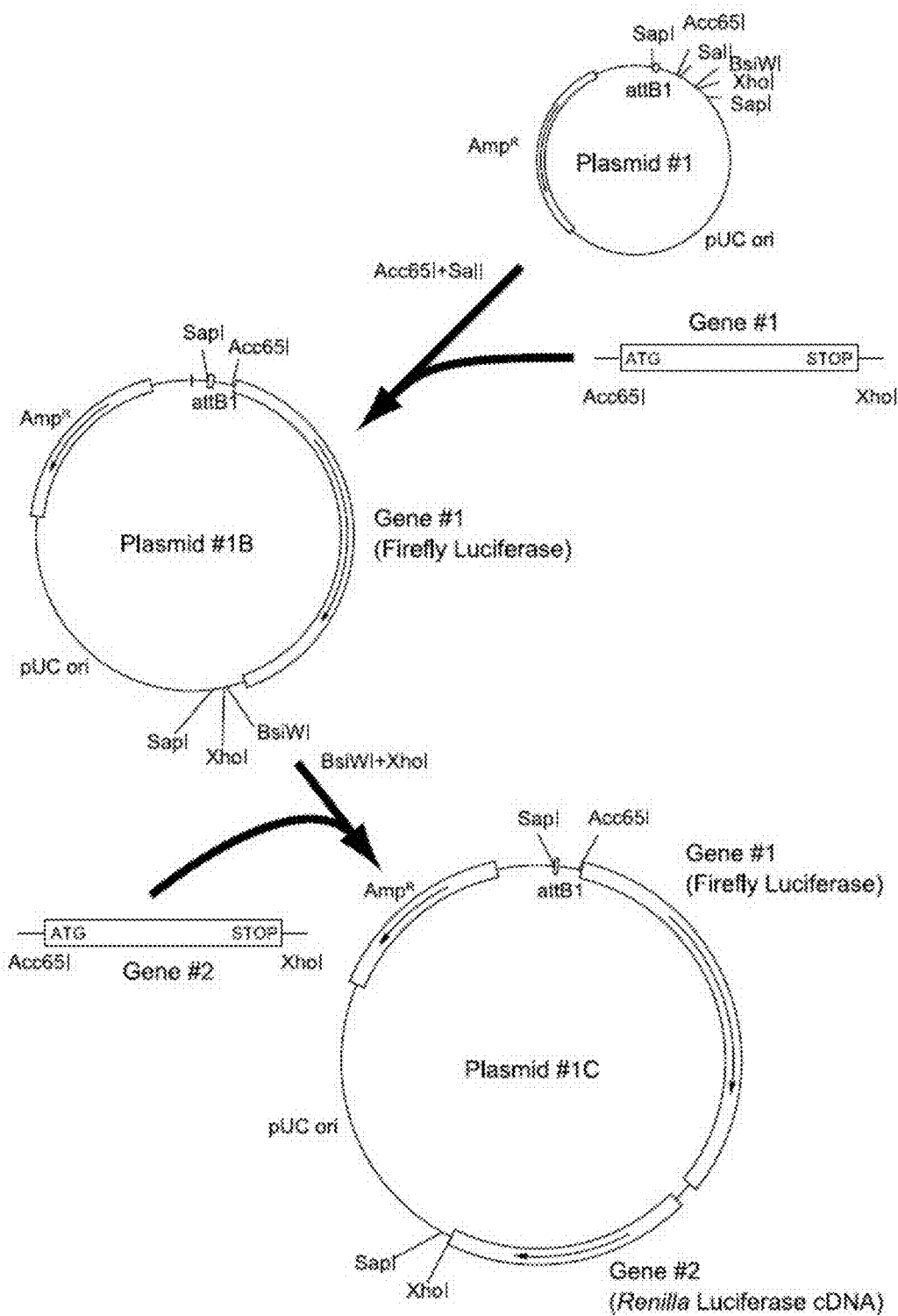
FIG. 8 illustrates a method of connecting two exogenous gene cDNAs.
Figure 9:
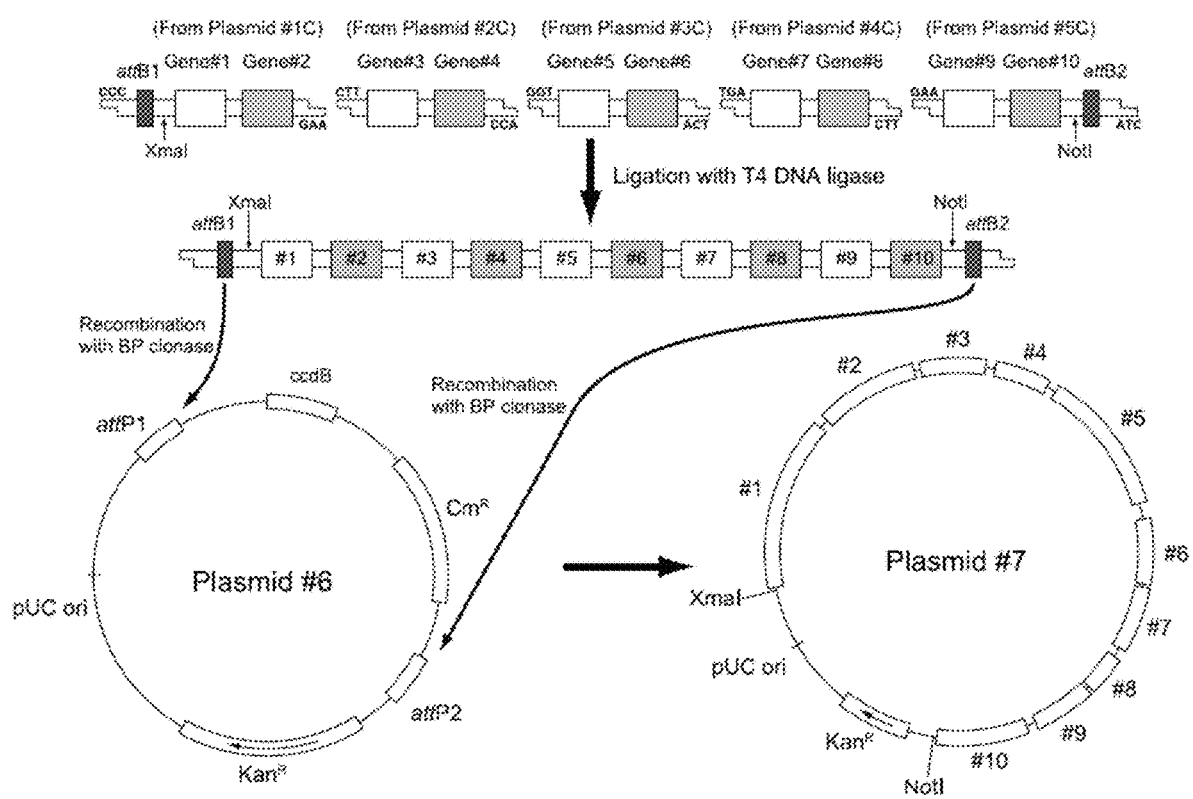
FIG. 9 illustrates a method of connecting ten exogenous gene cDNAs.

Next, five DNA fragments each carrying two cDNAs linked in this manner are connected to prepare a DNA carrying a total of ten cDNAs (FIG. 7, FIG. 8 and FIG. 9). In Examples, a DNA fragment carrying two linked cDNAs prepared in the above section 6-2. was cleaved by a restriction endonuclease called SapI and isolated. The protruding end structure of the DNA cleaved by SapI has such a structure that three nucleotides are protruded on 5' side, and by setting the sequence of three nucleotides arbitrarily, 4×4×4=64 patterns of protruding end structure can be selected (FIG. 7) (FIG. 9). Therefore, it is possible to bind five DNA fragments accurately as designed and to collect them as one DNA molecule (FIG. 9). In this case, cDNAs of genes to be installed are designed so that recognition site by SapI, in addition to recognition sites by restriction endonuclease A, restriction endonuclease B, restriction endonuclease C, and restriction endonuclease D are absent within its sequence (FIG. 7).

The restriction endonuclease having the characteristic of generating any given single-stranded protruding end structure in the sequence represented by NN or NNN on the terminus generated by digestion is not limited to SapI, and the equivalent results are obtained with various restriction endonucleases including BbsI, BbvI, BcoDI, BfuAI, BsaI, BsmBI, BsmFI, BtgZI, EarI, FokI, HgaI, and SfaNI. The equivalent effect can be obtained also with AlwNI, BglI, BstAPI, BstXI, DraIII, SfiI and the like having an indefinite sequence in the recognition site. This step is not necessarily cloning by a restriction endonuclease, and a method using homologous recombination (In-Fusion HD Cloning System (TAKARA-Bio, Inc) or Gibson Assembly System (New England Biolabs, Inc)) can also be employed. The step of incorporating into a circular plasmid DNA after connecting ten cDNAs can be achieved also by covalent bonding using ordinary T4 DNA ligase without using the method of incorporating into pDONR-221 or the like by homologous recombination (Gateway System (Life Technologies, Inc.)) shown in Examples. Also it is possible to prepare a DNA molecule carrying any of one to ten genes by the method shown in FIG. 9.

6-4. Regulation of Expression Level of Exogenous Gene

Generally, in the case of inserting plural exogenous genes in a negative-sense single-stranded RNA gene expression system containing genes respectively encoding a set of RNA-dependent RNA polymerase (PolS and PolL), single-stranded RNA binding protein (N), and RNA polymerase activity regulating protein (C), it is known that the expression level is higher as the position is closer to upstream 3' terminal site. The stealth RNA gene expression system of the present invention also shows this trend. In the present invention, since a large number of exogenous genes can be incorporated in any order in the manner of integrating cassettes, the genes can be conveniently arranged in the order of the desired expression levels. Also the expression levels of the proteins generated from respective genes can be regulated by changing the translation efficiency (FIG. 20).

7. Synthesis of Stealth RNA

Figure 10:
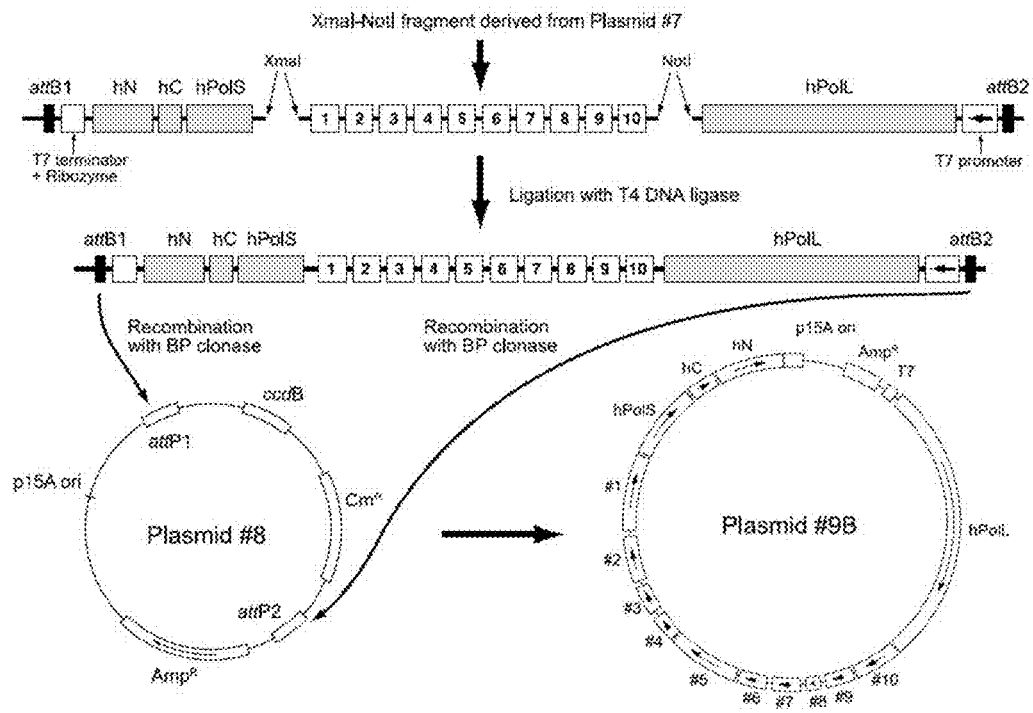
FIG. 10 illustrates a method of constructing a template cDNA for preparing a stealth RNA gene expression system into which ten exogenous genes are incorporated.

Next, the DNA fragment in which ten cDNAs are linked, prepared in the above section 6., and a gene encoding single-stranded RNA binding protein (hN), a gene encoding protein that regulates activity of RNA polymerase (hC), and genes encoding an RNA-dependent RNA polymerase (hPolL and hPolS) having codons optimized for human cells in the manner as described in the above section 5. (hereinafter, also referred to "humanized", and "h" is added to the abbreviated name of the protein) were linked to prepare a circular template cDNA for synthesizing a stealth RNA (FIG. 10). The structure of the stealth RNA can be selected from a negative strand and a positive strand depending on the position of the promoter recognized by the RNA polymerase. Here, the RNA having the same orientation as the mRNA expressed from the gene installed on the stealth RNA is defined as a positive strand, and the RNA having the orientation complementary to the mRNA is defined as a negative strand, and FIG. 10 illustrates preparation of a template for synthesizing a negative-sense RNA by using T7 RNA polymerase. Downstream the T7 promoter (Non-Patent Document 50), a ribozyme derived from anti genome of human hepatitis D virus for cleaving RNA and creating an accurate end (Non-Patent Document 51) and a transcription termination signal of T7 RNA polymerase (Non-Patent Document 50) are arranged so that RNA corresponding to the entire length of the stealth RNA can be synthesized. The enzyme used for synthesis of RNA is not limited to T7 RNA polymerase, but any DNA-dependent RNA polymerase that can be used in *Escherichia coli* or animal cells can be used. For example, T3 RNA polymerase derived from *Escherichia*

*coli* T3 phage (Non-Patent Document 52) and SP6RNA polymerase derived from salmonella SP6 phage (Non-Patent Document 53) can also be used in combination with the promoter and the transcription termination point recognized by these enzymes. The ribozyme is used for accurately cleaving 3' terminus of RNA, and not only the ribozyme derived from anti genome of human hepatitis D virus as used in Examples, but also a ribozyme derived from genome of human hepatitis D virus (Non-Patent Document 51), a hairpin ribozyme of tobacco ringspot virus (Non-Patent Document 54), and a short inhibitory RNA (siRNA) capable of cleaving RNA in cells (Patent Document 55) can be used.

The cDNA complementary to the entire length of the stealth RNA cDNA is cloned into a plasmid having a replication origin derived from p15A (Non-Patent Document 56). Since the plasmid having a replication origin derived from p15A is maintained in a low copy number state in *Escherichia coli*, not only it is advantageous for stably retaining a large DNA fragment in *Escherichia coli*, but also it can coexist in *Escherichia coli* with a plasmid for expressing N protein having a replication origin derived from ColE1 in the method 2 for reconstituting the stealth RNA gene expression system (Non-Patent Document 56). In Examples, the plasmid having a replication origin derived from p15A carries ampicillin resistance, and the plasmid having a replication origin derived from ColE1 carries kanamycin resistance, and the two plasmids are maintained in the same *Escherichia coli* by double selection of ampicillin and kanamycin, however, the combination of antibiotics is not limited to this example. Regarding the combination of plasmids, a plasmid having a replication origin derived from F factor in place of the replication origin derived from p15A, and a plasmid having a replication origin derived from pUC in place of the replication origin derived from ColE1 can be used.

8. Reconstruction of Stealth RNA Gene Expression System 8-1. Conventional Reconstruction Method Reconstruction of a stealth RNA gene expression system composed of a negative-sense single-stranded RNA and a protein that binds to the RNA can be achieved in two methods. The first method is a technique using a virus having genome of a negative-sense single-stranded RNA, and known as a vector reconstituting method using the virus, wherein a positive-sense single-stranded RNA complementary to the negative-sense single-stranded RNA is expressed in animal cells by using T7 RNA polymerase, and simultaneously, three proteins, NP (N), P (PolS), and L (PolL) are expressed in the cells, and thus a stealth RNA gene expression system of a positive-sense RNA is reconstituted (FIG. 11) (Non-Patent Document 57, and Patent Document 3). The merit of this method lies in the convenience that by using animal cells expressing T7 RNA polymerase stably, reconstitution can be achieved only by introducing the plasmid DNA which is a material into the cells. On the other hand, it is also known that since a plasmid containing a template cDNA for synthesizing a positive-sense single-stranded RNA, and three plasmids carrying genes for expressing three proteins, NP, P, and L are simultaneously introduced into cells, gene recombination often occurs among these DNA molecules, and mutation is inserted into the structure of the negative-sense single-stranded RNA to be prepared (Non-Patent Document 57). In Examples of Patent Document 3, plasmids for expressing M, F, and HN proteins are further added so as to increase the efficiency of reconstitution.

8-2. Reconstruction Method Developed in the Present Invention

Figure 12:
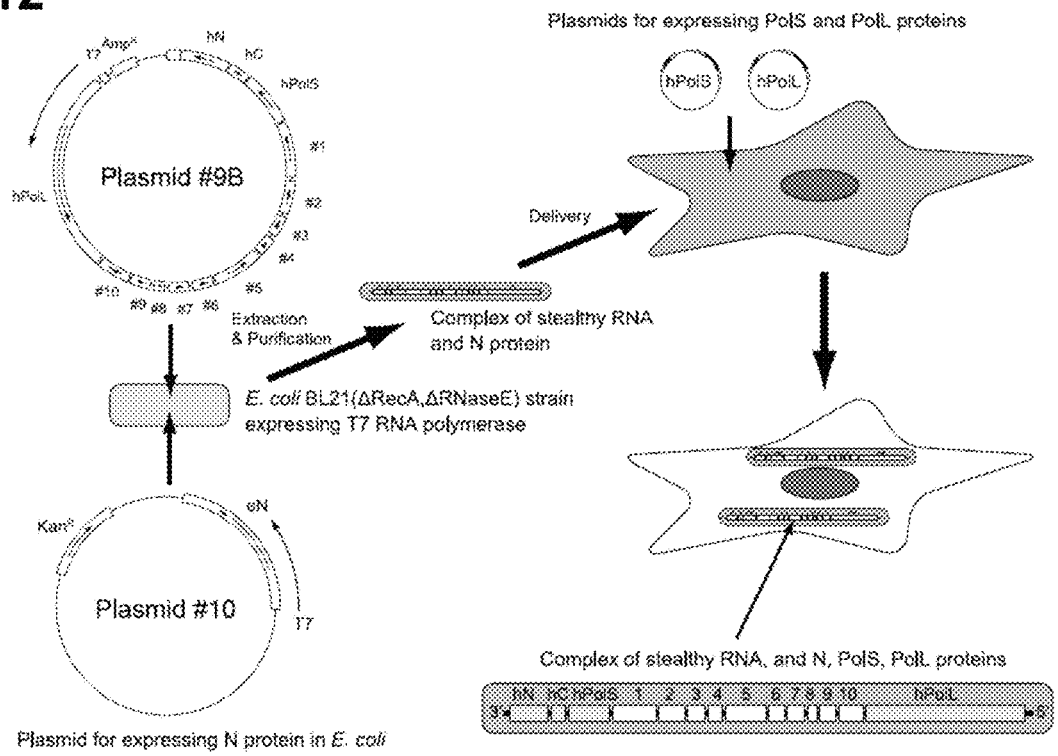
FIG. 12 illustrates a second method for reconstituting a stealth RNA gene expression system from a template cDNA.

In the second method, first, a complex of a negative-sense single-stranded RNA and a NP protein (N) having a single-stranded RNA binding ability is prepared in *Escherichia coli*, and the complex is introduced into animal cells in which P (PolS) protein and L (PolL) protein are expressed, to reconstitute a stealth RNA gene expression system (FIG. 12). In this method, first, mRNAs encoding N protein and a stealth RNA are synthesized by T7 RNA polymerase respectively from two plasmids that can coexist in *Escherichia coli*, and the single-stranded RNA binding protein (N) and the stealth RNA are co-expressed in *Escherichia coli* to produce a complex. Although the method of reconstituting an RNA virus by using an RNA-protein complex isolated from a naturally occurring RNA virus as a material is disclosed in Non-Patent Document 58, the method developed in the present invention enables reconstitution using a stealth RNA synthesized by gene recombination techniques as a material. Although this method disadvantageously requires a larger number of processes and is more complicated as compared with the first method, this method makes it possible to reconstitute a stealth RNA gene expression system without introducing mutation into genome RNA by using *Escherichia coli* in which a gene involved in homologous recombination (RecA) and a gene encoding RNase (RNaseE) are disrupted (Non-Patent Document 59).

That is, the method for reconstituting a stealth RNA gene expression system developed in the present invention is a method of preparing a complex of a negative-sense single-stranded RNA and a protein having a single-stranded RNA bindability (for example, NP protein (N)) in host cells expressing T7 RNA polymerase in advance, and introducing the complex into animal cells in which the RNA-dependent RNA polymerase (for example, P (PolS) protein and L (PolL) protein) is expressed to reconstitute a stealth RNA gene expression system. Preferably, as host cells, *Escherichia coli* in which RecA gene and RNaseE gene are disrupted and T7 RNA polymerase is expressed is used.

Figure 13:
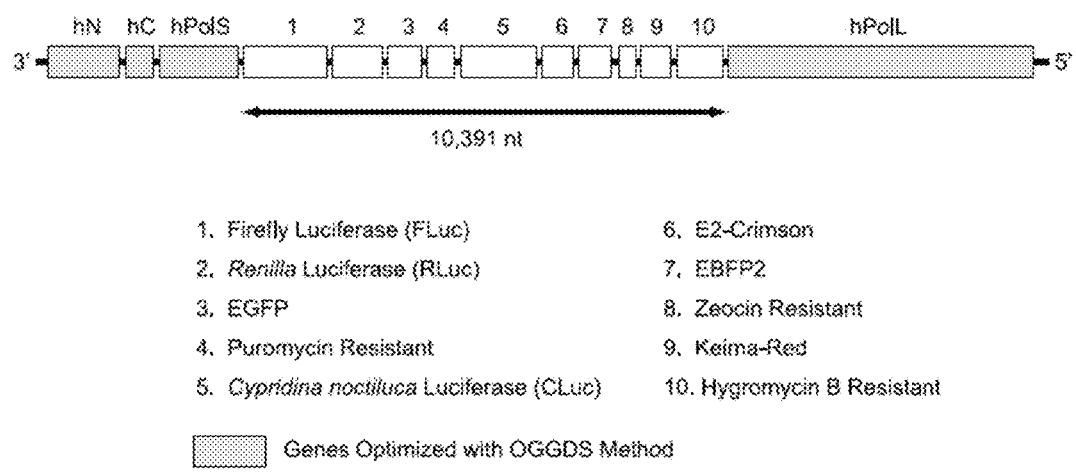
FIG. 13 illustrates a genome structure of a stealth RNA gene expression system carrying ten exogenous gene cDNAs.
Figure 14:
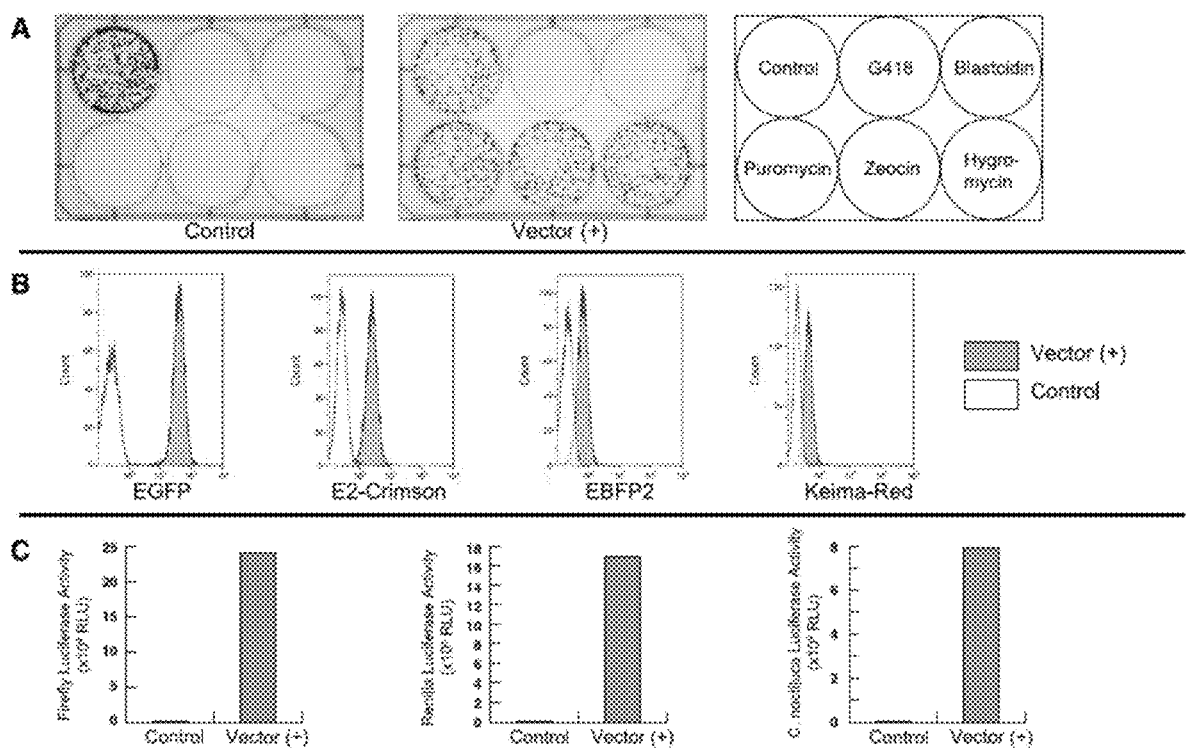
FIG. 14 illustrates gene expression activity of a stealth RNA gene expression system carrying ten exogenous gene cDNAs.

Subsequently, using the stealth RNA carrying ten genes synthesized by the method shown in the above section 7., a stealth RNA gene expression system is constructed by any of the methods described in the above section 8. (FIG. 13). It was confirmed that the gene expression system having a negative-sense single-stranded RNA prepared in this manner can persistently express all the ten installed genes by stable expression of three drug resistance characters (puromycin resistance, Zeocin resistance, and hygromycin resistance), four fluorescent proteins (EGFP, E2-Crimson, EBFP2, and Keima-Red), and three luciferases (firefly luciferase, Renilla luciferase, and *Cypridina noctiluca* luciferase) (FIG. 14).

Figure 16:
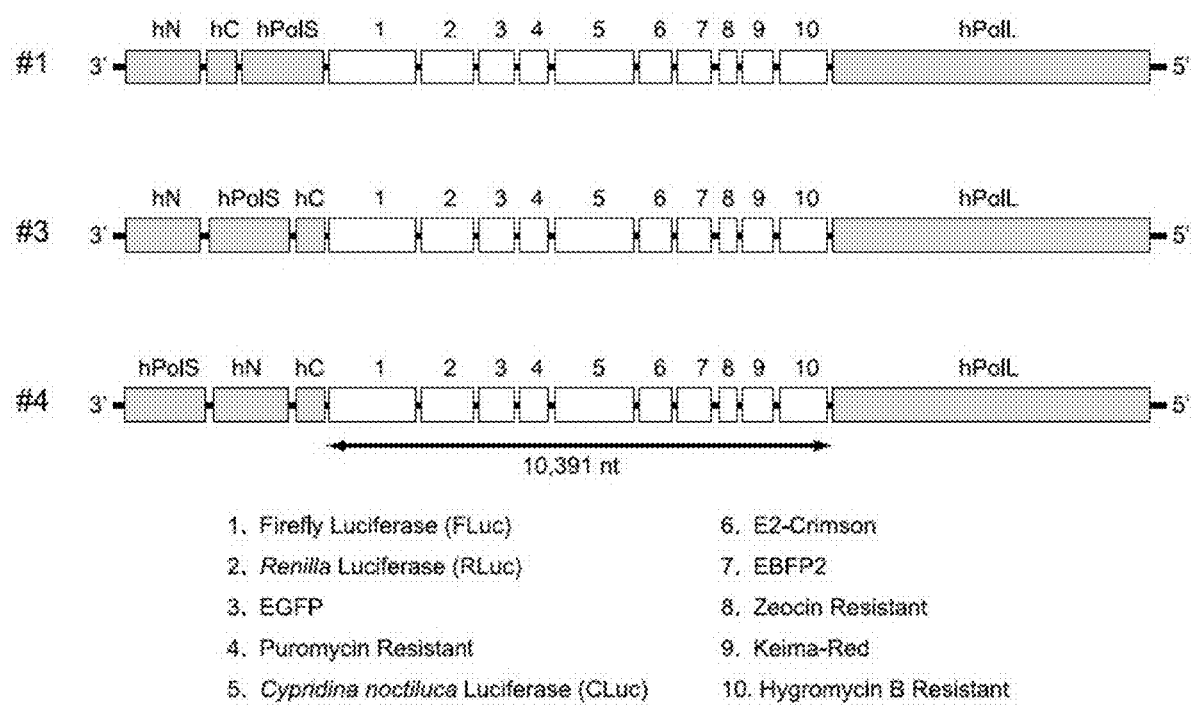
FIG. 16 illustrates a genome structure of a stealth RNA gene expression system carrying ten exogenous gene cDNAs, prepared while the arrangement of N, C, PolS (P) genes is changed.

8-3. Order of Linking RNA-Binding Protein (hN, hC, hPol) Genes in Stealth RNA Gene Expression System In the stealth RNA gene expression system of the present invention, the positions on the stealth RNA of the gene encoding single-stranded RNA binding protein (hN), the gene encoding protein that regulates activity of RNA polymerase (hC), and the gene encoding an RNA-dependent RNA polymerase (hPolS) are not limited to the order of hN-hC-hPolS from 3' terminal side shown in FIG. 13. For example, a stealth RNA gene expression system can be constructed while the order is changed as is hN-hPolS-hC or hPolS-hN-hC (FIG. 16).

8-4. Need for Mutation in Virus-Derived Protein Genes in Stealth RNA Gene Expression System In the stealth RNA gene expression system, there is no need of existence of specific mutation in the proteins expressed from the humanized gene encoding single-stranded RNA binding protein (hN), the humanized gene encoding protein that regulates activity of RNA polymerase (hC), and the humanized genes encoding an RNA-dependent RNA polymerase (hPolS, hPolL).

As described in the above section 3-3., in the conventional technique, introduction of a mutation for suppressing PAMP activity into the virus-derived RNA-dependent RNA polymerase or the like has been used as the most effective means for avoiding the innate immune system.

However, in the present invention, since any active PAMP is removed from the virus-derived protein gene by codon optimization according to the method shown in the above section 5., it is not necessary to preliminarily introduce a mutation into a virus-derived protein in a protein level. For example, even when genes expressing NP, P, C and L proteins derived from Sendai virus Z strain which is a wild-type paramyxovirus known to have strong interferon inducibility are used, they can be used as a material for the stealth RNA gene expression system through optimization by the method shown in the above section 5. For example, as the gene that expresses L protein shown as "hPol" in (FIG. 16), a gene sequence derived from Z strain is optimized for human cells and used.

9. Verification of Activity of Inducing Innate Immune System 9-1. Comparison with Innate Immune System Avoiding Effect in Conventional Art Next, for comparing the activity of inducing the innate immune system in gene introduction between the stealth RNA vector carrying the stealth RNA gene expression system and a conventional art, a stealth RNA vector carrying exactly the same four genes (Keima-Red, Blasticidin S resistant gene, EGFP, and Kusabira-Orange) as the persistent expression type Sendai virus vector which is a conventional art described in FIG. 1B of Non-Patent Document 7 was prepared. Genes were introduced into human primary culture fibroblasts using these two vectors, and the amount of interferon beta mRNA after 24 hours was quantified by the Real-Time PCR method (FIG. 17). Induction by the stealth RNA vector was within five times the amount of interferon β mRNA in normal cells although it does not carry V gene that suppresses the innate immune system. On the other hand, in the conventional art, induction of 47 times compared with normal cells was observed although V gene is contained (FIG. 17). This results reveal that in the stealth RNA gene expression system, activation of the innate immune system could be avoided even under the condition where a factor that inhibits the innate immune system is absent.

9-2. Further Avoidance of Activation of Inmate Immune System

Activity of inducing the innate immune system is also influenced by the kind of the cells retaining the stealth RNA gene expression system, or the strength of gene expression from the stealth RNA gene expression system. For example, interferon beta is little induced in human-derived HeLa cells, while it is strongly induced in human-derived 293 cells. As the gene expression is strengthened for production of biopharmaceuticals, the induction of interferon beta is strengthened. In the case of production of biopharmaceuticals using a stealth RNA gene expression system, since mutation of RNA genome (Non-Patent Document 39) by activity of cytoplasmic adenosine deaminase induced by interferon (Adenosine deaminase acting on RNA, ADAR1) is problematic, it is desired to further suppress the innate immune system inducing activity remaining in the stealth RNA gene expression system.

This object can be achieved by additionally carrying a factor that suppresses the innate immune system on the stealth RNA gene expression system (FIG. 18 and FIG. 19). As such a factor, a deletion mutant of "molecular pattern characteristic of pathogenic microorganism (Pathogen-associated molecular pattern, PAMP)" receptor RIG-I existing in cytoplasm (RIG-IC) (Non-Patent Document 71), C-terminal region of Sendai virus V protein (Non-Patent Document 72), and PSMA7 which is a constituent of proteasome (Non-Patent Document 73) can be recited.

10. Regulation of Gene Expression Level

Next, how the level of gene expression in the stealth RNA gene expression system varies by regulating the expression of factors involved in transcription and replication installed on the vector was examined (FIG. 20, FIG. 21). FIG. 20 indicates positive-sense RNA sequences. Expression of each factor can be regulated by altering the efficiency of translation from mRNA to protein. The simplest means for modifying the translation efficiency is to change the 5' noncoding sequence directly in front of the translation initiation codon (AUG). It is considered that the highest translation efficiency in animal cells is achieved when the sequence directly in front of AUG is 5'-CCACC-3' (SEQ ID NO: 18) (Non-Patent Document 60). On the other hand, it is possible to reduce the translation efficiency by inserting a short coding region on 5' upstream side (Non-Patent Document 61). In Examples, a vector in which expressions of single-stranded RNA binding protein (hN) and protein that regulates activity of RNA polymerase (hC) are suppressed to 40% and 23%, respectively while expression of RNA-dependent RNA polymerase (hPolS and hPolL) is kept constant was prepared, and expressions of firefly luciferase installed thereon were compared (FIG. 20). Expression of the installed luciferase gene increased by suppressing the expression of hN or hC, and increase in gene expression of up to 79 times was observed by combining expression suppression of hN and expression suppression of hC.

Regulation of gene expression level as described above can be conducted only by regulation of the expression level of the protein that regulates activity of RNA polymerase (hC) (FIG. 21). In this case, the stealth RNA gene expression system can be reconstructed even when hC gene is deleted, and the gene expression level is maximum, and hence, hC gene is not an essential element for the stealth RNA gene expression system. However, proliferation of cells will be strongly inhibited when the expression of the installed gene is too strong, and hence it is practical to realize gene expression adapted to the purpose by expressing hC protein at an appropriate level.

As important characteristics in the gene expression system, selectivity of optimum expression level depending on the purpose is recited. For example, in cell-reprogramming, cell death is induced when the expression of the transcription factors is too strong. In production of biopharmaceuticals, the production efficiency is deteriorated when the expression is weak. Generally, it is difficult to alter the expression level of the vector in a gene expression system using an RNA virus. In contrast, in the stealth RNA gene expression system, it is possible to alter the strength of the expression freely depending on the use purpose by finely regulating the expression balance of the individual constituents.

Next, an attempt was made to prepare a vector particle capable of introducing the stealth RNA gene expression system into various animal cells by enclosing therein the stealth RNA gene expression system completed through the processes described above. When three proteins M, F, and HN of paramyxovirus were expressed in BHK cells having the stealth RNA gene expression system in cytoplasm by using a strong SRα promoter, vector particles having gene introduction activity were detected in the culture supernatant of the cells. The infectivity titer was about $10^7$ infectious units/mL, and high activity comparable to that by a conventional persistent expression type Sendai virus vector was obtained. This vector particle adsorbs to the cell surface by the activities of F and HN proteins, and is capable of introducing the content, namely, the stealth RNA gene expression system into the cytoplasm by the fusion of membranes. Since this process does not require cell division, the gene can be introduced into non dividing cells.

While the cell specificity and the species specificity of the cells for which gene introduction can be made are determined by the origin of F and HN proteins, genes could be introduced into a very wide range of human cells and animal cells including blood cells of peripheral blood when F and HN proteins of Sendai virus were used.

11. Removal of Vector

Figure 23:
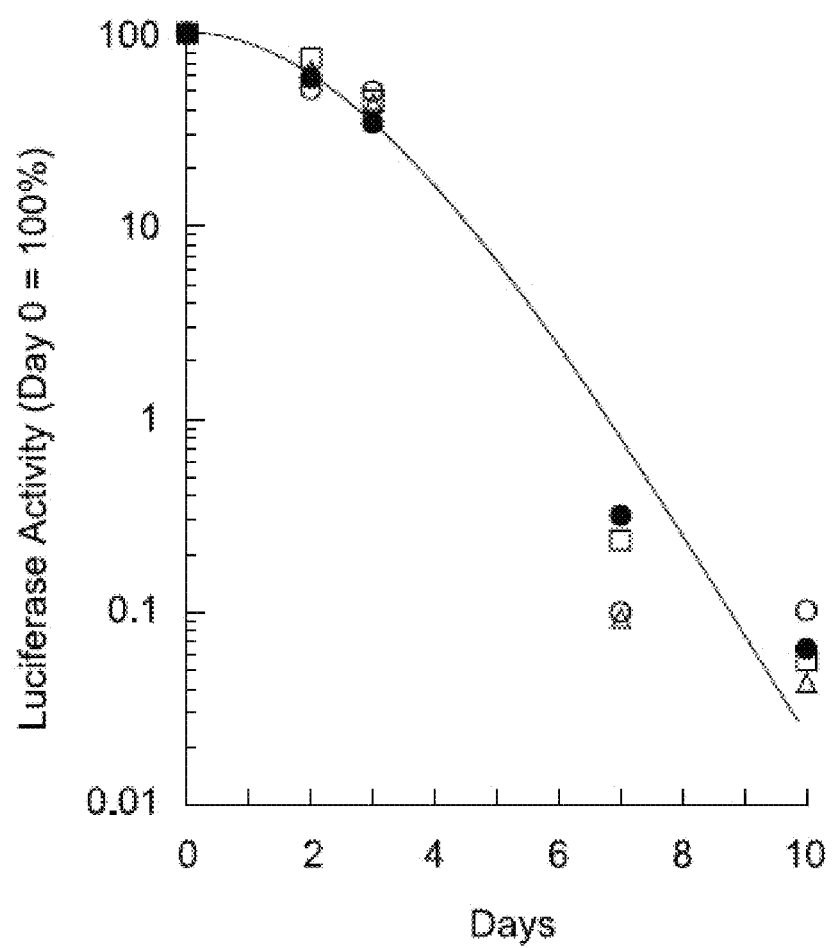
FIG. 23 illustrates removal of a stealth RNA gene expression system from cells.

In a persistent expression type Sendai virus vector which is a conventional art, rapid vector removal is successfully achieved by suppressing the activity of RNA-dependent RNA polymerase by siRNA (Patent Document 3, and Non-Patent Document 7). Thus, whether a vector in the stealth RNA gene expression system can be removed by a similar method was examined (FIG. 23). Since the base sequence of humanized RNA-dependent RNA polymerase (hPolL) possessed by the stealth RNA gene expression system is different from that in the persistent expression type Sendai virus vector which is a conventional art, three siRNAs were newly synthesized, and the activities thereof were examined. Removal could be achieved in the same manner as in the conventional art by using one of the three siRNAs (target sequence is SEQ ID NO: 46) (FIG. 23). Thus, it was found that for the stealth RNA gene expression system of the present invention, the vector removing method by RNAi that has been used in a conventional persistent expression type Sendai virus vector can be applied. Likewise, the removing method using micro RNA (miRNA) is also applicable, and as described, for example, in Patent Document 3, removal can be achieved by reaction with endogenous miRNA by inserting a target sequence of micro RNA (miRNA) into the 3' noncoding region or the 5' noncoding region of the exogenous gene.

12. Use of Stealth RNA Expression System of the Present Invention

The negative-sense single-stranded stealth RNA vector used in the stealth RNA expression system of the present invention can carry six or more, further up to ten any given genes such as human-derived genes, and can carry a length of 5,000 nucleotides, further a length of up to 15,000 nucleotides.

Since the system is stealthy, namely the system is capable of avoiding activation of an innate immune system in animal cells such as human cells, and removal of the vector can be easily conducted, a wide variety of uses including cell-reprogramming technology requiring simultaneous introduction of plural genes, gene therapy including giant gene, regenerative medicine, production of biopharmaceuticals and the like are conceivable.

Specifically, the following embodiments are conceivable.

(1) Application to the technique of preparing iPS cells of high quality for clinical use in regenerative medicine with high efficiency When six or more genes for reprogramming animal cells such as human cells, for example, a total of six genes including four Yamanaka factors (KLF4, OCT4, SOX2 and c-Myc)+BRG1+BAF155 for converting into iPS cells are installed, the length amounts to 13, 132 nucleotides. When six genes, OCT4, KLF4, SOX2, c-MYC, NANOG, and LIN28 are installed, the length amounts to 7,000 nucleotides.

Actually, these six genes were installed on the stealth RNA vector of the present invention (FIG. 25), and expressed in human embryonic fibroblasts, and initialization efficiency exceeding 40% was achieved (Example 21). It has been confirmed that the order of four Yamanaka factors (KLF4, OCT4, SOX2 and c-Myc) to be installed on in this case can be appropriately changed (data not shown).

A similar experiment was conducted in the absence of animal components (Xeno-free) and feeder cells (Feeder-free) by using human peripheral blood cells as a material, and as a result, higher initialization than the conventional method could be conducted (data not shown).

Also by carrying the four genes, KLF4, OCT4, SOX2, and c-MYC, and CHD1 gene encoding a chromatin remodeling factor (a total of 9,907 nucleotide length), and further adding TET1 gene encoding DNA demethylase (a total of 11,203 nucleotide length), it is possible to increase the initialization efficiency.

As other possible combinations, by expressing a total of eight genes including further added two oocyte-specific histones in human somatic cells, it is possible to prepare human iPS cells efficiently.

(2) Application to regenerative medicine utilizing direct reprogramming technology for creating useful cells of nerve cells, neural stem cells, stem cells, pancreatic beta cells and the like from human tissue cells (blood, skin, placenta and the like)

For example, in the technique of reprogramming human fibroblasts into motor nerves, three genes, HB9, ISL1, and NGN2 can be added to four genes, LHX3, ASCL1, BRN2, and MYT1L, and a total of seven genes (9,887 nucleotide length) can be installed.

(3) Production of Biopharmaceuticals Made Up of Plural Subunits

It is useful for producing immunoglobulins G, and M because the genes correspond thereto are giant, and the subunits are required to be expressed simultaneously in the same cell, and regulation of the expression amount of each subunit is required.

Actually, an H (μ) chain gene, an L (κ, λ) chain gene and a J gene of human immunoglobulin were installed on the stealth RNA vector of the present invention (FIG. 24), and human immunoglobulin M was produced by using BHK cells (Example 22). In that case, the present inventors also succeeded in expressing H chain, L chain, and μ chain in a ratio of roughly 1:1:0.2 by considering the order in which the genes are installed.

The present inventors also succeeded in expressing human bi specific antibody by carrying four cDNAs of human immunoglobulin (two H chains and two L chains) on the stealth RNA vector of the present invention (Example 23).

(4) Application to Expression of Drug-Discovery Target Protein Made Up of Plural Subunits For example, by carrying six subunits, gp91phox, p22phox, Rac, p47phox, p67phox, and p40phox on the stealth RNA vector of the present invention, and expressing them simultaneously, it is possible to express NADPH oxidase of the drug-discovery target enzyme (Nox2).

Figure 24:
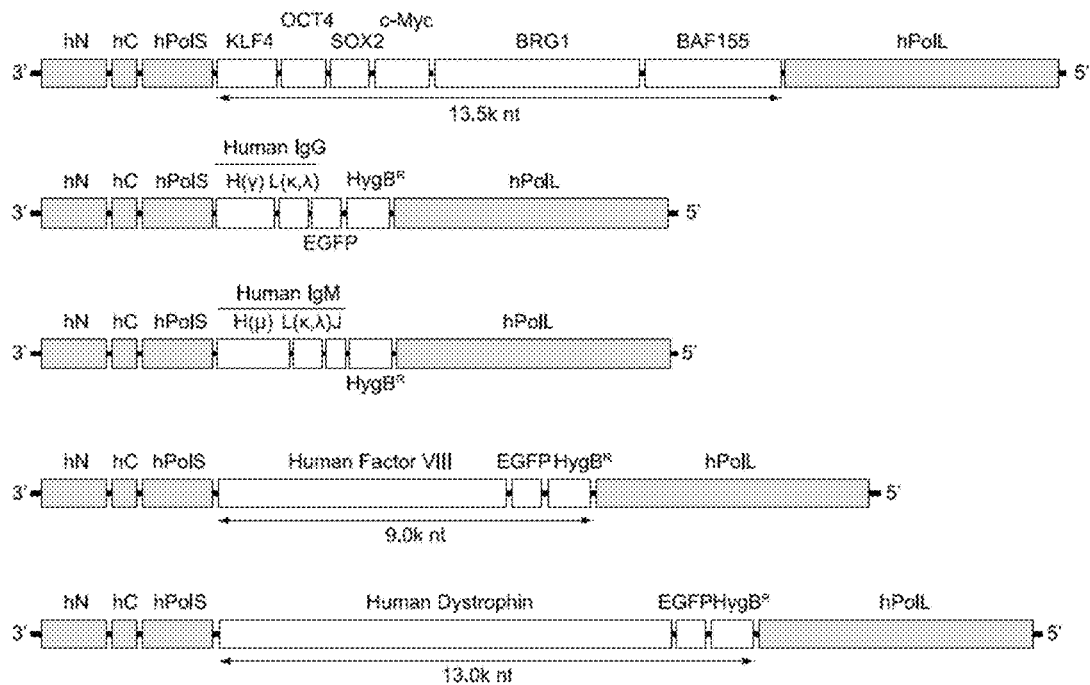
FIG. 24 illustrates genome structures of stealth RNA vectors prepared heretofore.

(5) Use as gene therapy vector for disease for which responsible gene is giant gene, by carrying the giant gene on stealth RNA vector of the present invention and expressing it persistently Specifically, cDNA of blood coagulation factor VIII which is a product of gene responsible for hemophiliaA (7053 nucleotide length) and cDNA of dystrophin which is a product of gene responsible for Duchenne muscular dystrophy (11058 nucleotide length) can be used while they are installed on the stealth RNA vector of the present invention (FIG. 24).

EXAMPLES

Hereinafter, the present invention will be described more specifically by way of Examples, however, it is to be noted that the present invention is not limited to these Examples.

Other terms and concepts in the present invention are based on the meanings of the terms that are commonly used in the art, and various techniques used for carrying out the present invention can be carried out easily and securely by a person skilled in the art according to known literature and the like except for the techniques of which source is particularly specified. Various analyses were conducted according to the methods described in the instruction manuals, catalogues and the like of the employed analytical instruments, reagents or kits.

The contents described in the conventional art literature, patent publications, patent application specifications cited in the present description are referred to as if they were described in the present invention.

Example 1

Preparation of DNA Fragments Carrying Ten Exogenous Genes (1)

The following genes were amplified by PCR to have a structure of Acc65I-cDNA-XhoI and sub-cloned (FIG. 7).
1) Firefly luciferase: (GenBank Accession Number AY738224)
2) Renilla luciferase: (GenBank Accession Number AY738228)
3) Enhanced Green Fluorescent Protein (EGFP): (GenBank Accession Number U55761)
4) Puromycin resistant gene (synthesized while codons were optimized for human cells): Non-Patent Document 62, SEQ ID NO: 47
5) *Cypridina noctiluca* luciferase: Non-Patent Document 63 (GenBank Accession Number AB177531)
6) E2-Crimson: derived from pE2-Crimson (Clontech Laboratories, Inc), SEQ ID NO: 48
7) Enhanced Blue Fluorescent Protein 2 (EBFP2): Non-Patent Document (GenBank Accession Number EF517318)
8) Zeocin resistant gene (synthesized while codons were optimized for human cells): Non-Patent Document 65, SEQ ID NO: 49
9) dKeima-Red: Non-Patent Document 66 (GenBank Accession Number 10) Hygromycin B resistant gene (synthesized while codons were optimized for human cells): Non-Patent Document 67, SEQ ID NO: 50

Example 2

Preparation of DNA Fragment Carrying Ten Exogenous Genes (2)

Next, the following plasmids were prepared.

All the nucleic acids used in the present Example are DNA fragments, and a sequence specified as a negative-sense RNA sequence in the sequencing listings such as SEQ ID NO: 1 or SEQ ID NO: 4 means a corresponding DNA sequence. This also applies to other Examples using a DNA fragment.
1) Plasmid #1

Between the ApaI cleavage site and the StuI cleavage site of plasmid LITMUS38i (New England BioLab, Inc), a DNA having the following structure is cloned: SapI cleavage site-attB1 (SEQ ID NO: 51)-SEQ ID NO: 1-SEQ ID NO: 24-Acc65I cleavage site-SalI cleavage site-SEQ ID NO: 25-SEQ ID NO: 4-ctt-SEQ ID NO: 1-SEQ ID NO: 26-BsiWI cleavage site-XhoI cleavage site-SEQ ID NO: 27-SEQ ID NO: 4-SapI cleavage site
2) Plasmid #2

Between the ApaI cleavage site and the StuI cleavage site of plasmid LITMUS38i, a DNA having the following structure is cloned: SapI cleavage site-SEQ ID NO: 1-SEQ ID NO: 28-Acc65I cleavage site-SalI cleavage site-SEQ ID NO: 29-SEQ ID NO: 4-ctt-SEQ ID NO: 1-SEQ ID NO: 30-BsiWI cleavage site-XhoI cleavage site-SEQ ID NO: 31-SEQ ID NO: 4-SapI cleavage site
3) Plasmid #3

Between the ApaI cleavage site and the StuI cleavage site of plasmid LITMUS38i, a DNA having the following structure is cloned: SapI cleavage site-SEQ ID NO: 1-SEQ ID NO: 32-Acc65I cleavage site-SalI cleavage site-SEQ ID NO: 33-SEQ ID NO: 4-ctt-SEQ ID NO: 1-SEQ ID NO: 34-BsiWI cleavage site-XhoI cleavage site-SEQ ID NO: 35-SEQ ID NO: 4-SapI cleavage site
4) Plasmid #4

Between the ApaI cleavage site and the StuI cleavage site of plasmid LITMUS38i, a DNA having the following structure is cloned: SapI cleavage site-SEQ ID NO: 1-SEQ ID NO: 36-Acc65I cleavage site-SalI cleavage site-SEQ ID NO: 37-SEQ ID NO: 4-ctt-SEQ ID NO: 1-SEQ ID NO: 38-BsiWI cleavage site-XhoI cleavage site-SEQ ID NO: 39-SEQ ID NO: 4-SapI cleavage site
5) Plasmid #5

Between the ApaI cleavage site and the StuI cleavage site of plasmid LITMUS38i, a DNA having the following structure is cloned: SapI cleavage site-SEQ ID NO: 1-SEQ ID NO: 36-Acc65I cleavage site-SalI cleavage site-SEQ ID NO: 37-SEQ ID NO: 4-ctt-SEQ ID NO: 1-SEQ ID NO: 38-BsiWI cleavage site-XhoI cleavage site-SEQ ID NO: 39-SEQ ID NO: 4-attB2 (SEQ ID NO: 52)-SapI cleavage site Example 3

Preparation of DNA Fragments Carrying Ten Exogenous Genes (3) (see FIG. 8)

Next, the following plasmids were prepared.
1) Plasmid #1C

Between Acc65I-SalI of plasmid #1, an Acc65I-XhoI fragment containing firefly luciferase gene was cloned to prepare plasmid #1B. Further, between BsiWI-XhoI of plasmid #1B, an Acc65I-XhoI fragment containing Renilla luciferase gene was cloned to prepare plasmid #1C.

2) Plasmid #2C

Between Acc65I-SalI of plasmid #2, an Acc65I-XhoI fragment containing EGFP gene was cloned to prepare plasmid #2B. Further, between BsiWI-XhoI of plasmid #2B, an Acc65I-XhoI fragment containing puromycin resistant gene was cloned to prepare plasmid #2C.

3) Plasmid #3C

Between Acc65I-SalI of plasmid #3, an Acc65I-XhoI fragment containing *Cypridina noctiluca* luciferase gene was cloned to prepare plasmid #3B. Further, between BsiWI-XhoI of plasmid #3B, an Acc65I-XhoI fragment containing E2-Crimson gene was cloned to prepare plasmid #3C.

4) Plasmid #4C

Between Acc65I-SalI of plasmid #4, an Acc65I-XhoI fragment containing EBFP2 gene was cloned to prepare plasmid #4B. Further, between BsiWI-XhoI of plasmid #4B, an Acc65I-XhoI fragment containing Zeocin resistant gene was cloned to prepare plasmid #4C.

5) Plasmid #5C

Between Acc65I-SalI of plasmid #5, an Acc65I-XhoI fragment containing dKeima-Red gene was cloned to prepare plasmid #5B. Further, between BsiWI-XhoI of plasmid #5B, an Acc65I-XhoI fragment containing hygromycin B resistant gene was cloned to prepare plasmid #5C.

Example 4

Preparation of DNA Fragments Carrying Ten Exogenous Genes (4) (see FIG. 9)

A total of 500 ng including 100 ng of a DNA fragment containing firefly luciferase gene and Renilla luciferase gene cut out from plasmid #1C with SapI, 100 ng of a DNA fragment containing EGFP gene and puromycin resistant gene cut out from plasmid #2C with SapI, 100 ng of a DNA fragment containing *Cypridina noctiluca* luciferase gene and E2-Crimson gene cut out from plasmid #3C with SapI, 100 ng of a DNA fragment containing EBFP2 gene and Zeocin resistant gene cut out from plasmid #4C with SapI, and 100 ng of a DNA fragment containing dKeima-Red gene and hygromycin B resistant gene cut out from plasmid #5C with SapI was dissolved in 5 µL of H$_2$O, and the solution was mixed with 5 µL of Ligation-Convenience Kit (NIPPON GENE Co., Ltd.) and allowed to react at 16° C. for 60 minutes. After purification, the product was dissolved in 7 µL of H$_2$O, and 1 µL of plasmid #6 (pDONR-221, Life Technologies, Inc.) (150 ng) and 2 µL of BP Clonase2 (Life Technologies, Inc.) were added and allowed to react at 25° C. for 2 hours, and then the product was introduced into *Escherichia coli* DH-5α, and a kanamycin resistant colony was isolated to prepare plasmid #7.

Example 5

Preparation of Template DNA for Forming Stealth RNA Carrying Ten Exogenous Genes (see FIG. 10)

Plasmid #8 is prepared by replacing the kanamycin resistant gene of plasmid pACYC177 having a replication origin of p15A (Non-Patent Document 56) with a DNA fragment containing attB1-chloramphenicol resistant gene-attB2 of pDONR-221. The DNA fragment in which attB1, T7 terminator, and HDV ribozyme are connected in sequence on 5' side of a DNA containing hN-hC-hPolS optimized with OptimumGen Gene Design System (SEQ ID NO: 53) was synthesized by GenScript. Similarly, the DNA in which T7 promoter and attB2 are connected on 3' side of a DNA containing hPolL optimized with OptimumGen Gene Design System (SEQ ID NO: 54) was synthesized. A total of 300 ng including 100 ng of a DNA fragment containing attB1-T7 terminator-HDV ribozyme-hN-hC-hPolS in this order cut out with BamHI and XmaI, 100 ng of a DNA fragment containing ten genes cut out from plasmid #7 with XmaI and NotI, and 100 ng of a DNA fragment containing hPolL-T7 promoter-attB2 in this order cut out with NotI and SalI was dissolved in 5 µL of H$_2$O, and the solution was mixed with 5 µL of Ligation-Convenience Kit and allowed to react at 16° C. for 60 minutes. After purification, the product was dissolved in 7 µL of H$_2$O, and 1 µL of plasmid #8 (150 ng) and 2 µL of BP Clonase2 were added and allowed to react at 25° C. for 16 hours, and then the product was introduced into *Escherichia coli* HST-08 (Takara Bio Co.), and an ampicillin resistant colony was isolated to prepare plasmid #9B which is to be a template for synthesizing a negative-sense stealth RNA.

A template DNA for synthesizing a positive-sense stealth RNA is prepared by replacing T7 promoter with T7 terminator. Specifically, a total of 300 ng including 100 ng of a DNA fragment containing attB1-17 promoter-hN-hC-hPolS in this order, 100 ng of a DNA fragment containing ten genes cut out from plasmid #7 with XmaI and NotI, and 100 ng of a DNA fragment containing hPolL-HDV ribozyme-T7 terminator-attB2 in this order cut out with NotI and SalI was dissolved in 5 µL of H$_2$O, and the solution was mixed with 5 µL of Ligation-Convenience Kit and allowed to react at 16° C. for 60 minutes. After purification, the product was dissolved in 7 µL of H$_2$O, and 1 µL of plasmid #8 (150 ng) and 2 µL of BP Clonase2 were added and allowed to react at 25° C. for 16 hours, and then the product was introduced into *Escherichia coli* HST-08, and an ampicillin resistant colony was isolated to prepare plasmid #9A which is to be a template for synthesizing a positive-sense stealth RNA.

Example 6

Figure 11:
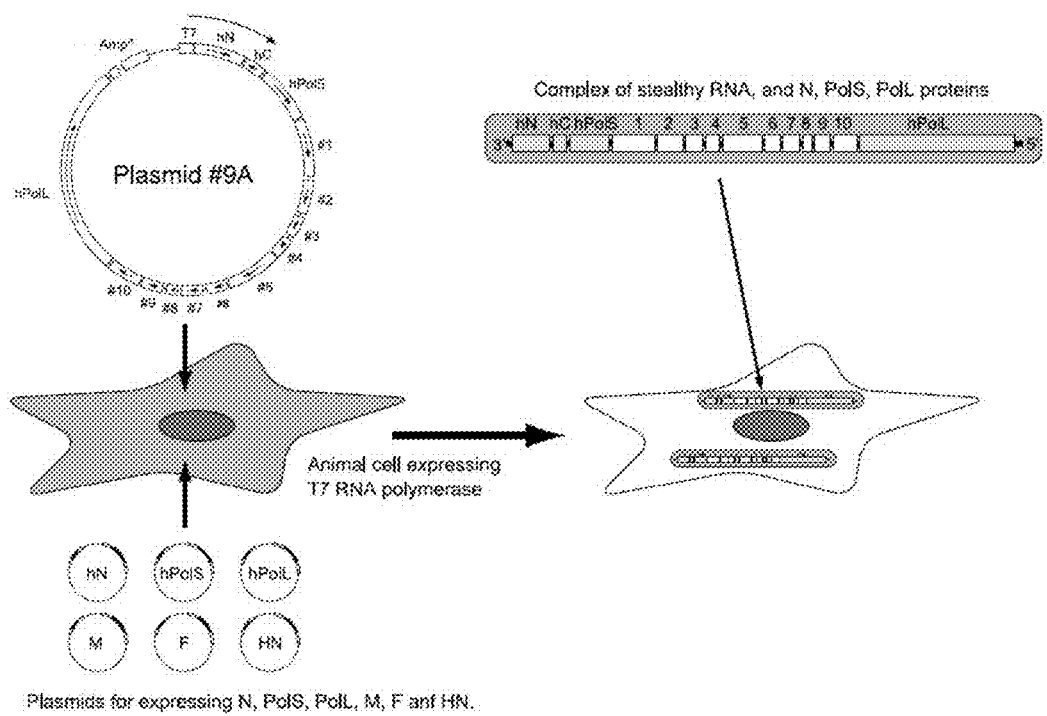
FIG. 11 illustrates a first method for reconstituting a stealth RNA gene expression system from a template cDNA.

Reconstitution of Stealth RNA Gene Expression System Carrying Ten Exogenous Genes (Method 1) (see FIG. 11)

Method 1 was conducted according to the method described in Patent Document 3 and Non-Patent Document 7.

Specifically, as BHK/T7/151M (SE) cells, BHK-21 cells derived from hamster in which T7 RNA polymerase and M protein are stably expressed were prepared in the following manner. BHK-21 cells were obtained from RIKEN BioResource Center. A cDNA synthesized by optimizing codons of T7 RNA polymerase gene (Non-Patent Document 74) for animal cells (Sequence information 77) was installed on a retrovirus vector pCX4neo (Non-Patent Document 75, GenBank Accession Number AB086385), and introduced into BHK-21 cells, and then selected in 10% FCS-containing DMEM culture medium containing 800 µg/mL of G-418 was conducted, and BHK/T7 cells were obtained. Next, M gene of Sendai virus temperature-sensitive mutant Clone 151 strain (GenBank Accession Number NM_011046) was installed on a retrovirus vector pCX4pur (Non-Patent Document 75, GenBank Accession Number AB086386), and introduced into BHK-21/T7 cells, and then selection in 10% FCS-containing DMEM culture medium containing 200 µg/mL of Puromycin was conducted, and thus BHK/T7/151M (SE) cells were obtained.

Expression vectors used in reconstitution were prepared in the following manner. A plasmid pCMV-NP for expressing NP protein, a plasmid pCMV-P for expressing P protein, an plasmid pCMV-L for expressing L protein, and plasmid pCMV-Furin for expressing mouse Furin were prepared by respectively connecting NP gene, P gene, and L gene (GenBank Accession Number M30202.1) of Sendai virus Z strain, and mouse Furin cDNA (Non-Patent Document 76, GenBankAccession Number NM_011046) downstream of the enhancer and the promoter of the Immediate Early gene of Cytomegalovirus (Non-Patent Document 77). A plasmid pSRD-HN-Fmut (Non-Patent Document 78) for expressing F and HN proteins is a plasmid in which F and HN genes of Sendai virus Z strain are connected downstream the SRα promoter (Non-Patent Document 79). pMKIT-151M was prepared by connecting M gene of Sendai virus temperature-sensitive mutant Clone 151 strain downstream the SRα promoter.

BHK/T7/151M (SE) cells stably expressing M protein were seeded on a 6-well plate at $5\times10^3$ cells/well, and cultured for 24 hours, and then washed. Plasmid #9A, a plasmid pCMV-NP for expressing NP protein, a plasmid pCMV-P for expressing P protein, a plasmid pCMV-L for expressing L protein, a plasmid pSRD-HN-Fmut for expressing F and HN protein, and a plasmid pCMV-Furin for expressing mouse Furin were suspended in 300 μL of OptiMEM (Life Technologies, Inc.) in a quantitative ratio of 2 μg, 1 μg, 1 μg, 1 μg, 2 μg, and 20 ng, respectively, and the suspension was mixed with 300 μL of OptiMEM containing 10 μL of Lipofectamine LTX (Life Technologies, Inc.) and left at room temperature for 20 minutes. The culture medium thus prepared was added to cells and the cells were cultured for 4 hours. After washing the cells again, a 10% FCS-containing DMEM culture medium was further added, and the cells were further cultured at 32° C. for 3 days. Then the cells were transferred to a 10% FCS-containing DMEM culture medium containing 300 μg/mL of hygromycin B, and cultivation was continued, and BHK/#9A cells were separated. Occurrence of the reconstitution of the stealth RNA gene expression system was confirmed by the expression of EGFP and Keima-Red.

Example 7

Reconstitution of Stealth RNA Gene Expression System Carrying Ten Exogenous Genes (Method 2) (see FIG. 12)

*Escherichia coli* E-AIST7 strain which is a double deletion mutant of RecA and RNaseE was prepared by disrupting RNase E gene and Rec A gene of *Escherichia coli* BL21 (DE3) strain (Non-Patent Document 68) in this order. Deletion mutation of C-terminus of RNase E (rne131) was introduced into RNase E gene (Non-Patent Document 59), and complete deletion mutation was introduced into Rec A gene. The gene disruption was conducted by using Quick & Easy *E. coli* Gene Deletion Kit available from Gene Bridges GmbH according to the protocol of the kit. Plasmid #10 for expressing single-stranded RNA binding protein (N) in *Escherichia coli* was prepared by carrying N gene having codons optimized for *Escherichia coli* (eN) (SEQ ID NO: 55) on plasmid pET-24a (+) (Merck KGaA).

Plasmid #9B and plasmid #10 were introduced into *Escherichia coli* E-AIST7 strain, and an E-AIST7/N/9B strain was prepared by selection with ampicillin and kanamycin. E-AIST7/N/9B strain was cultured at 30° C., and at $OD_{600}$=0.3, 0.5 mM IPTG was added to induce expression of T7 RNA polymerase, and cultured for 3 hours and *Escherichia coli* was collected. The collected cells were suspended in 10 mL of 10% Sucrose, 50 mM Tris-HCl (pH 7.5), 2 mM $MgCl_2$, and after addition of 150 k units of rLysozome (Merck KGaA) and 25 units of Benzonase (Merck KGaA), the cells were treated at 30° C. for 30 minutes, and protoplasts were collected. The protoplasts were broken with 50 mM Tris-HCl (pH 7.5), 2 mM $MgCl_2$, 50 mM CHAPS, and a supernatant from centrifugation at 4,500 rpm for 10 minutes was centrifuged at 25,000 rpm for 60 minutes with a Beckman SW41Ti rotor, and an RNA-N protein complex was collected as a precipitate. The RNA-N protein complex was further suspended in 28% calcium chloride, and centrifuged at 37,000 rpm for 45 hours with a Beckman SW41Ti rotor, and thus the RNA-N protein complex was purified.

BHK/T7/151M (SE) cells were seeded on a 6-well plate at $5\times10^3$ cells/well, and cultured for 24 hours, and then each 1 μg of plasmid pCMV-P for expressing P protein, and plasmid pCMV-L for expressing L protein were introduced by Lipofectamine LTX. After another 24 hours, 5 μg of the RNA-N protein complex was mixed with 10 μL of a Pro-DeliverIN reagent (OZ Biosciences) and introduced into the cells. From after 24 hours, the cells were transferred to a 10% FCS-containing DMEM culture medium containing 300 μg/mL of hygromycin B and cultivation was continued, and BHK/#9A2 cells were separated. Occurrence of reconstitution of the stealth RNA gene expression system was confirmed by the expression of EGFP and Keima-Red.

Example 8

Preparation of Stealth RNA Vector #1 Carrying Ten Exogenous Genes

For $5.0\times10^3$ BHK/#9A cells (or BHK/#9A2 cells), pMKIT-151M, pSRD-HN-Fmut, and pCMV-Furin which are defective gene expression plasmids were introduced in a ratio of 2 μg, 2 μg, and 30 ng with Lipofectamine LTX, and after washing the cells after 4 hours, a 10% FCS-containing DMEM culture medium was added, and the cells were further cultured at 32° C. for 4 days. Then the culture supernatant containing stealth RNA vector #1 (FIG. 13) was collected, and filtered through a 0.45 μm filter, and the vector was concentrated by ultra centrifugation as necessary. The vector suspension was rapidly frozen with liquid nitrogen, and stored at −80° C. The activity of the vector was assayed by an indirect fluorescent antibody method by an anti-NP protein antibody by using $LLCMK_2$ cells derived from monkey kidney (Non-Patent Document 7). The infectivity titer of the stealth RNA vector obtained by the present method was about $10^7$ infectious units/mL, and equivalent or higher activity was obtained as compared with a conventional persistent expression type Sendai virus vector.

Example 9

Gene Expression by Stealth RNA Vector Carrying Ten Exogenous Genes (see FIG. 14)

HeLa cells were infected with stealth RNA vector #1 prepared in (Example 8) at MOI=3, and HeLa/#9 cells were established by selection in a 10% FCS-containing DMEM culture medium containing 100 μg/mL of hygromycin B. The drug resistance of these cells was selected by puromycin (1.5 μg/mL), Zeocin (100 μg/mL), hygromycin B (100 μg/mL), G418 (800 μg/mL), and Blasticidin S (10 μg/mL), and the survival rate was measured by a colony assay. It was confirmed HeLa/#9 cells showed resistance selectively to puromycin, Zeocin, and hygromycin B and expressed the resistance characters to these three drugs unlike the negative control HeLa cells that are sensitive to all of these antibiotics (FIG. 14, upper stage).

Expression of fluorescent proteins in HeLa/#9 cells was measured with a flow cytometer (Gallios, Beckman Coulter). Observation conditions of individual fluorescent proteins are as follows. EBFP2: excitation 405 nm, detection 450 nm; Keima-Red: excitation 405 nm, detection 620 nm; EGFP: excitation 488 nm, detection 530 nm; E2-Crimson: excitation 638 nm, detection 660 nm. It was confirmed that HeLa/#9 cells significantly express four fluorescent proteins as compared with HeLa cells not having a vector (FIG. 14, middle stage).

Expression of luciferase in HeLa/#9 cells was examined by detecting the emission with a luminometer (Promega, Corp.) by using the following reagents. Firefly luciferase and Renilla luciferase: Dual-Luciferase Reporter Assay System (Promega, Corp.); *Cypridina noctiluca* luciferase: Bio-Lux Cypridina Luciferase Assay Kit (New England Biolabs, Inc.). Activity of any luciferase was not detected in HeLa cells not having a vector, but high activity was detected in HeLa/#9 cells (FIG. 14, lower stage).

Example 10

Figure 15:
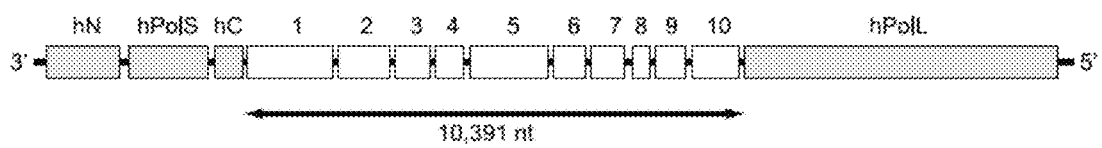
FIG. 15 illustrates a genome structure of a stealth RNA gene expression system carrying ten exogenous gene cDNAs, prepared while the base sequences of the nucleic acid are optimized in a different manner from FIG. 13.

Preparation of Stealth RNA Vector #2 Carrying Ten Exogenous Genes (FIG. 15)

A vector was prepared in the same manner as described in (Example 8) and verified in the manner as described in (Example 9) except that hN, hC, hPolS, hPolL genes used for preparation of the template cDNA were optimized by GeneGPS Expression Optimization Technology, and three genes, hN, hC, and hPolS were installed in the order of hN-hPolS-hC. The DNA fragment in which attB1 and T7 promoter are connected in this order on 5' side of the DNA containing hN-hPolS-hC (SEQ ID NO: 78) was synthesized by DNA 2.0. Similarly, the DNA fragment in which HDV ribozyme, T7 terminator, and attB2 are connected on 3' side of the DNA containing hPolL (SEQ ID NO: 79) was synthesized by DNA 2.0.

Example 11

Preparation of Stealth RNA Vectors #3 and #4 (FIG. 16) Carrying Ten Exogenous Genes A vector was prepared in the same manner as described in (Example 8) and verified in the manner as described in (Example 9) except that three genes, hN, hC, and hPolS optimized by OptimumGen Gene Design System was installed in the order of hN-hPolS-hC (#3) or in the order of hPolS-hN-hC (#4). The DNA fragment in which attB1 and T7 promoter are connected in this order on 5' side of the DNA containing hN-hPolS-hC (SEQ ID NO: 80), the DNA fragment in which attB1 and T7 promoter are connected in this order on 5' side of the DNA containing hPolS-hN-hC (SEQ ID NO: 81), and the DNA fragment in which HDV ribozyme, T7 terminator, and attB2 are connected on 3' side of the DNA containing hPolL (SEQ ID NO: 82) were synthesized by GenScript.

Example 12

Preparation of Stealth RNA Vector #5 Carrying Four Exogenous Genes

Blasticidin S resistant gene (Non-Patent Document 69) (SEQ ID NO: 56) and Kusabira-Orange gene (Non-Patent Document 70) (GenBank Accession Number AB128819) were amplified to have a structure of Acc65I-cDNA-XhoI by PCR, and sub-cloned (FIG. 7). Plasmid #5D is obtained by cloning the DNA having the following structure between the ApaI cleavage site and the StuI cleavage site of LITMUS38i. However, the SapI digested end is different from that of plasmid #5: SapI cleavage site-SEQ ID NO: 1-SEQ ID NO: 36-Acc65I cleavage site-SalI cleavage site-SEQ ID NO: 37-SEQ ID NO: 4-ctt-SEQ ID NO: 1-SEQ ID NO: 38-BsiWI cleavage site-XhoI cleavage site-SEQ ID NO: 39-SEQ ID NO: 4-attB2-SapI cleavage site.

Between Acc65I-SalI of plasmid #1, an Acc65I-XhoI fragment containing dKeima-Red gene was cloned to prepare plasmid #1D. Further, between BsiWI-XhoI of plasmid #1D, an Acc65I-XhoI fragment containing Blasticidin S resistant gene was cloned to prepare plasmid #1E. Further, between Acc65I-SalI of plasmid #5D, an Acc65I-XhoI fragment containing EGFP gene was cloned to prepare plasmid #5E. Further, between BsiWI-XhoI of plasmid #5E, an Acc65I-XhoI fragment containing Kusabira-Orange gene was cloned to prepare plasmid #5F.

A total of 200 ng including 100 ng of a DNA fragment containing dKeima-Red gene and Blasticidin S resistant gene cut out from plasmid #1E with SapI, and 100 ng of a DNA fragment containing EGFP gene and Kusabira-Orange gene cut out from plasmid #5F with SapI was dissolved in 5 μL of H$_2$O, and the solution was mixed with 5 μL of Ligation-Convenience Kit and allowed to react at 16° C. for 60 minutes. After purification, the product was dissolved in 7 μL of H$_2$O, and 1 μL of plasmid #6 (150 ng) and 2 μL of BP Clonase2 were added and allowed to react at 25° C. for 2 hours, and then the product was introduced into *Escherichia coli* DH-5α, and a kanamycin resistant colony was isolated to prepare plasmid #11. Preparation of stealth RNA vector #5 using the DNA fragment containing four genes cut out from plasmid #11 with XmaI and NotI was conducted in the manner as described in (Example 5) to (Example 8).

Example 13

Figure 17:
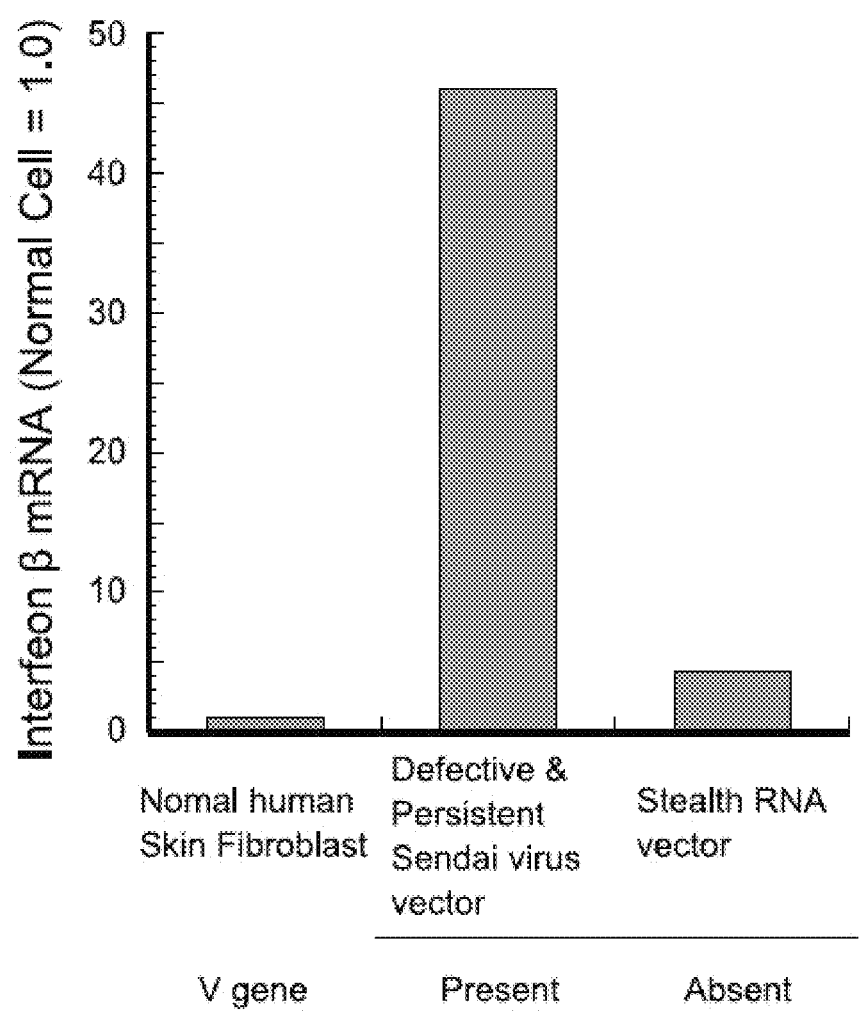
FIG. 17 illustrates interferon induction activity of a stealth RNA vector.

Induction of IFN-β Gene by Stealth RNA Vector (FIG. 17)

Defective and persistent Sendai virus vector SeVdp (KR/Bsr/EGFP/KO) is described in Non-Patent Document 7. Primary culture human skin-derived fibroblasts were infected with stealth RNA vector #5 prepared in (Example 12), and SeVdp (KR/Bsr/EGFP/KO) vector at MOI=3 each. Under this condition, both of the vectors could introduce genes into about 80% of the cells. At 24 hours after infection with the vectors, total RNA of cells was extracted by using ISOGEN Kit (NIPPON GENE Co., Ltd.), and genomic DNA was degraded by using Deoxy ribonuclease (RT Grade) (NIPPON GENE Co., Ltd.). Next, using this RNA as a template, First strand cDNA synthesis was conducted by reverse transcription reaction by using SuperScriptIII First-Strand Synthesis System for RT-PCR (Life Technologies, Inc.) and oligo (dT) 20. Further, by using Sso Advanced Universal SYBR Green Supermix (Bio-Rad), and using the first strand cDNA as a template, an expression amount of IFN-βmRNA was analyzed by the real-time PCR method using Gene Specific Primers (GSP) of a reference gene or interferon beta gene, and CFX96 Real-Time System (Bio-Rad).

Example 14

Preparation of Stealth RNA Gene Expression Systems #6, #7, #8, #9 and #10 Carrying Six Exogenous Genes (FIG. 20 and FIG. 22)

Plasmid #2D was obtained by cloning the DNA having the following structure between the ApaI cleavage site and the StuI cleavage site of plasmid LITMUS38i. However, the SapI digested end is different from that of plasmid #2: SapI cleavage site-SEQ ID NO: 1-SEQ ID NO: 28-Acc65I cleavage site-SalI cleavage site-SEQ ID NO: 29-SEQ ID NO: 4-ctt-SEQ ID NO: 1-SEQ ID NO: 30-BsiWI cleavage site-XhoI cleavage site-SEQ ID NO: 31-SEQ ID NO: 4-SapI cleavage site.

Between Acc65I-SalI of plasmid #2D, an Acc65I-XhoI fragment containing EGFP gene was cloned to prepare plasmid #2E. Further, between BsiWI-XhoI of plasmid #2E, an Acc65I-XhoI fragment containing puromycin resistant gene was cloned to prepare plasmid #2F.

A total of 300 ng including 100 ng of a DNA fragment containing firefly luciferase gene and Renilla luciferase gene cut out from plasmid #1C with SapI, 100 ng of a DNA fragment containing EGFP gene and puromycin resistant gene cut out from plasmid #2F with SapI, and 100 ng of a DNA fragment containing dKeima-Red gene and hygromycin B resistant gene cut out from plasmid #5C with SapI was dissolved in 5 µL of H$_2$O, and the solution was mixed with 5 µL of Ligation-Convenience Kit and allowed to react at 16° C. for 60 minutes. After purification, the product was dissolved in 7 µL of H$_2$O, and 1 µL of plasmid #6 (150 ng) and 2 µL of BP Clonase2 were added and allowed to react at 25° C. for 2 hours, and then the product was introduced into *Escherichia coli* DH-5α, and a kanamycin resistant colony was isolated to prepare plasmid #12. Preparation of stealth RNA gene expression systems #6, #7 and #8 (FIG. 20) (Example 16) and #9 and #10 (FIG. 22) (Example 18) using the DNA fragment containing six genes cut out from plasmid #12 with XmaI and NotI was conducted in the manner as described in (Example 5), (Example 6) and (Example 8).

Example 15

Figure 18:
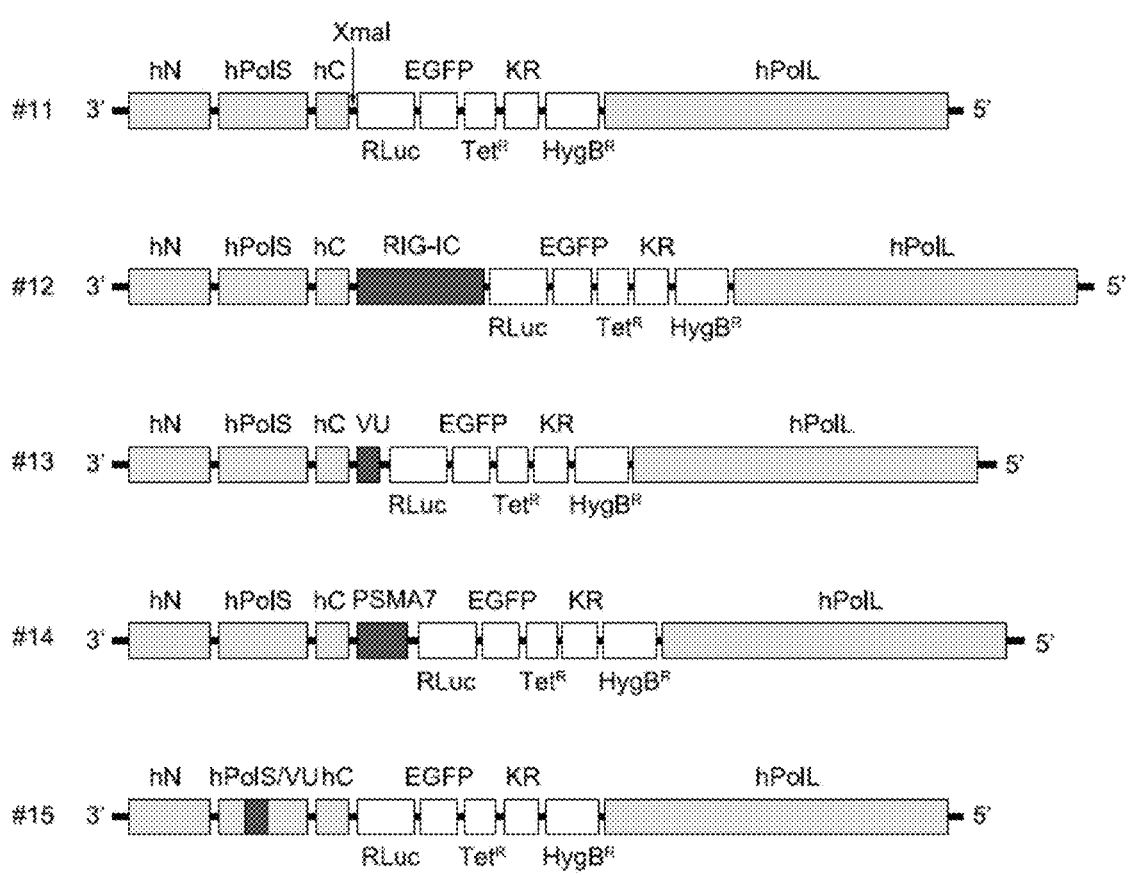
FIG. 18 illustrates a genome structure of a stealth RNA gene expression system carrying an additional factor for completely avoiding an innate immunity inducibility.

Preparation of Stealth RNA Gene Expression Systems #11, #12, #13, #14 and #15 Carrying Five Exogenous Genes (FIG. 18)

Plasmid #13 carrying five genes was prepared in the manner as described in (Example 14) except that among the genes installed on plasmid #12 in (Example 14), firefly luciferase gene was deleted, and puromycin resistant gene was replaced by tetracycline resistant gene derived from plasmid pBR322 (GenBank Accession Number J01749.1).

These five exogenous genes were installed on stealth RNA vector #3 (FIG. 16) carrying three genes, hN, hC, and hPolS in the order of hN-hPolS-hC, and stealth RNA gene expression system #11 carrying five exogenous genes were prepared. Further, in the XmaI site of this stealth RNA gene expression system, a gene cassette containing codon-optimized RIG-IC (SEQ ID NO: 83), a gene cassette containing codon-optimized C-terminal region of Sendai virus V protein (SEQ ID NO: 84), or a gene cassette containing codon-optimized PSMA7 which is a constituent of proteasome (SEQ ID NO: 85) was inserted, and thus stealth RNA gene expression systems #12, *13 and #14 carrying five exogenous genes were prepared. Stealth RNA gene expression system #15 carrying five exogenous genes is designed to express V protein by replacing part of hPolS gene of hN-hPolS-hC gene with P gene of non-optimized Sendai virus Z strain (SEQ ID NO: 86).

Figure 19:
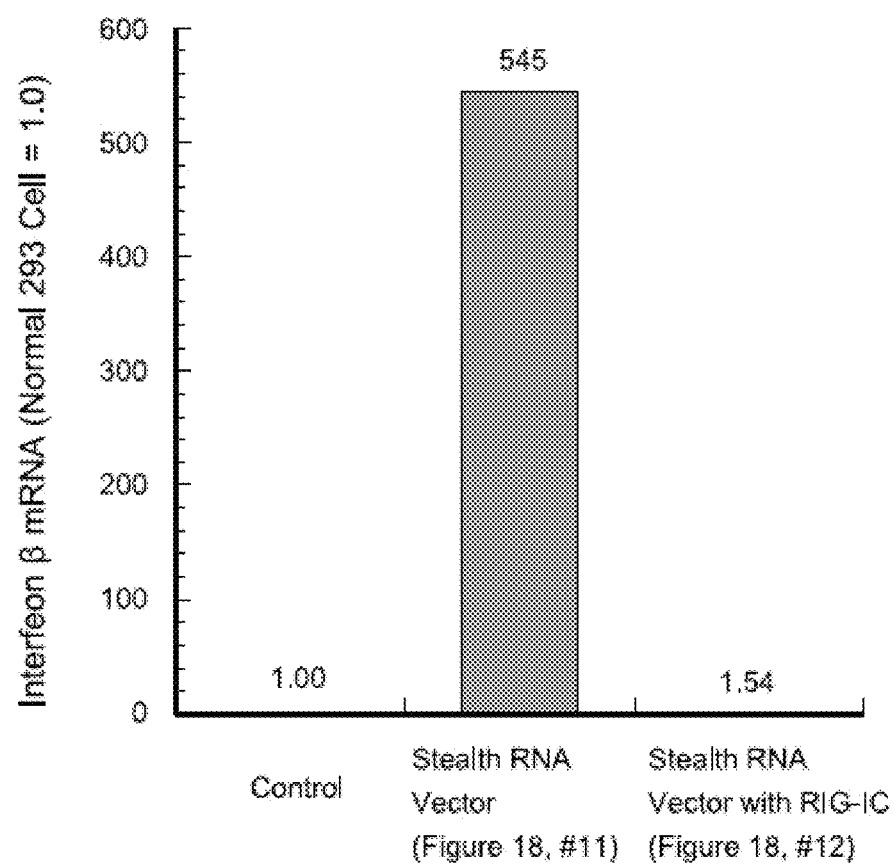
FIG. 19 illustrates interferon inducibility by a stealth RNA vector carrying an additional factor.

From cells containing these stealth RNA gene expression systems, stealth RNA vectors were prepared according to Example 8, and introduced into human-derived 293 cells, and interferon inducibility was measured. In FIG. 19, stealth RNA vectors #11 and #12 were compared as representative, and it was shown that by adding RIG-IC gene, induction of interferon beta remaining in the stealth RNA vector is almost completely suppressed.

Example 16

Analysis of Influence of Variation in Expression Efficiency of N Protein and C Protein on Expression of Exogenous Genes Installed on Stealth RNA Gene Expression System (see FIG. 20)

In front of the translation initiation codon (AUG) of firefly luciferase cDNA encoded by pGL4.12 (Promega Corporation) (GenBank Accession Number AY738224), an RNA sequence (SEQ ID Nos: 114, 115 or 116) corresponding to SEQ ID NO: 57, SEQ ID NO: 58 or SEQ ID NO: 59 was inserted, and firefly luciferase was expressed in HeLa cells by using a CMV promoter, and activity of luciferase was examined by using Dual-Luciferase Reporter Assay System (FIG. 20). It was demonstrated that when an another initiation codon is placed at out-frame position and upstream to the authentic translation initiation codon, the translating frame is shifted from the original translating frame of the protein, and the translation efficiency is deteriorated.

Next, stealth RNA gene expression systems #6, #7 and #8 in which a base sequence on 5' upstream side of the translation initiation codon of hN mRNA and hC mRNA was modified were examined for their gene expression ability. In stealth RNA gene expression system #6, a so-called "Kozak sequence (SEQ ID NO: 114)" which is believed to provide the highest translation efficiency is positioned on 5' upstream side of the translation initiation codon (AUG) of hN mRNA and hC mRNA. In stealth RNA gene expression system #7, 5' upstream side of the translation initiation codon of hN mRNA is replaced by "Kozak sequence (SEQ ID NO: 114)" (Non-Patent Document 60), and 5' upstream side of the translation initiation codon of hC mRNA is replaced by the base sequence of SEQ ID NO: 116 that lowers the translation efficiency to 23%. In stealth RNA gene expression system #8, 5' upstream side of the translation initiation codon of hN mRNA is replaced by the base sequence of SEQ ID NO: 115 that lowers the translation efficiency to 40%, and 5' upstream side of the translation initiation codon of hC mRNA is replaced by the base sequence of SEQ ID NO: 116 that lowers the translation efficiency to 23%. In this experiment, activity of luciferase was examined in BHK/T7/151M (SE) cells that stably retain stealth RNA gene expression systems #6, #7 or #8, by using Dual-Luciferase Reporter Assay System (FIG. 20).

Example 17

Preparation of Stealth RNA Gene Expression Systems #16 and #17 Carrying Five Exogenous Genes (FIG. 21)

Stealth RNA gene expression system #11 in which three genes, hN, hC, and hPolS are installed in the order of hN-hPolS-hC, and five exogenous genes are installed has been described in (Example 15). In hC gene of this vector, the translation efficiency is lowered to 23% by modification of the sequence of 5' untranslated region (FIG. 21). Stealth RNA gene expression system #16 is a system in which hC gene is removed from #11. The stealth RNA gene expression system #17 is a system in which the 5' untranslated sequence of hC gene in #11 is replaced by the Kozak sequence to achieve 100% of the translation efficiency.

As can be realized from the expression of EGFP shown in FIG. 21, the gene expression level of the stealth RNA gene expression system can be regulated by changing the translation efficiency of hC gene. Although hC gene is not an essential element for reconstitution of a stealth RNA gene expression system, lack of hC gene results in very strong expression of exogenous genes, and thus proliferation of cells is suppressed. Therefore, it is realistic to obtain gene expression of the practical level by allowing a certain degree of expression of hC gene.

Example 18

Analysis of Influence of Packaging Signal on Genome 3' Side of Stealth RNA Gene Expression System on Production of Vector Particle (see FIG. 22)

Stealth RNA gene expression system #9 is a system in which sequence D on 3' side of genome RNA (SEQ ID NO: 17) is deleted from stealth RNA gene expression system #6 (FIG. 20). Stealth RNA gene expression system #10 is a system in which sequence D on 3' side of genome RNA (SEQ ID NO: 17) is deleted from stealth RNA gene expression system #7 (FIG. 20). In BHK/T7/151M (SE) cells stably retaining these stealth RNA gene expression systems, proteins M, F, and HN were expressed in the manner as described in (Example 5), and the gene introduction ability of the stealth RNA vector collected in the supernatant was assayed by an indirect fluorescent antibody method using an anti-NP protein antibody and $LLCMK_2$ cells (Non-Patent Document 7).

Further, this sequence of 18 nucleotides was replaced by an arbitrarily selected partial sequence of mRNA derived from House-keeping gene recited in (Table 1) ((5) of FIG. 2 (SEQ ID NO: 75)), and no variation was observed in the particle formation efficiency (data not shown).

From the above, it can be considered that the region having a length of 18 nucleotides from the 97th to 114th nucleotides from 3' terminus of the genome or a region having a partial length thereof is an essential for packaging for particle formation in the negative-sense single-stranded RNA. In any case, it can be concluded that the region having a length of 18 nucleotides or a region having a partial length thereof at this position is "packaging signal region" that is essential for the stealth RNA gene expression system to be incorporated into the virus-like particle, although it is not essential for transcription and replication from the negative-sense single-stranded RNA as a template.

Example 19

Variation with Time of Luciferase Activity when HeLa Cells Retaining Stealth RNA Gene Expression System are Treated with siRNA (see FIG. 23)

Stealth RNA vector #6 was prepared from stealth RNA gene expression system #6 (FIG. 20), and gene introduction into HeLa cells and selection with hygromycin B were conducted, and thus HeLa/#3 cell strain was established. HeLa/#3 cells were seeded on a 48-well plate at $1.0 \times 10^4$/well, and on the next day, siRNA targeting a target sequence of PolL gene (SEQ ID NO: 46) was mixed with an introducing reagent RNAiMAX (Life Technologies, Inc.) in a final concentration 100 nM and introduced into the cells. Luciferase activity was measured overtime, and in all the four independent experiments, luciferase activity was suppressed to about 0.1% in 10 days. This reveals that the stealth RNA gene expression system was removed from cells efficiently.

Example 20

Preparation of Stealth RNA Vector Carrying Giant Gene (see FIG. 24)

Stealth RNA vectors carrying various exogenous genes can be prepared by producing "transcription cassettes" each consisting of two genes in the same manner as in (Example 1) to (Example 2), sequentially linking the "transcription cassettes" in the same manner as in (Example 3) to (Example 5), and preparing in the same manner as in (Example 6) or (Example 7) and (Example 8). Names and base sequences of exogenous genes that can be installed as such a giant exogenous gene are as follows. Human KLF4: SEQ ID NO: 60, human OCT4: SEQ ID NO: 61, human SOX2: SEQ ID NO: 62, human c-Myc: SEQ ID NO: 63, human BRG1: SEQ ID NO: 64, human BAF155: SEQ ID NO: 65, human immunoglobulin G H chain: SEQ ID NO: 66, human immunoglobulin G L chain: SEQ ID NO: 67, human immunoglobulin M clone 2G9 H chain: SEQ ID NO: 68, human immunoglobulin M clone 2G9 L chain: SEQ ID NO: 69, human immunoglobulin M J chain: SEQ ID NO: 70, human blood coagulation factor VIII: SEQ ID NO: 71, and human dystrophin: SEQ ID NO: 72.

RNA expression systems carrying these genes as exogenous genes can be introduced into target cells in the technique corresponding to the procedure described in the foregoing Examples. By expressing plural exogenous genes simultaneously in the same cell, it becomes possible to add a desired modification such as cell-reprogramming to the introduced cells.

Example 21

Figure 25:
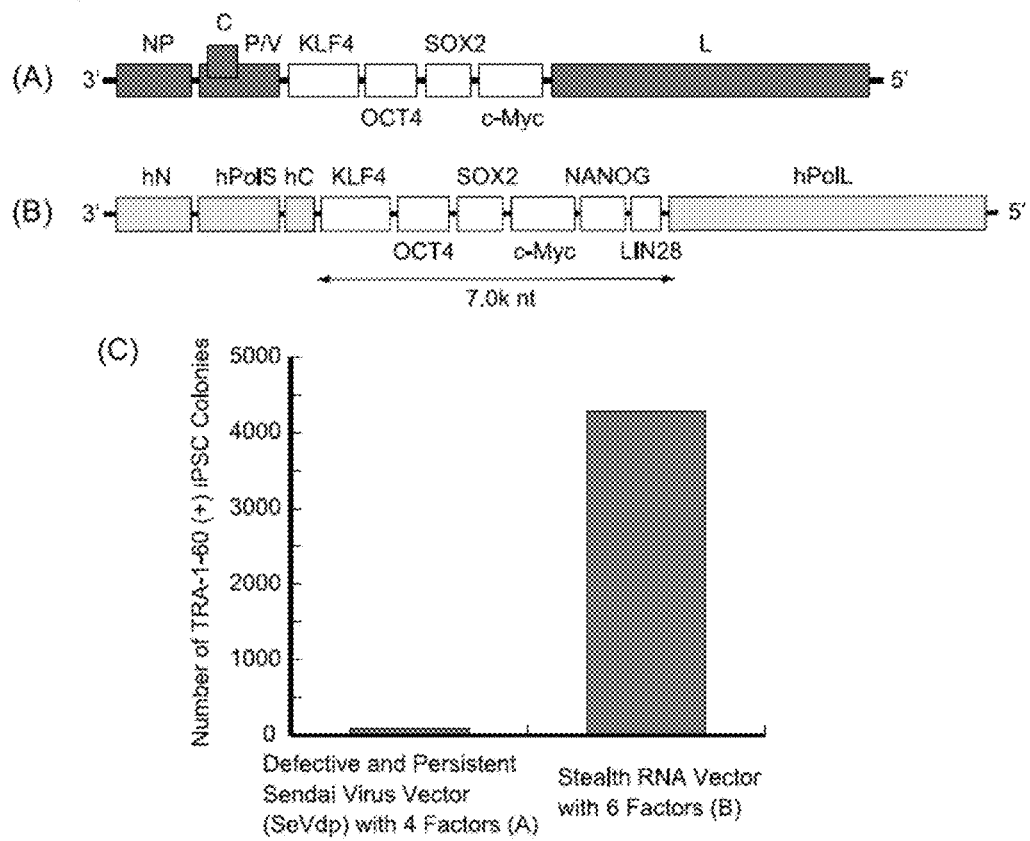
FIG. 25 illustrates a preparation efficiency of induced pluripotent stem cells (iPS cells) by a stealth RNA vector carrying six reprogramming genes.

Induction of Induced Pluripotent Stem Cells (iPS Cells) by Stealth RNA Vector Carrying Six Reprogramming Genes (FIG. 25)

The capability of carrying six or more genes and expressing them securely, which is a feature of the stealth RNA vector would be particularly effective for cell-reprogramming in which human somatic cells are initialized and converted to iPS cells. Thus, the present inventors prepared a stealth RNA vector simultaneously expressing a total of six reprogramming genes by adding reprogramming genes NANOG and LIN28 (Patent Document 2, and Non-Patent Document 2) having complementary functions to the combination of four reprogramming genes, KLF4, OCT4, SOX2, and c-MYC that was first reported as a method for making human induced pluripotent stem cells (Patent Document 1, and Non-Patent Document 1), and compared the cell-reprogramming activity between the stealth RNA vector and the "persistent expression type Sendai virus vector simultaneously carrying the four reprogramming genes (KLF4, OCT4, SOX2 and c-MYC)" having the highest reprogramming efficiency among the iPS cell preparation techniques that have been reported heretofore (Patent Document 3, Patent Document 4, and Non-Patent Document 7) (FIG. 25A).

Stealth RNA vector #23 carrying six reprogramming genes (FIG. 25B) was prepared according to Example 6 and Example 8 by binding human KLF4 (SEQ ID NO: 60), human OCT4 (SEQ ID NO: 61), human SOX2 (SEQ ID NO: 62), human c-MYC (SEQ ID NO: 63), human NANOG (SEQ ID NO: 87), and human LIN28 (SEQ ID NO: 88) in this order by the method shown in Example 14, and incorporating the genes into stealth RNA vector #3 of FIG. 16.

Preparation of iPS cells was conducted according to Patent Document 3. To be more specific, TIG3 cells derived from human embryonic fibroblasts were seeded on a 12-well plate at $1.0 \times 10^5$ cells/well, and on the next day, a Sendai virus vector for persistent expression carrying KLF4, OCT4, SOX2, and c-MYC (FIG. 25A), and a stealth RNA vector carrying KLF4, OCT4, SOX2, c-MYC, NANOG, and LIN28 (FIG. 25B) were added into the culture medium in the condition of MOI (Multiplicity of Infection)=3, and left still for 2 hours at room temperature, and then cultured overnight at 37° C. to infect the cells. MEF treated with mitomycin C was prepared as feeder cells on a gelatin-coated dish, and the aforementioned cells transfected with the vector were seeded thereon, and cultured in a culture medium for human multipotent stem cells StemFitAK03 (Ajinomoto, Co., Inc.). At days after gene introduction, cells were stained with AlexaFluor488-labeled anti-TRA-1-60 antigen antibody (Merck-Millipore), and the number of clones of TRA-1-60 positive iPS cells appeared from $1\times10^4$ TIG-3 cells was counted (FIG. 25C). While 85 clones of iPS cell clones appeared by the four-factor-carrying vector (reprogramming efficiency 0.85%), 4290 clones of iPS cell clones appeared by the six-factor-carrying vector (reprogramming efficiency 42.9%), revealing the effectiveness of the stealth RNA vector carrying six genes. The total nucleotide length of genes used in the present Example is 7.0 kb, and this size cannot be realized by a method using a conventional RNA vector.

Example 22

Figure 26:
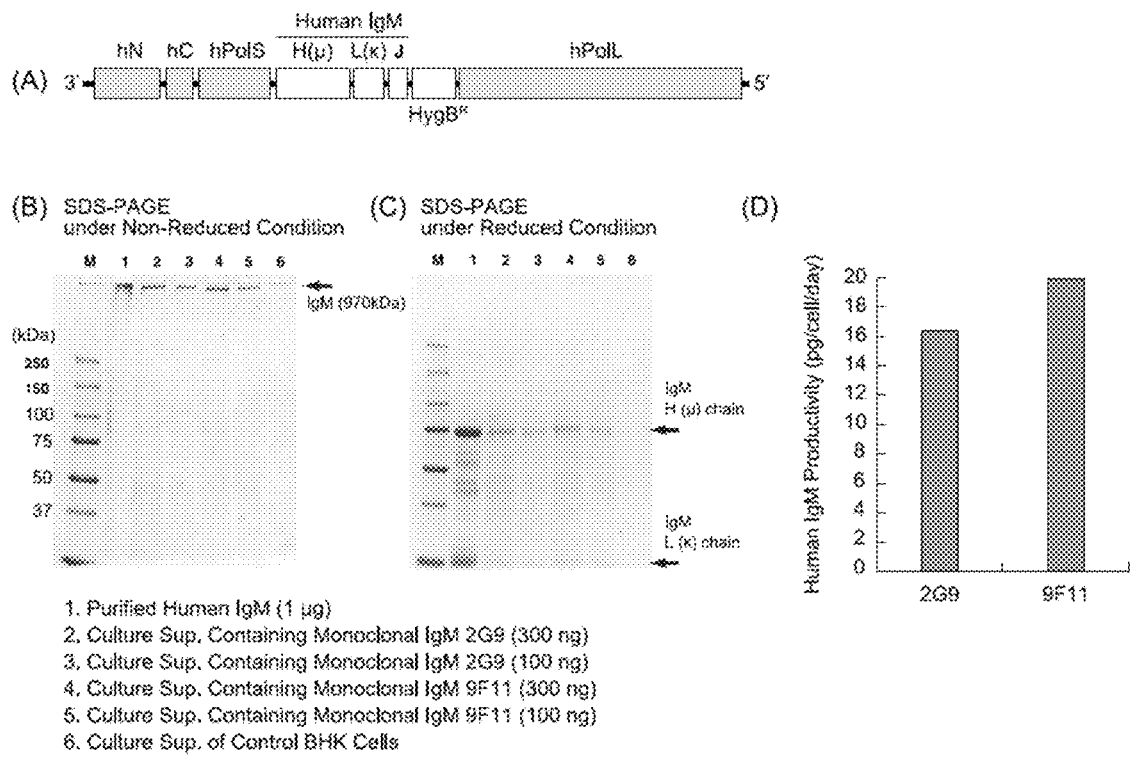
FIG. 26 illustrates expression of immunoglobulin M by a stealth RNA gene expression system.

Production of Human Immunoglobulin M by Simultaneous Expression of H Chain, L Chain, and J Chain of Human Immunoglobulin M (IgM) (FIG. 26)

As a representative product for which simultaneous expression of plural polypeptides is required in the field of production of biopharmaceuticals, antibody drugs are recited. While the commercial production technology of immunoglobulin G (IgG) capable of expressing and producing H chain and L chain has been already established, production of IgM for which simultaneous expression of three genes encoding H chain, L chain, and J chain are required is not still easy today (Non-Patent Document 84). It is known that in IgM, there is an antibody having strong anti tumor activity that is not present in IgG (Non-Patent Document 85), and establishment of a production method of IgM is industrially very significant. Thus, the present inventors attempted to produce an IgM having a molecular weight of 950 k Dalton by carrying three genes that encode H chain, L chain and J chain of human IgM on a stealth RNA vector and expressing them simultaneously.

In Example 22, human monoclonal IgM antibodies 9F11 and 2G9 that react with the cells infected with human immunodeficiency virus (HIV) (Non-Patent Document 86) were selected as a material, and a set of H chain gene (SEQ ID NO: 89) and L chain gene (SEQ ID NO: 90) of 9F11 antibody, J chain gene (SEQ ID NO: 70), and hygromycin B resistant gene (SEQ ID NO: 50), or a set of H chain gene (SEQ ID NO: 68) and L chain gene (SEQ ID NO: 69) of 2G9 antibody, J chain gene (SEQ ID NO: 70), and hygromycin B resistant gene (SEQ ID NO: 50) were linked in this order according to Example 12, and installed on stealth RNA vector #8 of FIG. 20, to obtain stealth RNA vectors #23 and #20. Then gene introduction into BHK cells derived from hamster acclimated to a serum-free culture medium, Opti-Pro SFM (Life Technologies, Inc.) for protein production was conducted in the condition of MOI=3, and selection was conducted by adding 100 µg/mL hygromycin B. After renewing the culture medium, cells were collected after 24 hours of culture, and the culture supernatant was collected.

The amount of human IgM in the culture supernatant was quantified by an anti-human IgM ELISA kit (Bethyl Laboratories, Inc.), and 9.17 µg/mL of IgM was detected when the gene set of 2G9 was introduced, and 11.15 µg/mL of IgM was detected when the gene set of 9F11 was introduced. IgM in the culture supernatant of BHK cells into which genes were not introduced was under or equal to the detection limit. Expression efficiency per cell per day (pg/cell/day) converted from the above amount was 16.38 pg/cell/day for 2G9, and 19.91 pg/cell/day for 9F11 (FIG. 26).

Then, the culture supernatants containing 300 ng and 100 ng of IgM were analyzed by SDS polyacrylamide gel electrophoresis using 4-20% Gradient Gel (Bio-Rad), and stained with BioSafe Coomasie G250 stain (Bio-Rad). Under a non-reduced condition, a band was detected at the position of 970 kDa as is the same with native human IgM, and under a reduced condition, bands were detected at the positions of H chain of molecular weight of 75 kDa and L chain of 25 kDa. This reveals that an IgM molecule in which 21 polypeptides are bound, that is the same with the native one is generated.

In Non-Patent Document 84, analytical results in four clones of cells stably expressing IgM obtained as a result of gene amplification with methotrexate by using CHO-DG44 cells and HEK293 cells are described, and the expression efficiency was 25.00, 3.59, 4.60, and 0.21 pg/cell/day, respectively. This reveals that by using a stealth RNA vector, it is possible to easily realize production at an equivalent or higher level compared with expression of IgM achieved by gene amplification that requires several months.

Example 23

Figure 27:
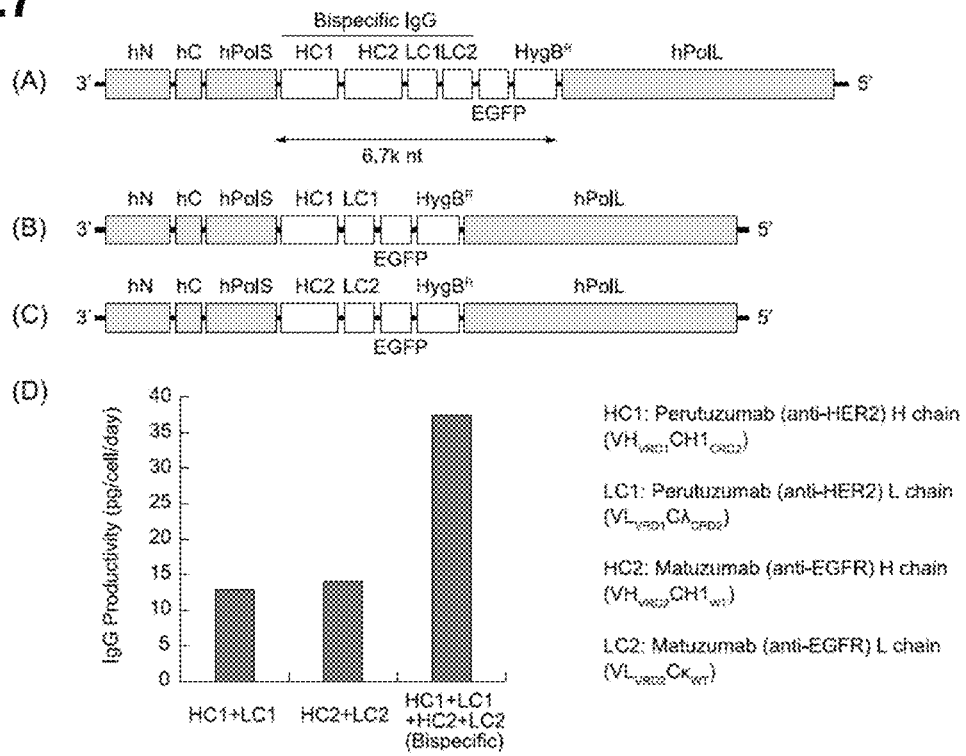
FIG. 27 illustrates expression of a bi-specific antibody molecule by a stealth RNA gene expression system.

Production of Human Bispecific Antibody by Simultaneous Expression of Four cDNAs (FIG. 27)

Recently, bi specific antibodies capable of recognizing two different antigens attract attentions in the field of biopharmaceuticals as a molecule that greatly extends the possibility of the existing antibody drugs. A bi specific antibody is a tetramer made up of H chain (A) and L chain (A) that recognize antigen A, and H chain (B) and L chain (B) that recognize antigen B, and is prepared by introducing a mutation so that H chain (A) and L chain (B), or H chain (B) and L chain (A) are difficult to bind each other, and introducing a mutation so that binding between H chain (A) and H chain (B) is stronger than binding between H chains (A) or binding between H chains (B), and then expressing four genes encoding H chain (A), L chain (A), H chain (B), and L chain (B) simultaneously (Non-Patent Document 87). Since it is very difficult to obtain a cell strain that simultaneously expresses four polypeptides by gene amplification after simultaneous introduction of these four genes into cells, it is normally produced by transient gene expression. In the present Example, the present inventors attempted to prepare HE Design LK that simultaneously recognizes HER2 and an epithelial growth factor receptor (EGFR) among the bi specific antibodies described in Non-Patent Document 87.

H chain HC1 (VH$_{VRD1}$CH1$_{CRD2}$) gene (SEQ ID NO: 91) and L chain LC1 (VL$_{VRD1}$Cλ$_{CRD2}$) gene (SEQ ID NO: 92) of anti-HER2 antibody, and H chain HC2 (VH$_{VRD2}$CH1$_{WT}$) gene (SEQ ID NO: 93) and L chain LC2 (VL$_{VRD2}$Cκ$_{WT}$) gene (SEQ ID NO: 94) of anti-EGFR antibody disclosed in Non-Patent Document 87 were linked together with EGFP gene and hygromycin B resistant gene according to Example 14, and installed on stealth RNA vector #8 (FIG. 20) to prepare stealth RNA vector #24. For comparison, vector #25 for expressing only H chain and L chain of anti-HER2 antibody (FIG. 27B) and vector #26 for expressing only H chain and L chain of anti-EGFR antibody (FIG. 27C) were prepared according to Example 12.

Using these vectors, genes were introduced into BHK cells derived from hamster acclimated to Opti-Pro SFM (Life Technologies, Inc.) by the method of Example 22, and an amount of human IgG in the culture supernatant of stably expressing cells was quantified by an anti-human IgG ELISA kit (Bethyl Laboratories, Inc.). In contrast with the combination of only HC1 and LC1 (12.93 pg/cell/day), or the combination of HC2 and LC2 (14.02 pg/cell/day) that is poor in activity of forming a tetramer, significantly high (37.45 pg/cell/day) antibody production was observed when four genes, HC1, LC1, HC2, and LC2 were installed. This suggests that the bi specific antibody is produced efficiently. This expression level is comparable to the gene expression level in a general cell strain established by CHO cells using gene amplification (about 90 pg/cell/day at maximum) (Non-Patent Document 88). This suggests that as a method for stably producing a bi specific antibody for which a stably expressing cell strain has been difficult to be obtained by conventional methods, the stealth RNA vector is very useful. The total nucleotide length of the genes used in the present Example is 6.7 k nucleotides, and this size cannot be realized by a method using a conventional RNA vector.

INDUSTRIAL APPLICABILITY

The present invention is useful in various industrial fields including reprogramming of human cells including preparation of induced pluripotent stem cells (iPS cells), production of protein drugs, gene therapy by various genes including giant genes, and expression of drug-discovery target molecules.

What is claimed is:

1. A DNA-based tandem cassette having two cloning sites A and B, the tandem cassette being composed of (1) multimerization site A, (2) transcription start signal A, (3) noncoding sequence A1, (4) cloning site A, (5) noncoding region A2, (6) transcription termination signal A, (7) transcription start signal B, (8) noncoding sequence B1, (9) cloning site B, (10) noncoding region B2, (11) transcription termination signal B, and (12) multimerization site B in order from the 5' terminus, the multimerization site A of the (1), and multimerization site B of the (12) being DNAs that are identical to or different from each other and each containing a recognition site by restriction endonuclease and/or a recognition site by site-specific recombinase, the transcription start signal A of the (2), and transcription start signal B of the (7) being DNAs that are identical to or different from each other and each containing a transcription start signal recognized by the RNA-dependent RNA polymerase when transcribed to RNA, the noncoding sequence A1 of the (3), noncoding region A2 of the (5), noncoding sequence B of the (8), and noncoding region B2 of the (10) being DNAs that are identical to or different from one another and each becoming RNA that is not recognized by an innate immune system of a host cell when transcribed to RNA, the cloning site A of the (4), and cloning site B of the (9) being DNAs that are identical to or different from each other and each containing one or more recognition sites by restriction endonuclease and/or recognition sites by site-specific recombinase, the transcription termination signal A of the (6), and transcription termination signal B of the (11) being DNAs that are identical to or different from each other and each containing a transcription termination signal recognized by the RNA-dependent RNA polymerase when transcribed to RNA, wherein the noncoding sequence A1 of the (3), the noncoding region A2 of the (5), the noncoding sequence B1 of the (8), and the noncoding region B2 of the (10) are identical to or different from one another, and each of the sequences A1, A2, B1 and B2 is a DNA sequence having 5 to 49 nucleotides in length that is to be transcribed into a partial mRNA of an animal gene that is not recognized by the innate immune system of the host cell, and one of human genes identical to or different from each other is inserted into the cloning site A of the (4), and cloning site B of the (9).

2. The tandem cassette according to claim 1, wherein the cloning site A of the (4) contains a recognition site by restriction endonuclease A, and a recognition site by restriction endonuclease C in order from 5' terminal side, and the cloning site B of the (9) contains a recognition site by restriction endonuclease D, and a recognition site by restriction endonuclease B in order from 5' terminal side, provided that the restriction endonuclease A and the restriction endonuclease D give single-stranded protruding ends of the same order, and the restriction endonuclease C and the restriction endonuclease B give single-stranded protruding ends of the same sequence.

3. The tandem cassette according to claim 1, wherein both of the multimerization site A of the (1), and multimerization site B of the (12) are DNAs containing a recognition site by a restriction endonuclease giving a single-stranded protruding end of any sequence represented by NN or NNN.

* * * * *